United States Patent
Loehn et al.

(10) Patent No.: US 8,846,712 B2
(45) Date of Patent: Sep. 30, 2014

(54) 6-(4-HYDROXY-PHENYL)-3-STYRYL-1H-PYRAZOLO[3,4-B]PYRIDINE-4-CARBOXYLIC ACID AMIDE DERIVATIVES AS KINASE INHIBITORS

(75) Inventors: Matthias Loehn, Frankfurt am Main (DE); Maria Mendez-Perez, Frankfort am Main (DE); Stefania Pfeiffer-Marek, Frankfurt am Main (DE); Aimo Kannt, Frankfurt am Main (DE); Guillaume Begis, Paris (FR); Olivier Duclos, Paris (FR); Federic Jeannot, Paris (FR)

(73) Assignee: Sanofi, Paris (FR)

( * ) Notice: Subject to any disclaimer, the term of this patent is extended or adjusted under 35 U.S.C. 154(b) by 146 days.

(21) Appl. No.: 13/230,365

(22) Filed: Sep. 12, 2011

(65) Prior Publication Data

US 2013/0065894 A1    Mar. 14, 2013

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl.
USPC .......................................... 514/303; 546/120

(58) Field of Classification Search
USPC .......................................... 514/303; 546/120
See application file for complete search history.

(56) References Cited

U.S. PATENT DOCUMENTS

| 2013/0085128 A1 | 4/2013 | Hatchel et al. |
|---|---|---|
| 2013/0150340 A1 | 6/2013 | Plettenburg et al. |

FOREIGN PATENT DOCUMENTS

| AU | 617324 | 12/1988 |
|---|---|---|
| EP | 0 296 110 A2 | 12/1988 |
| EP | 296110 | 12/1988 |
| EP | 657458 | 12/1994 |
| EP | 0 657 458 A1 | 6/1995 |
| EP | 1354882 | 10/2003 |
| WO | WO 95/17182 | 6/1995 |
| WO | WO 95/17182 A1 | 6/1995 |
| WO | WO 00/58307 | 10/2000 |
| WO | WO 00/58307 A2 | 10/2000 |
| WO | WO 02/38561 | 5/2002 |
| WO | WO 02/38561 A1 | 5/2002 |
| WO | WO 2005/009389 | 2/2005 |
| WO | WO 2005/009389 A2 | 2/2005 |
| WO | WO 2005/028480 | 3/2005 |
| WO | WO 2005/028480 A2 | 3/2005 |
| WO | WO 2005/058307 | 6/2005 |
| WO | WO 2008/125945 | 10/2008 |
| WO | WO 2008/125945 A2 | 10/2008 |
| WO | WO2008/144253 A1 | 11/2008 |
| WO | WO2010/011772 A2 | 1/2010 |
| WO | WO2010/129668 A1 | 11/2010 |

OTHER PUBLICATIONS

Chemical Abstract Services (CAS) STN Records, Apr. 13, 2011-Apr. 17, 2011, American Chemical Society.*
U.S. Appl. No. 13/660,366, filed Oct. 25, 2012, Plettenburg, et al.
European Search Report dated Nov. 7, 2011 issued in EP 11 30 6130.
International Search Report and Written Opinion dated Oct. 20, 2011 issued in PCT/EP2011/065719.

* cited by examiner

*Primary Examiner* — Sarah Pihonak

(57) ABSTRACT

The present invention relates to pyrazolo[3,4-b]pyridine compounds of the formula I,

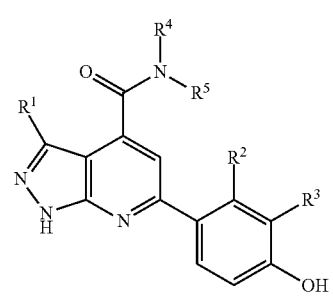

in which $R^1$, $R^2$, $R^3$, $R^4$ and $R^5$ are defined as indicated below. The compounds of the formula I are kinase inhibitors, and are useful for the treatment of diseases associated with diabetes and diabetic complications, such as, diabetic nephropathy, diabetic neuropathy and diabetic retinopathy, for example. The invention furthermore relates to the use of compounds of the formula I, in particular as active ingredients in pharmaceuticals, and pharmaceutical compositions comprising them.

7 Claims, No Drawings

6-(4-HYDROXY-PHENYL)-3-STYRYL-1H-PYRAZOLO[3,4-B]PYRIDINE-4-CARBOXYLIC ACID AMIDE DERIVATIVES AS KINASE INHIBITORS

The present invention relates to pyrazolo[3,4-b]pyridine compounds of the formula I,

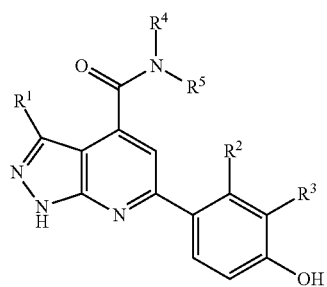

in which $R^1$, $R^2$, $R^3$, $R^4$ and $R^5$ are defined as indicated below. The compounds of the formula I are kinase inhibitors, and are useful for the treatment of diseases associated with diabetes and diabetic complications, e.g., diabetic nephropathy, diabetic neuropathy and diabetic retinopathy, for example. The invention furthermore relates to the use of compounds of the formula I, in particular as active ingredients in pharmaceuticals, and pharmaceutical compositions comprising them.

Protein kinase C (PKC) comprises a family of several related isoenzymes that function as serine/threonine kinases. PKC plays an important role in intercellular and intracellular signaling, gene expression, and in the control of cell differentiation and growth. Currently, at least ten isoforms of PKC are known which are different in regulation, tissue distribution, and enzymatic specificity (Newton A C. Regulation of the ABC kinases by phosphorylation: protein kinase C as a paradigm. Biochem J 2003; 370(Pt 2):361-371; Newton A C. Protein kinase C: poised to signal. Am J Physiol Endocrinol Metab 2010; 298(3):E395-E402; Nishizuka Y. Studies and prospectives of the protein kinase c family for cellular regulation. Cancer 1989; 63(10):1892-1903; Nishizuka Y. The Albert Lasker Medical Awards. The family of protein kinase C for signal transduction. JAMA 1989; 262(13):1826-1833). The PKC family of isoenzymes are grouped into three subclasses based on the domain composition of the regulatory moiety: (1) conventional PKCs (alpha, beta-II, and beta-I), (2) novel PKCs (delta, epsilon, gamma, eta and theta) and (3) atypical PKCs (zeta and iota/lambda) (Newton A C. Regulation of the ABC kinases by phosphorylation: protein kinase C as a paradigm. Biochem J 2003; 370(Pt 2):361-371; Mellor H, Parker P J. The extended protein kinase C superfamily. Biochem J 1998; 332 (Pt 2):281-292). PKC is a membrane-associated enzyme that is regulated by several distinct factors, such as membrane phospholipids, calcium, and membrane lipids, e.g. diacylglycerol (Newton A C. Regulation of the ABC kinases by phosphorylation: protein kinase C as a paradigm. Biochem J 2003; 370(Pt 2):361-371; Newton A C. Protein kinase C: poised to signal. Am J Physiol Endocrinol Metab 2010; 298(3):E395-E402; Mellor H, Parker P J. The extended protein kinase C superfamily. Biochem J 1998; 332 (Pt 2):281-292; Kishimoto A, Kikkawa U, Ogita K, Shearman M S, Nishizuka Y. The protein kinase C family in the brain: heterogeneity and its implications. Ann NY Acad Sci 1989; 568: 181-186; Nishizuka Y. Calcium, phospholipid turnover and transmembrane signalling. Philos Trans R Soc Lond B Biol Sci 1983; 302(1108):101-112). All PKC isoforms have an autoinhibitory pseudosubstrate sequence that is N-terminal to the C1 domain, which functions as a diacylglycerol sensor. Atypical PKCs have a diacylglycerol non-responsive C1 domain. Conventional PKCs have a C2 domain that serves as a $Ca^{2+}$-regulated phospholipid-binding module. The C2 domain in novel PKCs binds neither $Ca^{2+}$ nor membrane phospholipids. Based on the structural differences conventional PKCs require membrane phospholipids, calcium and diacylglycerol for complete activation. Novel PKCs do not require calcium but diacylglycerol for activation. The zeta and iota/lambda forms of PKC are independent of both calcium and diacylglycerol for their activation (Newton A C. Regulation of the ABC kinases by phosphorylation: protein kinase C as a paradigm. Biochem J 2003; 370(Pt 2):361-371; Newton A C. Lipid activation of protein kinases. J Lipid Res 2009; 50 Suppl:S266-S271).

PKC is involved in the regulation of smooth muscle contractility. Upon stimulation PKC phosphorylates the regulatory myosin light chain ($MLC_{20}$) and inhibits the myosin associated phosphatase (MYPT). Phosphorylation of $MLC_{20}$ and inhibition of MYPT leads to an increased activity of the acto-myosin complex and to vasoconstriction in different vascular beds, e.g. resistance-sized, retinal, cerebral, coronary, conduit arteries and veins (Merkel L A, Rivera L M, Colussi D J, Perrone M H. Protein kinase C and vascular smooth muscle contractility: effects of inhibitors and down-regulation. J Pharmacol Exp Ther 1991; 257(1):134-140; Sehic E, Malik K U. Influence of protein kinase C activators on vascular tone and adrenergic neuroeffector events in the isolated rat kidney. J Pharmacol Exp Ther 1989; 251(2):634-639). Overexpressed or overactivated PKC detrimentally affects heart function. Upon activation PKC affects the intracellular calcium homeostasis which results in reduced myocardial contractility and relaxation of the myocardium. Overall this effect leads to myocardial contractile insufficiency (Connelly K A, Kelly D J, Zhang Y, Prior D L, Advani A, Cox A J, That K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137). Moreover, activated PKC mediates organ damage during end-organ injuries, e.g. during ischemia in heart (Connelly K A, Kelly D J, Zhang Y, Prior D L, Advani A, Cox A J, That K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137; Hambleton M, Hahn H, Pleger S T, Kuhn M C, Klevitsky R, Carr A N, Kimball T F, Hewett T E, Dorn G W, Koch W J, Molkentin J D. Pharmacological- and gene therapy-based inhibition of protein kinase Calpha/beta enhances cardiac contractility and attenuates heart failure. Circulation 2006; 114(6): 574-582) or kidney (Tuttle K R. Protein kinase C-beta inhibition for diabetic kidney disease. Diabetes Res Clin Pract 2008; 82 Suppl 1:S70-S74; Anderson P W, McGill J B, Tuttle K R. Protein kinase C beta inhibition: the promise for treatment of diabetic nephropathy. Curr Opin Nephrol Hypertens 2007; 16(5):397-402). PKC and especially the PKC-beta II isoform is overexpressed or overactivated in diabetes in various different types of tissue and exerts its deleterious effect to the cells, tissues and endorgans, e.g. kidney (Tuttle K R. Protein kinase C-beta inhibition for diabetic kidney disease. Diabetes Res Clin Pract 2008; 82 Suppl 1:S70-S74; Anderson P W, McGill J B, Tuttle K R. Protein kinase C beta inhibition: the promise for treatment of diabetic nephropathy. Curr Opin Nephrol Hypertens 2007; 16(5):397-402; Tuttle K R, Bakris G L, Toto R D, McGill J B, Hu K, Anderson P W. The effect of ruboxistaurin on nephropathy in type 2 diabetes. Diabetes Care 2005; 28(11):2686-2690; Kelly D J, Zhang Y, Hepper C, Gow R M, Jaworski K, Kemp B E, Wilkinson-Berka J L, Gilbert R E. Protein kinase C beta inhibition attenuates the progression of experimental diabetic nephropathy in the presence of continued hypertension. Diabetes 2003; 52(2):512-518), heart (Connelly K A, Kelly D J, Zhang Y, Prior D L, Advani A, Cox A J, That K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137; Guo M, Wu M H, Korompai F, Yuan S Y. Upregulation of PKC genes and isozymes in cardiovascular tissues during early stages of experimental diabetes. Physiol Genomics 2003; 12(2):139-146), or in tissues like the retina (Aiello L P, Clermont A, Arora V, Davis M D, Sheetz M J, Bursell S E. Inhibition of PKC beta by oral administration of ruboxistaurin is well tolerated and ameliorates diabetes-induced retinal hemodynamic abnormalities in patients. Invest Ophthalmol V is Sci 2006; 47(1):86-92; Aiello L P. The potential role of PKC beta in diabetic retinopathy and macular edema. Surv Ophthalmol 2002; 47 Suppl 2:S263-S269; Kimura M, Ishizawa M, Miura A, itaya S, Kanoh Y, Yasuda K, Uno Y, Morita H, Ishizuka T. Platelet protein kinase C isoform content in type 2 diabetes complicated with retinopathy and nephropathy. Platelets 2001; 12(3):138-143) or neuronal tissue (Krishnan S T, Rayman G. New treatments for diabetic neuropathy: symptomatic treatments. Curr Diab Rep 2003; 3(6):459-467; Kim H, Sasaki T, Maeda K, Koya D, Kashiwagi A, Yasuda H. Protein kinase Cbeta selective inhibitor LY333531 attenuates diabetic hyperalgesia through ameliorating cGMP level of dorsal root ganglion neurons. Diabetes 2003; 52(8):2102-2109; Cotter M A, Jack A M, Cameron N E. Effects of the protein kinase C beta inhibitor LY333531 on neural and vascular function in rats with streptozotocin-induced diabetes. Clin Sci (Lond) 2002; 103(3):311-321; Nakamura J, Kato K, Hamada Y, Nakayama M, Chaya S, Nakashima E, Naruse K, Kasuya Y, Mizubayashi R, Miwa K, Yasuda Y, Kamiya H, lenaga K, Sakakibara F, Koh N, Hotta N. A protein kinase C-beta-selective inhibitor ameliorates neural dysfunction in streptozotocin-induced diabetic rats. Diabetes 1999; 48(10):2090-2095) or in platelets (Assert R, Scherk G, Bumbure A, Pirags V, Schatz H, Pfeiffer A F. Regulation of protein kinase C by short term hyperglycaemia in human platelets in vivo and in vitro. Diabetologia 2001; 44(2):188-195; Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Kimura M, Ishizawa M, Miura A, Itaya S, Kanoh Y, Yasuda K, Uno Y, Morita H, Ishizuka T. Platelet protein kinase C isoform content in type 2 diabetes complicated with retinopathy and nephropathy. Platelets 2001; 12(3):138-143; Oskarsson H J, Hofineyer T G, Coppey L, Yorek M A. Effect of protein kinase C and phospholipase A2 inhibitors on the impaired ability of human diabetic platelets to cause vasodilation. Br J Pharmacol 1999; 127(4):903-908) or induces endothelial dysfunction (Chiasson V L, Quinn M A, Young K J, Mitchell B M. Protein kinase Cbetall-mediated phosphorylation of endothelial nitric oxide synthase threonine 495 mediates the endothelial dysfunction induced by FK506 (tacrolimus). J Pharmacol Exp Ther 2011; 337(3):718-723; Xu Y, Wang S, Feng L, Zhu Q, Xiang P, He B. Blockade of PKC-beta protects HUVEC from advanced glycation end products induced inflammation. Int Immunopharmacol 2010; 10(12):1552-1559; Geraldes P, King G L. Activation of protein kinase C isoforms and its impact on diabetic complications. Circ Res 2010; 106(8):1319-1331; Nacci C, Tarquinio M, Montagnani M. Molecular and clinical aspects of endothelial dysfunction in diabetes. Intern Emerg Med 2009; 4(2):107-116). Furthermore, it has been suggested that PKC signalling is involved in tumour formation (Gonelli A, Mischiati C, Guerrini R, Voltan R, Salvadori S, Zauli G. Perspectives of protein kinase C (PKC) inhibitors as anti-cancer agents. Mini Rev Med Chem 2009; 9(4):498-509; Ali A S, Ali S, El-Rayes B F, Philip P A, Sarkar F H. Exploitation of protein kinase C: a useful target for cancer therapy. Cancer Treat Rev 2009; 35(1):1-8), e.g. in hematological tumours (Mischiati C, Melloni E, Corallini F, Milani D, Bergamini C, Vaccarezza M. Potential role of PKC inhibitors in the treatment of hematological malignancies. Curr Pharm Des 2008; 14(21):2075-2084; Cheson B D, Zwiebel J A, Dancey J, Murgo A. Novel therapeutic agents for the treatment of myelodysplastic syndromes. Semin Oncol 2000; 27(5):560-577; Deng X, Kornblau S M, Ruvolo P P, May W S, Jr. Regulation of Bcl2 phosphorylation and potential significance for leukemic cell chemoresistance. J Natl Cancer Inst Monogr 2001; (28):30-37), in glioma formation (Baltuch G H, Dooley N P, Villemure J G, Yong V W. Protein kinase C and growth regulation of malignant gliomas. Can J Neurol Sci 1995; 22(4):264-271; Blobe G C, Obeid L M, Hannun Y A. Regulation of protein kinase C and role in cancer biology. Cancer Metastasis Rev 1994; 13(3-4):411-431; Bredel M, Pollack I F. The role of protein kinase C (PKC) in the evolution and proliferation of malignant gliomas, and the application of PKC inhibition as a novel approach to anti-glioma therapy. Acta Neurochir (Wien) 1997; 139(11):1000-1013), in gastric and intestinal cancer (Atten M J, GodoyRomero E, Attar B M, Milson T, Zopel M, Holian O. Resveratroi regulates cellular PKC alpha and delta to inhibit growth and induce apoptosis in gastric cancer cells. Invest New Drugs 2005; 23(2):111-119; Fahrmann M. Targeting protein kinase C (PKC) in physiology and cancer of the gastric cell system. Curr Med Chem 2008; 15(12):1175-1191), in skin cancer (Birt D F, Yaktine A, Duysen E. Glucocorticoid mediation of dietary energy restriction inhibition of mouse skin carcinogenesis. J Nutr 1999; 129 (2S Suppl):571S-574S; Birt D F, Przybyszewski J, Wang W, Stewart J, Liu Y. Identification of molecular targets for dietary energy restriction prevention of skin carcinogenesis: an idea cultivated by Edward Bresnick. J Cell Biochem 2004; 91(2):258-264), lung cancer (Herbst R S, Oh Y, Wagle A, Lahn M. Enzastaurin, a protein kinase Cbeta-selective inhibitor, and its potential application as an anticancer agent in lung cancer. Clin Cancer Res 2007; 13(15 Pt 2):s4641-s4646; Herbst R S. Targeted therapy in non-small-cell lung cancer. Oncology (Williston Park) 2002; 16(9 Suppl 9):19-24) and others. PKC is an important signal transducer of events in autoimmune responses, e.g. in T-cell (Birchall A M, Bishop J, Bradshaw D, Cline A, Coffey J, Elliott L H, Gibson V M, Greenham A, Hallam T J, Harris W. Ro 32-0432, a selective and orally active inhibitor of protein kinase C prevents T-cell activation. J Pharmacol Exp Ther 1994; 268 (2):922-929; Isakov N, Altman A. Protein kinase C(theta) in T cell activation. Annu Rev Immunol 2002; 20:761-794) or B-cell (Shinohara H, Kurosaki T. Comprehending the complex connection between PKCbeta, TAK1, and IKK in BCR signaling. Immunol Rev 2009; 232(1):300-318; Venkataraman C, Chen X C, Na S, Lee L, Neote K, Tan S L. Selective role of PKCbeta enzymatic function in regulating cell survival mediated by B cell antigen receptor cross-linking. Immunol Lett 2006; 105(1):83-89) linked autoimmune signalling, and in inflammatory processes. The above mentioned effects of the PKC-mediated signalling leads to induction or promotion of the progression of asthma (Boschelli D H. Small molecule inhibitors of PKCTheta as potential antiinflammatory therapeutics. Curr Top Med Chem 2009; 9(7): 640-654), chronic obstructive pulmonary disease (Mercer B A, D'Armiento J M. Emerging role of MAP kinase pathways as therapeutic targets in COPD. Int J Chron Obstruct Pulmon Dis 2006; 1(2):137-150; Adcock I M, Chung K F, Caramori G, Ito K. Kinase inhibitors and airway inflammation. Eur J Pharmacol 2006; 533(1-3):118-132; Dempsey E C, Cool C D, Littler C M. Lung disease and PKCs. Pharmacol Res 2007; 55(6):545-559; Ishii M, Kurachi Y. Muscarinic acetylcholine receptors. Curr Pharm Des 2006; 12(28):3573-3581; Medina-Tato D A, Watson M L, Ward S G. Leukocyte navigation mechanisms as targets in airway diseases. Drug Discov Today 2006; 11(19-20):866-879), pulmonary hypertension (Agbani E O, Coats P, Mills A, Wadsworth R M. Peroxynitrite stimulates pulmonary artery endothelial and smooth muscle cell proliferation: involvement of ERK and PKC. Pulm Pharmacol Ther 2011; 24(1):100-109; Littler C M, Wehling C A, Wick M J, Fagan K A, Cool C D, Messing R O, Dempsey E C. Divergent contractile and structural responses of the murine PKC-epsilon null pulmonary circulation to chronic hypoxia. Am J Physiol Lung Cell Mol Physiol 2005; 289(6):L1083-L1093), retinopathy, like retinal ischemia and neovascularization (Galvez M I. Protein kinase C inhibitors in the treatment of diabetic retinopathy. Review. Curr Pharm Biotechnol 2011; 12(3):386-391; Schwartz S G, Flynn H W, Jr., Aiello L P. Ruboxistaurin mesilate hydrate for diabetic retinopathy. Drugs Today (Barc) 2009; 45(4):269-274), nephropathy, including hypertension-induced (Kelly D J, Edgley A J, Zhang Y, That K, Tan S M, Cox A J, Advani A, Connelly K A, Whiteside C I, Gilbert R E. Protein kinase C-beta inhibition attenuates the progression of nephropathy in non-diabetic kidney disease. Nephrol Dial Transplant 2009; 24(6):1782-1790; Hayashi K, Wakino S, Ozawa Y, Homma K, Kanda T, Okubo K, Takamatsu I, Tatematsu S, Kumagai H, Saruta T. Role of protein kinase C in Ca channel blocker-induced renal arteriolar dilation in spontaneously hypertensive rats—studies in the isolated perfused hydronephrotic kidney. Keio J Med 2005; 54(2):102-108; Kelly D J, Zhang Y, Hepper C, Gow R M, Jaworski K, Kemp B E, Wilkinson-Berka J L, Gilbert R E. Protein kinase C beta inhibition attenuates the progression of experimental diabetic nephropathy in the presence of continued hypertension. Diabetes 2003; 52(2):512-518), non-hypertension-induced, and diabetic nephropathies (Danis R P, Sheetz M J. Ruboxistaurin: PKC-beta inhibition for complications of diabetes. Expert Opin Pharmacother 2009; 10(17):2913-2925; Tuttle K R. Protein kinase C-beta inhibition for diabetic kidney disease. Diabetes Res Clin Pract 2008; 82 Suppl 1:S70-S74), renal failure (Danis R P, Sheetz M J. Ruboxistaurin: PKC-beta inhibition for complications of diabetes. Expert Opin Pharmacother 2009; 10(17):2913-2925; Yamagishi S, Fukami K, Ueda S, Okuda S. Molecular mechanisms of diabetic nephropathy and its therapeutic intervention. Curr Drug Targets 2007; 8(8):952-959) and myocardial infarction (Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Rohilla A, Singh G, Singh M, Bala kP. Possible involvement of PKC-delta in the abrogated cardioprotective potential of ischemic preconditioning in hyperhomocysteinemic rat hearts. Biomed Pharmacother 2010; 64(3):195-202; Liu Q, Chen X, Macdonnell S M, Kranias E G, Lorenz J N, Leitges M, Houser S R, Molkentin J D. Protein kinase C{alpha}, but not PKC{beta} or PKC {gamma}, regulates contractility and heart failure susceptibility: implications for ruboxistaurin as a novel therapeutic approach. Circ Res 2009; 105(2):194-200; Yonezawa T, Kurata R, Kimura M, Inoko H. PKC delta and epsilon in drug targeting and therapeutics. Recent Pat DNA Gene Seq 2009; 3(2):96-101) cardiac hypertrophy and failure (Ferreira J C, Brum P C, Mochly-Rosen D. betaIIPKC and epsilonPKC isozymes as potential pharmacological targets in cardiac hypertrophy and heart failure. Mol Cell Cardiol 2010; Palaniyandi S S, Sun L, Ferreira J C, Mochly-Rosen D. Protein kinase C in heart failure: a therapeutic target?Cardiovasc Res 2009; 82(2):229-239), coronary heart disease, artherosclerosis, restenosis (Ding R Q, Tsao J, Chai H, Mochly-Rosen D, Zhou W. Therapeutic potential for protein kinase C inhibitor in vascular restenosis. J Cardiovasc Pharmacol Ther 2011; 16(2):160-167; Schleicher E, Friess U. Oxidative stress, AGE, and atherosclerosis. Kidney Int Suppl 2007; (106):S17-S26), diabetes, diabetic complications, glucose utilization and metabolic syndrome (Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Geraldes P, King G L. Activation of protein kinase C isoforms and its impact on diabetic complications. Circ Res 2010; 106(8):1319-1331; Danis R P, Sheetz M J. Ruboxistaurin: PKC-beta inhibition for complications of diabetes. Expert Opin Pharmacother 2009; 10(17):2913-2925), immune diseases (Baler G, Wagner J. PKC inhibitors: potential in T cell-dependent immune diseases. Curr Opin Cell Biol 2009; 21(2):262-267; Mecklenbrauker i, Saijo K, Zheng N Y, Leitges M, Tarakhovsky A. Protein kinase Cdelta controls self-antigen-induced B-cell tolerance. Nature 2002; 416(6883):860-865; Wilkinson S E, Hallam T J. Protein kinase C: is its pivotal role in cellular activation over-stated?Trends Pharmacol Sci 1994; 15(2):53-57; Costello R, Mawas C, Olive D. Differential immuno-suppressive effects of metabolic inhibitors on T-lymphocyte activation. Eur Cytokine Netw 1993; 4(2):139-146), like psoriasis (Sommerer C, Zeier M. AEB071—a promising immuno-suppressive agent. Clin Transplant 2009; 23 Suppl 21:15-18; Rasmussen H H, Celis J E. Evidence for an altered protein kinase C (PKC) signaling pathway in psoriasis. J Invest Dermatol 1993; 101(4):560-566; Fisher G J, Tavakkol A, Leach K, Burns D, Basta P, Loomis C, Griffiths C E, Cooper K D, Reynolds N J, Elder J T. Differential expression of protein kinase C isoenzymes in normal and psoriatic adult human skin: reduced expression of protein kinase C-beta II in psoriasis. J Invest Dermatol 1993; 101(4):553-559), rheumatoid athritis (Healy A M, Izmailova E, Fitzgerald M, Walker R, Hattersley M, Silva M, Siebert E, Terkelsen J, Picarella D, Pickard M D, LeClair B, Chandra S, Jaffee B. PKC-theta-deficient mice are protected from Th1-dependent antigen-induced arthritis. J Immunol 2006; 177(3):1886-1893; Ji J D, Tassiulas I, Park-Min K H, Aydin A, Mecklenbrauker I, Tarakhovsky A, Pricop L, Salmon J E, Ivashkiv L B. Inhibition of interleukin 10 signaling after Fc receptor ligation and during rheumatoid arthritis. J Exp Med 2003; 197(11):1573-1583; Kehlen A, Thiele K, Riemann D, Langner J. Expression, modulation and signalling of IL-17 receptor in fibroblast-like synoviocytes of patients with rheumatoid arthritis. Clin Exp Immunol 2002; 127(3):539-546), or other autoimmune disorders (Zanin-Zhorov A, Dustin M L, Blazar B R. PKC-theta function at the immunological synapse: prospects for therapeutic targeting. Trends Immunol 2011; 32(8):358-363), central nervous system disorders (Liang J, Takeuchi H, Jin S, Noda M, Li H, Doi Y, Kawanokuchi J, Sonobe Y, Mizuno T, Suzumura A. Glutamate induces neurotrophic factor production from microglia via protein kinase C pathway. Brain Res 2010; 1322:8-23; Bastianetto S, Zheng W H, Quirion R. Neuroprotective abilities of resveratrol and other red wine constituents against nitric oxide-related toxicity in cultured hippocampal neurons. Br J Pharmacol 2000; 131(4):711-720), cerebral ischemia or cerebral vasospasm (Bu X, Zhang N, Yang X, Liu Y, Du J, Liang J, Xu Q, Li J. Proteomic analysis of cPKCbetaII-interacting proteins involved in HPC-induced neuroprotection against cerebral ischemia of mice. J Neurochem 2011; 117(2):346-356), neuropathies and pain, e.g. neuropathic pain (Nakajima A, Tsuboi Y, Suzuki I, Honda K, Shinoda M, Kondo M, Matsuura S, Shibuta K, Yasuda M, Shimizu N, Iwata K. PKC-gamma in Vc and C1/C2 is involved in trigeminal neuropathic pain. J Dent Res 2011; 90(6):777-781; Malmberg A B, Chen C, Tonegawa S, Basbaum A I. Preserved acute pain and reduced neuropathic pain in mice lacking PKCgamma. Science 1997; 278(5336):279-283), cancer development and progression, neoplasia where inhibition of protein kinase C has been shown to inhibit tumor cell growth and metastasis (Kim J, Thorne S H, Sun L, Huang B, Mochly-Rosen D. Sustained inhibition of PKCalpha reduces intravasation and lung seeding during mammary tumor metastasis in an in vivo mouse model. Oncogene 2011; 30(3):323-333; Spindler K L, Lindebjerg J, Lahn M, Kjaer-Frifeldt S, Jakobsen A. Protein kinase C-beta II (PKC-beta II) expression in patients with colorectal cancer. Int J Colorectal Dis 2009; 24(6):641-645; Guo K, Li Y, Kang X, Sun L, Cui J, Gao D, Liu Y. Role of PKCbeta in hepatocellular carcinoma cells migration and invasion in vitro: a potential therapeutic target. Clin Exp Metastasis 2009; 26(3):189-195), angiogenesis (Nakamura S, Chikaraishi Y, Tsuruma K, Shimazawa M, Hara H. Ruboxistaurin, a PKCbeta inhibitor, inhibits retinal neovascularization via suppression of phosphorylation of ERK1/2 and Akt. Exp Eye Res 2010; 90(1):137-145; Ali A S, Ali S, El-Rayes B F, Philip P A, Sarkar F H. Exploitation of protein kinase C: a useful target for cancer therapy. Cancer Treat Rev 2009; 35(1):1-8; Tekle C, Giovannetti E, Sigmond J, Graff J R, Smid K, Peters G J. Molecular pathways involved in the synergistic interaction of the PKC beta inhibitor enzastaurin with the antifolate pemetrexed in non-small cell lung cancer cells. Br J Cancer 2008; 99(5):750-759; Mischiati C, Melloni E, Corallini F, Milani D, Bergamini C, Vaccarezza M. Potential role of PKC inhibitors in the treatment of hematological malignancies. Curr Pharm Des 2008; 14(21):2075-2084), platelet disorders leading to thrombosis (Gilio K, Harper M T, Cosemans J M, Konopatskaya O, Munnix I C, Prinzen L, Leitges M, Liu Q, Molkentin J D, Heemskerk J W, Poole A W. Functional divergence of platelet protein kinase C (PKC) isoforms in thrombus formation on collagen. J Biol Chem 2010; 285(30):23410-23419; Chari R, Getz T, Nagy B, Jr., Bhavaraju K, Mao Y, Bynagari Y S, Murugappan S, Nakayama K, Kunapuli S P. Protein kinase C[delta] differentially regulates platelet functional responses. Arterioscler Thromb Vasc Biol 2009; 29(5):699-705; Nagy B, Jr., Bhavaraju K, Getz T, Bynagari Y S, Kim S, Kunapuli S P. Impaired activation of platelets lacking protein kinase C-theta isoform. Blood 2009; 113(11):2557-2567; Harper M T, Poole A W. Isoform-specific functions of protein kinase C: the platelet paradigm. Biochem Soc Trans 2007; 35(Pt 5):1005-1008; Strehl A, Munnix I C, Kuijpers M J, van der Meijden P E, Cosemans J M, Feijge M A, Nieswandt B, Heemskerk J W. Dual role of platelet protein kinase C in thrombus formation: stimulation of pro-aggregatory and suppression of procoagulant activity in platelets. J Biol Chem 2007; 282(10):7046-7055; London F S. The protein kinase C inhibitor RO318220 potentiates thrombin-stimulated platelet-supported prothrombinase activity. Blood 2003; 102(7):2472-2481; Wheeler-Jones C P, Patel Y, Kakkar V V, Krishnamurthi S. Translocation of protein kinase C (PKC) in stimulated platelets: a role for aggregation in PKC degradation. Br J Pharmacol 1989; 98 Suppl:845P), and leukocyte aggregation (Hu H, Zhang W, Li N. Glycoprotein IIb/IIIa inhibition attenuates platelet-activating factor-induced platelet activation by reducing protein kinase C activity. J Thromb Haemost 2003; 1(8):1805-1812; Kotovuori A, Pessa-Morikawa T, Kotovuori P, Nortamo P, Gahmberg C G. ICAM-2 and a peptide from its binding domain are efficient activators of leukocyte adhesion and integrin affinity. J Immunol 1999; 162(11):6613-6620; Lorenz H M, Lagoo A S, Hardy K J. The cell and molecular basis of leukocyte common antigen (CD45)-triggered, lymphocyte function-associated antigen-1-/intercellular adhesion molecule-1-dependent, leukocyte adhesion. Blood 1994; 83(7):1862-1870).

Until now, mainly staurosporine derivatives have been described as PKC inhibitors in the prior art, for example Ruboxistaurin (e.g. EP 657458), Enzastaurin (e.g. WO 9517182), Midostaurin (e.g. EP 296110) or Sotrastaurin (e.g. WO 2002038561). Only very few PKCβ inhibitors, which not derived from staurosporine have been described, such as 3-amido-pyrrolo[3,4-c]pyrazole-5(1H, 4H,6H)carbaldehydes in WO 2008125945.

However, there continues to be a need for further effective low molecular weight PKCβ inhibitors, in particular in view of safety and selectivity. The present invention satisfies this need by providing the pyrazolo[3,4-b]pyridine compounds of the formula I.

Pyrazolo[3,4-b]pyridine derivatives which are useful for pharmaceutical applications, have already been disclosed, for example in WO 2005028480 (Neurogen Corp. and Aventis Pharmaceuticals Inc.), in WO 2005009389 (Exelixis Inc.) or in WO 2000058307 (Neurogen Corp.).

Accordingly, a subject of the present invention is a compound of the formula I,

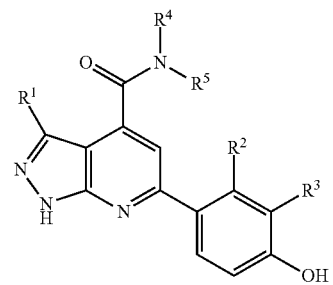

I wherein
R$^1$ is a) a residue of the formula Ia

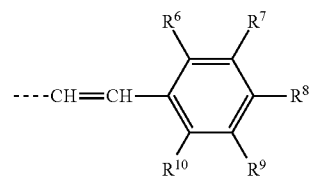

Ia wherein
R$^6$ is H, F, Cl, (C$_1$-C$_3$)-alkyl or O—(C$_1$-C$_3$)-alkyl, wherein (C$_1$-C$_3$)-alkyl is unsubstituted or substituted by one to five F;
R$^7$ is H, F, Cl, (C$_1$-C$_3$)-alkyl or O—(C$_1$-C$_3$)-alkyl, wherein (C$_1$-C$_3$)-alkyl is unsubstituted or substituted by one to five F, or is CN, $(C_0-C_2)$-alkylene-$SO_2(C_1-C_3)$-alkyl, $(C_0-C_2)$-alkylene-$N((C_1-C_4)$-alkyl$)_2$, CO—N$((C_1-C_4)$-alkyl$)_2$, 1-pyrrolidinyl, 1-piperidinyl, 1-pyrrolidinyl-2-on, 1-piperidinyl-2-on, or 4-morpholinyl;

$R^8$ is H, F, Cl, $(C_1-C_5)$-alkyl or O—$(C_1-C_8)$-alkyl, wherein $(C_1-C_3)$-alkyl is unsubstituted or substituted by one to five F, or is CN, OH, O-phenyl, $SO_2(C_1-C_3)$-alkyl, CO—$(C_1-C_4)$-alkyl, CO—N$((C_1-C_4)$-alkyl$)_2$, CO-1-piperidinyl, CO-1-pyrrolidinyl, or CO-4-morpholinyl;

$R^9$ is H, F, $CH_3$, or O—$CH_3$;

$R^{10}$ is H; or $R^6$ and $R^7$ form, together with the two carbon atoms, to which they are attached, a five to six membered heterocycloalkyl ring, which contains one or two identical or different heteroatoms selected from nitrogen and oxygen, and wherein said heterocycloalkyl is unsubstituted or mono-substituted by $(C_1-C_4)$-alkyl or oxo (=O); or $R^7$ and $R^8$ form, together with the two carbon atoms, to which they are attached, a five to six membered heterocycloalkyl ring, which contains one or two identical or different heteroatoms selected from nitrogen and oxygen, and wherein said heterocycloalkyl is unsubstituted or mono-substituted by $(C_1-C_4)$-alkyl or oxo (=O);

b) ethylene-phenyl, wherein phenyl is unsubstituted or substituted by one or two identical or different substituents selected from F, Cl, $CH_3$, O—$CH_3$, $CF_3$, O—$CF_3$, CN, $SO_2CH_3$, CO—$CH_3$, and CO—N$((CH_3)_2$;

c) 2-phenylcyclopropyl, wherein phenyl is unsubstituted or substituted by one or two identical or different substituents selected from F, Cl, $CH_3$, O—$CH_3$, $CF_3$, O—$CF_3$, CN, $SO_2CH_3$, CO—$CH_3$, and CO—N$((CH_3)_2$;

d) ethylene-$(C_5-C_7)$cycloalkyl;

$R^2$ is H, F, Cl, or $CH_3$;

$R^3$ is H, F, or O—$CH_3$;

$R^4$ is piperidin-4-yl, piperidin-3-yl or pyrrolidin-3-yl, which are unsubstituted or monosubstituted by $(C_1-C_3)$-alkyl, which is unsubstituted or substituted by one to five F;

$R^5$ is H; or $R^4$ and $R^5$ together with the nitrogen carrying them denote a) a residue of the formula Ib

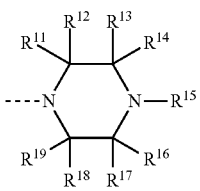

wherein $R^{11}$ is H, $(C_3-C_5)$-cycloalkyl, $(C_1-C_4)$-alkylene-OH or $(C_1-C_4)$-alkyl, which is unsubstituted or substituted by one to five F;

$R^{12}$ is H, or $(C_1-C_4)$-alkyl, $R^{13}$ is H, $(C_1-C_4)$-alkyl, or $(C_3-C_5)$-cycloalkyl;

$R^{14}$ is H, or $(C_1-C_4)$-alkyl; or $R^{13}$ and $R^{14}$ together with the C-atom carrying them is 1'-spiro-cyclo-$(C_3-C_6)$-alkyl; and $R^{15}$ is H, $CH_2$—CO—N$((C_1-C_4)$-alkyl$)_2$, CO—$(C_1-C_6)$-alkyl, CO—$(C_1-C_4)$-alkylene-OH, CO—$(C_1-C_4)$-alkylene-O—$CH_3$, CO—$CH_2$-4-morpholinyl, CO—O—$(C_1-C_4)$-alkyl, CO—N$((C_1-C_4)$-alkyl$)_2$, $(C_3-C_6)$cycloalkyl, or pyridyl;

$R^{16}$ is H, or $(C_1-C_4)$-alkyl;

$R^{17}$ is H, or $CH_3$;

$R^{18}$ is H, or $CH_3$;

$R^{19}$ is H;

b) a 9 to 11 membered spiro-heterocycloalkyl containing 2 nitrogen atoms, which is attached via a nitrogen atom;

in any of its stereoisomeric forms, or a mixture of stereoisomeric forms in any ratio, or a physiologically acceptable salt thereof, or a physiologically acceptable solvate of any of them.

Another group of embodiments are compounds of the formula I wherein $R^1$ is a) a residue of the formula Ia

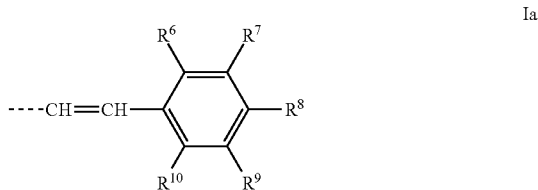

wherein $R^6$ is H, F, Cl, $(C_1-C_3)$-alkyl or O—$(C_1-C_3)$-alkyl, wherein $(C_1-C_3)$-alkyl is unsubstituted or substituted by one to five F; or $R^6$ is H, F, Cl, $CH_3$, $CF_3$, or O—$CH_3$; or $R^6$ is H;

$R^7$ is H, F, Cl, $(C_1-C_3)$-alkyl or O—$(C_1-C_3)$-alkyl, wherein $(C_1-C_3)$-alkyl is unsubstituted or substituted by one to five F, or is CN, $SO_2(C_1-C_3)$-alkyl, N$((C_1-C_4)$-alkyl$)_2$, 1-piperidinyl, or 4-morpholinyl; or $R^7$ is H, F, Cl, $CH_3$, $CF_3$, CN, O—$CH_3$, $SO_2CH_3$, N$(CH_3)_2$, 1-piperidinyl, or 4-morpholinyl; or $R^7$ is H;

$R^8$ is H, F, Cl, $(C_1-C_8)$-alkyl or O—$(C_1-C_5)$-alkyl, wherein $(C_1-C_3)$-alkyl is unsubstituted or substituted by one to five F, or is OH, O-phenyl, $SO_2(C_1-C_3)$-alkyl, CO—$(C_1-C_4)$-alkyl, CO—N$((C_1-C_4)$alkyl$)_2$; or $R^8$ is H, F, Cl, $CH_3$, $CH_2CH_3$, $CH(CH_3)_2$, $C(CH_3)_3$, $CF_3$, OH, O—$CH_3$, O—$C_2H_5$, O—$CHF_2$, O—$CF_3$, O-phenyl, $SO_2CH_3$, CO—$CH_3$, or CO—N$(CH_3)_2$; or $R^8$ is H;

$R^9$ is H, F, $CH_3$, O—$CH_3$; or $R^9$ is H;

$R^{10}$ is H; or $R^7$ and $R^8$ together are

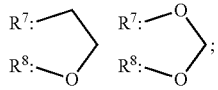

b) ethylene-phenyl, wherein phenyl is unsubstituted or substituted by one to two identical or different substituents selected from F, Cl, $OH_3$, O—$CH_3$, $CF_3$, O—$CF_3$, CN, $SO_2CH_3$, CO—$CH_3$, and CO—N$((CH_3)_2$; or $R^1$ is phenethyl.

Another group of embodiments are compounds of the formula I wherein $R^2$ is H, F, $CH_3$, or $R^2$ is H, $CH_3$ or $R^2$ is H, F, or $R^2$ is H.

Another group of embodiments are compounds of the formula I wherein $R^3$ is H, O—$CH_3$, or $R^3$ is H.

Another group of embodiments are compounds of the formula I wherein $R^4$ is piperidin-4-yl, piperidin-3-yl or pyrrolidin-3-yl, which are unsubstituted or monosubstituted by $(C_1-C_3)$-alkyl, which is unsubstituted or substituted by one to five F; or $R^4$ is 4-methyl-piperidin-4-yl and
$R^5$ is H.

Another group of embodiments are compounds of the formula I wherein
$R^4$ and $R^5$ together with the nitrogen carrying them denote
a) a residue of the formula Ib

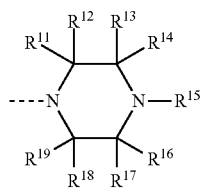

wherein
$R^{11}$ is H, $CH_3$, $(C_3$-$C_4)$-alkyl, or $(C_3$-$C_4)$-cycloalkyl; or $R^{11}$ is H, $CH_3$, or $(CH_2)_3$—$CH_3$; or $R^{11}$ is H;
$R^{12}$ is H;
$R^{13}$ is H, $(C_1$-$C_4)$-alkyl, or $(C_3$-$C_4)$-cycloalkyl; or $R^{13}$ is H, $CH_3$, or $CH_2$—$CH(CH_3)_2$; or $R^{13}$ is H or $CH_3$; or $R^{13}$ is H;
$R^{14}$ is H, or $CH_3$; or $R^{14}$ is H; or
$R^{13}$ and $R^{14}$ together with the C-atom carrying them is 1'-spiro-cyclo-$(C_3$-$C_6)$-alkyl; preferably 1'-spiro-cyclopentyl; and
$R^{15}$ is H, $CH_2$—CO—$N((C_1$-$C_4)$-alkyl$)_2$, CO—$(C_1$-$C_6)$-alkyl, CO—$(C_1$-$C_4)$-alkylene-OH, CO—$(C_1$-$C_4)$-alkylene-O—$CH_3$, CO—$CH_2$-4-morpholinyl, CO—O—$(C_1$-$C_4)$-alkyl, CO—N(—$(C_1$-$C_4)$-alkyl$)_2$, —$(C_3$-$C_6)$-cycloalkyl, or pyridyl; or $R^{15}$ is H, $CH_2$—CO—$N(CH_3)_2$, CO—$CH(C_2H_5)_2$, CO—$C(CH_3)_2$—OH, CO—$C(CH_3)_2$—$CH_2$—OH, CO—$(CH_2)_2$—O—$CH_3$, CO—$CH_2$-4-morpholinyl, CO—$CH_3$, CO—$N(CH_3)_2$, cyclopropyl, or 3-pyridyl; or $R^{15}$ is H;
$R^{16}$ is H, or $(C_1$-$C_4)$-alkyl; or $R^{16}$ is H, or $CH_3$; or $R^{16}$ is H;
$R^{17}$ is H;
$R^{18}$ is H;
$R^{19}$ is H;
b) a 9 to 11 membered spiro-heterocycloalkyl containing two nitrogen atoms, which is attached via a nitrogen atom, or $R^1$ is (2,7-Diaza-spiro[4.4]non-2-yl).

Another group of embodiments are compounds of the formula I wherein
$R^1$ is a) a residue of the formula Ia

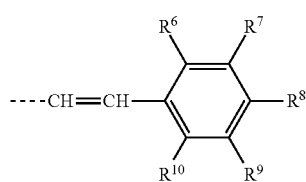

wherein
$R^6$ is H, F, Cl, $CH_3$, $CF_3$, or O—$CH_3$;
$R^7$ is H, F, Cl, $CH_3$, $CH_2$—$SO_2$—$CH_3$, $CF_3$, CN, $CH_2$—N$(CH_3)_2$, CO—$N(CH_3)_2$, O—$CH_3$, $SO_2CH_3$, $N(CH_3)_2$, 1-pyrrolidinyl, 1-piperidinyl, 4-morpholinyl, or 1-pyrrolidinyl-2-on;

$R^8$ is H, F, Cl, $CH_3$, $CH_2CH_3$, $CH(CH_3)_2$, $C(CH_3)_3$, $CF_3$, CN, OH, $OCH_3$, O—$C_2H_5$, O—$CHF_2$, O—$CF_3$, O-phenyl, $SO_2CH_3$, CO—$CH_3$, CO—$N(CH_3)_2$, or CO-1-piperidinyl;
$R^9$ is H, Cl, F, $CH_3$, or O—$CH_3$;
$R^{10}$ is H; or
$R^6$ and $R^7$ together are

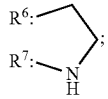

or
$R^7$ and $R^8$ together are

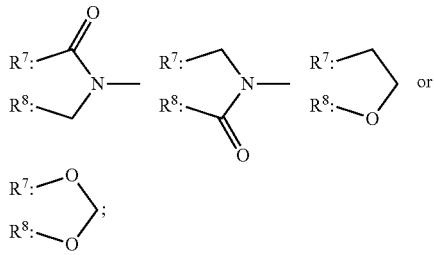

b) phenethyl;
c) 2-phenylcycopropyl;
d) 2-cyclohexylethyl; or
$R^2$ is H, F, Cl, or $CH_3$; or
$R^3$ is H, F, or O—$CH_3$; or
$R^4$ is 4-methyl-piperidin-4-yl;
$R^5$ is H; or
$R^4$ and $R^5$ together with the nitrogen carrying them denote
a) a residue of the formula Ib

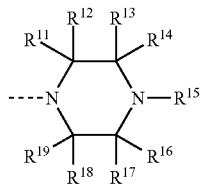

wherein
$R^{11}$ is H, $CH_3$, $C_2H_5$, $(CH_2)_3$—$CH_3$, or $CH_2$—OH;
$R^{12}$ is H, or $CH_3$;
$R^{13}$ is H, $CH_3$, or $CH_2$—$CH(CH_3)_2$;
$R^{14}$ is H, or $CH_3$; or
$R^{13}$ and $R^{14}$ together with the C-atom carrying them is 1'-spiro-cyclopentyl; and
$R^{15}$ is H, $CH_2$—CO—$N(CH_3)_2$, CO—$CH(C_2H_5)_2$, CO—$C(CH_3)_2$—OH, CO—$C(CH_3)_2$—$CH_2$—OH, CO—$(CH_2)_2$—O—$CH_3$, CO—$CH_2$-4-morpholinyl, CO—$OCH_3$, CO—$N(CH_3)_2$, cyclopropyl, or CO-3-pyridyl;
$R^{16}$ is H, or $CH_3$;
$R^{17}$ is H;
$R^{18}$ is H;
$R^{19}$ is H;

b) (2,7-Diaza-spiro[4.4]non-2-yl) (=Bsp 60).

Another group of embodiments are compounds of the formula I
wherein
$R^1$ is a) a residue of the formula Ia

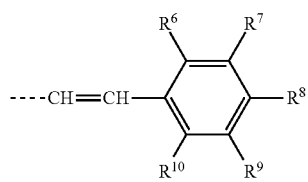

Ia wherein
$R^6$ is H, F, C, $CH_3$, $CF_3$, or $O-CH_3$;
$R^7$ is H, F, Cl, $CH_3$, $CF_3$, CN, $O-CH_3$, $SO_2CH_3$, $N(CH_3)_2$, 1-piperidinyl, or 4-morpholinyl;
$R^8$ is H, F, Cl, $CH_3$, $CH_2CH_3$, $CH(CH_3)_2$, $C(CH_3)_3$, $CF_3$, OH, $O-CH_3$, $O-C_2H_5$, $O-CHF_2$, $O-CF_3$, O-phenyl, $SO_2CH_3$, $CO-CH_3$, or $CO-N(CH_3)_2$;
$R^9$ is H, F, $OH_3$, or $O-CH_3$;
$R^{10}$ is H; or
$R^7$ and $R^8$ together are

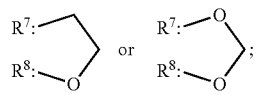

b) phenethyl;
$R^2$ is H, or $CH_3$;
$R^3$ is H, or $O-CH_3$;
$R^4$ is 4-methyl-piperidin-4-yl;
$R^5$ is H; or
$R^4$ and $R^5$ together with the nitrogen carrying them denote
a) a residue of the formula Ib

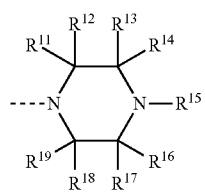

Ib wherein
$R^{11}$ is H, $CH_3$, or $(CH_2)_3-CH_3$;
$R^{12}$ is H;
$R^{13}$ is H, $CH_3$, or $CH_2-CH(CH_3)_2$;
$R^{14}$ is H, or $CH_3$; or
$R^{13}$ and $R^{14}$ together with the C-atom carrying them is 1'-spiro-cyclopentyl; and
$R^{15}$ is H, $CH_2-CO-N(CH_3)_2$, $CO-CH(C_2H_5)_2$, $CO-C(CH_3)_2-OH$, $COC(CH_3)_2-CH_2-OH$, $CO-(CH_2)_2-O-CH_3$, $CO-CH_2$-4-morpholinyl, $CO-OCH_3$, $CO-N(CH_3)_2$, cyclopropyl, or 3-pyridyl;
$R^{16}$ is H, or $CH_3$;
$R^{17}$ is H;
$R^{11}$ and $R^{12}$ together with the C-atoms carrying them are 1'-spirocyclopentyl;
$R^{18}$ is H;

$R^{19}$ is H;
b) (2,7-Diaza-spiro[4.4]non-2-yl).

Another group of embodiments are compounds of the formula I
wherein
$R^1$ is a residue of the formula Ia

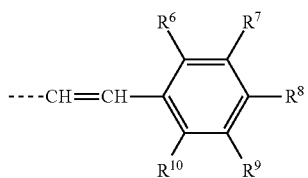

Ia wherein
$R^6$ is H, F, Cl, $CH_3$, $CF_3$, or $O-CH_3$;
$R^7$ is H, F, Cl, $CH_3$, $CF_3$, N,$O-CH_3$, $SO_2CH_3$, $N(CH_3)_2$, 1-piperidinyl, or 4-morpholinyl;
$R^8$ is H, F, Cl, $CH_3$, $CH_2CH_3$, $CH(CH_3)_2$, $C(CH_3)_3$, $CF_3$, OH, $O-CH_3$, $O-C_2H_5$, $O-CHF_2$, $O-CF_3$, O-phenyl, $SO_2CH_3$, $CO-CH_3$, or $CO-N(CH_3)_2$;
$R^9$ is H, F, $CH_3$, or $O-CH_3$;
$R^{10}$ is H;
$R^2$ is H;
$R^3$ is H;
$R^4$ and $R^5$ together with the nitrogen carrying them denote a residue of the formula Ib

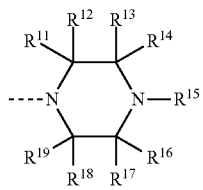

Ib wherein
$R^{11}$ is H, $CH_3$, or $(CH_2)_3-CH_3$;
$R^{12}$ is H;
$R^{13}$ is H, $CH_3$, or $CH_2-CH(CH_3)_2$;
$R^{14}$ is H, or $CH_3$; or
$R^{13}$ and $R^{14}$ together with the C-atom carrying them is 1'-spiro-cyclopentyl; and
$R^{15}$ is H;
$R^{16}$ is H, or $CH_3$;
$R^{17}$ is H;
$R^{11}$ and $R^{12}$ together with the C-atoms carrying them are 1'-spirocyclopentyl;
$R^{18}$ is H;
$R^{19}$ is H.

Another group of embodiments are compounds selected from the group consisting of
1
[3-[(E)-2-(4-Chloro-phenyl)-vinyl]-6-(4-hydroxy-phenyl)-1H-pyrazolo[3,4-b]pyridin-4-yl]-piperazin-1-yl-methanone
2
[6-(4-Hydroxy-phenyl)-3-((E)-styryl)-1H-pyrazolo[3,4-b]pyridin-4-yl]-piperazin-1-yl-methanone
3
(2,2-Dimethyl-piperazin-1-yl)-[6-(4-hydroxy-phenyl)-3-(styryl)-1H-pyrazolo[3,4-b]pyridin-4-yl]-methanone 4
(3,3-Dimethyl-piperazin-1-yl)-[6-(4-hydroxy-phenyl)-3-((E)-styryl)-1H-pyrazolo[3,4-b]pyridin-4-yl]-methanone
5
[6-(4-Hydroxy-phenyl)-3-((E)-styryl)-1H-pyrazolo[3,4-b]pyridin-4-yl]-((S)-3-isobutylpiperazin-1-yl)-methanone
6
[6-(4-Hydroxy-phenyl)-3-((E)-styryl)-1H-pyrazolo[3,4-b]pyridin-4-yl]-((S)-2-methyl-piperazin-1-yl)-methanone
7
[6-(4-Hydroxy-2-methyl-phenyl)-3-((E)-styryl)-1H-pyrazolo[3,4-b]pyridin-4-yl]-piperazin-1-yl-methanone
8
((2S,5R)-2,5-Dimethyl-piperazin-1-yl)-[6-(4-hydroxy-phenyl)-3-((E)-styryl)-1H-pyrazolo[3,4-b]pyridin-4-yl]-methanone
9
[6-(4-Hydroxy-3-methoxy-phenyl)-3-((E)-styryl)-1H-pyrazolo[3,4-b]pyridin-4-yl]-piperazin-1-yl-methanone
10
((S)-2-Ethyl-piperazin-1-yl)-[6-(4-hydroxy-phenyl)-3-((E)-styryl)-1H-pyrazolo[3,4-b]pyridin-4-yl]-methanone
11
[6-(2-Fluoro-4-hydroxy-phenyl)-3-((E)-styryl)-1H-pyrazolo[3,4-b]pyridin-4-yl]-((S)-2-methyl-piperazin-1-yl)-methanone
12
[6-(3-Fluoro-4-hydroxy-phenyl)-3-(styryl)-1H-pyrazolo[3,4-b]pyridin-4-yl]-piperazin-1-yl-methanone
13
[6-(2-Chloro-4-hydroxy-phenyl)-3-(styryl)-1H-pyrazolo[3,4-b]pyridin-4-yl]-piperazin-1-yl-methanone
14
[3-[2-(3-Dimethylaminomethyl-phenyl)-vinyl]-6-(4-hydroxy-phenyl)-1H-pyrazolo[3,4-b]pyridin-4-yl]-piperazin-1-yl-methanone
15
{6-(4-Hydroxy-phenyl)-3-[2-(3-methanesulfonylmethyl-phenyl)-vinyl]-1H-pyrazolo[3,4-b]pyridin-4-yl}-piperazin-1-yl-methanone
16
((R)-2-Hydroxymethyl-piperazin-1-yl)-[6-(4-hydroxy-phenyl)-3-((E)-styryl)-1H-pyrazolo[3,4-b]pyridin-4-yl]-methanone
17
[6-(4-Hydroxy-phenyl)-3-phenethyl-1H-pyrazolo[3,4-b]pyridin-4-yl]-piperazin-1-yl-methanone
18
[6-(4-Hydroxy-phenyl)-3-((1R,2R)-2-phenyl-cyclopropyl)-1H-pyrazolo[3,4-b]pyridin-4-yl]-piperazin-1-yl-methanone
19
(6-(4-Hydroxy-phenyl)-3-{2-[4-(piperidine-1-carbonyl)-phenyl]-vinyl}-1H-pyrazolo[3,4-b]pyridin-4-yl)-piperazin-1-yl-methanone
20
1-(3-{2-[6-(4-Hydroxy-phenyl)-4-(piperazine-1-carbonyl)-1H-pyrazolo[3,4-b]pyridin-3-yl]-vinyl}-phenyl)-pyrrolidin-2-one
21
[6-(4-Hydroxy-phenyl)-3-((E)-2-p-tolyl-vinyl)-1H-pyrazolo[3,4-b]pyridin-4-yl]-piperazin-1-yl-methanone
22
{6-(4-Hydroxy-phenyl)-3-[(E)-2-(3-methanesulfonyl-phenyl)-vinyl]-1H-pyrazolo[3,4-b]pyridin-4-yl}-piperazin-1-yl-methanone
23
[3-[(E)-2-(3-Dimethylamino-phenyl)-vinyl]-6-(4-hydroxy-phenyl)-1H-pyrazolo[3,4-b]pyridin-4-yl]-piperazin-1-yl-methanone
24
{6-(4-Hydroxy-phenyl)-3-[(E)-2-(4-methanesulfonyl-phenyl)-vinyl]-1H-pyrazolo[3,4-b]pyridin-4-yl}-piperazin-1-yl-methanone
25
3-{(E)-2-[6-(4-Hydroxy-phenyl)-4-(piperazine-1-carbonyl)-1H-pyrazolo[3,4-b]pyridin-3-yl]-vinyl}-benzonitrile
26
{6-(4-Hydroxy-phenyl)-3-[(E)-2-(3-piperidin-1-yl-phenyl)-vinyl]-1H-pyrazolo[3,4-b]pyridin-4-yl}-piperazin-1-yl-methanone
27
{6-(4-Hydroxy-phenyl)-3-[(E)-2-(3-morpholin-4-yl-phenyl)-vinyl]-1H-pyrazolo[3,4-b]pyridin-4-yl}-piperazin-1-yl-methanone
28
{6-(4-Hydroxy-phenyl)-3-[2-(3-pyrrolidin-1-yl-phenyl)-vinyl]-1H-pyrazolo[3,4-b]pyridin-4-yl}-piperazin-1-yl-methanone
29
4-{2-[6-(4-Hydroxy-phenyl)-4-(piperazine-1-carbonyl)-1H-pyrazolo[3,4-b]pyridin-3-yl]-vinyl}-2-methyl-benzonitrile
30
[3-[2-(3-Chloro-5-piperidin-1-yl-phenyl)-vinyl]-6-(4-hydroxy-phenyl)-1H-pyrazolo[3,4-b]pyridin-4-yl]-piperazin-1-yl-methanone
31
3-{2-[6-(4-Hydroxy-phenyl)-4-(piperazine-1-carbonyl)-1H-pyrazolo[3,4-b]pyridin-3-yl]-vinyl}-N,N-dimethyl-benzamide
32
5-{2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one
33
[3-[2-(2,3-Dihydro-1H-indol-7-yl)-vinyl]-6-(4-hydroxy-phenyl)-1H-pyrazolo[3,4-b]pyridin-4-yl]-piperazin-1-yl-methanone
34
3-{2-[4-(2,2-Dimethyl-piperazine-1-carbonyl)-6-(4-hydroxy-phenyl)-1H-pyrazolo[3,4-b]pyridin-3-yl]-vinyl}-N,N-dimethyl-benzamide
35
6-{2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one
36
[3-(2-Cyclohexyl-ethyl)-6-(4-hydroxy-phenyl)-1H-pyrazolo[3,4-b]pyridin-4-yl]-piperazin-1-yl-methanone
37
[3-[(E)-2-(4-Fluoro-phenyl)-vinyl]-6-(4-hydroxy-phenyl)-1H-pyrazolo[3,4-b]pyridin-4-yl]-piperazin-1-yl-methanone
38
[6-(4-Hydroxy-phenyl)-3-((E)-2-m-toyl-vinyl)-1H-pyrazolo[3,4-b]pyridin-4-yl]-piperazin-1-yl-methanone
39
[3-[(E)-2-(2,4-Dichloro-phenyl)-vinyl]-6-(4-hydroxy-phenyl)-1H-pyrazolo[3,4-b]pyridin-4-yl]-piperazin-1-yl-methanone 40 [3-[(E)-2-(3,5-Dimethyl-phenyl)-vinyl]-6-(4-hydroxy-phenyl)-1H-pyrazolo[3,4-b]pyridin-4-yl]-piperazin-1-yl-methanone
41 [3-[(E)-2-(4-Difluoromethoxy-phenyl)-vinyl]-6-(4-hydroxy-phenyl)-1H-pyrazolo[3,4-b]pyridin-4-yl]-piperazin-1-yl-methanone
42 {6-(4-Hydroxy-phenyl)-3-[(E)-2-(4-trifluoromethyl-phenyl)-vinyl]-1H-pyrazolo[3,4-b]pyridin-4-yl}-piperazin-1-yl-methanone
43 [3-[(E)-2-(2,4-Dimethoxy-phenyl)-vinyl]-6-(4-hydroxy-phenyl)-1H-pyrazolo[3,4-b]pyridin-4-yl]-piperazin-1-yl-methanone
44 {6-(4-Hydroxy-phenyl)-3-[(E)-2-(4-phenoxy-phenyl)-vinyl]-1H-pyrazolo[3,4-b]pyridin-4-yl}-piperazin-1-yl-methanone
45 [3-[(E)-2-(3,4-Dichloro-phenyl)-vinyl]-6-(4-hydroxy-phenyl)-1H-pyrazolo[3,4-b]pyridin-4-yl]-piperazin-1-yl-methanone
46 {6-(4-Hydroxy-phenyl)-3-[(E)-2-(3-trifluoromethyl-phenyl)-vinyl]-1H-pyrazolo[3,4-b]pyridin-4-yl}-piperazin-1-yl-methanone
47 [3-[(E)-2-(4-Hydroxy-3-methyl=phenyl)-vinyl]-6-(4-hydroxy-phenyl)-1H-pyrazolo[3,4-b]pyridin-4-yl]-piperazin-1-yl-methanone
48 [3-[(E)-2-(3-Chloro-phenyl)-vinyl]-6-(4-hydroxy-phenyl)-1H-pyrazolo[3,4-b]pyridin-4-yl]-piperazin-1-yl-methanone
49 [3-[(E)-2-(2,4-Dimethyl-phenyl)-vinyl]-6-(4-hydroxy-phenyl)-1H-pyrazolo[3,4-b]pyridin-4-yl]-piperazin-1-yl-methanone
50 [3-[(E)-2-(2,5-Dimethyl-phenyl)-vinyl]-6-(4-hydroxy-phenyl)-1H-pyrazolo[3,4-b]pyridin-4-yl]-piperazin-1=yl-methanone
51 {6-(4-Hydroxy-phenyl)-3-[(E)-2-(4-isopropyl-phenyl)-vinyl]-1H-pyrazolo[3,4-b]pyridin-4-yl}-piperazin-1-yl-methanone
52 [3-[(E)-2-(2-Chloro-4-fluoro-phenyl)-vinyl]-6-(4-hydroxy-phenyl)-1H-pyrazolo[3,4-b]pyridin-4-yl]-piperazin-1-yl-methanone
53 [3-[(E)-2-(4-Ethyl-phenyl)-vinyl]-6-(4-hydroxy-phenyl)-1H-pyrazolo[3,4-b]pyridin-4-yl]-piperazin-1-yl-methanone
54 [3-[(E)-2-(4-tert-Butyl-phenyl)-vinyl]-6-(4-hydroxy-phenyl)-1H-pyrazolo[3,4-b]pyridin-4-yl]-piperazin-1-yl-methanone
55 [3-[(E)-2-(3-Fluoro-4-methyl-phenyl)-vinyl]-6-(4-hydroxy-phenyl)-1H-pyrazolo[3,4-b]pyridin-4-yl]-piperazin-1-yl-methanone
56 {6-(4-Hydroxy-phenyl)-3-[(E)-2-(3-methoxy-phenyl)-vinyl]-1H-pyrazolo[3,4-b]pyridin-4-yl}-piperazin-1-yl-methanone
57 1-(4-{(E)-2-[6-(4-Hydroxy-phenyl)-4-(piperazine-1-carbonyl)-1H-pyrazolo[3,4-b]pyridin-3-yl]-vinyl}-phenyl)-ethanone
58 {6-(4-Hydroxy-phenyl)-3-[(E)-2-(4-trifluoromethoxy-phenyl)-vinyl]-1H-pyrazolo[3,4-b]pyridin-4-yl}-piperazin-1-yl-methanone
59 [3-[(E)-2-(3,4-Difluoro-phenyl)-vinyl]-6-(4-hydroxy-phenyl)-1H-pyrazolo[3,4-b]pyridin-4-yl]-piperazin-1-yl-methanone
60 {6-(4-Hydroxy-phenyl)-3-[(E)-2-(2-methoxy-phenyl)-vinyl]-1H-pyrazolo[3,4-b]pyridin-4-yl}-piperazin-1-yl-methanone
61 [3-[(E)-2-(4-Fluoro-2-methyl-phenyl)-vinyl]-6-(4-hydroxy-phenyl)-1H-pyrazolo[3,4-b]pyridin-4-yl]-piperazin-1-yl-methanone
62 {6-(4-Hydroxy-phenyl)-3-[(E)-2-(3,4,5-trimethoxy-phenyl)-vinyl]-1H-pyrazolo[3,4-b]pyridin-4-yl}-piperazin-1-yl-methanone
63 [3-[(E)-2-(2-Fluoro-4-methyl-phenyl)-vinyl]-6-(4-hydroxy-phenyl)-1H-pyrazolo[3,4-b]pyridin-4-yl]-piperazin-1-yl-methanone
64 [3-[(E)-2-(2,3-Dihydro-benzofuran-5-yl)-vinyl]-6-(4-hydroxy-phenyl)-1H-pyrazolo[3,4-b]pyridin-4-yl]-piperazin-1-yl-methanone
65 [3-((E)-2-Benzo[1,3]dioxol-5-yl-vinyl)-6-(4-hydroxy-phenyl)-1H-pyrazolo[3,4-b]pyridin-4-yl]-piperazin-1-yl-methanone
66 4-{(E)-2-[6-(4-Hydroxy-phenyl)-4-(piperazine-1-carbonyl)-1H-pyrazolo[3,4-b]pyridin-3-yl]-vinyl}-N,N-dimethyl-benzamide
67 [3-[(E)-2-(4-Ethoxy-phenyl)-vinyl]-6-(4-hydroxy-phenyl)-1H-pyrazolo[3,4-b]pyridin-4-yl]-piperazin-1-yl-methanone
68 {6-(4-Hydroxy-phenyl)-3-[(E)-2-(2-trifluoromethyl-phenyl)-vinyl]-1H-pyrazolo[3,4-b]pyridin-4-yl}-piperazin-1-yl-methanone
69 [6-(4-Hydroxy-phenyl)-3-((E)-2-o-tolyl-vinyl)-1H-pyrazolo[3,4-b]pyridin-4-yl]-piperazin-1-yl-methanone
70 [3-[2-(3,5-Dichloro-phenyl)-vinyl]-6-(4-hydroxy-phenyl)-1H-pyrazolo[3,4-b]pyridin-4-yl]-piperazin-1-yl-methanone
71 [3-[(E)-2-(3-fluoro-phenyl)-vinyl]-6-(4-hydroxy-phenyl)-1H-pyrazolo[3,4-b]pyridin-4-yl]-piperazin-1-yl-methanone
72 [3-[(E)-2-(2-Fluoro-phenyl)-vinyl]-6-(4-hydroxy-phenyl)-1H-pyrazolo[3,4-b]pyridin-4-yl]-piperazin-1-yl-methanone 73 {6-(4-Hydroxy-phenyl)-3-[(E)-2-(4-methoxy-3-methyl-phenyl)-vinyl]-1H-pyrazolo[3,4-b]pyridin-4-yl}-piperazin-1-yl-methanone
74 4-[6-(4-Hydroxy-phenyl)-3-((E)-styryl)-1H-pyrazolo[3,4-b]pyridine-4-carbonyl]-piperazine-1-carboxylic acid dimethylamide
75 6-(4-Hydroxy-phenyl)-3-((E)-styryl)-1H-pyrazolo[3,4-b]pyridine-4-carboxylic acid (4-methyl-piperidin-4-yl)-amide
76 ((S)-2-Butyl-piperazin-1-yl)-[6-(4-hydroxy-phenyl)-3-((E)-styryl)-1H-pyrazolo[3,4-b]pyridin-4-yl]-methanone
77 ((R)-2-Butyl-piperazin-1-yl)-[6-(4-hydroxy-phenyl)-3-((E)-styryl)-1H-pyrazolo[3,4-b]pyridin-4-yl]-methanone
78 (2,7-Diaza-spiro[4.4]non-2-yl)-[6-(4-hydroxy-phenyl)-3-((E)-styryl)-1H-pyrazolo[3,4-b]pyridin-4-yl]-methanone
79 (6,9-Diaza-spiro[4.5]dec-9-yl)-[6-(4-hydroxy-phenyl)-3-((E)-styryl)-1H-pyrazolo[3,4-b]pyridin-4-yl]-methanone
80 2-Ethyl-1-{4-[6-(4-hydroxy-phenyl)-3-((E)-styryl)-1H-pyrazolo[3,4-b]pyridine-4-carbonyl]-piperazin-1-yl}-butan-1-one
81 1-{4-[6-(4-Hydroxy-phenyl)-3-((E)-styryl)-1H-pyrazolo[3,4-b]pyridine-4-carbonyl]-piperazin-1-yl}-2-morpholin-4-yl-ethanone
82 4-[6-(4-Hydroxy-phenyl)-3-((E)-styryl)-1H-pyrazolo[3,4-b]pyridine-4-carbonyl]-piperazine-1-carboxylic acid methyl ester
83 [6-(4-Hydroxy-phenyl)-3-((E)-styryl)-1H-pyrazolo[3,4-b]pyridin-4-yl]-[4-(pyridine-3-carbonyl)-piperazin-1-yl]-methanone
84 2-{4-[6-(4-Hydroxy-phenyl)-3-((E)-styryl)-1H-pyrazolo[3,4-b]pyridine-4-carbonyl]-piperazin-1-yl}-N,N-dimethyl-acetamide
85 (4-Cyclopropyl-piperazin-1-yl)-[6-(4-hydroxy-phenyl)-3-((E)-styryl)-1H-pyrazolo[3,4-b]pyridin-4-yl]-methanone
86 2-Hydroxy-1-{4-[6-(4-hydroxy-phenyl)-3-((E)-styryl)-1H-pyrazolo[3,4-b]pyridine-4-carbonyl]-piperazin-1-yl}-2-methyl-propan-1-one
87 3-Hydroxy-1-{4-[6-(4-hydroxy-phenyl)-3-((E)-styryl)-1H-pyrazolo[3,4-b]pyridine-4-carbonyl]-piperazin-1-yl}-2,2-dimethyl-propan-1-one
88 1-{4-[6-(4-Hydroxy-phenyl)-3-((E)-styryl)-1H-pyrazolo[3,4-b]pyridine-4-carbonyl]-piperazin-1-yl}-3-methoxy-propan-1-one
Another group of embodiments are compounds selected from the group consisting of
[6-(4-hydroxyphenyl)-3-(2-phenylethenyl)-1H-pyrazolo[3,4-b]pyridin-4-yl](4-methyl-1-piperazinyl)-methanone
(4,7-Diaza-spiro[2.5]oct-4-yl)-[6-(4-hydroxy-phenyl)-3-((E)-styryl)-1H-pyrazolo[3,4-b]pyridin-4-yl]-methanone.
Another group of embodiments are compounds selected from the group consisting of 1 [3-[(E)-2-(4-Chloro-phenyl)-vinyl]-6-(4-hydroxy-phenyl)-1H-pyrazolo[3,4-b]pyridin-4-yl]-piperazin-1-yl-methanone
2 [6-(4-Hydroxy-phenyl)-3-((E)-styryl)-1H-pyrazolo[3,4-b]pyridin-4-yl]-piperazin-1-yl-methanone
4 (3,3-Dimethyl-piperazin-1-yl)-[6-(4-hydroxy-phenyl)-3-((E)-styryl)-1H-pyrazolo[3,4-b]pyridin-4-yl]-methanone
5 [6-(4-Hydroxy-phenyl)-3-((E)-styryl)-1H-pyrazolo[3,4-b]pyridin-4-yl]-((S)-3-isobutylpiperazin-1-yl)-methanone
6 [6-(4-Hydroxy-phenyl)-3-((E)-styryl)-1H-pyrazolo[3,4-b]pyridin-4-yl]-((S)-2-methyl piperazin-1-yl)-methanone
7 [6-(4-Hydroxy-2-methyl-phenyl)-3-((E)-styryl)-1H-pyrazolo[3,4-b]pyridin-4-yl]-piperazin-1-yl-methanone
8 ((2S,5R)-2,5-Dimethyl-piperazin-1-yl)-[6-(4-hydroxy-phenyl)-3-((E)-styryl)-1H-pyrazolo[3,4-b]pyridin-4-yl]-methanone
9 [6-(4-Hydroxy-3-methoxy-phenyl)-3-((E)-styryl)-1H-pyrazolo[3,4-b]pyridin-4-yl]-piperazin-1-yl-methanone
17 [6-(4-Hydroxy-phenyl)-3-phenethyl-1H-pyrazolo[3,4-b]pyridin-4-yl]-piperazin-1-yl-methanone
21 [6-(4-Hydroxy-phenyl)-3-((E)-2-p-tolyl-vinyl)-1H-pyrazolo[3,4-b]pyridin-4-yl]-piperazin-1-yl-methanone
22 {6-(4-Hydroxy-phenyl)-3-[(E)-2-(3-methanesulfonyl-phenyl)-vinyl]-1H-pyrazolo[3,4-b]pyridin-4-yl}-piperazin-1-yl-methanone
23 [3-[(E)-2-(3-Dimethylamino-phenyl)-vinyl]-6-(4-hydroxy-phenyl)-1H-pyrazolo[3,4-b]pyridin-4-yl]-piperazin-1-yl-methanone
24 {6-(4-Hydroxy-phenyl)-3-[(E)-2-(4-methanesulfonyl-phenyl)-vinyl]-1H-pyrazolo[3,4-b]pyridin-4-yl}-piperazin-1-yl-methanone
25 3-{(E)-2-[6-(4-Hydroxy-phenyl)-4-(piperazine-1-carbonyl)-1H-pyrazolo[3,4-b]pyridin-3-yl]-vinyl}-benzonitrile
26 {6-(4-Hydroxy-phenyl)-3-[(E)-2-(3-piperidin-1-yl-phenyl)-vinyl]-1H-pyrazolo[3,4-b]pyridin-4-yl}-piperazin-1-yl-methanone
27 {6-(4-Hydroxy-phenyl)-3-[(E)-2-(3-morpholin-4-yl-phenyl)-vinyl]-1H-pyrazolo[3,4-b]pyridin-4-yl}-piperazin-1-yl-methanone
37 [3-[(E)-2-(4-fluoro-phenyl)-vinyl]-6-(4-hydroxy-phenyl)-1H-pyrazolo[3,4-b]pyridin-4-yl]-piperazin-1-yl-methanone
38 [6-(4-Hydroxy-phenyl)-3-((E)-2-m-tolyl-vinyl)-1H-pyrazolo[3,4-b]pyridin-4-yl]-piperazin-1-yl-methanone
39 [3-[(E)-2-(2,4-Dichloro-phenyl)-vinyl]-6-(4-hydroxy-phenyl)-1H-pyrazolo[3,4-b]pyridin-4-yl]-piperazin-1-yl-methanone 40 [3-[(E)-2-(3,5-Dimethyl-phenyl)-vinyl]-6-(4-hydroxy-phenyl)-1H-pyrazolo[3,4-b]pyridin-4-yl]-piperazin-1-yl-methanone 41 [3-[(E)-2-(4-Difluoromethoxy-phenyl)-vinyl]-6-(4-hydroxy-phenyl)-1H-pyrazolo[3,4-b]pyridin-4-yl]-piperazin-1-yl-methanone 42 {6-(4-Hydroxy-phenyl)-3-[(E)-2-(4-trifluoromethyl-phenyl)-vinyl]-1H-pyrazolo[3,4-b]pyridin-4-yl}-piperazin-1-yl-methanone 43 [3-[(E)-2-(2,4-Dimethoxy-phenyl)-vinyl]-6-(4-hydroxy-phenyl)-1H-pyrazolo[3,4-b]pyridin-4-yl]-piperazin-1-yl-methanone 44 {6-(4-Hydroxy-phenyl)-3-[(E)-2-(4-phenoxy-phenyl)-vinyl]-1H-pyrazolo[3,4-b]pyridin-4-yl}-piperazin-1-yl-methanone 45 [3-[(E)-2-(3,4-Dichloro-phenyl)-vinyl]-6-(4-hydroxy-phenyl)-1H-pyrazolo[3,4-b]pyridin-4-yl]-piperazin-1-yl-methanone 46 {6-(4-Hydroxy-phenyl)-3-[(E)-2-(3-trifluoromethyl-phenyl)-vinyl]-1H-pyrazolo[3,4-b]pyridin-4-yl}-piperazin-1-yl-methanone 47 [3-[(E)-2-(4-Hydroxy-3-methyl-phenyl)-vinyl]-6-(4-hydroxy-phenyl)-1H-pyrazolo[3,4-b]pyridin-4-yl]-piperazin-1-yl-methanone 48 [3-[(E)-2-(3-Chloro-phenyl)-vinyl]-6-(4-hydroxy-phenyl)-1H-pyrazolo[3,4-b]pyridin-4-yl]-piperazin-1-yl-methanone 49 [3-[(E)-2-(2,4-Dimethyl-phenyl)-vinyl]-6-(4-hydroxy-phenyl)-1H-pyrazolo[3,4-b]pyridin-4-yl]-piperazin-1-yl-methanone 50 [3-[(E)-2-(2,5-Dimethyl-phenyl)-vinyl]-6-(4-hydroxy-phenyl)-1H-pyrazolo[3,4-b]pyridin-4-yl]-piperazin-1-yl-methanone 51 {6-(4-Hydroxy-phenyl)-3-[(E)-2-(4-isopropyl-phenyl)-vinyl]-1H-pyrazolo[3,4-b]pyridin-4-yl}-piperazin-1-yl-methanone 52 [3-[(E)-2-(2-Chloro-4-fluoro-phenyl)-vinyl]-6-(4-hydroxy-phenyl)-1H-pyrazolo[3,4-b]pyridin-4-yl]-piperazin-1-yl-methanone 53 [3-[(E)-2-(4-Ethyl-phenyl)-vinyl]-6-(4-hydroxy-phenyl)-1H-pyrazolo[3,4-b]pyridin-4-yl]-piperazin-1-yl-methanone 54 [3-[(E)-2-(4-tert-Butyl-phenyl)-vinyl]-6-(4-hydroxy-phenyl)-1H-pyrazolo[3,4-b]pyridin-4-yl]-piperazin-1-yl-methanone 55 [3-[(E)-2-(3-Fluoro-4-methyl-phenyl)-vny]-6-(4-hydroxy-phenyl)-1H-pyrazolo[3,4-b]pyridin-4-yl]-piperazin-1-yl-methanone 56 {6-(4-Hydroxy-phenyl)-3-[(E)-2-(3-methoxy-phenyl)-vinyl]-1H-pyrazolo[3,4-b]pyridin-4-yl}-piperazin-1-yl-methanone 57 1-(4-{(E)-2-[6-(4-Hydroxy-phenyl)-4-(piperazine-1-carbonyl)-1H-pyrazolo[3,4-b]pyridin-3-yl]-vinyl}-phenyl)-ethanone 58 {6-(4-Hydroxy-phenyl)-3-[(E)-2-(4-trifluoromethoxy-phenyl)-vinyl]-1H-pyrazolo[3,4-b]pyridin-4-yl}-piperazin-1-yl-methanone 59 [3-[(E)-2-(3,4-Difluoro-phenyl)-vinyl]-6-(4-hydroxy-phenyl)-1H-pyrazolo[3,4-b]pyridin-4-yl]-piperazin-1-yl-methanone 60 {6-(4-Hydroxy-phenyl)-3-[(E)-2-(2-methoxy-phenyl)-vinyl]-1H-pyrazolo[3,4-b]pyridin-4-yl}-piperazin-1-yl-methanone 61 [3-[(E)-2-(4-Fluoro-2-methyl-phenyl)-vinyl]-6-(4-hydroxy-phenyl)-1H-pyrazolo[3,4-b]pyridin-4-yl]-piperazin-1-yl-methanone 62 {6-(4-Hydroxy-phenyl)-3-[(E)-2-(3,4,5-trimethoxy-phenyl)-vinyl]-1H-pyrazolo[3,4-b]pyridin-4-yl}-piperazin-1-yl-methanone 63 [3-[(E)-2-(2-Fluoro-4-methyl-phenyl)-vinyl]-6-(4-hydroxy-phenyl)-1H-pyrazolo[3,4-b]pyridin-4-yl]-piperazin-1-yl-methanone 64 [3-[(E)-2-(2,3-Dihydro-benzofuran-5-yl)-vinyl]-6-(4-hydroxy-phenyl)-1H-pyrazolo[3,4-b]pyridin-4-yl]-piperazin-1-yl-methanone 65 [3-((E)-2-Benzo[1,3]dioxol-5-yl-vinyl)-6-(4-hydroxy-phenyl)-1H-pyrazolo[3,4-b]pyridin-4-yl]-piperazin-1-yl-methanone 66 4-{(E)-2-[6-(4-Hydroxy-phenyl)-4-(piperazine-1-carbonyl)-1H-pyrazolo[3,4-b]pyridin-3-yl]-vinyl}-1N,N-dimethyl-benzamide 67 [3-[(E)-2-(4-Ethoxy-phenyl)-vinyl]-6-(4-hydroxy-phenyl)-1H-pyrazolo[3,4-b]pyridin-4-yl]-piperazin-1-yl-methanone 68 {6-(4-Hydroxy-phenyl)-3-[(E)-2-(2-trifluoromethyl-phenyl)-vinyl]-1H-pyrazolo[3,4-b]pyridin-4-yl}-piperazin-1-yl-methanone 69 [6-(4-Hydroxy-phenyl)-3-((E)-2-o-tolyl-vinyl)-1H-pyrazolo[3,4-b]pyridin-4-yl]-piperazin-1-yl-methanone 71 [3-[(E)-2-(3-Fluoro-phenyl)-vinyl]-6-(4-hydroxy-phenyl)-1H-pyrazolo[3,4-b]pyridin-4-yl]-piperazin-1-yl-methanone 72 [3-[(E)-2-(2-Fluoro-phenyl)-vinyl]-6-(4-hydroxy-phenyl)-1H-pyrazolo[3,4-b]pyridin-4-yl]-piperazin-1-yl-methanone 73 {6-(4-Hydroxy-phenyl)-3-[(E)-2-(4-methoxy-3-methyl-phenyl)-vinyl]-1H-pyrazolo[3,4-b]pyridin-4-yl}-piperazin-1-yl-methanone 74
4-[6-(4-Hydroxy-phenyl)-3-((E)-styryl)-1H-pyrazolo[3,4-b]pyridine-4-carbonyl]-piperazine-1-carboxylic acid dimethylamide
75
6-(4-Hydroxy-phenyl)-3-((E)-styryl)-1H-pyrazolo[3,4-b]pyridine-4-carboxylic acid (4-methyl-piperidin-4-yl)-amide
76
((S)-2-Butyl-piperazin-1-yl)-[6-(4-hydroxy-phenyl)-3-((E)-styryl)-1H-pyrazolo[3,4-b]pyridin-4-yl]-methanone
77
((R)-2-Butyl-piperazin-1-yl)-[6-(4-hydroxy-phenyl)-3-((E)-styryl)-1H-pyrazolo[3,4-b]pyridin-4-yl]-methanone
78
(2,7-Diaza-spiro[4.4]non-2-yl)-[6-(4-hydroxy-phenyl)-3-((E)-styryl)-1H-pyrazolo[3,4-b]pyridin-4-yl]-methanone
79
(6,9-Diaza-spiro[4.5]dec-9-yl)-[6-(4-hydroxy-phenyl)-3-((E)-styryl)-1H-pyrazolo[3,4-b]pyridin-4-yl]-methanone
80
2-Ethyl-1-{4-[6-(4-hydroxy-phenyl)-3-((E)-styryl)-1H-pyrazolo[3,4-b]pyridine-4-carbonyl]-piperazin-1-yl}-butan-1-one
81
1-{4-[6-(4-Hydroxy-phenyl)-3-((E)-styryl)-1H-pyrazolo[3,4-b]pyridine-4-carbonyl]-piperazin-1-yl}-2-morpholin-4-yl-ethanone
82
4-[6-(4-Hydroxy-phenyl)-3-((E)-styryl)-1H-pyrazolo[3,4-b]pyridine-4-carbonyl]-piperazine-1-carboxylic acid methyl ester
83
[6-(4-Hydroxy-phenyl)-3-((E)-styryl)-1H-pyrazolo[3,4-b]pyridin-4-yl]-[4-(pyridine-3-carbonyl)-piperazin-1-yl]-methanone
84
2-{4-[6-(4-Hydroxy-phenyl)-3-((E)-styryl)-1H-pyrazolo[3,4-b]pyridine-4-carbonyl]-piperazin-1-yl}-N,N-dimethyl-acetamide
85
(4-Cyclopropyl-piperazin-1-yl)-[6-(4-hydroxy-phenyl)-3-((E)-styryl)-1H-pyrazolo[3,4b]pyridin-4-yl]-methanone
86
2-Hydroxy-1-{4-[6-(4-hydroxy-phenyl)-3-((E)-styryl)-1H-pyrazolo[3,4-b]pyridine-4-carbonyl]-piperazin-1-yl}-2-methyl-propan-1-one
87
3-Hydroxy-1-{4-[6-(4-hydroxy-phenyl)-3-((E)-styryl)-1H-pyrazolo[3,4-b]pyridine-4-carbonyl]-piperazin-1-yl}-2,2-dimethyl-propan-1-one
88
1-{4-[6-(4-Hydroxy-phenyl)-3-((E)-styryl)-1H-pyrazolo[3,4-b]pyridine-4-carbonyl]-piperazin-1-yl}-3-methoxy-propan-1-one Another group of embodiments are compounds selected from the series consisting of
3
(2,2-Dimethyl-piperazin-1-yl)-[6-(4-hydroxy-phenyl)-3-(styryl)-1H-pyrazolo[3,4-b]pyridin-4-yl]-methanone
10
((S)-2-Ethyl-piperazin-1-yl)-[6-(4-hydroxy-phenyl)-3-((E)-styryl)-1H-pyrazolo[3,4-b]pyridin-4-yl]-methanone
11
[6-(2-Fluoro-4-hydroxy-phenyl)-3-((E)-styryl)-1H-pyrazolo[3,4-b]pyridin-4-yl]-((S)-2-methyl-piperazin-1-yl)-methanone
12
[6-(3-Fluoro-4-hydroxy-phenyl)-3-(styryl)-1H-pyrazolo[3,4-b]pyridin-4-yl]-piperazin-1-yl-methanone
13
[6-(2-Chloro-4-hydroxy-phenyl)-3-(styryl)-1H-pyrazolo[3,4-b]pyridin-4-yl]-piperazin-1-yl-methanone
14
[3-[2-(3-Dimethylaminomethyl-phenyl)-vinyl]-6-(4-hydroxy-phenyl)-1H-pyrazolo[3,4-b]pyridin-4-yl]-piperazin-1-yl-methanone
15
{6-(4-Hydroxy-phenyl)-3-[2-(3-methanesulfonylmethyl-phenyl)-vinyl]-1H-pyrazolo[3,4-b]pyridin-4-yl}-piperazin-1-yl-methanone
16
((R)-2-Hydroxymethyl-piperazin-1-yl)-[6-(4-hydroxy-phenyl)-3-((E)-styryl)-1H-pyrazolo[3,4-b]pyridin-4-yl]-methanone
18
[6-(4-Hydroxy-phenyl)-3-((1R,2R)-2-phenyl-cyclopropyl)-1H-pyrazolo[3,4-b]pyridin-4-yl]-piperazin-1-yl-methanone
19
(6-(4-Hydroxy-phenyl)-3-{2-[4-(piperidine-1-carbonyl)-phenyl]-vinyl}-1H-pyrazolo[3,4-b]pyridin-4-yl)-piperazin-1-yl-methanone
20
1-(3-{2-[6-(4-Hydroxy-phenyl)-4-(piperazine-1-carbonyl)-1H-pyrazolo[3,4-b]pyridin-3-yl]-vinyl}-phenyl)-pyrrolidin-2-one
28
{6-(4-Hydroxy-phenyl)-3-[2-(3-pyrroidin-1-yl-phenyl)-vinyl]-1H-pyrazolo[3,4-b]pyridin-4-yl}-piperazin-1-yl-methanone
29
4-{2-[6-(4-Hydroxy-phenyl)-4-(piperazine-1-carbonyl)-1H-pyrazolo[3,4-b]pyridin-3-yl]-vinyl}-2-methyl-benzonitrile
30
[3-[2-(3-Chloro-5-piperidin-1-yl-phenyl)-vinyl]-6-(4-hydroxy-phenyl)-1H-pyrazolo[3,4-b]pyridin-4-yl]-piperazin-1-yl-methanone
31
3-{2-[6-(4-Hydroxy-phenyl)-4-(piperazine-1-carbonyl)-1H-pyrazolo[3,4-b]pyridin-3-yl]-vinyl}-N,N-dimethyl-benzamide
32
5-{2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one
33
[3-[2-(2,3-Dihydro-1H-indol-7-yl)-vinyl]-6-(4-hydroxy-phenyl)-1H-pyrazolo[3,4-b]pyridin-4-yl]-piperazin-1-yl-methanone
34
3-{2-[4-(2,2-Dimethyl-piperazine-1-carbonyl)-6-(4-hydroxy-phenyl)-1H-pyrazolo[3,4-b]pyridin-3-yl]-vinyl}-N,N-dimethyl-benzamide
35
6-{2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one
36
[3-(2-Cyclohexyl-ethyl)-6-(4-hydroxy-phenyl)-1H-pyrazolo[3,4-b]pyridin-4-yl]-piperazin-1-yl-methanone 70 [3-[2-(3,5-Dichloro-phenyl)-vinyl]-6-(4-hydroxy-phenyl)-1H-pyrazolo[3,4-b]pyridin-4-yl]-piperazin-1-yl-methanone Structural elements such as groups, substituents, hetero ring members, numbers or other features, for example alkyl groups, groups like $R^1$, $R^2$, $R^3$ etc., which can occur several times in the compounds of the formula I, can all independently of one another have any of the indicated meanings and can in each case be identical to or different from one another. For example, the alkyl groups in a dialkylamino group can be identical or different.

As used here, the terms "including" and "comprising" are used in their open, non-limiting sense. As used herein, the terms "$(C_1-C_8)$" or "$(C_5-C_8)$" and so forth, refer to moieties having 1 to 8 or 5 to 8 carbon atoms, respectively. Within terms like "$(C_0-C_6)$-alkyl" or "$(C_0-C_6)$-alkylen" "$C_0$-alkyl" or "$(C_0)$-alkylen" refer to a bond, or in case of an unsubstituted "$(C_0)$-alkyl" it refers to a hydrogen.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkinyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (=alkoxy groups, O-alkylgroups), alkyloxycarbonyl groups or alkyl-substituted amino groups, or when they are substituted. Depending on the respective definition, the number of carbon atoms in an alkyl group can be 1, 2, 3, 4, 5, 6, 7 or 8, or 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl, heptyl and octyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Independently of one another and independently of any other substituents, alkyl groups, divalent alkyl groups, alkenyl groups, alkynyl groups, cycloalkyl groups and heterocycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, —C(CH$_3$)$_2$—CF$_2$—, —CF$_2$—C(CH$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy.

The term "alkanediyl" or "alkylene", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkindiyl", as used herein, refers to divalent hydrocarbon radicals, which contain at least one carbon-carbon triple bond. As far as applicable, the preceding explanations regarding alkyl, alkenyl and alkinyl groups apply correspondingly to alkanediyl, alkenediyl and alkindiyl groups, which thus can likewise be linear and branched. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—.

The term "cycloalkyl", as used herein, unless otherwise indicated, refers to a monovalent radical of a saturated or partially saturated hydrocarbon ring system, which can be monocyclic, bicyclic or tricyclic, i.e. which can contain one, two or three rings. The bicyclic or tricyclic ring system can be a fused ring system, in which two adjacent rings share two adjacent carbon atoms. The bicyclic or tricyclic ring system can be a spiro ring system or a di-spiro-ring system, in which two adjacent rings share a single carbon atom. The tricyclic ring system can also be a bicyclic spiro ring system, to which another ring is fused, that means that the latter ring and the ring in the spiro ring system, to which it is attached, share two adjacent carbon atoms; herein the latter ring can be an aromatic, saturated or partially saturated ring. The bicyclic or tricyclic system can also be a non-fused or bridged ring system, in which two adjacent rings share two non-adjacent carbon atoms. The bicyclic or tricyclic ring can be attached by any ring atom except a spiro- or a bridgehead atom.

In a monocyclic cycloalkyl group the number of ring carbon atoms can be 3, 4, 5, 6, 7 or 8. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 5, in another embodiment 6. Examples of cycloalkyl groups are cyclopropyl, cyclobutyl, cyclopentyl, cyclohexyl, cycloheptyl and cyclooctyl.

In a bicyclic cycloalkyl group the number of ring carbon atoms can be 6, 7, 8, 9, 10, 11 or 12. In one embodiment of the invention, the number of ring carbon atoms in a bicyclic cycloalkyl group can be 7, 8, 9, 10 or 11, in another embodiment 8, 9 or 10. In a tricyclic cycloalkyl group the number of ring carbon atoms can be 7, 8, 9, 10, 11, 12, 13, 14 or 15. In one embodiment of the invention, the number of ring carbon atoms in a tricyclic cycloalkyl group can be 10, 11 or 12.

Exemplary bicyclic or tricyclic fused ring cycloalkyls are derived from, but not limited to, the following ring systems: bicyclo[3.1.0]hexane, bicyclo[4.1.0]heptane, bicycle-[5.1.0]octane, bicyclo[3.2.0]heptane, bicyclo[4.2.0]octane, octahydro-pentalene, octahydro-indene, decahydro-azulene, decahydro-naphthalene, decahydro-benzocycloheptene, dodecahydro-heptalene, 1,2,3,3a,4,6a-hexahydro-pentalene, 1,2,3,4-tetrahydro-pentalene, 2,3,3a,4,5,7a-hexahydro-1H-indene, 2,3,3a,4,7,7a-hexahydro-1H-indene, 3a,4,5,6,7,7a-hexahydro-1H-indene, 4,5,6,7-tetrahydro-1H-indene, indane, 1,2,3,4,4a,5,6,8a-octahydro-naphthalene, 1,2,3,4,4a,5,8,8a-octahydronaphthalene, 1,2,4a,5,8,8a-hexahydro-naphthalene, 1,4,4a,5,8,8a-hexahydronaphthalene, 1,2,3,4-tetrahydro-naphthalene, 2,3,4,4a,5,6,9,9a-octahydro-1H-benzocycloheptene, 2,3,4,4a,5,9a-hexahydro-1H-benzocycloheptene, 4,4a,5,6,7,8,9,9a-octahydro-1H-benzocycloheptene, 6,7,8,9-tetrahydro-5H-benzocycloheptene, 1,2,3,4,5,5a,6,7,8,10a-decahydro-heptalene, dodecahydro-as-indacene and 2,3,3a,4,9,9a-hexahydro-1H-cyclopenta[b]naphthalene:

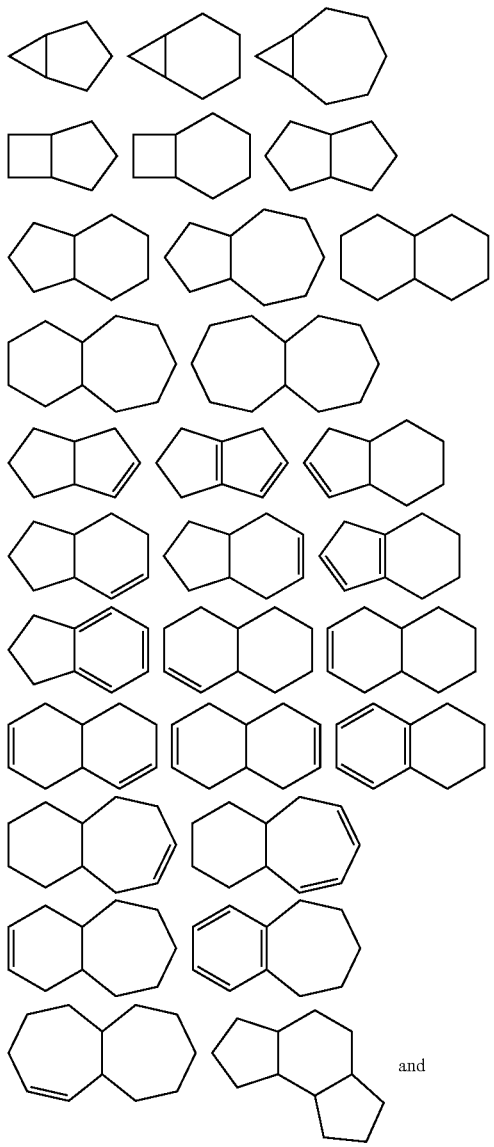

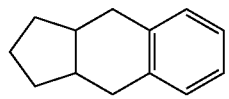

Exemplary bicyclic or tricyclic spiro ring cycloalkyls are derived from, but not limited to, the following ring systems: spiro[2.4]heptane, spiro[2.5]octane, spiro[2.6]nonane, spiro[3.3]heptane, spiro[3.4]octane, spiro[3.5]nonane, spiro[3.6]decane, spiro[4.4]nonane, spiro[4.5]decane, spiro[4.6]undecane, spiro[5.5]undecane, spiro[5.6]dodecane, spiro[6.6]tridecane, dispiro[2.2.4.2]dodecane, dispiro[2.2.3.2]undecane, dispiro-[2.1.4.2]undecane and spiro[5.5]undec-2-ene:

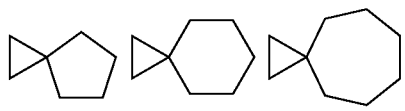

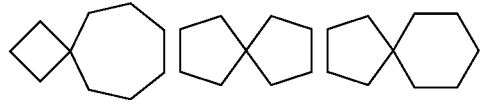

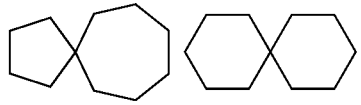

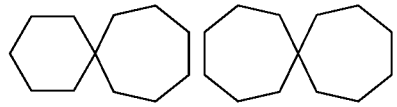

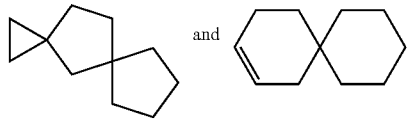

and

Exemplary cycloalkyls, in which a ring is fused to one ring of a bicyclic spiro system, are derived from, but not limited to, the following ring systems:

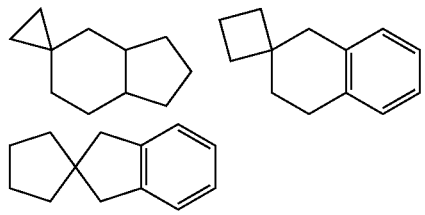

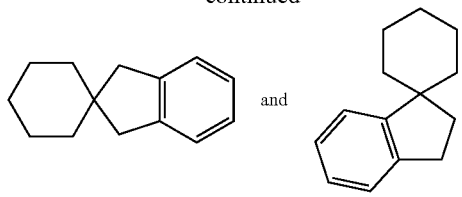

Exemplary non-fused or bridged bicyclic or tricyclic ring cycloalkyls are derived from, but not limited to, the following ring systems: bicyclo[2.2.1]heptane, bicyclo[2.2.2]octane, bicyclo[3.2.1]octane, bicyclo[3.2.2]nonane and adamantane.

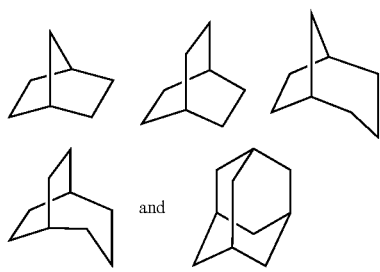

The term "heterocycloalkyl" or "heterocyclyl", as used herein, unless otherwise indicated, refers to a cycloalkyl as defined above, in which 1, 2, 3 or 4 carbon atoms are replaced by nitrogen, oxygen or sulfur atoms, provided that a spiro atom is always a carbon atom and a bridgehead atom is either a carbon or a nitrogen atom and provided that the heterocycloalkyl system is stable and suitable as a subgroup for the desired purpose of the compound of the formula I such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 2, in another embodiment 1, wherein the ring heteroatoms can be identical or different. The heterocycloalkyl group can be attached by any ring carbon atom or saturated ring nitrogen atom, with the exception of spiro- or bridgehead atoms. A ring sulfur atom in a heterocycloalkyl group can carry zero, one or two oxo groups, it is a non-oxidized sulfur atom S in case it does not carry any oxo group, or it is an S(O) group (=sulfoxide group, S-oxide group) in case it carries one oxo group, or it is an S(O)$_2$ group (=sulfone group, S,S-dioxide group) in case it carries two oxo groups.

Exemplary monocyclic heterocycloalkyls are derived from, but not limited to, the following ring systems: aziridine, oxirane, azetidine, oxetane, pyrrolidine, tetrahydrofurane, tetrahydrothiophene, 4,5-dihydrothiazole, piperidine, piperazine, morpholine, thiomorpholine, tetrahydropyran, 1,4-dioxane, 1,4-oxathiane, 1,2,3,6-tetrahydropyridine, azepane, 2,3,4,7-tetrahydro-1H-azepine, 2,7-dihydro-1H-azepine, 1,4-diazepane, 1,4-oxazepane, 1,4-thiazepane and 1,4-dioxepane:

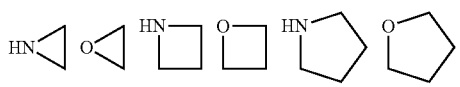

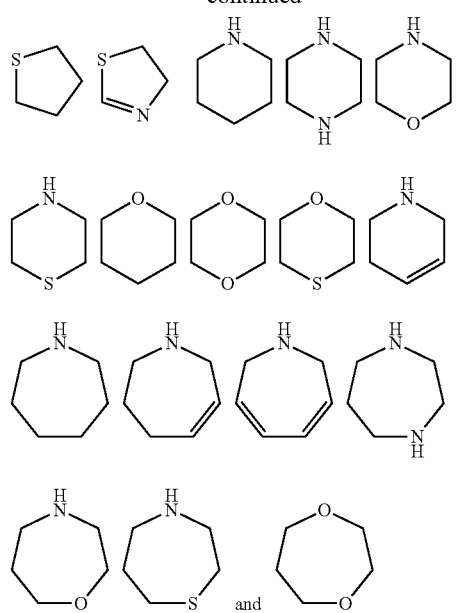

In one embodiment monocyclic heterocycloalkyls are derived from azetidine, pyrrolidine, piperidine, piperazine, morpholine or 1,4-diazepane:

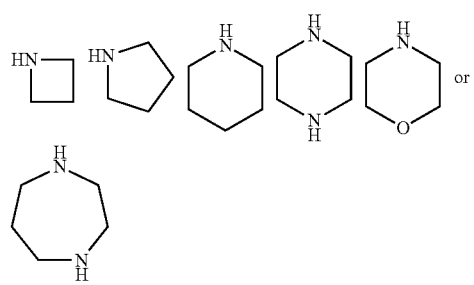

Exemplary bicyclic fused ring heterocycloalkyls are derived from, but not limited to, the following ring systems: 3-aza-bicyclo[3.1.0]hexane, 2-aza-bicyclo[4.1.0]heptane, 2-oxa-5-aza-bicyclo[5.1.0]octane, 3-aza-bicyclo[3.2.0]heptane, 2-aza-bicyclo[4.2.0]-octane, octahydro-pyrrolo[3,4-c]pyrrole, octahydro-pyrrolo[3,4-b]pyrrole, octahydro-pyrrolo[3,4-b]pyridine, octahydro-thieno[3,4-b]pyrazine, octahydro-furo[3,4-b]pyridine, octahydro-cyclopenta[1,4]oxazine, octahydro-pyrrolo[1,2-a]pyrimidine, octahydro-pyrrolo[1,2-a]pyrazine, octahydro-cyclopenta[e][1,4]oxazepine, decahydro-quinoxaline, decahydro-[1,6]naphthyridine, octahydro-benzo[1,4]oxazine, octahydro-benzo[1,4]thiazine, octahydro-pyrido[1,2-a]pyrazine, octahydro-pyrano[3,2-b]pyridine, decahydro-1-oxa-9-azabenzocycloheptene, 1,2,3,3a,6,6a-hexahydro-cyclopenta-[b]pyrrole, 5,6-dihydro-4H-cyclopenta[b]thiophene, 2,3,4,4a,7,7a-hexahydro-1H-[2]pyrindine, 2,4a,5,6,7,7a-hexahydro-1H-[1]pyrindine, 2,3,3a,4,7,7a-hexahydro-1H-indole, 1,2,3,4-tetrahydro-quinoxaline, 4,5,6,7-tetrahydro-benzofuran, benzo[1,3]dioxole, 3,4,4a,7,8,8a-hexahydro-2H-benzo[1,4]oxazine, 1,2,3,4,4a,5,8,8a-octahydro-quinoxaline, 4a,5,8,8a-tetrahydro-2H-thiopyrano[3,2-b]pyridine and 1,2,3,4-tetrahydro-[1,5]naphthyridine:

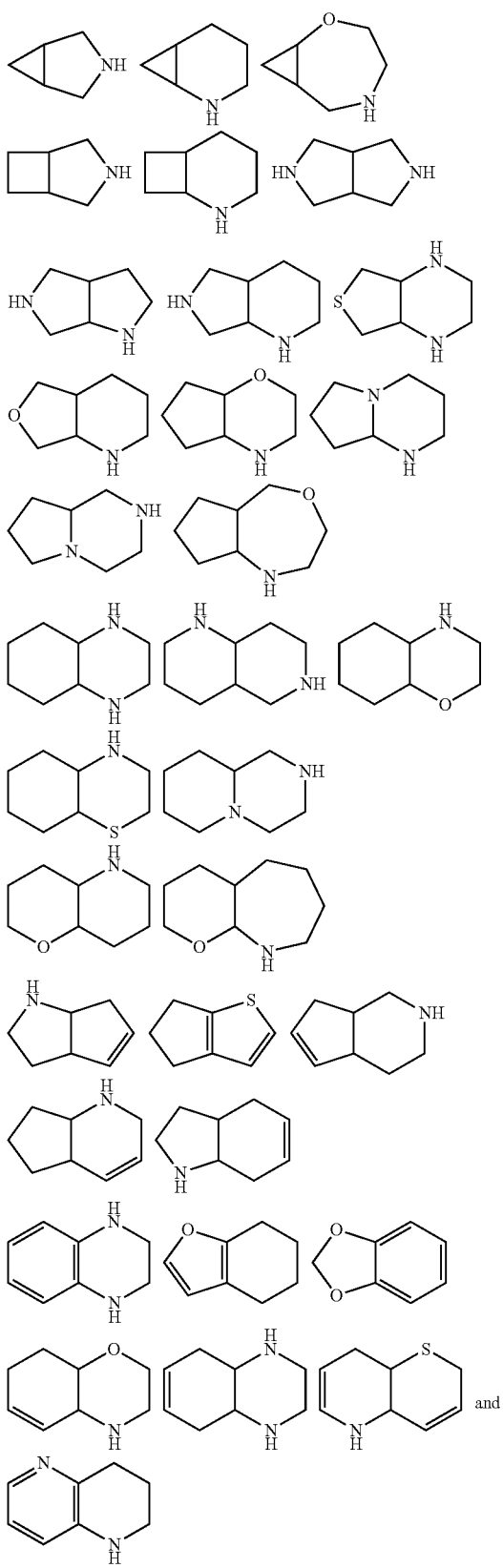

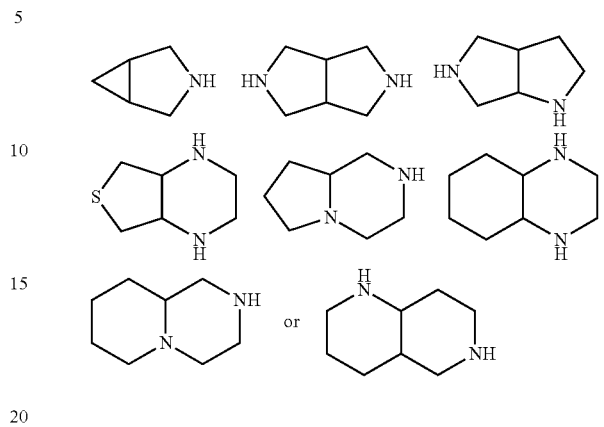

dro-thieno[3,4-b]pyrazine, octahydro-pyrrolo[1,2-a]pyrazine, decahydro-quinoxaline, octahydro-pyrido[1,2-a]pyrazine or decahydro-[1,6]naphthyridine:

Exemplary bicyclic or tricyclic spiro ring heterocycloalkyls are derived from, but not limited to, the following ring systems: 4-aza-spiro[2.4]heptane, 5-aza-spiro[3.4]octane, 1-aza-spiro[4.4]nonane, 7-oxa-1-aza-spiro[4.4]nonane, 7-thia-1-aza-spiro[4.4]-nonane, 4-aza-spiro[2.5]octane, 5-aza-spiro[2.5]octane, 6-aza-spiro[2.5]octane, 5-aza-spiro[3.5]nonane, 6-aza-spiro[3.5]nonane, 7-aza-spiro[3.5]nonane, 4,7-diaza-spiro[2.5]octane, 5,8-diaza-spiro[3.5]nonane, 6,9-diaza-spiro[4.5]decane, 1,4-diaza-spiro[5.5]undecane, 2-oxa-6,9-diaza-spiro[4.5]decane, 2-oxa-6-aza-spiro[4.5]decane, 2,7-diaza-spiro[3.5]nonane, 3,9-diaza-spiro[5.5]undecane, 1-oxa-4,9-diaza-spiro-[5.5]undecane, 1-oxa-4,8-diaza-spiro[5.5]undecane, 1-thia-4,9-diaza-spiro[5.5]undecane, 1-thia-4,8-diaza-spiro[5.5]undecane, 4,8-diaza-spiro[2.6]nonane, 5,8-diaza-spiro[3.6]decane, 2-aza-spiro[5.5]undec-7-ene, 6,9-diaza-spiro[4.6]undecane, 4-azadispiro[2.1.4.2]undecane, 4,10-diaza-dispiro[2.2.3.2]undecane and 4,11-diaza-dispiro[2.2.4.2]dodecane:

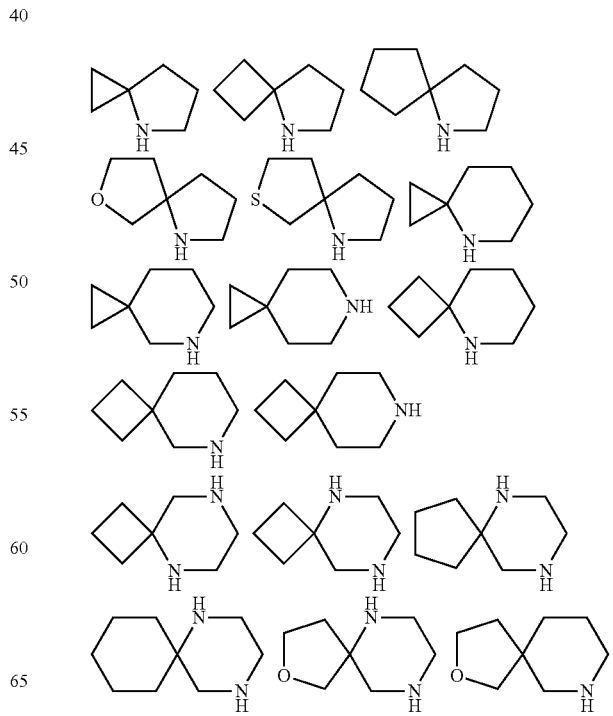

In one embodiment bicyclic fused ring heterocycloalkyls are derived from 3-aza-bicyclo[3.1.0]hexane, octahydro-pyrrolo[3,4-c]pyrrole, octahydro-pyrrolo[3,4-b]pyrrole, octahy-

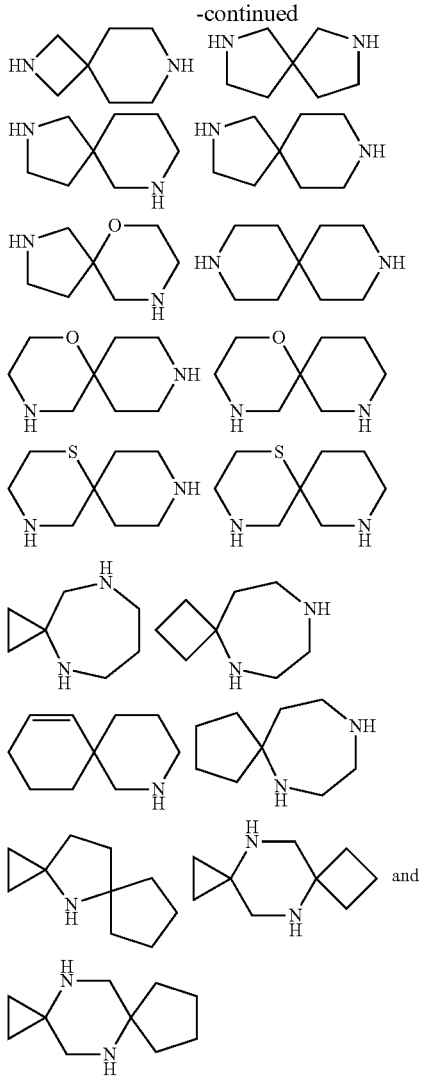

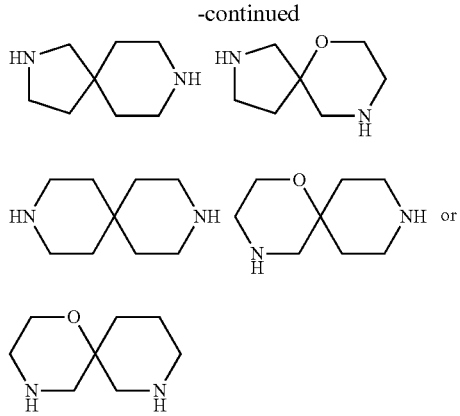

Exemplary heterocycloalkyls, in which a ring is fused to one ring of a bicyclic spiro system, are derived from, but not limited to, the following ring systems: octahydrospiro[cyclopentane-1,2'(3'H)-quinoxalin], 1',4'-dihydro-spiro[cyclopentane-1,2'(3'H)quinoxalin], 1',2',4,5-tetrahydro-spiro[furan-3(2H), 3'-[3H]indol], 1,3-dihydro-spiro[indene-2,2'-piperazine], 2,3-dihydro-spiro[1H-indene-1,4'-piperidin] and 1,2-dihydro-5-spiro[3H-indole-3,4'-piperidin]:

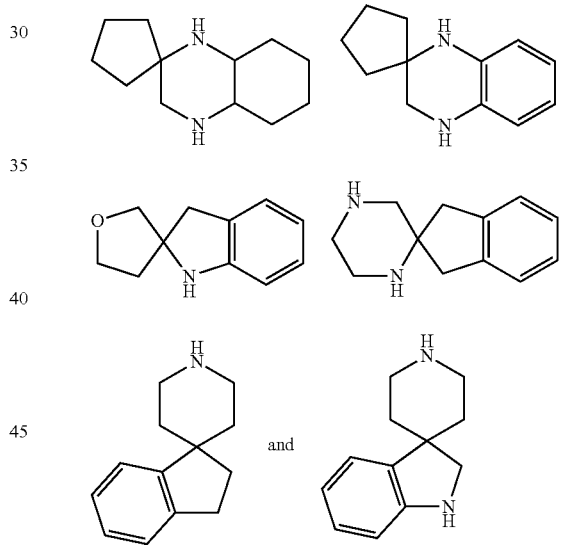

In one embodiment bicyclic or tricyclic spiro ring heterocycloalkyls are derived from 4,7-diaza-spiro[2.5]octane, 6-aza-spiro[3.5]nonane, 5,8-diaza-spiro[3.5]nonane, 6,9-diaza-spiro[4.5]decane, 2,7-diaza-spiro[3.5]nonane, 2,7-diaza-spiro[4.4]nonane, 2,7-diaza-spiro[4.5]decane, 2,8-diaza-spiro[4.5]decane, 6-oxa-2,9-diaza-spiro[4.5]decane, 3,9-diaza-spiro[5.5]undecane, 1-oxa-4,9-diaza-spiro[5.5]undecane or 1-oxa-4,8-diaza-spiro[5.5]undecane:

In one embodiment heterocycloalkyls, in which a ring is fused to one ring of a bicyclic spiro system, are derived from 3-dihydro-spiro[indene-2,2'-piperazine], 2,3-dihydro-spiro[1H-indene-1,4'-piperidin] or 1,2-dihydro-5-spiro[3H-indole-3,4'-piperidin]:

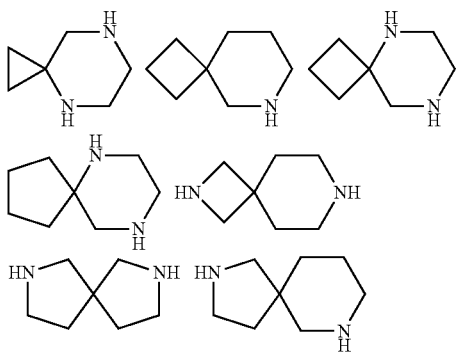

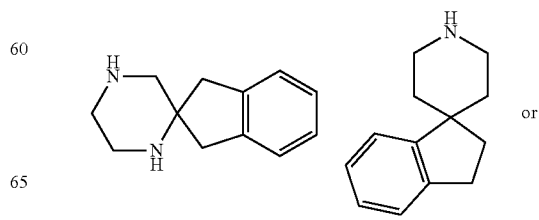

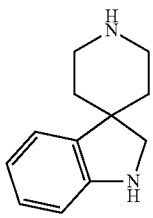

Exemplary non-fused or bridged bicyclic or tricyclic ring heterocycloalkyls are derived from, but not limited to, the following ring systems: 2-aza-bicyclo[2.2.1]heptane, 1-aza-bicyclo[2.2.2]octane, 8-aza-bicyclo[3.2.1]octane, 3-aza-bicyclo[3.2.1]octane, 9-aza-bicyclo[3.3.1]nonane, 2,5-diaza-bicyclo[2.2.1]heptane, 2,5-diaza-bicyclo[2.2.2]-octane, 3,8-diaza-bicyclo[3.2.1]octane and 3,7-diaza-bicyclo[3.3.1]nonane:

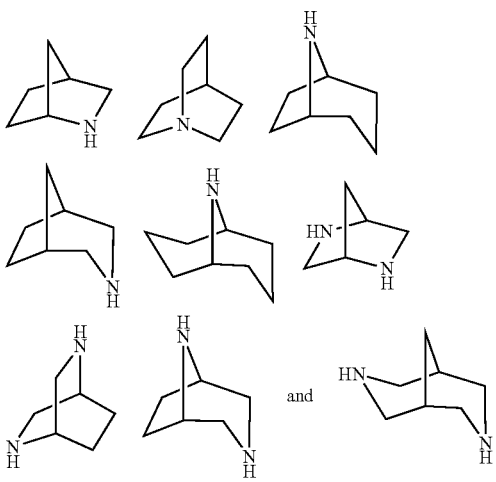

The term "aryl", as used herein, refers to a radical derived from an aromatic hydrocarbon by removal of one hydrogen, such as phenyl or naphthyl (=naphthalenyl).

The term "heteroaryl" or "hetaryl" as used herein, refers to a radical derived from an aromatic mono- or bicyclic ring system, in which 1, 2, 3, 4 or 5 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of the formula I such as use as a drug substance. Heteroaryl radicals are derived from 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene[1,3]benzoxazole, [1,3]benzothiazole, benzoimidazole, indazole, quinoline, isoquinoline, cinnoline, quinazoline, quinoxaline, phthalazine, different naphthyridines, e.g. [1,8]naphthyridine, different thienopyridines, e.g. thieno[2,3-b]pyridine and purine:

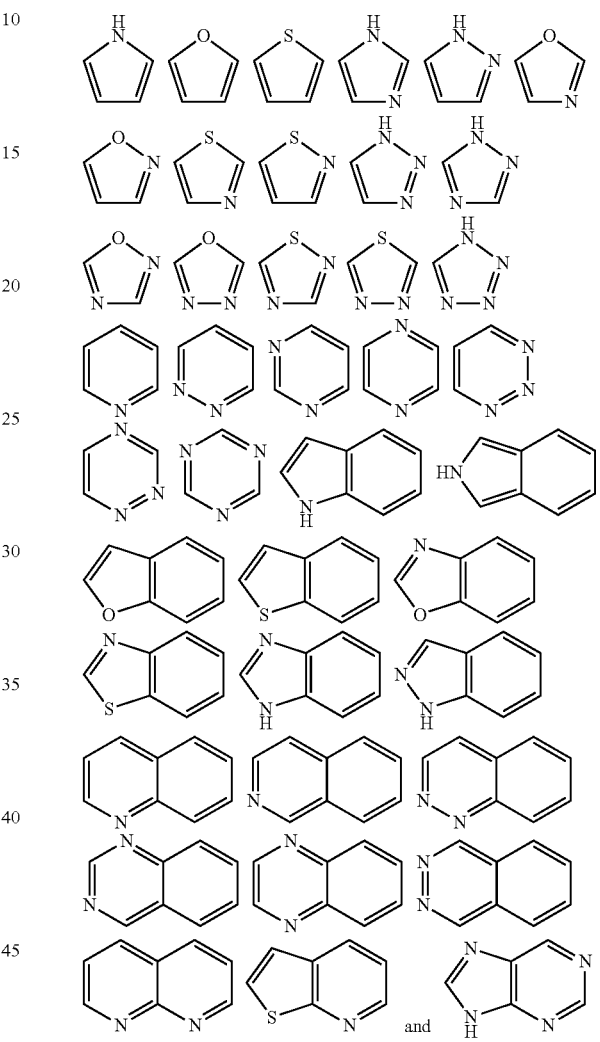

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on ring carbon atoms and/or on such ring nitrogen atoms. In one embodiment of the invention, substituents on such ring nitrogen atoms are chosen from ($C_1$-$C_4$)-alkyl groups, i.e. such ring nitrogen atoms in aromatic heterocycles carry a hydrogen atom or a ($C_1$-$C_4$)-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring or a quinoline ring, can in general also be present as N-oxide or as quaternary salt, for example as N—$(C_1$-$C_4)$-alkyl salt such as N-methyl salt, wherein in one embodiment of the invention the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring.

Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine, and in yet another embodiment it is fluorine.

When an oxo group is bonded to a carbon atom, it replaces two hydrogen atoms on a carbon atom of the parent system. Thus, if a $CH_2$ group in a chain or a ring is substituted by oxo, i.e. by a doubly bonded oxygen atom, it becomes a CO group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group, S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention furthermore includes all solvates of compounds of the formula I, for example hydrates or adducts with alcohols such as $(C_1$-$C_4)$-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

The compounds of the present invention, PKC inhibitors, can be widely combined with other pharmacologically active compounds, e.g., with all antihypertensives and nephroprotectives, mentioned in the Rote Liste 2011, antidiabetics mentioned in the Rote Liste 2011, chapter 12; all weight-reducing agents/appetite suppressants mentioned in the Rote Liste 2011, chapter 1; all diuretics mentioned in the Rote Liste 2011, chapter 36; all lipid-lowering agents mentioned in the Rote Liste 2011, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), insulin degludec, insulin aspart, polyethylene glycosidized (PEGylated) Insulin Lispro as described in WO2009152128, Humulin®, VIAject™, SuliXen® VIAject™ or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-Lyn™ (Generex Biotechnology), or Technosphere® insulin (MannKind) or Cobalamin™ oral insulin or ORMD-0801 or insulins or insulin precursors as described in WO2007128815, WO02007128817, WO2008034881, WO2008049711, WO2008145721, WO2009034117, WO02009060071, WO2009133099 or insulins which can be administered transdermally; additionally included are also those insulin derivatives which are bonded to albumin by a bifunctional linker, as described, for example, in WO2009121884;

GLP-1 derivatives and GLP-1 agonists, for example exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037811, WO2006037810 by Novo Nordisk A/S, in WO 01/04156 by Zealand or in WO 00/34331 by Beaufour-lpsen, pramlintide acetate (Symlin; Amylin Pharmaceuticals), inhalable GLP-1 (MKC-253 from MannKind) AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, WO2008148839, US2008299096, WO2008152403, WO2009030738, WO2009030771, WO2009030774, WO2009035540, WO2009058734, WO2009111700, WO2009125424, WO2009129696, WO2009149148, peptides, for example obinepitide (TM-30338), orally active GLP-1 analogs (e.g. NN9924 from Novo Nordisk), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, WO2009155257, WO2009155258, glycosylated GLP-1 derivatives as described in WO2009153960, and orally active hypoglycemic ingredients.

Antidiabetics also include gastrin analogs, for example TT-223.

Antidiabetics additionally include poly- or monoclonal antibodies directed, for example, against interleukin 1 beta (IL-1β), for example XOMA-052.

Antidiabetics additionally include peptides which can bind to the human pro-islet peptide (HIP) receptor, as described, for example, in WO2009049222.

Antidiabetics also include agonists of the glucose-dependent insulinotropic polypeptide (GIP) receptor, as described, for example, in WO2006121860.

Antidiabetics also include the glucose-dependent insulinotropic polypeptide (GIP), and also analogous compounds, as described, for example, in WO2008021560, WO2010016935, WO2010016936, WO2010016938, WO2010016940, WO2010016944.

Additionally included are analogs and theivatives of human pancreatic polypeptide, as described, for example, in WO02009007714.

Antidiabetics additionally include encapsulated insulin-producing porcine cells, for example DiabeCell®.

Antidiabetics also include analogs and theivatives of fibroblast growth factor 21 (FGF-21), as described, for example, in WO2009149171, WO2010006214.

The orally active hypoglycemic ingredients preferably include sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists,
potassium channel openers, for example pinacidil, cromakalim, diazoxide, diazoxide choline salt, or those as described in R. D. Carr et al., Diabetes 52, 2003, 2513.2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S,
active ingredients which act on the ATP-dependent potassium channel of the beta cells,
inhibitors of dipeptidyl peptidase-IV (DPP-IV),
insulin sensitizers,
inhibitors of liver enzymes involved in stimulating gluconeogenesis and/or
glycogenolysis,
modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC1 and/or ACC2) or
inhibitors of GSK-3 beta.

Also included are compounds which modify the lipid metabolism, such as active antihyperlipidemic ingredients and active antilipidemic ingredients,
HMG-CoA reductase inhibitors,
farnesoid X receptor (FXR) modulators,
fibrates,
cholesterol reabsorption inhibitors,
CETP inhibitors,
bile acid absorption inhibitors,
MTP inhibitors,
estrogen receptor gamma agonists (ERR γ agonists),
sigma-1 receptor antagonists,
antagonists of the somatostatin 5 receptor (SST5 receptor);
compounds which reduce food intake, and
compounds which increase thermogenesis.

In one embodiment of the invention, the compound of the formula I is administered in combination with insulin.

In another embodiment of the invention, the compound of the formula I is administered in combination with an insulin sensitizer, for example PN-2034 or ISIS-113715.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride, or those formulations as described, for example, in EP2103302.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin or one of its salts.

In a further embodiment, the compound of the formula I is administered in combination with a guanidine, for example benzylguanidine or one of its salts, or those guanidines as described in WO02009087395.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]-phenyl]methyl]-2,4-thiazolidinedione.

In one embodiment of the invention, the compound of the formula I is administered in combination with a PPAR gamma agonist, for example rosiglitazone, pioglitazone, JTT-501, GI 262570, R-483, CS-011 (rivoglitazone), DRL-17564, DRF-2593 (balaglitazone), INT-131, T-2384, or those as described in WO2005086904, WO2007060992, WO2007100027, WO2007103252, WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008110062, WO2008126731, WO2008126732, WO2008137105, WO2009005672, WO2009038681, WO2009046606, WO2009080821, WO2009083526, WO2009102226, WO2009128558, WO2009139340.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982, JP2009023975, WO2009033561, WO2009047240, WO2009072581, WO2009080248, WO2009080242, WO2009149819, WO2009149820, WO2009147121, WO2009153496, WO2010008299, WO2010014771.

In one embodiment of the invention, the compound of the formula I is administered in combination with a mixed PPAR alpha/gamma agonist, for example naveglitazar, aleglitazar, LY-510929, ONO-5129, E-3030, AVE 8042, AVE 8134, AVE 0847, AVE 0897, CKD-501 (lobeglitazone sulfate), MBX-213, KY-201, BMS-759509, or as described in WO 00/64888, WO 00/64876, WO031020269, WO2004024726, WO2007099553, US2007276041, WO2007085135, WO2007085136, WO2007141423, WO2008016175, WO2008053331, WO2008109697, WO2008109700, WO2008108735, WO2009026657, WO2009026658, WO2009149819, WO2009149820 or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861, WO2009012650, US2009137671, WO2009080223, WO2009149819, WO2009149820, WO2010000353.

In one embodiment of the invention, the compound of the formula I is administered in combination with a pan-SP- PARM (selective PPAR modulator alpha, gamma, delta), for example GFT-505, indeglitazar, or those as described in WO2008035359, WO2009072581.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017, US2009076129.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760, WO2009016118, WO2009016119, WO2009030715, WO2009045830, WO2009045831, WO2009127723.

In another embodiment, the compound of the formula I is administered in combination with an inhibitor of the interaction of liver glycogen phosphorylase with the protein PPP1R3 (GL subunit of glycogen-associated protein phosphatase 1 (PP1)), as described, for example, in WO2009030715.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244, WO2009057784, WO2009058662, WO2009058734, WO2009110520, WO2009120530, WO2009140342, WO2010019828.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754, US2008280875, WO2008136428, WO2008136444, WO2008149382, WO2008154563, WO2008156174, WO2008156757, US2009030046, WO2009018065, WO2009023718, WO2009039944, WO2009042435, WO2009046784, WO2009046802, WO2009047798, WO2009063821, WO2009081782, WO2009082152, WO2009083553, WO2009091014, US2009181981, WO2009092432, WO2009099080, WO2009106203, WO2009106209, WO2009109270, WO2009125873, WO2009127544, WO2009127546, WO2009128481, WO2009133687, WO2009140624, WO2010013161, WO2010015849, WO2010018800.

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628, WO2009012039, EP2058308, WO02009068467, WO2009068468.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, DSP-7238, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO02006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO02007071576, WO2007077508, WO2007087231, WO2007097931, WO02007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO02008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532, WO2010000469, WO2010015664.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a combination of a DPP-IV inhibitor with metformin hydrochloride, as described, for example, in WO2009121945.

In one embodiment, the compound of the formula I is administered in combination with a combination of a DPP-IV inhibitor with a GPR-119 agonist, as described, for example, in WO02009123992.

In one embodiment, the compound of the formula I is administered in combination with a combination of a DPP-IV inhibitor with miglitol, as described, for example, in WO2009139362.

In one embodiment, the compound of the formula I is administered in combination with a solid combination of a salt of sitagliptin with metformin hydrochloride.

In one embodiment, the compound of the formula I is administered in combination with a solid combination of alopliptin benzoate with pioglitazone hydrochloride.

In one embodiment, the compound of the formula I is administered in combination with a substance which enhances insulin secretion, for example KCP-265 (WO2003097064), or those as described in WO2007026761, WO2008045484, US2008194617, WO2009109259, WO2009109341.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 and/or 2 (SGLT1, SGLT2), for example KGA-2727, T-1095, SGL-0010, AVE 2268, SAR 7226, SGL-5083, SGL-5085, SGL-5094, ISIS-388626, sergliflozin, dapagliflozin or remogliflozin etabonate, canagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, US2008287529, WO2009026537, WO2009049731, WO2009076550, WO2009084531, WO2009096503, WO2009100936, WO2009121939, WO2009124638, WO2009128421, WO2009135673, WO2010009197, WO2010018435, WO2010018438 or by A. L. Handlon in Expert Opin. Ther. Patents (2005) 15(11), 1531-1540.

In a further embodiment of the invention, the compound of the formula I is administered in combination with a solid combination of an SGLT inhibitor with a DPP-IV inhibitor, as described in WO2009091082.

In one embodiment, the compound of the formula I is administered in combination with a stimulator of glucose transport, as described, for example, in WO2008136392, WO2008136393.

In one embodiment, the compound of the formula I is administered in combination with inhibitors of 11-beta-hydroxysteroid dehydrogenase 1 (11β-HSD1), for example BVT-2733, JNJ-25918646, INCB-13739, INCB-20817, DIO-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834. WO2007145835, WO2007146761, WO2008000950, WO2008000951, WO2008003611, WO2008005910, WO2008006702, WO2008006703, WO02008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924, WO2008130951, WO2008134221, WO2008142859, WO2008142986, WO02008157752, WO2009001817, WO2009010416, WO2009017664, WO2009020140, WO2009023180, WO2009023181, WO2009023664, WO2009026422, WO2009038064, WO2009045753, WO2009056881, WO2009059666, WO2009061498, WO2009063061, WO2009070497, WO2009074789, WO2009075835, WO2009088997, WO2009090239, WO2009094169, WO2009098501, WO2009100872, WO2009102428, WO2009102460, WO2009102761, WO2009106817, WO2009108332, WO2009112691, WO2009112845, WO2009114173, WO2009117109, US2009264401, WO2009118473, WO2009131669, WO2009132986, WO02009134384, WO2009134387, WO2009134392, WO2009134400, WO2009135581, WO2009138386, WO2010006940, WO2010010157, WO2010010174, WO2010011917.

In one embodiment, the compound of the formula I is administered in combination with inhibitors of protein tyrosine phosphatase-1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058, US2008004325, WO2008033455, WO2008033931, WO2008033932, WO2008033934, WO2008089581, WO2008148744, WO2009032321, WO2009109999, WO2009109998.

In a further embodiment, the compound of the formula I is administered in combination with stimulators of tyrosine kinase B (Trk-B), as described, for example, in WO2010014613.

In a further embodiment, the compound of the formula I is administered in combination with beta 3 agonists (also called beta-3 adrenoceptor agonists), as described, for example, in Physiol. Behav. 2004 Sep. 15; 82(2-3):489-96, J Clin Invest (1998) 101: 2387-93, Curr. Pharma. Des. 2001 September; 7(14):1433-49, Bioorganic & Medicinal Chemistry Letters volume 14, number 13, Jul. 5, 2004, pages 3525-3529 (BMS-201620).

In one embodiment of the invention, the compound of the formula I is administered in combination with an agonist of GPR109A (HM74A receptor agonists; NAR agonists (nicotinic acid receptor agonists)), for example nicotinic acid or extended release niacin in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007002557, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered in combination with a solid combination of niacin with simvastatin.

In another embodiment of the invention, the compound of the formula I is administered in combination with nicotinic acid or "extended release niacin" in conjunction with MK-0524A (laropiprant).

In a further embodiment of the invention, the compound of the formula I is administered in combination with nicotinic acid or "extended release niacin" in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with a solid combination of niacin with meloxicam, as described, for example, in WO2009149056.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056, WO2010012650.

In one embodiment, the compound of the formula I is administered in combination with modulators of GPR119 (G-protein-coupled glucose-dependent insulinotropic receptor), for example PSN-119-1, PSN-821, PSN-119-2, MBX-2982 or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702, WO2008130581, WO2008130584, WO2008130615, WO2008137435, WO2008137436, WO2009012275, WO2009012277, WO2009014910, WO02009034388, WO2009038974, WO2009050522, WO2009050523, WO2009055331, WO2009105715, WO2009105717, WO2009105722, WO2009106561, WO2009106565, WO2009117421, WO2009125434, WO2009126535, WO2009129036, US2009286812, WO2009143049, WO2009150144, WO2010001166, WO2010004343, WO2010004344, WO2010004345, WO2010004346, WO2010004347, WO2010004348, WO2010008739, WO2010006191, WO2010009183, WO2010009195, WO2010009207, WO2010009208, WO2010014593.

In a further embodiment, the compound of the formula I is administered in combination with modulators of GPR120, as described, for example, in EP1688138, WO2008066131, WO2008066131, WO2008103500, WO2008103501, WO2008139879, WO2009038204, WO2009147990, WO2010008831.

In another embodiment, the compound of the formula I is administered in combination with antagonists of GPR105, as described, for example, in WO2009000087, WO2009070873.

In a further embodiment, the compound of the formula I is administered in combination with agonists of GPR43, for example ESN-282.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837, WO2008122352, WO2008122357, WO2009009287.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002, or those as described in WO2008048866, WO20080488867, US2009062369.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064, EP-1992620, EP-1992621, EP1992624, EP-1992625, WO2008130312, WO2009007029, EP2020232, WO2009017452, WO2009035634, WO2009035684, WO2009038385, WO2009095787, WO2009095788, WO2009095789, WO2009095792, WO2009145814, US2009291982, WO2009154697, WO2009156857, WO2009156859, WO2009156860, WO2009156861, WO02009156863, WO2009156864, WO2009156865, WO2010013168, WO2010014794.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of phosphoinositide kinase-3 (PI3K), for example those as described in WO2008027584, WO2008070150, WO2008125833, WO2008125835, WO2008125839, WO2009010530, WO2009026345, WO2009071888, WO2009071890, WO2009071895.

In one embodiment, the compound of the formula I is administered in combination with an inhibitor of serum/glucocorticoid-regulated kinase (SGK), as described, for example, in WO2006072354, WO2007093264, WO2008009335, WO2008086854, WO2008138448.

In one embodiment, the compound of the formula I is administered in combination with a modulator of the glucocorticoid receptor, as described, for example, in WO2008057855, WO2008057856, WO2008057857, WO2008057859, WO2008057862, WO2008059867, WO2008059866, WO02008059865, WO2008070507, WO2008124665, WO2008124745, WO2008146871, WO2009015067, WO2009040288, WO2009069736, WO2009149139.

In one embodiment, the compound of the formula I is administered in combination with a modulator of the mineralocorticoid receptor (MR), for example drospirenone, or those as described in WO2008104306, WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator/modulator of the AMP-activated protein kinase (AMPK), as described, for example, in WO02007062568, WO2008006432, WO2008016278, WO2008016730, WO2008020607, WO2008083124, WO2008136642, WO2009019445, WO2009019446, WO2009019600, WO2009028891, WO2009065131, WO2009076631, WO2009079921, WO2009100130, WO2009124636, WO2009135580, WO2009152909.

In one embodiment, the compound of the formula I is administered in combination with an inhibitor of ceramide kinase, as described, for example, in WO2007112914, WO02007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "1-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075, WO2009056693, WO2009075277, WO2009089042, WO2009120801.

In another embodiment, the compound of the formula I is administered in combination with inhibitors of NF-kappaB (NFKB) activation, for example salsalate.

In a further embodiment, the compound of the formula I is administered in combination with inhibitors of ASK-1 (apoptosis signal-regulating kinase 1), as described, for example, in WO2008016131, WO2009123986.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, NCX-6560, or those as described in US2007249583, WO2008083551, WO2009054682.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222, JP2008273847, WO2008157270, US2008299118, US2008300235, WO2009005998, WO2009012125, WO2009027264, WO2009062874, US2009131409, US2009137554, US2009163552, WO2009127321, EP2128158.

In another embodiment of the invention, the compound of the formula I is administered in combination with a ligand of the liver X receptor (LXR), as described, for example, in WO2007092965, WO2008041003, WO2008049047, WO2008065754, WO2008073825, US2008242677, WO2009020683, US2009030082, WO2009021868, US2009069373, WO2009024550, WO2009040289, WO2009086123, WO2009086129, WO2009086130, WO2009086138, WO2009107387, US2009247587, WO2009133692, WO2008138438, WO2009144961, WO2009150109.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348; Trilipix™).

In one embodiment of the invention, the compound of the formula I is administered in combination with fibrates, for example the choline salt of fenofibrate (Trilipix™) and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia®, a solid combination of fenofibrate with metformin.

In another embodiment of the invention, the compound of the formula I is administered in combination with a solid combination of metformin with an MTP inhibitor, as described in WO2009090210.

In one embodiment of the invention, the compound of the formula I is administered in combination with a cholesterol reabsorption inhibitor, for example ezetimibe, tiqueside, pamaqueside, FM-VP4 (sitostanol/campesterol ascorbyl phosphate; Forbes Medi-Tech, WO2005042692, WO02005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300, WO2008104875, US2008280836, WO2008108486.

In one embodiment of the invention, the compound of the formula I is administered in combination with an NPC1L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. Nos. 6,992,067 or 7,205,290.

In a further embodiment of the invention, the further active ingredient is a diphenylazetidinone derivative, as described, for example, in U.S. Pat. Nos. 6,992,067 or 7,205,290, combined with a statin, for example simvastatin, fluvastatin, pravastatin, lovastatin, cerivastatin, atorvastatin, pitavastatin or rosuvastatin.

In one embodiment of the invention, the compound of the formula I is administered in combination with a solid combination of lapaquistat, a squalene synthase inhibitor, with atorvastatin.

In a further embodiment of the invention, the compound of the formula I is administered in combination with a conjugate consisting of the HMG-CoA reductase inhibitor atorvastatin with the renin inhibitor aliskiren (WO2009090158).

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO02007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO02008059513, WO2008070496, WO2008115442, WO2008111604, WO2008129951, WO2008141077, US2009118287, WO2009062371, WO2009071509.

In one embodiment of the invention, the compound of the formula I is administered in combination with bile acid reabsorption inhibitors (inhibitors of the intestinal bile acid transporter (IBAT)) (see, for example, U.S. Pat. Nos. 6,245,744, 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1 (G-protein-coupled bile acid receptor 1; TGR5), for example INT-777 or those as described, for example, in US20060199795, WO2007110237, WO2007127505, WO2008009407, WO2008067219, WO2008067222, FR2908310, WO2008091540, WO2008097976, US2009054304, WO2009026241, WO2009146772, WO2010014739, WO2010014836.

In one embodiment, the compound of the formula I is administered in combination with modulators of histone deacetylase, for example ursodeoxycholic acid, as described in WO2009011420.

In one embodiment, the compound of the formula I is administered in combination with inhibitors/modulators of the TRPM5 channel (TRP cation channel M5), as described, for example, in WO2008097504, WO2009038722.

In one embodiment, the compound of the formula I is administered in combination with inhibitors/modulators of the TRPA1 channel (TRP cation channel A1), as described, for example, in US2009176883, WO2009089083, WO2009144548.

In one embodiment, the compound of the formula I is administered in combination with inhibitors/modulators of the TRPV3 channel (TRP cation channel V3), as described, for example, in WO2009084034, WO2009130560.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with tocotrienol and insulin or an insulin derivative.

In one embodiment of the invention, the compound of the formula I is administered in combination with a chewing gum comprising phytosterols (Reductol™).

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, JTT-130, or those as described in WO2005085226, WO2005121091, WO2006010423, WO2006113910, WO2007143164, WO2008049806, WO2008049808, WO2008090198, WO2008100423, WO2009014674.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189, WO2009030746, WO2009030747, WO2009030750, WO2009030752, WO2009070130, WO2009081957, WO2009081957.

In a further embodiment of the invention, the compound of the formula I is administered in combination with an inhibitor of liver carnitine palmitoyltransferase-1 (L-CPT1), as described, for example, in WO2007063012, WO2007096251 (ST-3473), WO2008015081, US2008103182, WO2008074692, WO2008145596, WO2009019199, WO2009156479, WO2010008473.

In another embodiment of the invention, the compound of the formula I is administered in combination with an inhibitor of carnitin O-palmitoyltransferase II (CPT2), as described, for example, in US2009270500, US2009270505, WO2009132978, WO2009132979.

In a further embodiment of the invention, the compound of the formula I is administered in combination with a modulator of serine palmitoyltransferase (SPT), as described, for example, in WO2008031032, WO02008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO02005077907, JP2007022943, WO2008003424, WO2008132846, WO2008133288, WO2009136396.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with apolipoprotein (ApoB) SNALP, a therapeutic product which comprises an siRNA (directed against the ApoB gene).

In one embodiment of the invention, the compound of the formula I is administered in combination with a stimulator of the ApoA-1 gene, as described, for example, in WO2008092231.

In one embodiment of the invention, the compound of the formula I is administered in combination with a modulator of the synthesis of apolipoprotein C-III, for example ISIS-APOCIIIRx.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278, WO2009071099, WO2009086096, US2009247550.

In one embodiment of the invention, the compound of the formula I is administered in combination with an ABCA1 expression enhancer, as described, for example, in WO2006072393, WO2008062830, WO2009100326.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), for example CVT-3619 or those as described, for example, in EP1258247, EP1375508, WO2008028590, WO02008077050, WO2009050199, WO2009080197, WO2009100827, WO2009112155.

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923, WO2008070661, WO2009010871.

In a further embodiment of the invention, the compound of the formula I is administered in combination with a ligand of the adenosine A1/A2B receptors, as described, for example, in WO2008064788, WO02008064789, WO02009080198, WO2009100827, WO2009143992.

In one embodiment of the invention, the compound of the formula I is administered in combination with an adenosine A2B receptor antagonist (adenosine A2B R), as described in US2007270433, WO02008027585, WO02008080461, WO2009037463, WO2009037467, WO2009037468, WO2009118759.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833, WO2008065508, WO02008069500, WO2008070609, WO2008072850, WO2008079610, WO02008088688, WO2008088689, WO2008088692, US2008171761, WO2008090944, JP2008179621, US2008200461, WO2008102749, WO2008103382, WO2008121592, WO2009082346, US2009253725, JP2009196966, WO2009144554, WO2009144555, WO2010003624, WO2010002010.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833) or with modulators of mitochondrial glycerol-3-phosphate O-acyltransferase, described in WO2010005922.

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO02008112022, WO2009011872, WO02009049154, WO2009049157, WO2009049165, WO2009073772, WO2009097476, WO2009111207, WO2009129508, WO2009151800.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A) or velneperit or those as described in WO02009110510;

NPY-5 receptor antagonists/receptor modulators, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891, WO2008129007, WO2008134228, WO2009054434, WO2009095377, WO2009131096;

NPY-4 receptor antagonists, as described, for example, in WO02007038942;

NPY-2 receptor antagonists/modulators, as described, for example, in WO2007038943, WO2009006185, US2009099199, US2009099243, US2009099244, WO2009079593, WO2009079597;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947, WO2009080608;

NPY-2 receptor agonists, as described, for example, in WO2009080608;

derivatives of the peptide obestatin, as described by WO2006096847;

CB1R (cannabinoid receptor 1) antagonists/inverse agonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136571, WO2007136607, WO2007136571, U.S. Pat. No. 7,297, 710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, WO2998043544, WO2008044111, WO2008048648, EP1921072-A1, WO2008053341, WO2008056377, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO200812000, WO2008121257, WO2008127585, WO2008129157, WO2008130616, WO2008134300, US2008262066, US2008287505, WO2009005645, WO2009005646, WO2009005671, WO2009023292, WO2009023653, WO02009024819, WO2009033125, EP2042175, WO2009053548-WO02009053553, WO2009054923, WO2009054929, WO2009059264, WO2009073138, WO2009074782, WO2009075691, WO2009078498, WO2009087285, WO2009074782, WO2009097590, WO2009097995, WO2009097996, WO2009097998, WO2009097999, WO2009098400, WO2009106708, US2009239909, WO2009118473, US2009264436, US2009264476, WO2009130234, WO2009131814, WO2009131815, US2009286758, WO2009141532, WO2009141533, WO2009153569, WO2010003760, WO2010012437, WO2010019762;

cannabinoid receptor 1/cannabinoid receptor 2 (CB1/CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618, WO2009007697, WO2009012227, WO2009087564, WO2009093018, WO2009095752, WO2009120660, WO2010012964;

cannabinoid receptor 2 (CB2) modulating compounds, for example those as described, for example, in WO2008063625, WO2008157500, WO2009004171, WO02009032754, WO2009055357, WO2009061652, WO2009063495, WO2009067613, WO2009114566;

modulators of FAAH (fatty acid amide hydrolase), as described, for example, in WO2007140005, WO2008019357, WO2008021625, WO2008023720, WO2008030532, WO2008129129, WO2008145839, WO2008145843, WO2008147553, WO2008153752, WO2009011904, WO2009048101, WO2009084970, WO2009105220, WO2009109504, WO2009109743, WO2009117444, WO2009127944, WO2009138416, WO2009151991, WO2009152025, WO2009154785, WO2010005572, WO2010017079;

inhibitors of fatty acid synthase (FAS), as described, for example, in WO2008057585, WO2008059214, WO2008075064, WO2008075070, WO2008075077, WO2009079860;

inhibitors of LCE (long chain fatty acid elongase)/long chain fatty acid CoA ligase, as described, for example, in WO2008120653, WO2009038021, WO2009044788, WO2009081789, WO2009099086;

vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863, WO2008125295, WO2008125296, WO2008125337, WO2008125342, WO2008132600, WO2008133973, WO2009010529, WO2009010824, WO2009016241, WO2009023539, WO2009038812, WO2009050348, WO2009055629, WO2009055749, WO2009064449, WO2009081222, WO2009089057, WO2009109710WO2009112677, WO2009112678, WO2009112679, WO2009121036, WO2009124551, WO2009136625, WO2010002209;

modulators, ligands, antagonists or inverse agonists of the opioid receptors, for example GSK-982 or those as described, for example, in WO2007047397, WO2008021849, WO2008021851, WO2008032156, WO2008059335, WO02008125348, WO2008125349, WO2008142454, WO2009030962, WO2009103552, WO2009115257;

modulators of the "orphan opioid (ORL-1) receptor", as described, for example, in US2008249122, WO2008089201;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydropyrazolo[4,3-c]pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2004089307, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186-WO2008087190, WO2008090357, WO2008142319, WO2009015867, WO2009061411, US2009076029, US2009131465, WO2009071101, US2009305960, WO2009144432, WO2009151383, WO2010015972;

MC4 receptor modulators (melanocortin-4 receptor modulators), as described, for example, in WO2009010299, WO2009074157;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125, WO2008147518, WO2008150364, WO2009003993, WO2009003997, WO2009011775, WO2009016087, WO2009020642, WO2009058238, US2009186920, US2009203736, WO2009092642, WO2009100994, WO2009104155, WO2009124956, WO2009133522, WO2009156951, WO2010017260);

histamine H3 receptor antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208), or those as described in WO200064884, WO2005082893, WO2005123716, US2005171181 (e.g. PF-00389027), WO2006107661, WO2007003804, WO2007016496, WO2007020213, WO2007049798, WO2007055418, WO2007057329, WO2007062999, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EP1757594, WO2008068173, WO2008068174, US20080171753, WO2008072703, WO2008072724, US2008188484, US2008188486, US2008188487, WO2008109333, WO02008109336, WO2008126886, WO2008154126, WO2008151957, US2008318952, WO2009003003, WO2009013195, WO2009036132, WO2009039431, WO2009045313, WO2009058300, WO2009063953, WO2009067401, WO2009067405, WO2009067406, US2009163464, WO2009100120, WO2009105206, WO2009121812, WO2009126782, WO2010011653, WO2010011657);

histamine H1/histamine H3 modulators, for example betahistine or its dihydrochloride;

modulators of the histamine H3 transporter or of the histamine H3/serotonin transporter, as described, for example, in WO2008002816, WO2008002817, WO2008002818, WO2008002820;

modulators of vesicular monoamine transporter 2 (VMAT2), as described, for example, in WO2009126305;

histamine H4 modulators, as described, for example, in WO2007117399, US2009156613;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070, WO2010015628, WO2010015655);

CRF BP antagonists (e.g. urocortin);

urocortin agonists;

modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103, WO2008132162;

MSH (melanocyte-stimulating hormone) agonists;

MCH (melanine-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO02002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO02007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO02008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409, US2008269110, WO2008140239, WO2009021740, US2009011994, US2009082359, WO2009041567, WO2009076387, WO2009089482, WO2009103478, WO2009119726, WO2009120655, WO2009123194, WO2009137270, WO2009146365, WO2009154132);

CCK-A (CCK-1) modulators (for example {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525) or SR-146131 (WO 0244150) or SSR-125180) or those as described in WO2005116034, WO2007120655, WO2007120688, WO2007120718, WO2008091631;

serotonin reuptake inhibitors (e.g. dexfenfluramine), or those as described in WO2007148341, WO2008034142, WO2008081477, WO2008120761, WO2008141081, WO2008141082, WO2008145135, WO2008150848, WO2009043834, WO2009077858;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947 or those as described in WO2009016214, WO2009016215, WO2009077584, WO2009098208, WO2009098209, WO2009106769, WO2009109517, WO2009109518, WO2009109519, WO2009109608, WO2009145357, WO2009149258;

mixed serotoninergic and noradrenergic compounds (e.g. WO 00/71549); 5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118, WO2008150480;

dopamine antagonists, as described, for example, in WO2008079838, WO2008079839, WO2008079847, WO2008079848;

norepinephrine reuptake inhibitors, as described, for example, in US2008076724, WO2009062318;

5-HT1A receptor modulators, as described, for example, in WO2009006227, WO2009137679, WO2009137732;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO02003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213, WO2008007661, WO2008007664, WO2008009125, WO2008010073, WO02008108445, WO2009063991, WO02009063992, WO2009063993, WO2009079765);
5-HT6 receptor modulators, for example E-6837, BVT-74316, PF-3246799 or PRX-07034, or those as described, for example, in WO2005058858, WO2007054257, WO2007107373, WO2007108569, WO2007108742-744, WO2008003703, WO2008027073, WO2008034815, WO2008054288, EP1947085, WO2008084491, WO2008084492, WO2008092665, WO2008092666, WO2008101247, WO2008110598, WO2008116831, WO2008116833, WO2008117169, WO2008136017, WO2008147812, EP2036888, WO2009013010, WO2009034581, WO2009053997, WO2009056632, WO2009073118, WO2009115515, WO2009135925, WO2009135927, WO2010000456, WO2010012806, EP2145887;
agonists of estrogen receptor gamma (ERRγ agonists), as described, for example, in WO2007131005, WO2008052709;
agonists of estrogen receptor alpha (ERRα/ERR1 agonists), as described, for example, in WO2008109727;
agonists of estrogen receptor beta (ERRβ agonists), as described, for example, in WO2009055734, WO2009100335, WO2009127686;
sigma-1 receptor antagonists, as described, for example, in WO2007098953, WO2007098961, WO2008015266, WO2008055932, WO2008055933, WO2009071657;
muscarin 3 receptor (M3R) antagonists, as described, for example, in WO2007110782, WO2008041184;
bombesin receptor agonists (BRS-3 agonists), as described, for example, in WO2008051404, WO2008051405, WO2008051406, WO2008073311;
galanin receptor antagonists;
growth hormone (e.g. human growth hormone or AOD-9604);
growth hormone releasing compounds (tert-butyl 6-benzyloxy-1-(2-diisopropylaminoethylcarbamoyl)-3,4-dihydro-1H-isoquinoline-2-carboxylate (WO 01/85695));
growth hormone secretagogue receptor antagonists (ghrelin antagonists), for example A-778193, or those as described in WO2005030734, WO2007127457, WO2008008286, WO2009056707;
growth hormone secretagogue receptor modulators (ghrelin modulators), for example JMV-2959, JMV-3002, JMV-2810, JMV-2951, or those as described in WO2006012577 (e.g. YIL-781 or YIL-870), WO2007079239, WO2008092681, WO2008145749, WO2008148853, WO2008148854, WO2008148856, WO2009047558, WO2009071283, WO2009115503;
TRH agonists (see, for example, EP 0 462 884);
decoupling protein 2 or 3 modulators (as described, for example, in WO2009128583);
chemical decouplers (e.g. WO2008059023, WO2008059024, WO2008059025, WO2008059026);
leptin receptor agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);
leptin receptor modulators, as described, for example, in WO2009019427, WO2009071658, WO2009071668, WO2009071677, WO2009071678, WO2009147211, WO2009147216, WO2009147219, WO2009147221;

DA agonists (bromocriptin, bromocriptin mesylate, doprexin) or those as described in US2009143390;
lipase/amylase inhibitors (e.g. WO 00/40569, WO2008107184, WO2009049428, WO2009125819);
inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221, WO2008129319, WO2008141976, WO2008148840, WO2008148849, WO2008148851, WO2008148868, WO2009011285, WO2009016462, WO2009024821, US2009076275, WO2009040410, WO2009071483, WO2009081195, WO2009119534, WO2009126624, WO2009126861, WO2010007046, WO2010017040;
inhibitors of monoacylglycerol acyltransferase (2-acylglycerol O-acyltransferase; MGAT), as described, for example, in WO2008038768;
inhibitors of fatty acid synthase (FAS), for example C75, or those as described in WO2004005277, WO2008006113;
inhibitors of stearoyl-CoA delta9 desaturase (SCD1), as described, for example, in WO2007009236, WO2007044085, WO2007046867, WO2007046868, WO20070501124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349, WO2008128335, WO2008135141, WO2008139845, WO2008141455, US20080255130, US2008255161, WO2008141455, WO2009010560, WO2009016216, WO2009012573, WO2009024287, JP2009019013, WO2009037542, WO2009056556, WO2009060053, WO2009060054, WO2009070533, WO2009073973, WO2009103739, WO2009117659, WO2009117676, US2009253693, US2009253738, WO2009124259, WO2009126123, WO2009126527, WO2009129625, WO2009137201, WO2009150196, WO2009156484, WO2010006962, WO2010007482;
inhibitors of fatty acid desaturase 1 (delta5 desaturase), as described, for example, in WO2008089310;
inhibitors of monoglyceride lipase (MGL), as described in WO2008145842;
hypoglycemic/hypertriglyceridemic indoline compounds, as described in WO2008039087, WO2009051119;
inhibitors of "adipocyte fatty acid-binding protein aP2", for example BMS-309403 or those as described in WO2009028248;
activators of adiponectin secretion, as described, for example, in WO2006082978, WO02008105533, WO2008136173;
promoters of adiponectin production, as described, for example, in WO2007125946, WO2008038712;

modified adiponectins, as described, for example, in WO2008121009;

oxyntomodulin or analogs thereof (for example, TKS-1225);

oleoyl-estrone or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213, JP2009155261;

or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (S1P), for example PF-429242.

In a further embodiment of the invention, the compound of the formula I is administered in combination with a modulator of the "trace amine associated receptor 1" (TAAR1), as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, AGI-1067 (succinobucol), probucol, tocopherol, ascorbic acid, β-carotene or selenium, or those as described in WO2009135918.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In a further embodiment, the compound of the formula I is administered in combination with an activator of soluble guanylate cyclase (sGC), as described, for example, in WO2009032249.

In another embodiment, the compound of the formula I is administered in combination with an inhibitor of carboanhydrase type 2 (carbonic anhydrase type 2), for example those as described in WO2007065948, WO2009050252.

In another embodiment, the compound of the formula I is administered in combination with topiramat or a derivative thereof, as described in WO2008027557, US2009304789.

In a further embodiment, the compound of the formula I is administered in combination with a solid combination of topiramat with phentermin (Qnexa™).

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463, WO2009035159, WO2009035162.

In one embodiment, the compound of the formula I is administered in combination with a "c-Jun N-terminal kinase" inhibitor (JNK inhibitor), for example B1-78D3 or those as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with inhibitors of neutral endopeptidase (NEP inhibitors), as described, for example, in WO2009138122, WO2009135526.

In one embodiment, the compound of the formula I is administered in combination with modulators of the glucocorticoid receptor (GR), for example KB-3305 or those compounds as described, for example, in WO02005090336, WO2006071609, WO2006135826, WO2007105766, WO2008120661, WO2009040288, WO2009058944, WO2009108525, WO2009111214.

In one embodiment, the further active ingredient is varenicline tartrate, a partial agonist of the alpha 4-beta 2 nicotinic acetylcholine receptor.

In one embodiment, the further active ingredient is an agonist of the alpha 7-nicotinic acetylcholine receptor, as described, for example, in WO2009018551, WO2009071519, WO2009071576, WO2009071577.

In one embodiment, the further active ingredient is trodusquemine.

In one embodiment, the further active ingredient is a modulator of the enzyme SIRT1 and/or SIRT3 (an $NAD^+$-dependent protein deacetylase); this active ingredient may, for example, be resveratrol in suitable formulations, or those compounds as specified in WO2007019416 (e.g. SRT-1720), WO2008073451, WO2008156866, WO2008156869, WO2009026701, WO2009049018, WO2009058348, WO2009061453, WO2009134973, WO2009146358, WO2010003048.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2004000803, WO2006000804, WO2004000805, WO2004087655, WO2005113496, WO2007059871, WO2007107587, WO2007111994, WO2008052658, WO2008106600, WO2008113796, US2008280836, WO2009113952, US2009312302.

In a further embodiment, the compound of the formula I is administered in combination with inhibitors of SREBP (sterol regulatory element-binding protein), for example fatostatin, or those as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine. In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In another embodiment, the further active ingredient is a neuropeptide FF2 agonist, as described, for example, in WO2009038012.

In one embodiment, the further active ingredient is a nasal calcium channel blocker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936, WO2009107660.

In one embodiment, the further active ingredient is an inhibitor of the calcium metabolism, for example those as described in US2009124680.

In one embodiment, the further active ingredient is a blocker of the "T-type calcium channel", as described, for example, in WO2008033431, WO2008110008, US2008280900, WO2008141446, US2009270338, WO2009146540, US2009325979, WO2009146539.

In one embodiment, the further active ingredient is an inhibitor of KCNQ potassium channel 2 or 3, for example those as described in US2008027049, US2008027090.

In one embodiment, the further active ingredient is a modulator of KCNN potassium channel 1, 2 or 3 (modulators of the SK1, SK2 and/or SK3 channel), for example those as described in US2009036475.

In one embodiment, the further active ingredient is an inhibitor of the potassium Kv1.3 ion channel, for example those as described in WO2008040057, WO2008040058, WO2008046065, WO2009043117.

In one embodiment, the further active ingredient is a potassium channel modulator, for example those as described in WO2008135447, WO2008135448, WO2008135591, WO2009099820.

In a further embodiment, the further active ingredient is a hyperpolarization-activated cyclic nucleotide-gated (HCN) potassium-sodium channel inhibitor, for example those as described in US2009069296.

In another embodiment, the further active ingredient is an inhibitor of the sodiumpotassium-2 chloride (NKCCl) cotransporter, for example those as described in WO2009130735.

In another embodiment, the further active ingredient is a voltage-gated sodium channel inhibitor, for example those as described in WO2009049180, WO2009049181.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 3 (SSTR3), for example those as described in WO2009011836.

In one embodiment, the further active ingredient is a modulator of somatostatin receptor 5 (SSTR5), for example those as described in WO2008019967, US2008064697, US2008249101, WO2008000692, US2008293756, WO2008148710.

In one embodiment, the further active ingredient is a modulator of somatostatin receptor 2 (SSTR2), for example those as described in WO2008051272.

In one embodiment, the further active ingredient is a compound which is capable of reducing the amount of retinol-binding protein 4 (RBP4), for example those as described in WO2009051244, WO2009145286.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO02008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin 11 receptor antagonist, for example those as described in WO2008062905, WO2008067378, WO2008062905.

In one embodiment, the further active ingredient is an agonist of the sphingosine 1-phosphate receptor (S1P), for example those as described in WO2008064315, WO2008074820, WO2008074821, WO2008135522, WO2009019167, WO2009043013, WO2009080663, WO2009085847, WO2009151529, WO2009151621, WO2009151626, WO2009154737.

In one embodiment, the further active ingredient is an agent which retards gastric emptying, for example 4-hydroxyisoleucine (WO2008044770).

In one embodiment, the further active ingredient is a tryptophan-5-hydroxylase inhibitor-1 (TPH1 inhibitor), which modulates gastrointestinal motility, as described, for example, in WO02009014972.

In one embodiment, the further active ingredient is a muscle-relaxing substance, as described, for example, in WO02008090200.

In a further embodiment, the further active ingredient is an inhibitor of monoamine oxidase B (MAO-B), for example those as described in WO2008092091, WO2009066152.

In a further embodiment, the further active ingredient is an inhibitor of monoamine oxidase A (MAO-A), for example those as described in WO2009030968.

In another embodiment, the further active ingredient is an inhibitor of the binding of cholesterol and/or triglycerides to the SCP-2 protein (sterol carrier protein-2), for example those as described in US2008194658.

In a further embodiment, the further active ingredient is a compound which binds to the (β-subunit of the trimeric GTP-binding protein, for example those as described in WO2008126920.

In one embodiment, the further active ingredient is a urate anion exchanger inhibitor 1, as described, for example, in WO2009070740.

In one embodiment, the further active ingredient is a modulator of the ATP transporter, as described, for example, in WO2009108657.

In another embodiment, the further active ingredient is lisofylline, which prevents autoimmune damage to insulin-producing cells.

In yet another embodiment, the further active ingredient is an extract from *Bidens pilosa* with the ingredient cytopiloyne as described in EP1955701.

In one embodiment, the further active ingredient is an inhibitor of glucosylceramide synthase, as described, for example, in WO2008150486.

In a further embodiment of the invention, the further active ingredient is a glycosidase inhibitor, as described, for example, in WO2009117829, WO2009155753.

In another embodiment, the further active ingredient is an ingredient from the plant *Hoodia Gordonii*, as described in US2009042813, EP2044852.

In one embodiment, the further active ingredient is an antidiabetic, for example D-tagatose.

In one embodiment, the further active ingredient is a zinc complex of curcumin, as described in WO2009079902.

In one embodiment, the further active ingredient is an inhibitor of the "cAMP response element binding protein" (CREB), as described in WO2009143391.

In another embodiment, the further active ingredient is an antagonist of the bradykinin B1 receptor, as described in WO2009124746.

In a further embodiment, the further active ingredient is a compound which is capable of modulating diabetic peripheral neuropathy (DPN). Such modulators are, for example, FK-1706 or SB-509, or those as described in WO1989005304, WO2009092129, WO2010002956.

In one embodiment, the further active ingredient is a compound which is capable of modulating diabetic nephropathy. Such compounds are described, for example, in WO2009089545, WO2009153261.

In one embodiment, the further active ingredient is an inhibitor (e.g. an anti-CD38 antibody) of CD38, as described in US2009196825.

In one embodiment, the further active ingredient is an inhibitor of human fibroblast growth factor receptor 4 (FGFR4), as described, for example, in WO2009046141.

In a further embodiment of the invention, the further active ingredient is a compound which protects the beta cell, for example 14-alpha-lipoyl-andrographolide (AL-1).

In yet another embodiment of the invention, the further active ingredient is the INGAP (islet neogenesis associated protein) peptide, a peptide which reestablishes insulin production in patients with diabetes mellitus.

In one embodiment of the invention, the further active ingredient is a modulator of the CFTR (cystic fibrosis transmembrane conductance regulator), as described, for example, in US2009246137, US2009264433, US2009264441, US2009264471, US2009264481, US2009264486, WO2010019239.

In one embodiment of the invention, the further active ingredient is a compound which stimulates/modulates insulin release, for example those as described in WO2009109258, WO2009132739, US2009281057, WO2009157418.

In one embodiment of the invention, the further active ingredient is an extract from Hippophae rhamnoides, as described, for example, in WO2009125071.

In one embodiment of the invention, the further active ingredient is an from Huanglian and Ku Ding Cha, as described, for example, in WO2009133458.

In another embodiment, the further active ingredient is a root extract from *Cipadessa baccifera*, as described in US2009238900.

In one embodiment of the invention, the further active ingredients are borapetoside A and/or borapetoside C, which can be isolated from the plant SDH-V, a species of *Tinospora crispa*, as described, for example, in US2010016213.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered within the scope of protection conferred by the present invention.

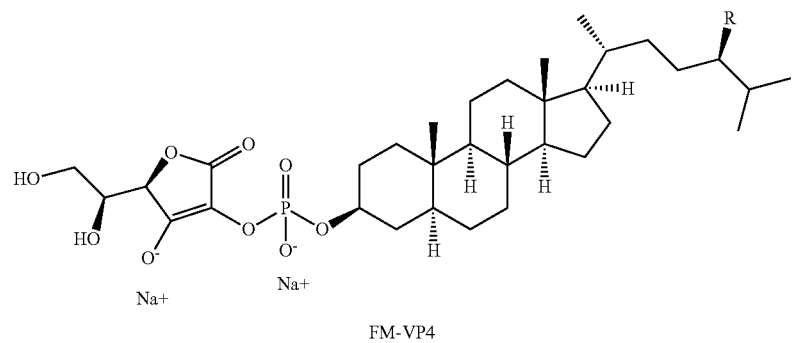
FM-VP4
R = CH₃; CH₂—CH₃
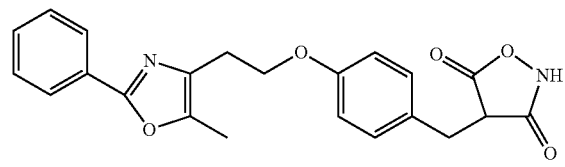
JTT-501
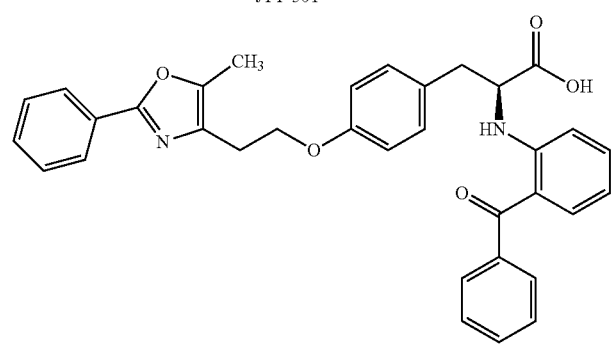
GI 262570
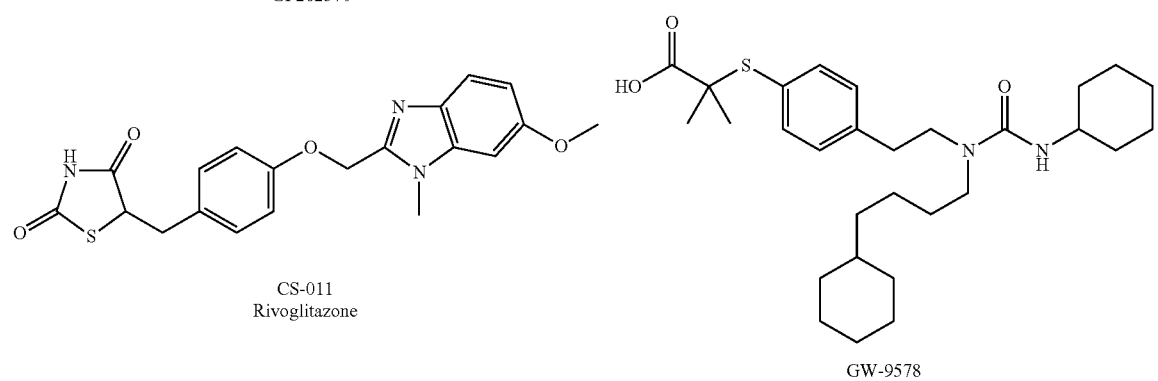
CS-011
Rivoglitazone
GW-9578
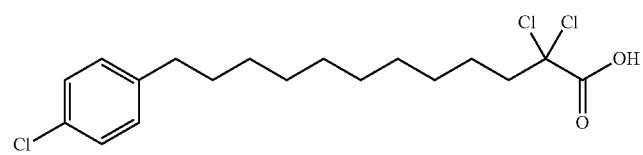
K-111
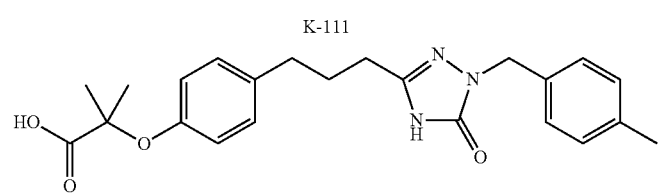
LY-518674

-continued
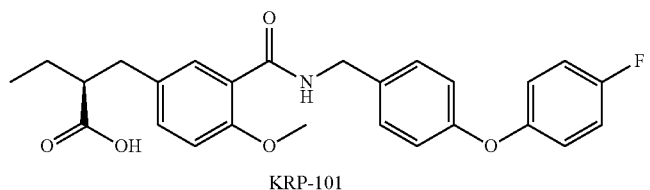
KRP-101
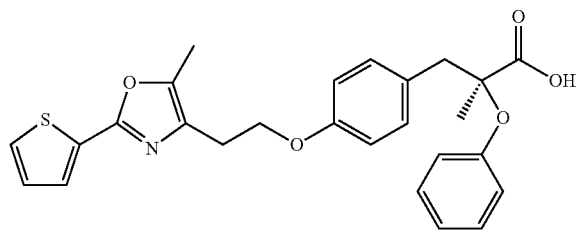
LY-510929
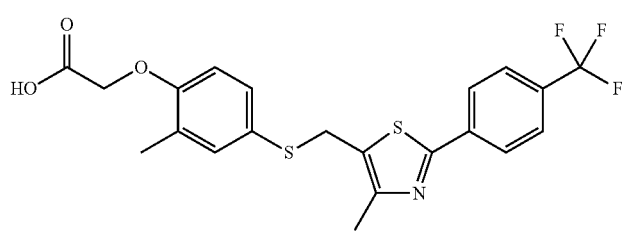
GW-501516
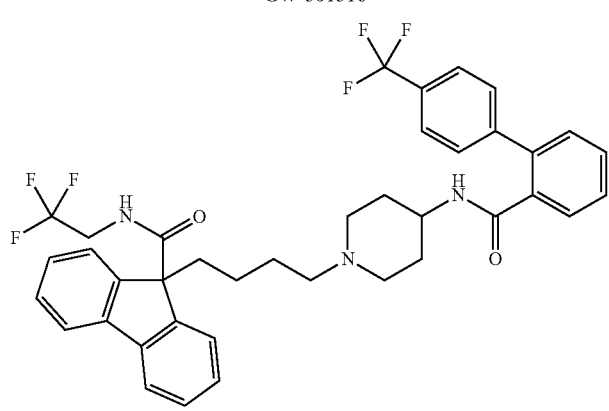
BMS-201038
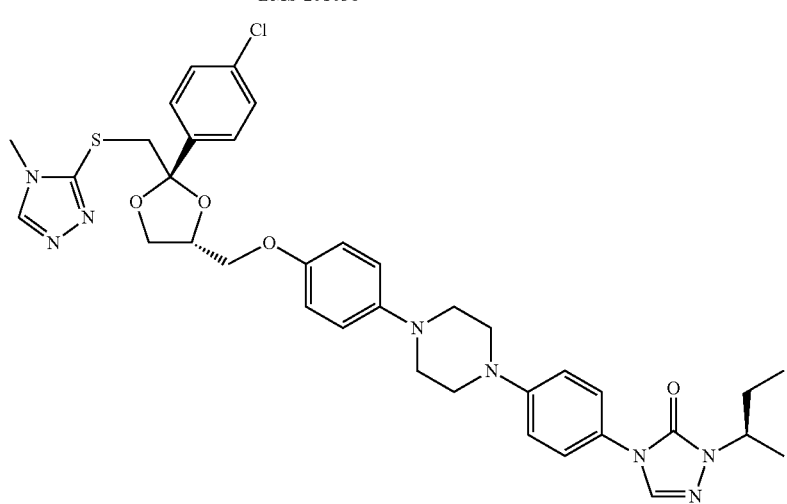
R-103757

-continued
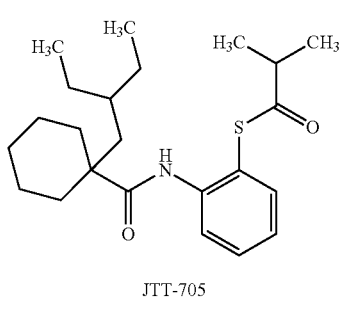
JTT-705
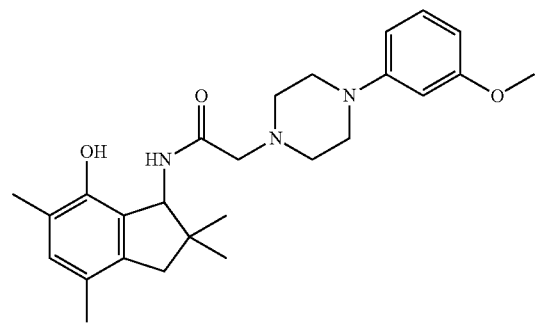
OPC-14117
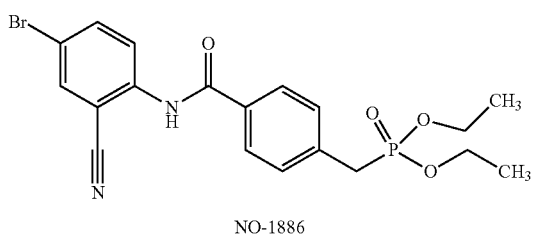
NO-1886
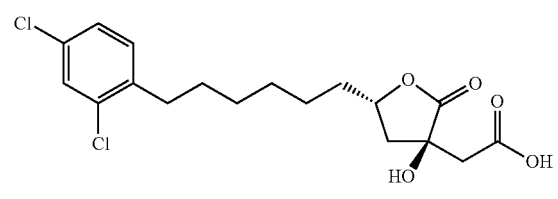
SB-204990
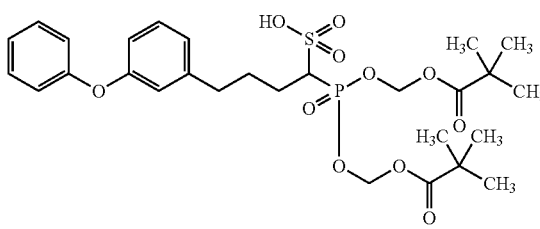
BMS-188494
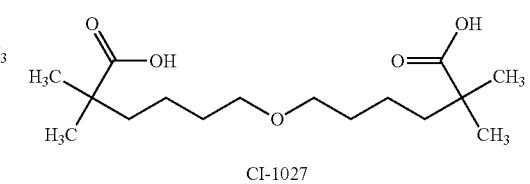
CI-1027
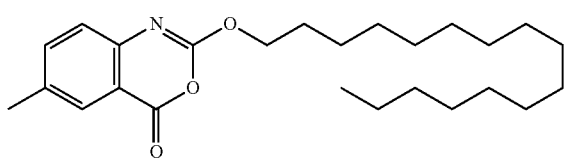
ATL-962
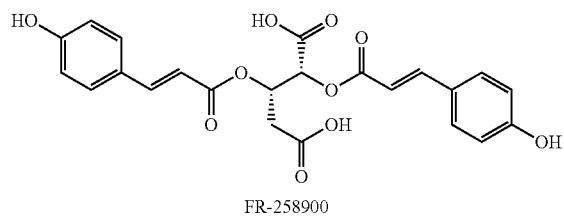
FR-258900
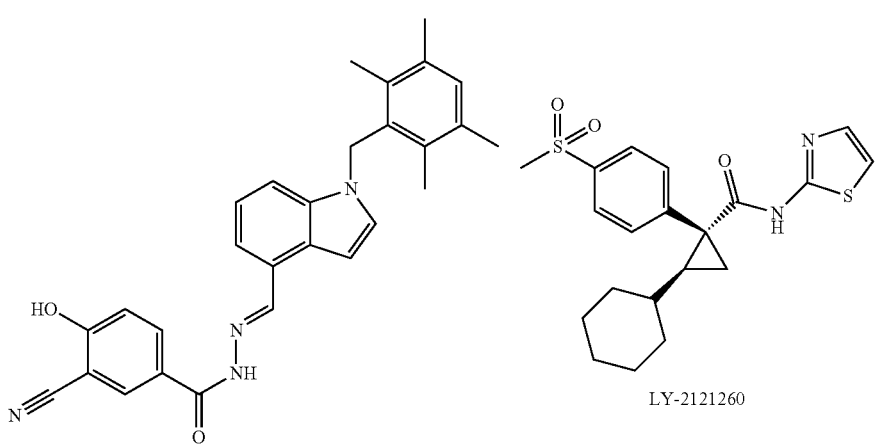
NNC-25-2504
LY-2121260

-continued
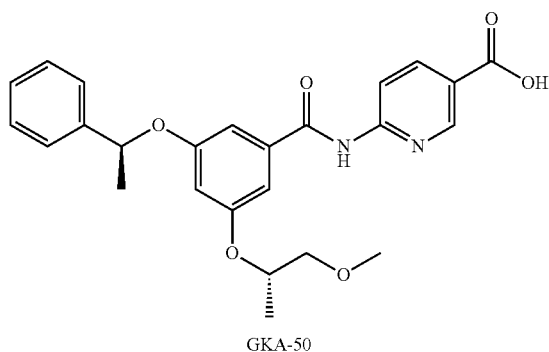
GKA-50
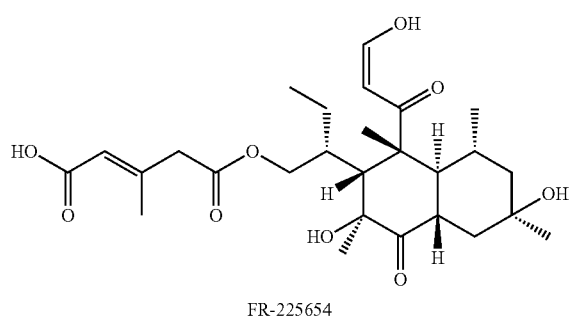
FR-225654
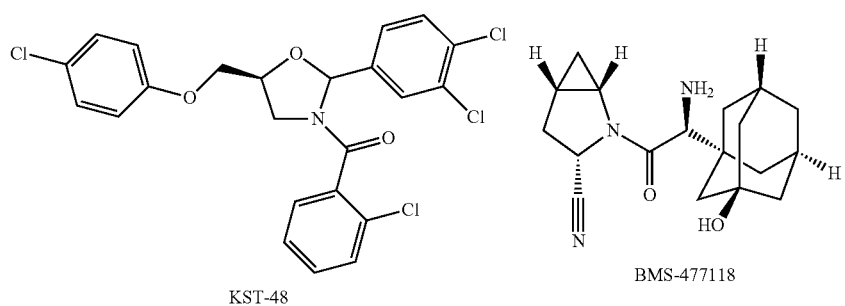
KST-48
BMS-477118
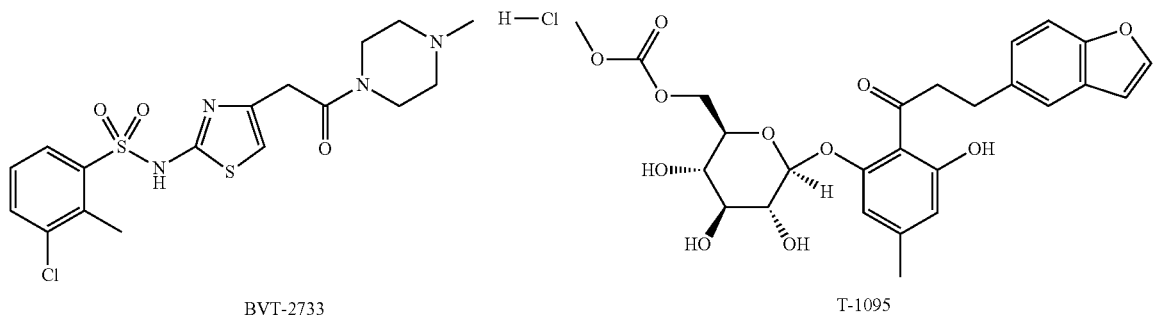
BVT-2733
T-1095
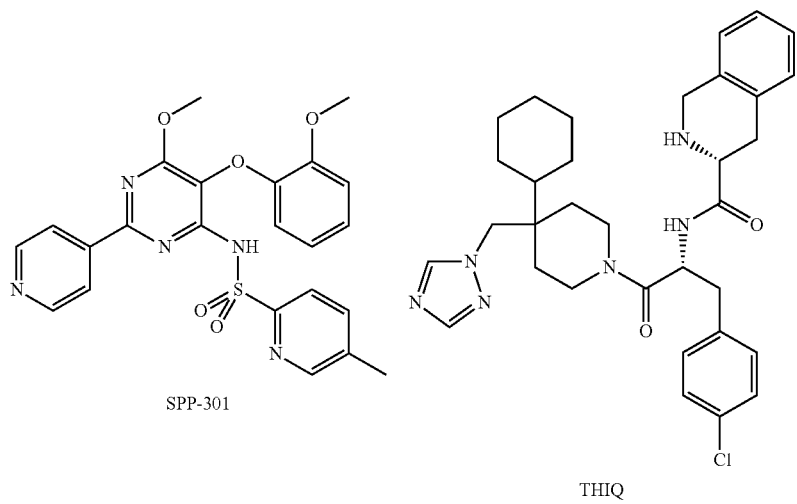
SPP-301
THIQ -continued
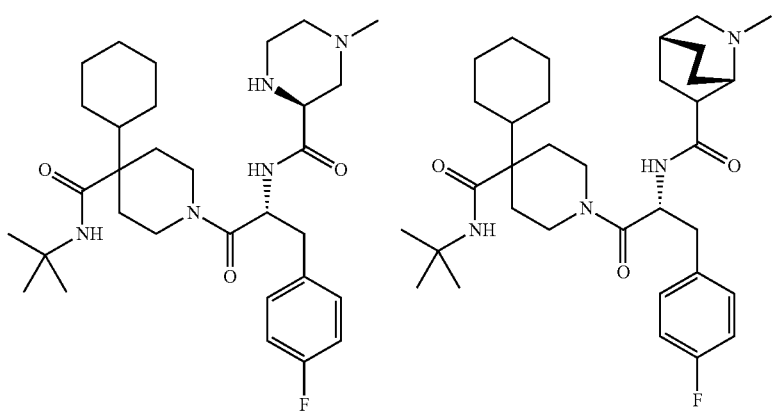
MB243
RY764
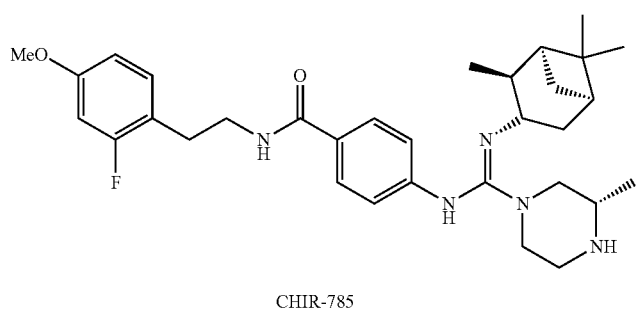
CHIR-785
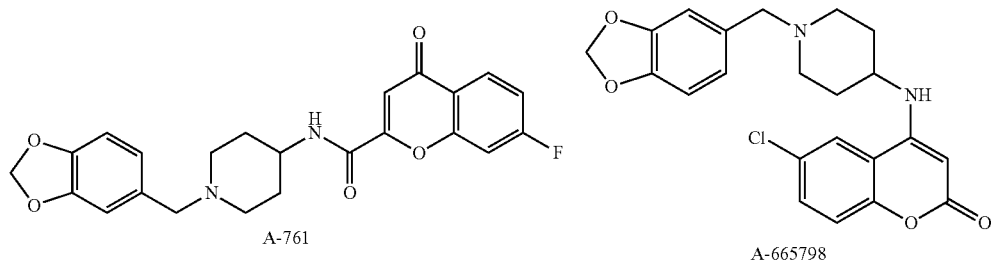
A-761
A-665798
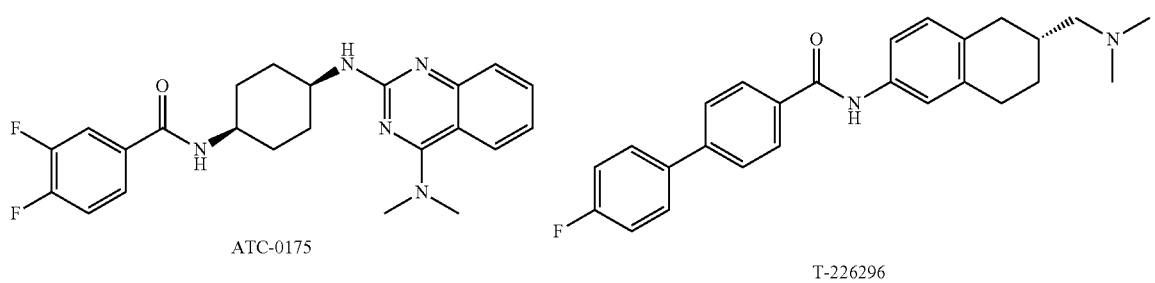
ATC-0175
T-226296
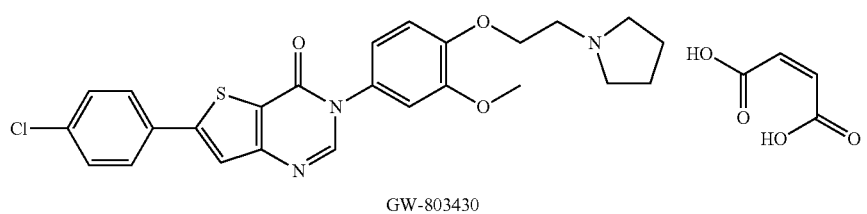
GW-803430

-continued
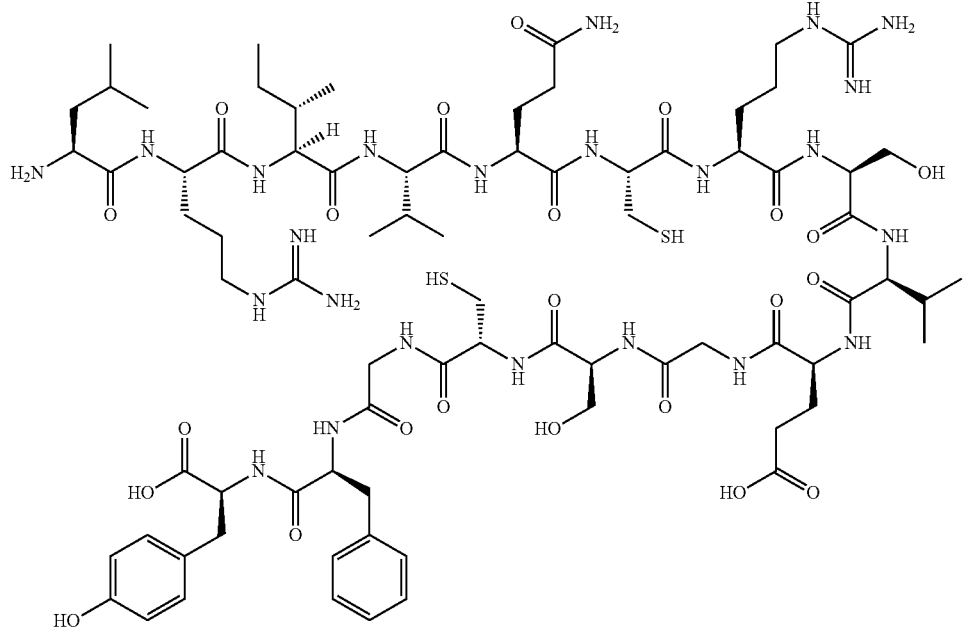
AOD-9604
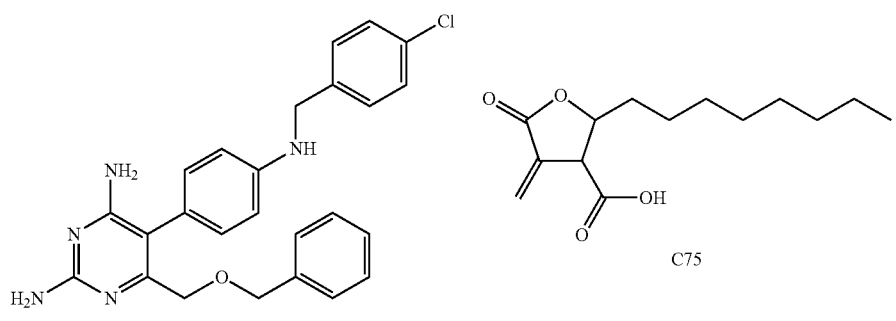
A-778193
C75
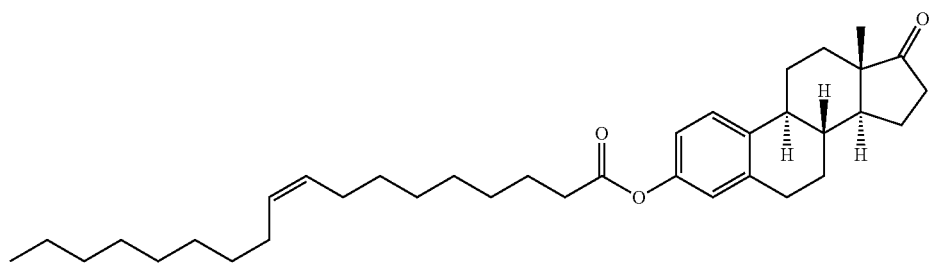
Oleoyl-Estron
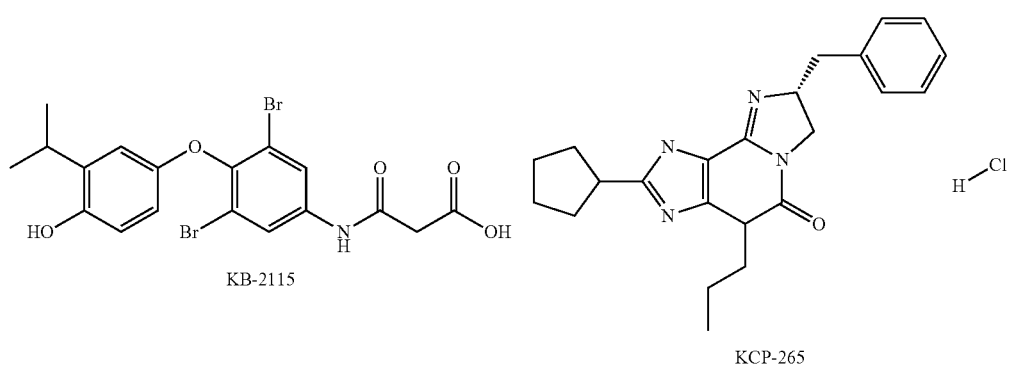
KB-2115
KCP-265

-continued
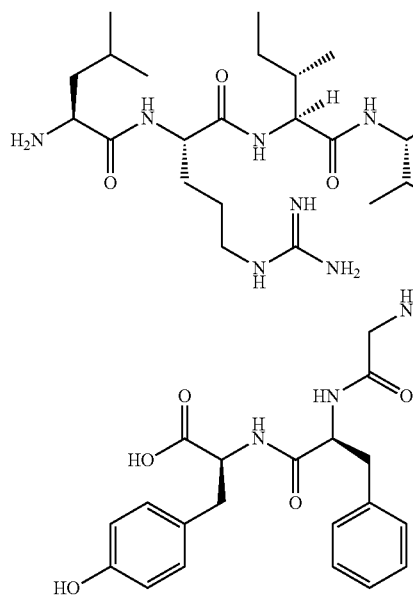
AOD-9604
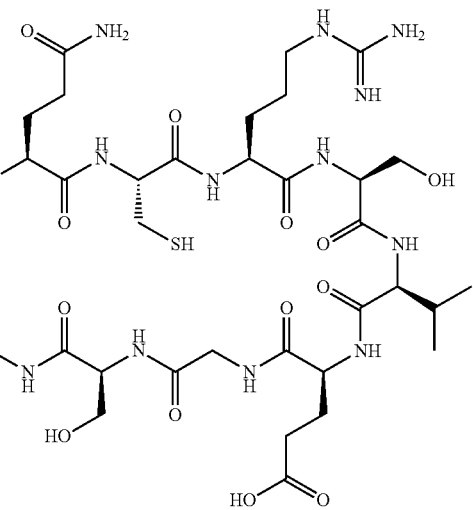
SMP-797
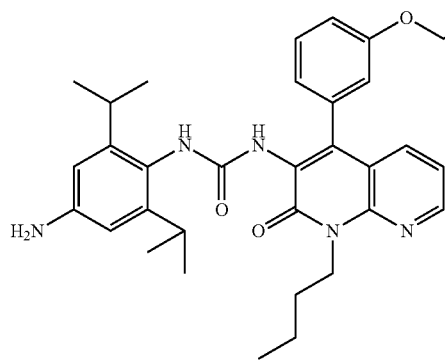
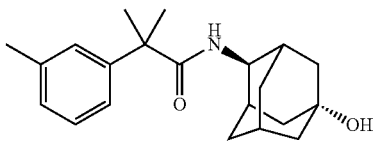
JNJ-25918646
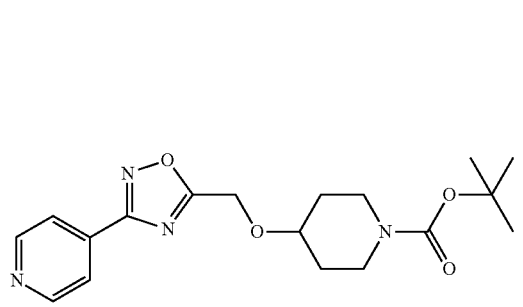
PSN-632408
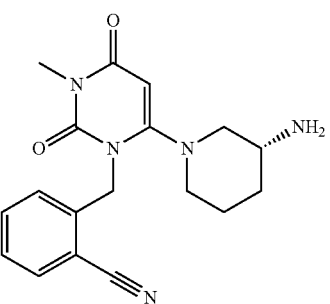
SYR-322
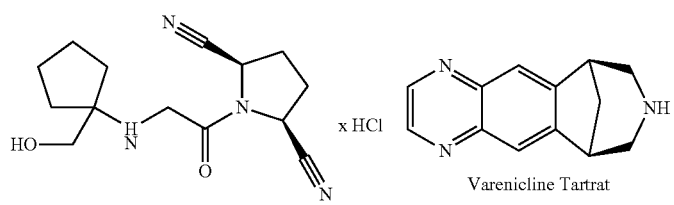
DP-893    Varenicline Tartrat -continued
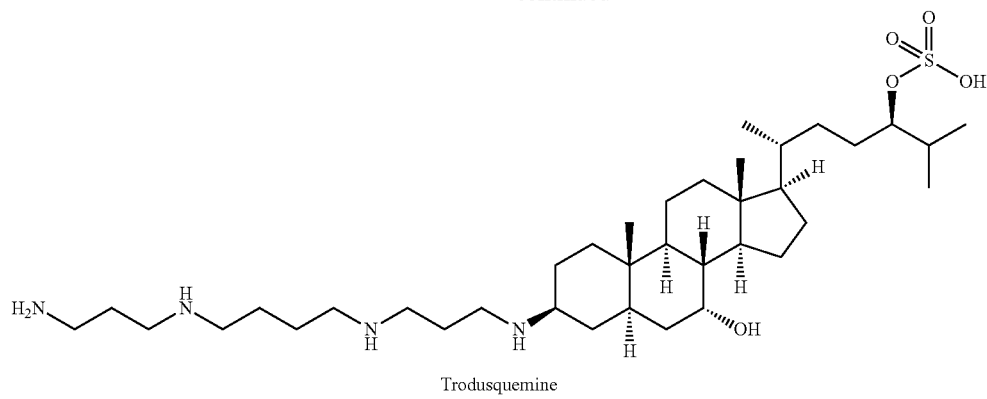
Trodusquemine
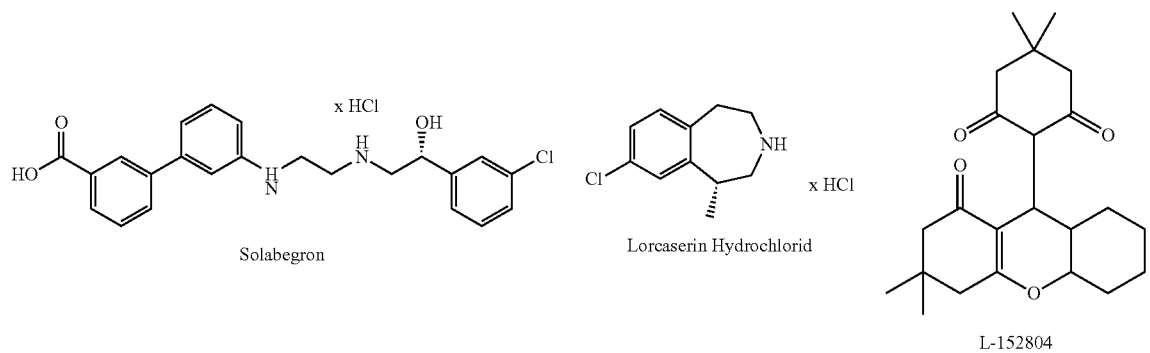
Solabegron    Lorcaserin Hydrochlorid    L-152804
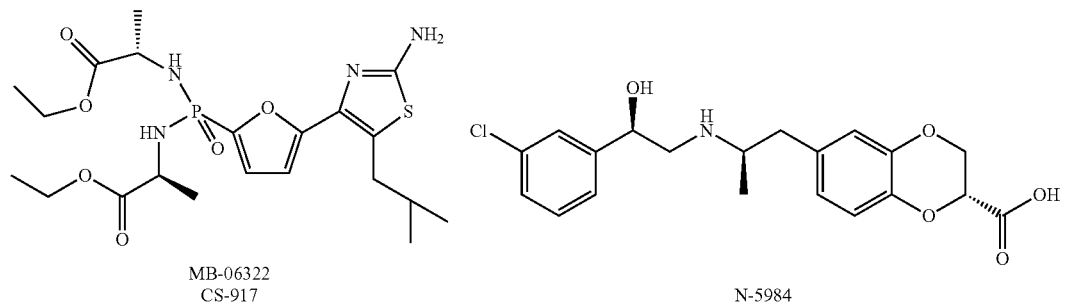
MB-06322
CS-917    N-5984
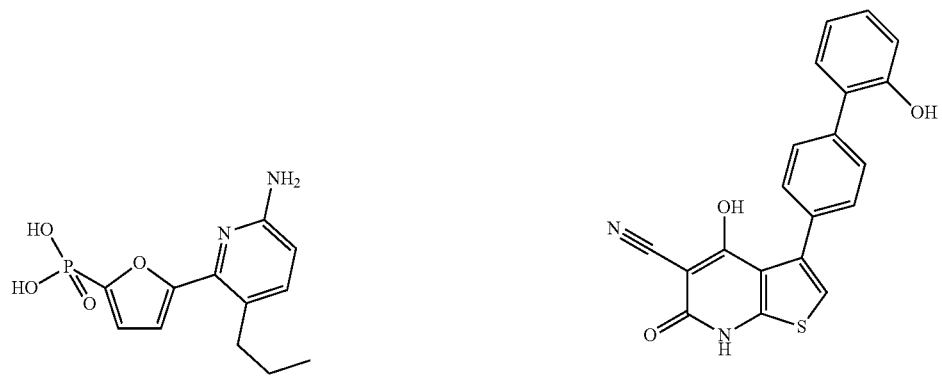
MB-07803    A-769662

-continued
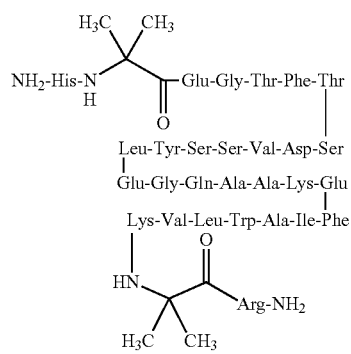
BIM-51077
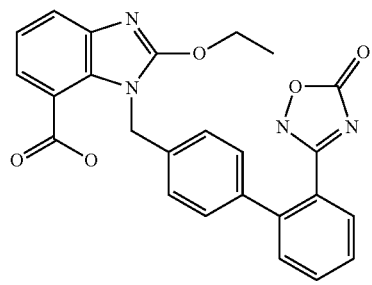
TAK-536
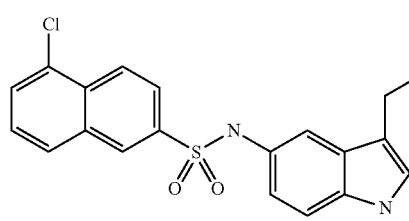
E-6837
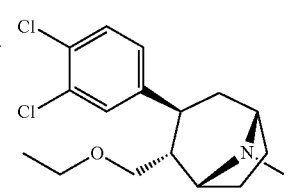
tesofensine
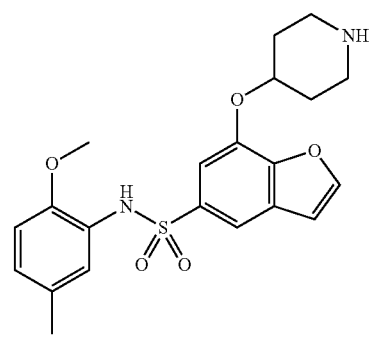
BVT-74316
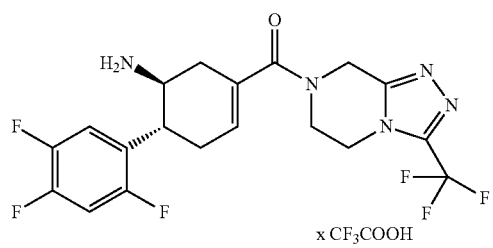
ABT-341
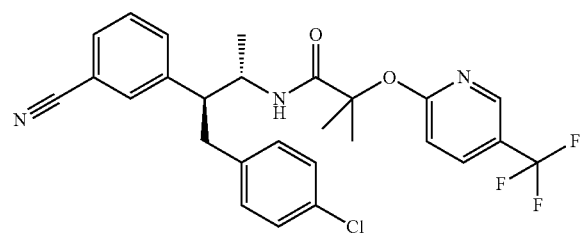
MK-0364
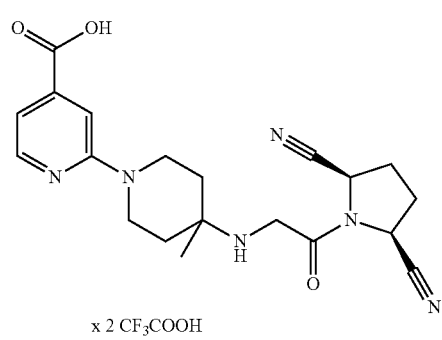
ABT-279
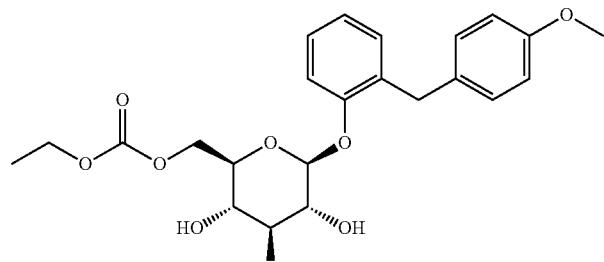
sergliflozin

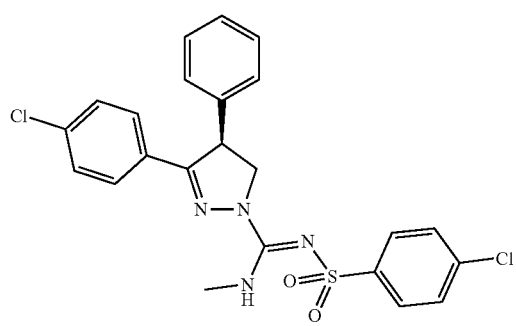
SLV-319
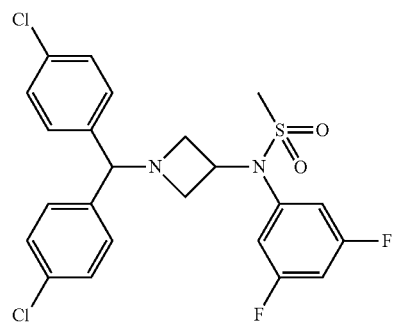
AVE 1625 (proposed INN: drinabant)
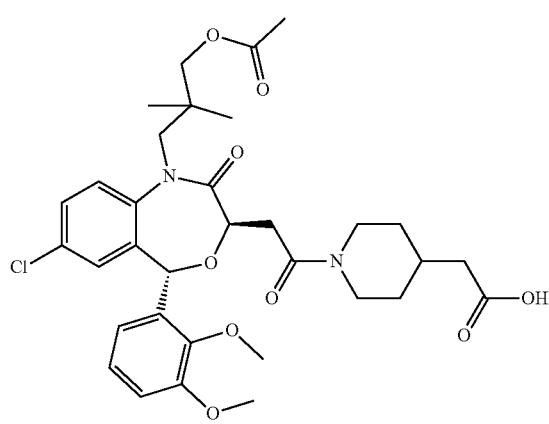
TAK-475 (lapaquistat acetate)
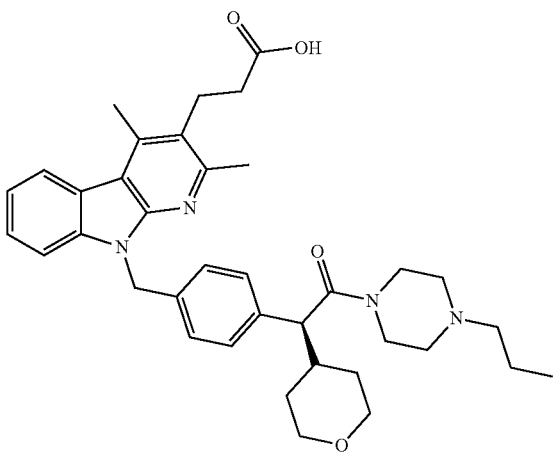
AS-1552133
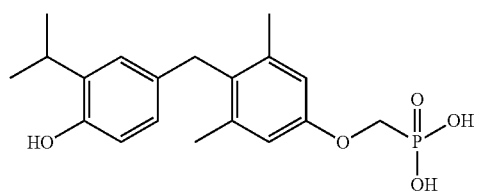
MB-07344
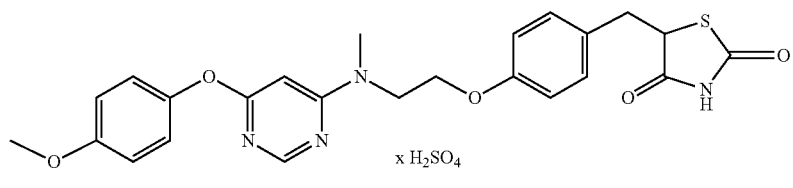
x H$_2$SO$_4$
CKD-501 (lobeglitazone sulfate)
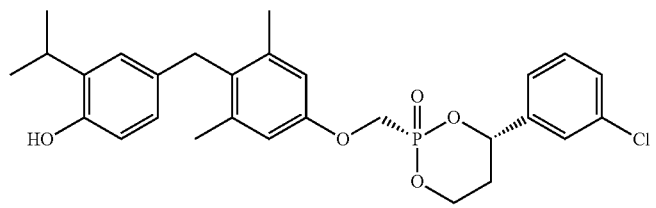
MB-07811
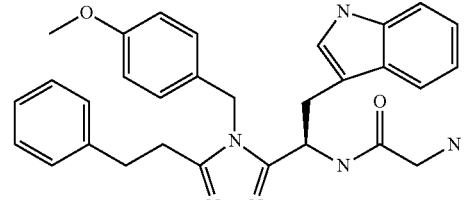
JMV-2959

-continued
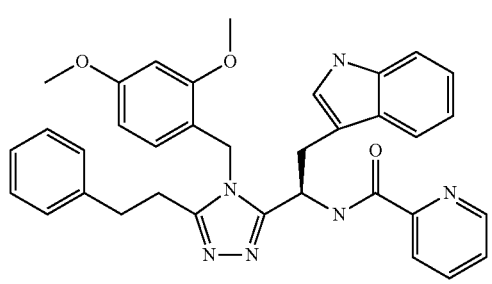
JMV-3002
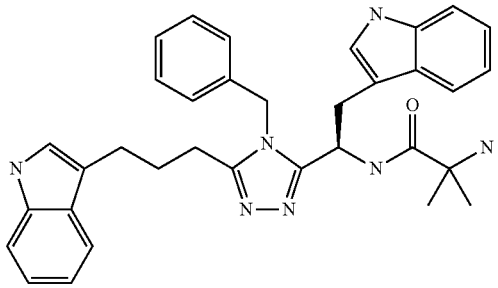
JMV-2810
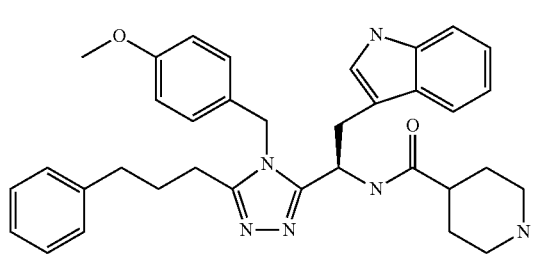
JMV-2951
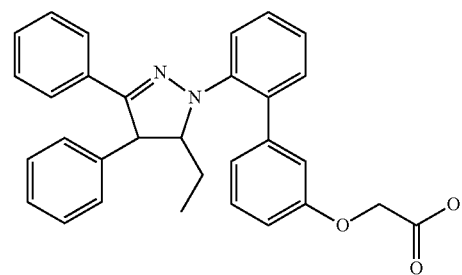
BMS-309403
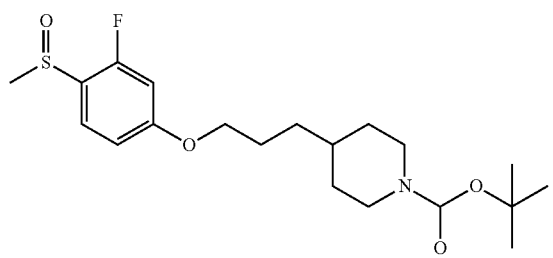
PSN-119-1
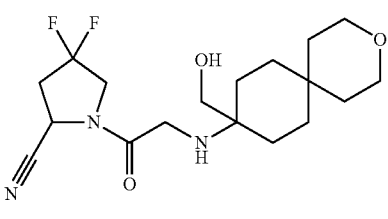
S-40755
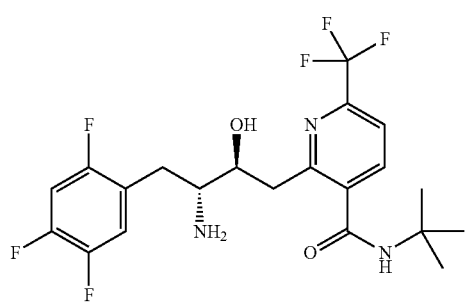
LY-2463665
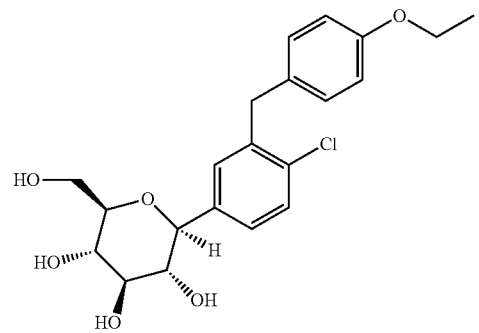
dapagliflozin, BMS-512148
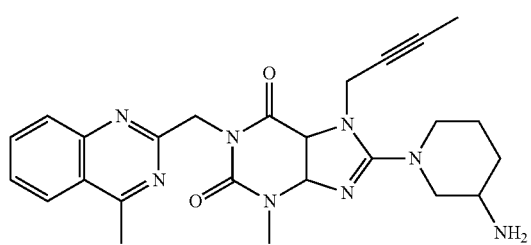
BI-1356
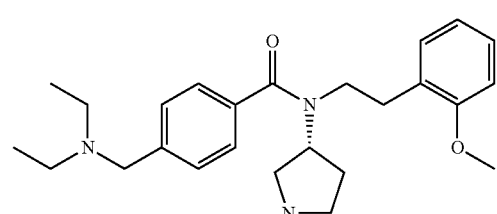
PF-429242

91
92
-continued
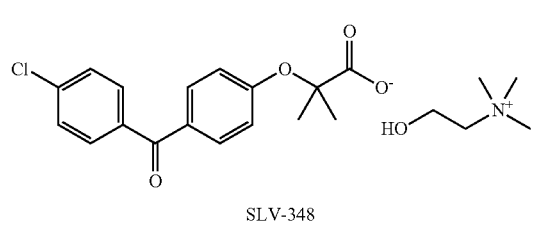
SLV-348
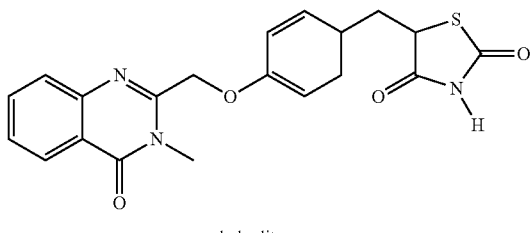
balaglitazone
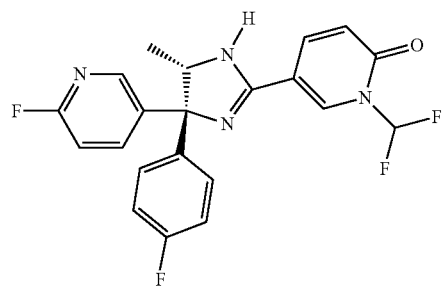
"NPY-5-BY"
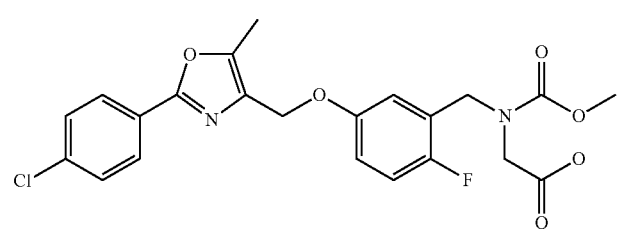
BMS-711939
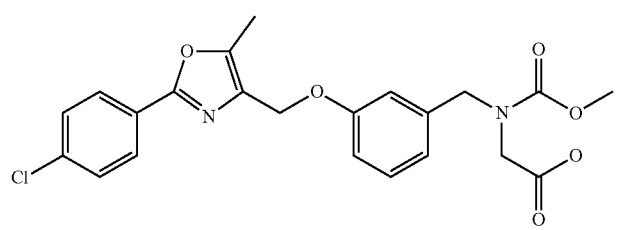
BMS-687453
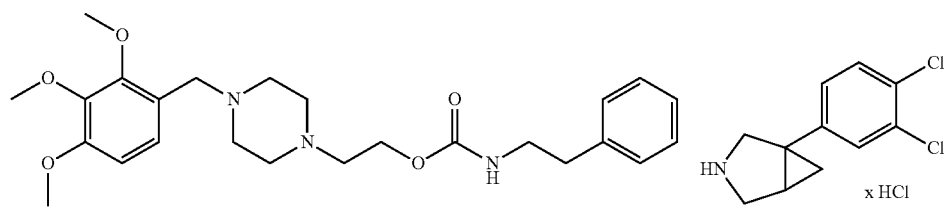
ST-3473     DOV-21947
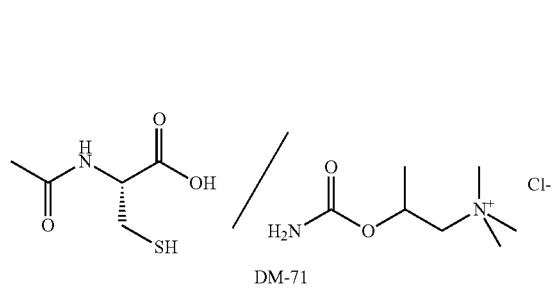
DM-71
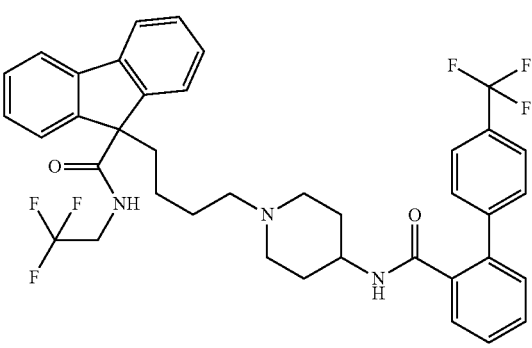
AEGR-733

-continued
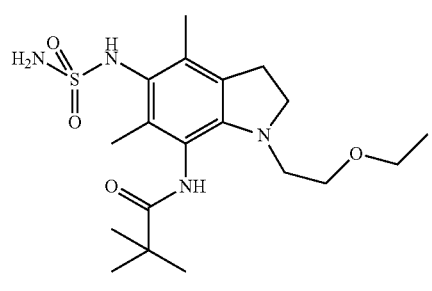
KY-382
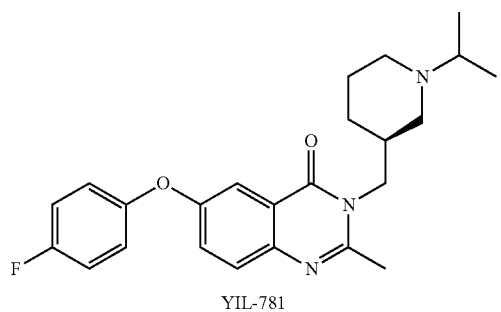
YIL-781
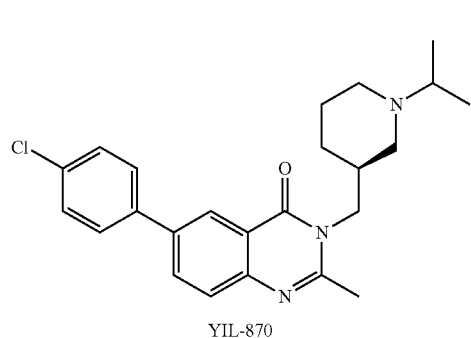
YIL-870
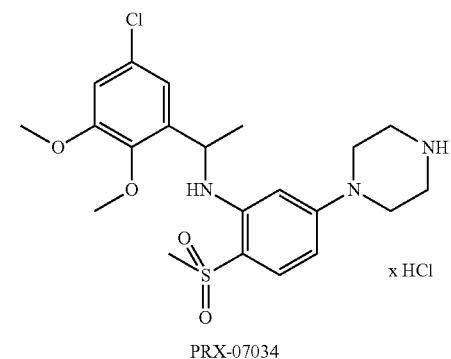
PRX-07034 x HCl
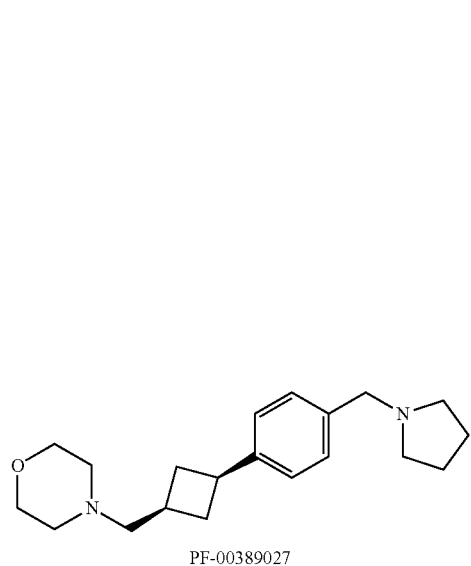
PF-00389027
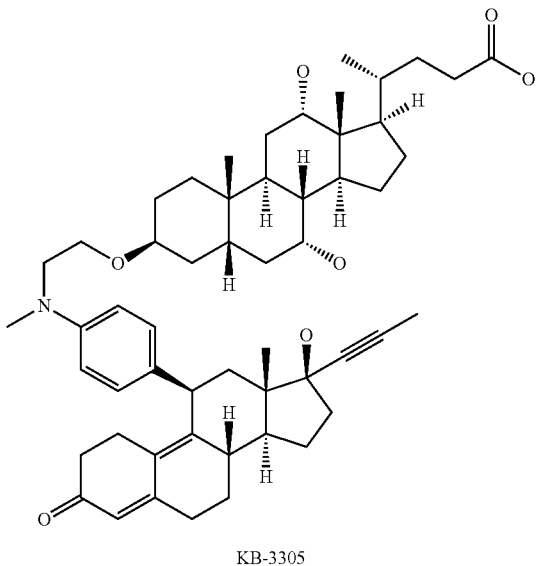
KB-3305
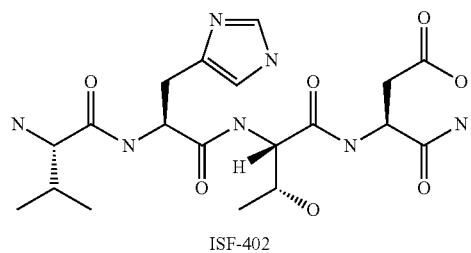
ISF-402
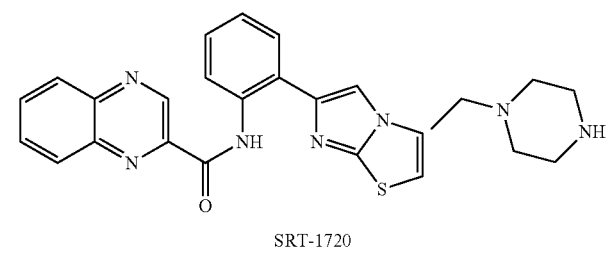
SRT-1720

-continued
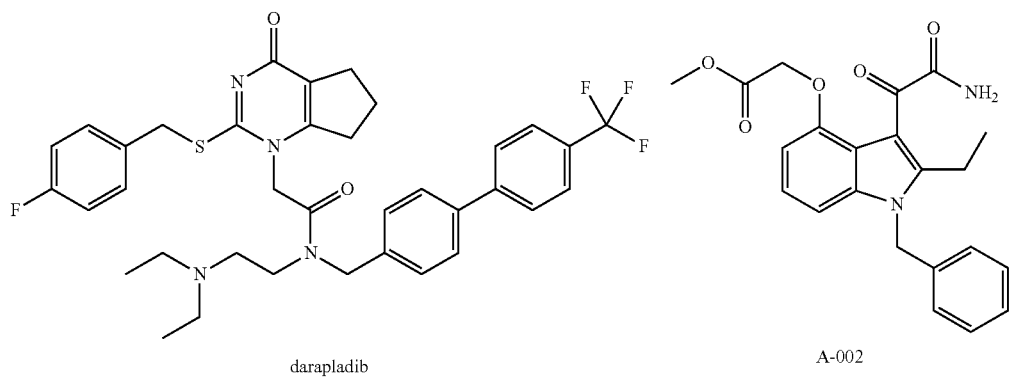
darapladib
A-002
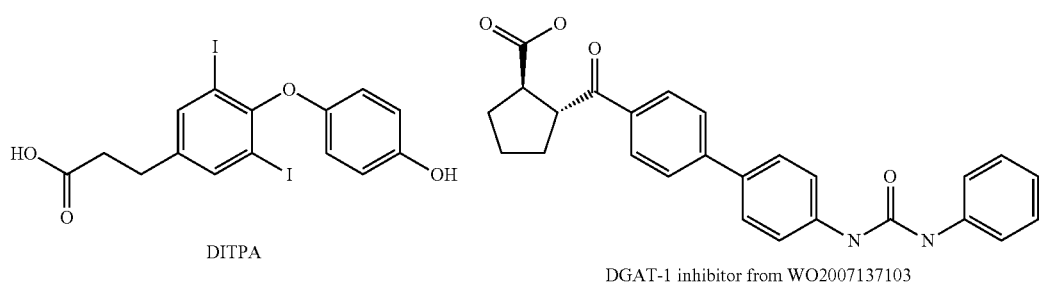
DITPA
DGAT-1 inhibitor from WO2007137103
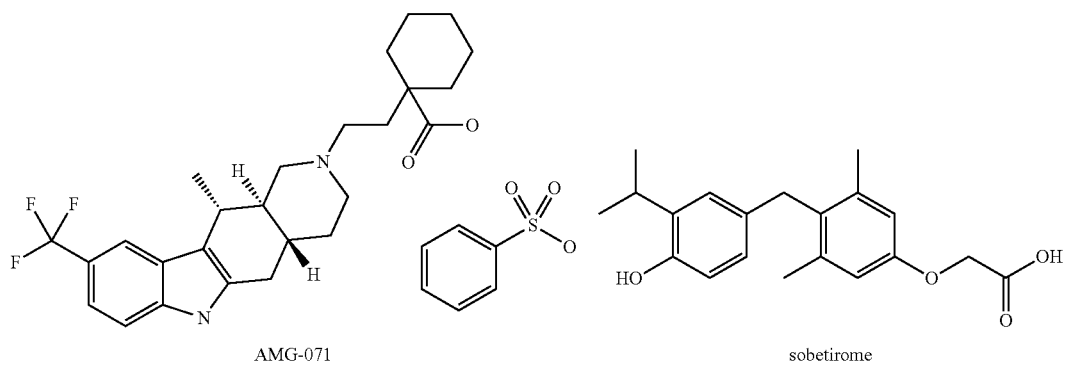
AMG-071
sobetirome
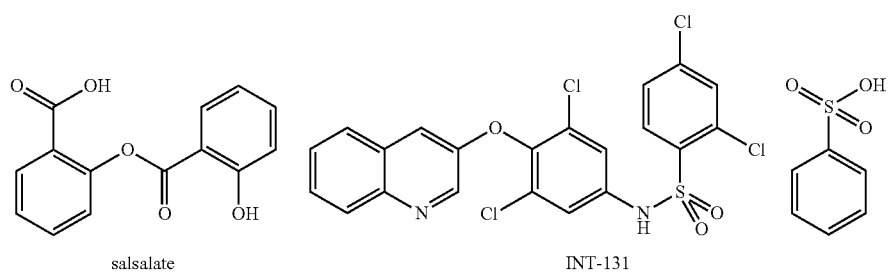
salsalate
INT-131

-continued
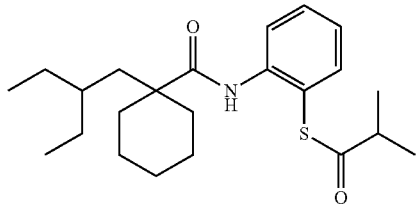
dalcetrapib
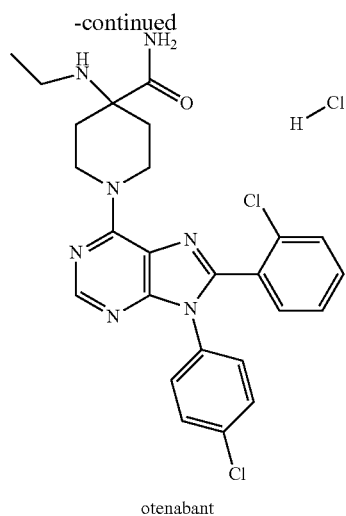
otenabant
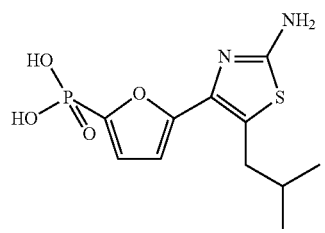
MB-07229
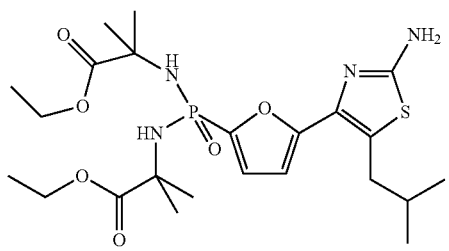
MB-07803
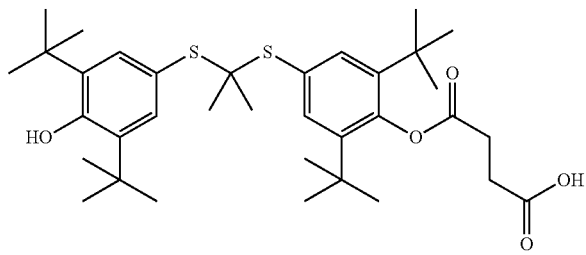
succinobucol
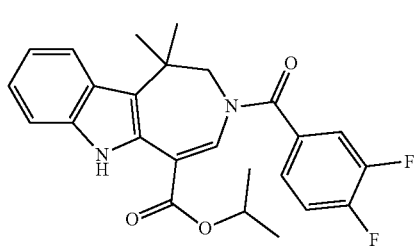
WAY-362450
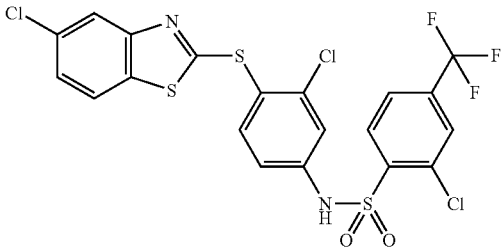
T-2384
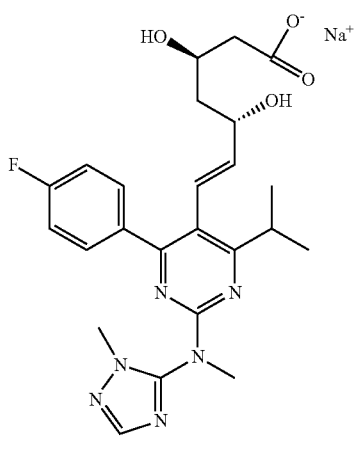
BMS-644950
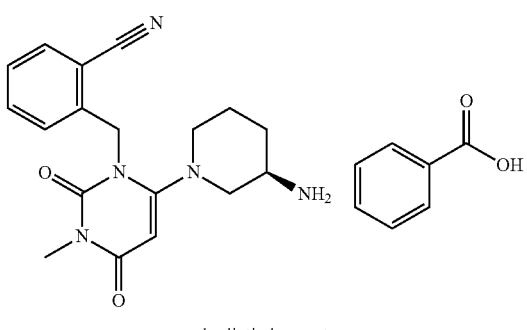
alogliptin benzoate -continued
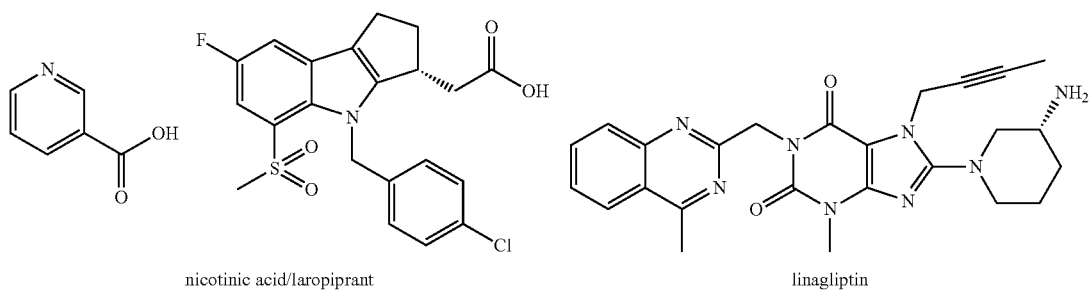
nicotinic acid/laropiprant
linagliptin
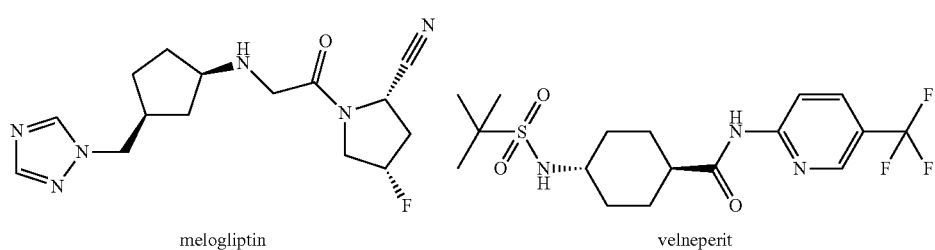
melogliptin
velneperit
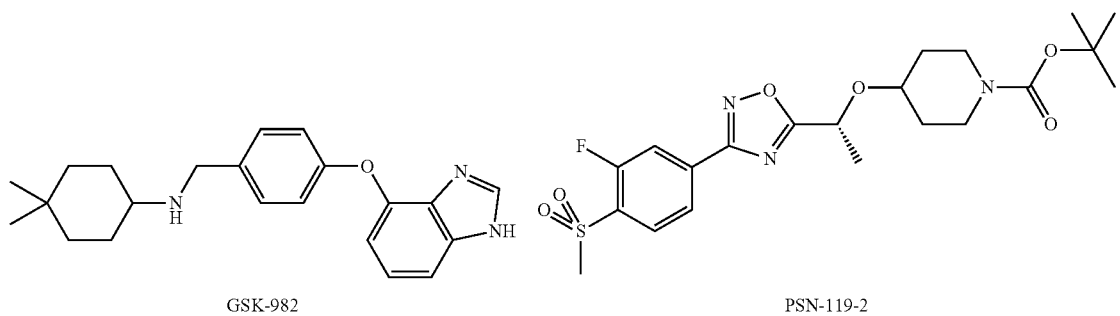
GSK-982
PSN-119-2
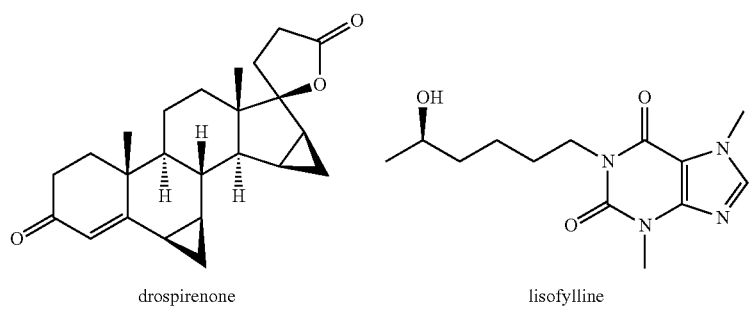
drospirenone
lisofylline
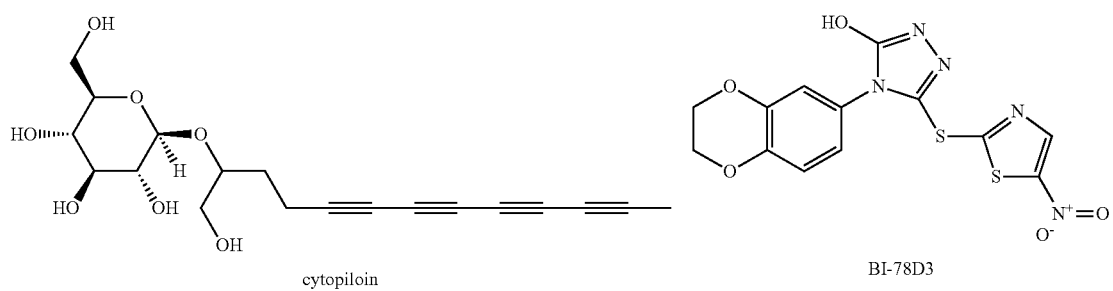
cytopiloin
BI-78D3

-continued
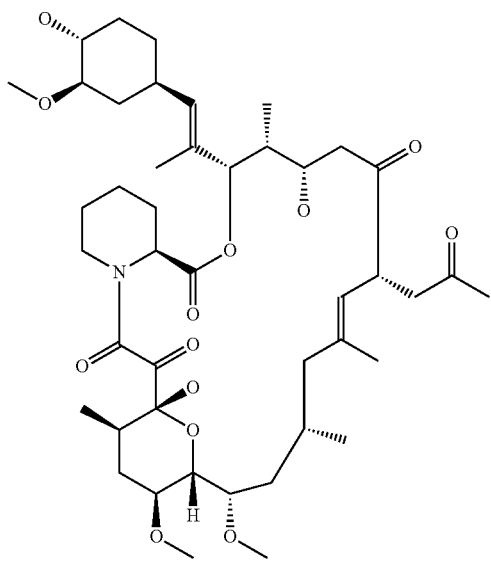
FK-1706
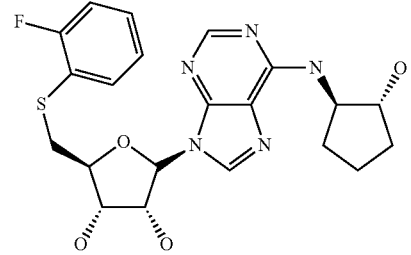
CVT-3619
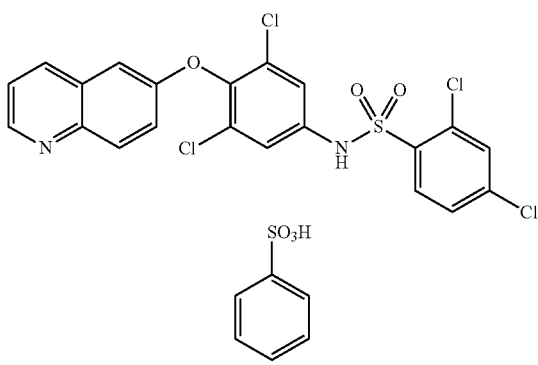
INT-131
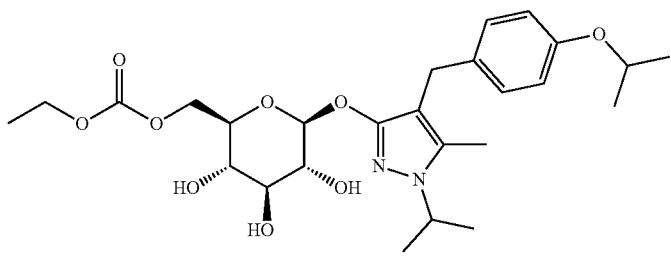
remogliflozin
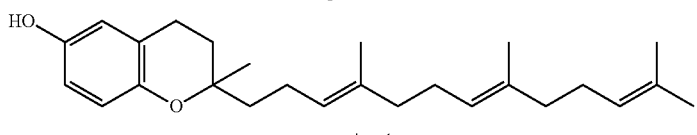
tocotrienol
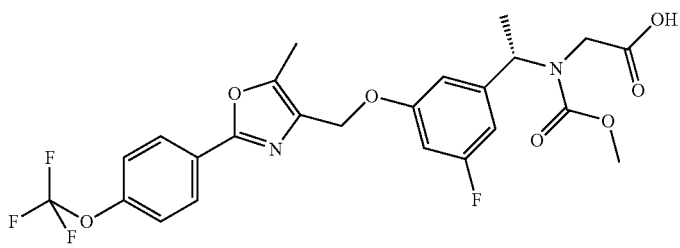
BMS-759509

-continued

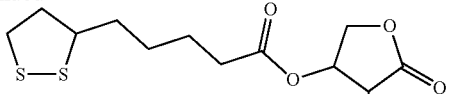

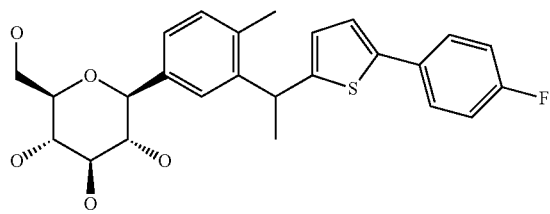

canagliflozin

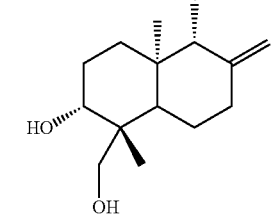

14-alpha-lipoyl-andrographolide (AL-1)

fatostatin

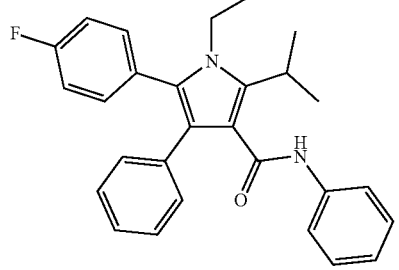

NCX-6560

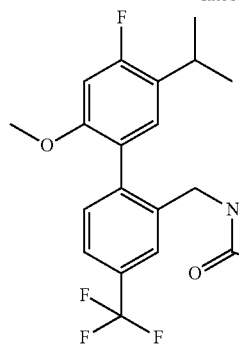

anacetrapib

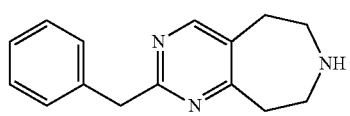

PF-3246799

Also suitable are the following active ingredients for combination preparations:
all antiepileptics specified in the Rote Liste 2011, chapter 15;
all antihypertensives specified in the Rote Liste 2011, chapter 17;
all hypotonics specified in the Rote Liste 2011, chapter 19;
all anticoagulants specified in the Rote Liste 2011, chapter 20;
all arteriosclerosis drugs specified in the Rote Liste 2011, chapter 25;
all beta receptors, calcium channel blockers and inhibitors of the renin angiotensin system specified in the Rote Liste 2011, chapter 27;
all diuretics and perfusion-promoting drugs specified in the Rote Liste 2011, chapter 36 and 37;
all withdrawal drugs/drugs for the treatment of addictive disorders specified in the Rote Liste 2011, chapter 39;
all coronary drugs and gastrointestinal drugs specified in the Rote Liste 2011, chapter 55 and 60;
all migraine drugs, neuropathy preparations and Parkinson's drugs specified in the Rote Liste 2011, chapter 61, 66 and 70.

It will be appreciated that every suitable combination of the compounds of the invention with one or more of the aforementioned compounds and optionally one or more other pharmacologically active substances is considered to be covered within the scope of protection conferred by the present invention.

PKC-inhibitors can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula I with a flavoring, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, also belong within the framework of the invention. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for longterm close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

PKC inhibitors can additionally be used in systems for local drug delivery, for example in coated stents for preventing or reducing in-stent restenosis or by applying them locally by means of a catheter. The appropriate administration form depends, among others, on the disease to be treated and on its severity.

The dosing of PKC inhibitors to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, 0.1 ng to 100 mg, typically 1 ng to 100 mg, per milliliter. Single doses may contain, for example, 1 mg to g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

The present invention provides novel and potent PKC inhibitors. The compounds of the present invention are selective to PKC over other kinases and are isozymeselective. Selective PKC inhibitors are useful in preventing and treating diseases associated with diabetes and diabetic complications (e.g. diabetic cardiomyopathy, diabetic nephropathy, diabetic micro- and macrovascular complications, diabetic neuropathy and diabetic retinopathy, preferably diabetic nephropathy, diabetic neuropathy and diabetic retinopathy), cardiovascular diseases, diseases associated with hypertension- and non-hypertension-related and ischemic and non-ischemic end-organ damage (e.g. mycardial infarction, coronary heart disease, atherosclerosis, cardiac and renal hypertrophy, stroke), diseases associated with inflammation and fibrosis, central nervous system disorders (e.g. neuropathic pain), dermatological diseases, autoimmune diseases (e.g. psoriasis, type 1 diabetes) and cancer (e.g. hematological tumours, glioma, gastric and intestinal cancer, skin cancer and lung cancer).

Another subject of the present invention are processes for the preparation of the compounds of the formula I and their salts and solvates, by which the compounds are obtainable and which are outlined in the following.

Scheme 1 shows a first process of preparing compounds of the formula I

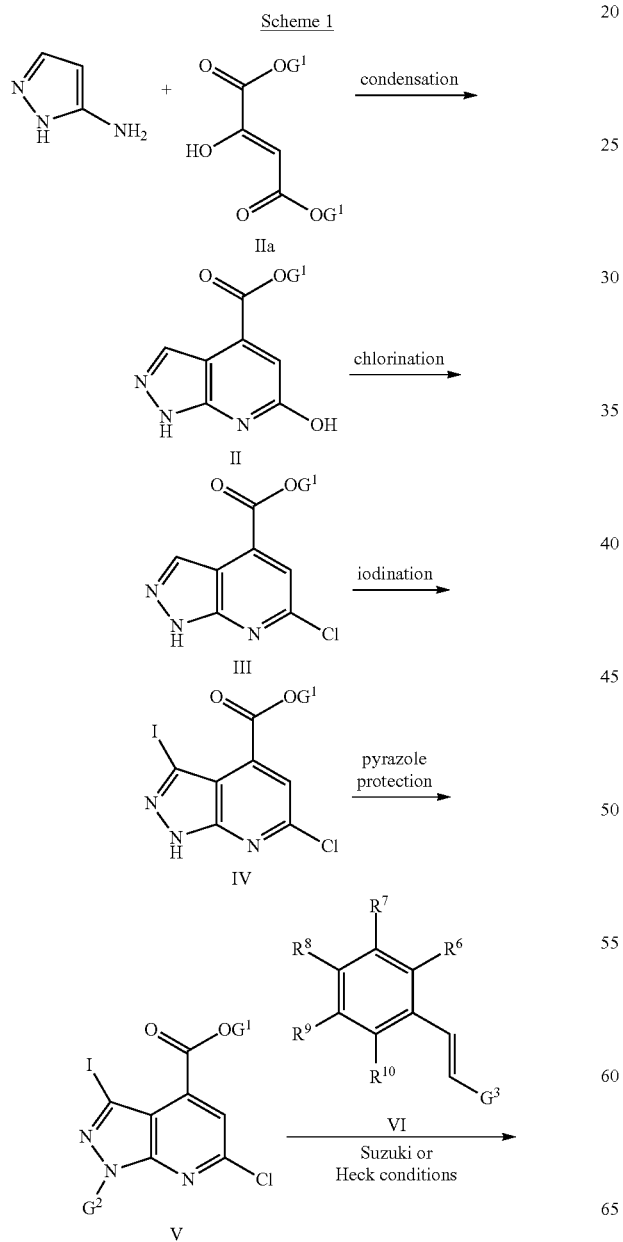

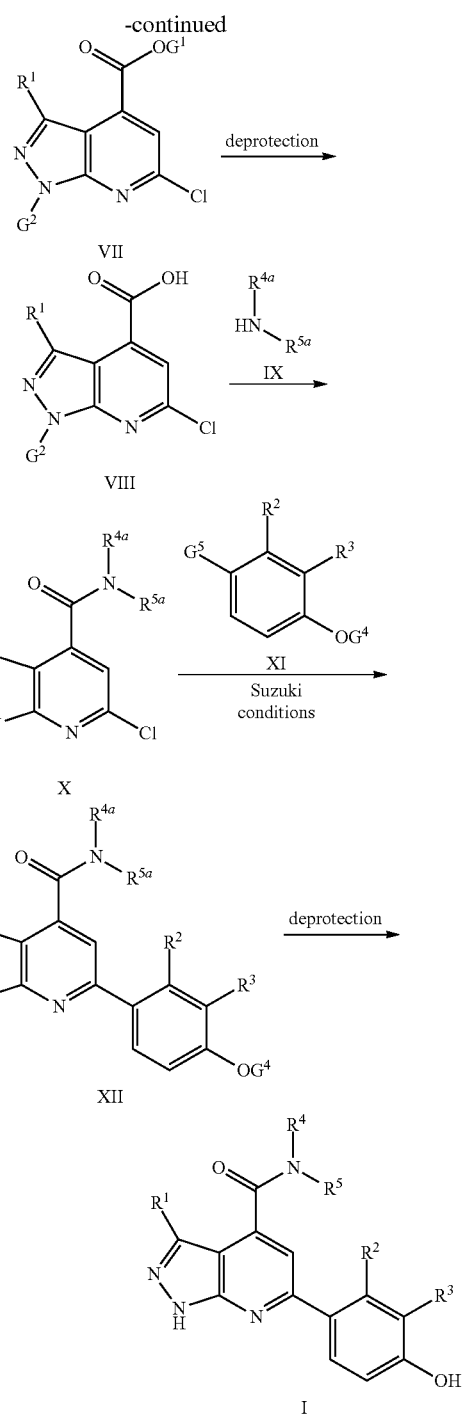

wherein $R^1$ is a residue of the formula Ia

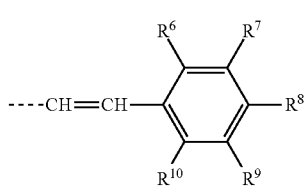

and the groups $R^2$, $R^3$, $R^4$, $R^5$, $R^6$, $R^7$, $R^8$ $R^9$ and $R^{10}$ in the compounds of the formulae VI, VII, VIII, IX, X, XI and XII are defined as above in the compounds of the formula I. The groups $R^{4a}$ and $R^{5a}$ in the compounds of formulae IX, X and XII are, independently of each other, either defined as the groups $R^4$ and $R^5$ in formula I, or they are precursors of the groups $R^4$ and $R^5$ in formula I, they can for example contain functional groups in protected form or functional groups which can be converted to obtain the final groups $R^4$ and $R^5$. The group $G^1$ in the compounds of formulae II, IIa, III, IV, V and VII is a protecting group for a carboxylic acid, such as, for example methyl, ethyl, propyl, tert-butyl or benzyl, preferably methyl or ethyl. The group $G^2$ in the compounds of formulae V, VII, VIII, X and XII is defined as a protecting group for a pyrazole nitrogen, such as, for example, a 2-tetrahydropyranyl-group, a trimethylsilylethoxymethyl-group, a benzyl group, a 4-methoxybenzyl, a 2,5-dimethoxybenzyl group, a trialkylsilyl-group such as tert-butyldimethylsilyl-group. The group $G^3$ in the compounds of formula VI is a hydrogen, a boronic acid or a boronic ester or cyclic

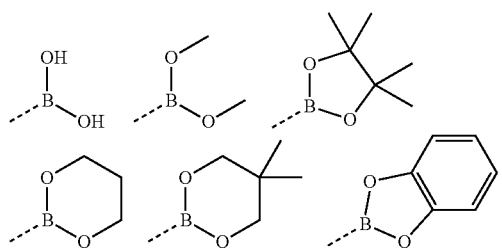

The group $G^4$ in the compounds of formulae XI and XII is defined as a hydrogen or a protecting group for a phenolic hydroxyl group, such as, for example, a trialkylsilyl-group such as tert-butyldimethylsilyl-group, a 2-tetrahydropyranyl-group, a benzyl group, a 4-methoxybenzyl or a 2,5-dimethoxybenzyl group. The group $G^5$ in the compounds of formula XI is a boronic acid or a boronic ester or cyclic boronic ester as described above.

As it is known to the skilled person the employed protection groups in the invention should be chosen in a manner to be compatible with the desired reaction conditions for all subsequent steps. All protection and deprotection reactions used in all above- and hereinafter-described transformations are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

Compounds of the formula II can be obtained by heating 3-aminopyrazole with a 2-oxo succinic acid derivative of formula IIa (or a tautomer and/or salt thereof) in the presence of an acid, such as aqueous hydrochloric acid or acetic acid or trifluoro acetic acid at temperatures from about 20° C. to about 120° C. The reaction can be carried out in neat conditions or in a suitable inert solvent. The reaction time is generally from 30 min to 48 h, preferably from 30 min to 16 h, depending on the composition of the mixture and the chosen temperature range. Depending on the solvents and conditions applied the preferred regioisomer of formula II can be easily isolated by precipitation from the reaction mixture.

Compounds of the formula III are obtained by reacting compounds of the formula II with a chlorinating agent such as phosphorous oxychloride. This reaction can be carried out in neat conditions or in a suitable inert solvent, for example a hydrocarbon, such as benzene or toluene, or a chlorinated hydrocarbon, such as 1,2-dichloroethane by heating at a tempearature between 50° C. to 110° C.

Subsequent iodination of compounds of the formula III to obtain compounds of the formula IV can be conducted by treatment with iodine in presence of a base such as $Na_2CO_3$, $NaHCO_3$, tBuOK in water or an inert organic solvent such as acetonitrile, dimethylformamide, tetrahydrofurane and dioxane or a mixture of solvents. Preferably this iodination reaction is performed with iodine in a saturated sodium hydrogencarbonate aqueous solution at room tempearature for 1 to 3 days to lead to compounds of the formula IV which can be subjected to protection on pyrazole ring nitrogen with an appropriate $G^2$ using conventional chemistry well known to those skilled in the art to give compounds of the formula V. If $G^2$ is a cyclic ether protecting group (e.g., a tetrahdropyran group), such groups may be applied and subsequently removed under known conditions. Such cyclic ethers may be attached to nitrogen moieties and hydroxyl groups via their enol ethers (e.g., 3,4-dihydro-2H-pyran) in the presence of a suitable acid (e.g., p-toluenesulfonic acid monohydrate or methanesulfonic acid), and solvent (e.g., dichloromethane). After functionalization of the C-3 position with iodine, and protection of the pyrazole ring nitrogen with a suitable protecting group $G^2$, the C-3 position of the pyrazole ring can be elaborated to a desired vinylic $R^1$ group through a Suzuki-type or Heck-type reaction using the appropriate catalyst, ligand, and vinyl aryl species to obtain a compound of formula VII.

A Suzuki-type reaction between compounds of the formula V with compounds of the formula VI wherein $G^3$ is a boronic acid or a boronic ester or cyclic boronic ester, is carried out in the presence of catalytic palladium compound, for example a palladium(II) salt such as palladium(II) acetate or palladium (II) chloride, which can be employed in the presence of a phosphine such as tricyclohexylphosphine or triphenylphosphine, or a palladium complex such as tetrakis(triphenylphosphine)palladium(0), palladium(0) bis(tri-tert-butylphosphine) or bis(triphenylphosphine)palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 110° C. The reaction time is generally from 30 min to 24 h, preferably from 30 min to 16 h, depending on the composition of the mixture and the chosen temperature range.

Depending on the chosen reaction conditions to carry out the Suzuki-type coupling reaction, an in situ deprotection of the carboxylic group of compounds of the formula VII can occur to give directly compounds of the formula VIII. If the $G^1$ protecting group is preserved in the chosen Suzuki conditions, a subsequent deprotection of the carboxylic group, preferably in basic media (e.g., aqueous sodium hydroxide) allow the transformation of compounds of the formula VII into compounds of the formula VIII.

Alternatively the vinylic linkage can be installed through a Heck-type reaction by heating compounds of the formula V with compounds of the formula VI wherein $G^3$ is a hydrogen in the presence of catalyst such as palladium(II) acetate, a ligand such as tri-o-tolylphosphine, a suitable base such as triethylamine or N,N-diisopropylethyl-amine, and a solvent such as acetonitrile or DMF to provide compounds of the formula VII. Subsequent removal of $G^1$ protecting group as described above affords compounds of the formula VIIII.

The reaction of the compounds of the formula VIII with an amine of the formula IX to form an amide of the formula X is generally performed in the presence of activating agents, such as CDI, DCC, EDC, HOAt, HOBt, HATU, TOTU, TBTU, BEP or combinations thereof, and optionally an additional base, such as TEA, DIPEA or N-methylmorpholine in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyrrolidinone or a in mixture of solvents. The reaction temperature in this case is generally from 30° C. to 200° C., preferably from −20° C. to 80° C., more preferably from 0° C. to 20° C. The reaction time is generally from 15 min to 6 days, preferably from 15 min to 16 h, depending on the composition of the mixture and the chosen temperature range. The acids of formula VIII can be subjected to the reaction in form of their salts, for example their sodium salts. They can also be transformed into an activated derivative prior to the coupling with the amine, for example into an acid chloride or an acid anhydride by standard transformations. The amines of formula IX can be subjected to the reaction in form of their salts, for example as hydrochloride or triflate salts, in which case usually an additional equivalent of the base is added to the reaction.

The reaction of the compound of the formula X with compounds of the formula XI to a compound of formula XII is a Suzuki-type reaction and is generally carried out as already described above in the presence of catalytic palladium compound, for example a palladium(II) salt such as palladium(II) acetate or palladium(II) chloride, which can be employed in the presence of a phosphine such as tricyclehexylphosphine or triphenylphosphine, or a palladium complex such as tetrakis(triphenylphosphine)palladium(0), palladium(0) bis(tri-tert-butylphosphin) or bis(triphenylphosphine)palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 120° C. The reaction time is generally from 30 min to 48 h, preferably from 30 min to 16 h, depending on the composition of the mixture and the chosen temperature range.

A compound of formula XII can be transformed into a compound of formula I in one step or in several steps depending of the meaning of the groups $G^2$, $G^4$, $R^{4a}$ and $R^{5a}$. If the groups $R^{4a}$ and/or $R^{5a}$ contain or if the groups $G^2$ and/or $G^4$ consist of protecting groups that can be cleaved by hydrogenation, e.g. a benzyl group or a 4-methoxybenzyl group, one step in the transformation of a compound of formula Ia to a compound of formula I can be a catalytic hydrogenation or a transfer hydrogenation. If the groups $R^{4a}$ and/or $R^{5a}$ contain or if the groups $G^2$ and/or $G^4$ consist of protecting groups that can be cleaved by treatment with acid, e.g. a 2-tetrahydropyranyl group, trimethylsilylethoxymethyl-group, a trialkylsilyl-group such as tert-butyldimethylsilyl-group, a 4-methoxybenzyl group, a 2,4-dimethoxybenzyl group or a tert-butoxycarbonyl group, one step in the transformation of a compound of formula XII to a compound of formula I can be an acidic deprotection. If the groups $R^{4a}$ and/or $R^{5a}$ contain or if the groups $G^2$ and/or $G^4$ consist of protecting groups that can be cleaved by treatment with a suitable fluoride source, for example tetrabutylammomium fluoride, e.g. a 2-trimethylsilylethoxymethyl-group, a trialkylsilyl-group such as tert-butyldimethylsilyl-group, one step in the transformation of a compound of formula XII to a compound of formula I can be an deprotection with a suitable fluoride source. All deprotection reactions used in the above-described transformation of compounds of the formula XII, in which the groups $R^{4a}$ and/or $R^{5a}$ contain or in which the groups $G^2$ and/or $G^4$ consist of protecting groups, to compounds of formula I are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

A transformation of a compound of formula XII, in which the groups $R^{4a}$ and/or $R^{5a}$ are precursors to the groups $R^4$ and/or $R^5$ into a compound of formula I can also include a functionalization or modification of contained functional groups according to standard procedures, for example by esterification, amidation, hydrolysis, etherification, alkylation, acylation, sulfonylation, reduction, oxidation, conversion into salts, and others. For example, a hydroxy group, which may be obtained from a protected hydroxy group by deprotection, can be esterified to give a carboxylic acid ester or a sulfonic acid ester, or etherified. Etherifications of hydroxy groups can favorably be performed by alkylation with the respective halogen compound, for example a bromide or iodide, in the presence of a base, for example an alkaline metal carbonate such potassium carbonate or cesium carbonate in an inert solvent, for example an amide like dimethylformamide or N-methylpyrrolidinone or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group, which may be obtained from a protected hydroxy group by deprotection, can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with a carboxylic acid in the presence of activating agents, such as CDI, DCC, EDC, HOAt, HOBt, HATU, TOTU, TBTU, BEP or combinations thereof, or for carbamoylation, for example by reaction with an isocyanate. A carboxylic ester group can be hydrolyzed under acidic or basic conditions to give a carboxylic acid. A carboxylic acid group can be activated or converted into a reactive derivative as mentioned afore and reacted with an alcohol or an amine or ammonia to give an ester or amide. A primary amide can be dehydrated to give a nitrile. A sulfur atom, for example in an alkyl-S— group or in a heterocyclic ring, can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example by means of a complex hydride such as lithium aluminium hydride, lithium borohydride or sodium borohydride. All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York.

Scheme 2 shows a second process of preparing compounds of the formula I starting from a compound of the formula V

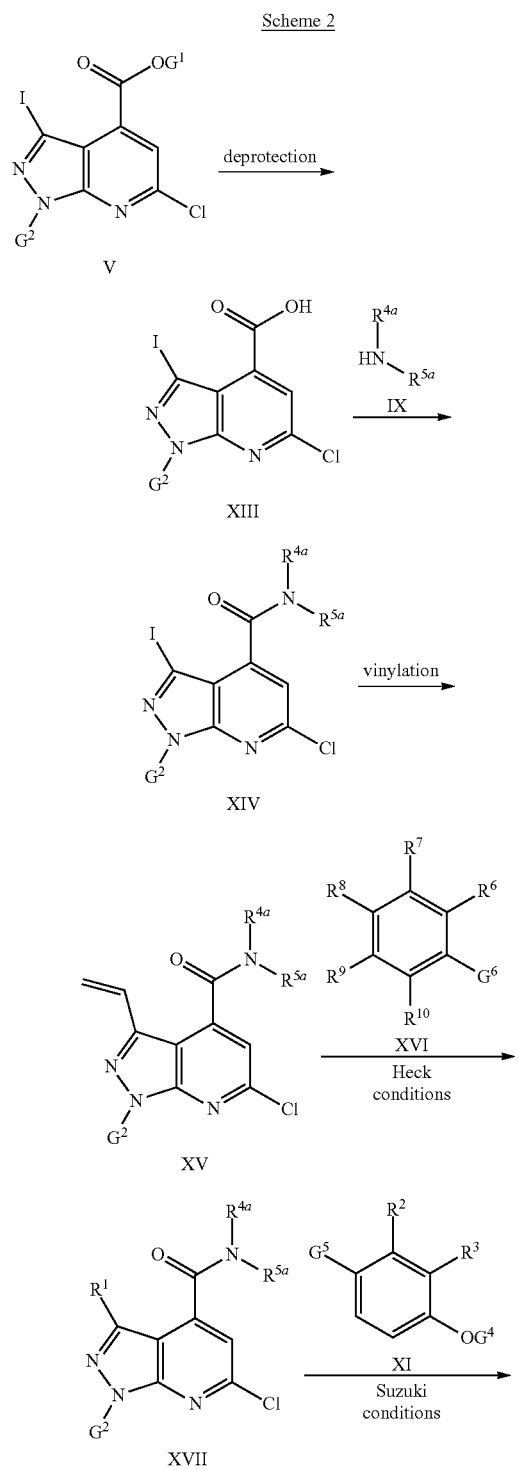

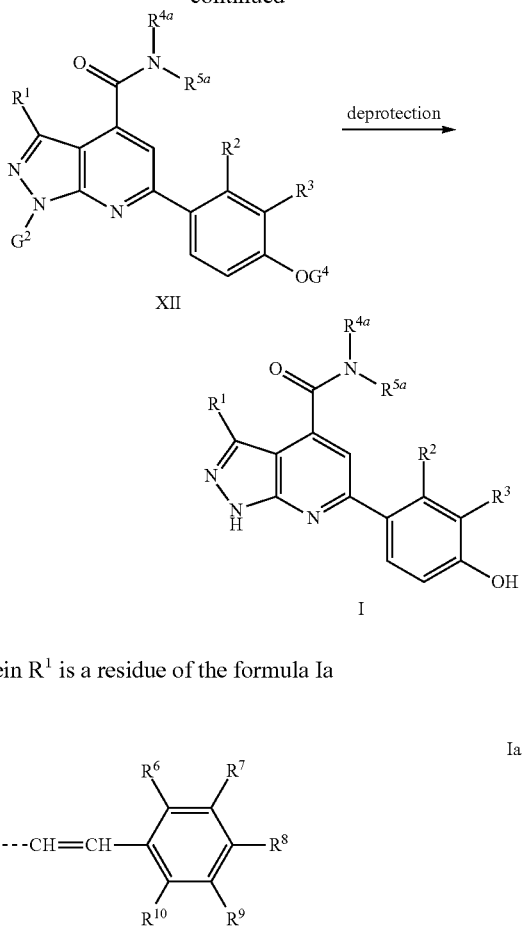

wherein $R^1$ is a residue of the formula Ia and the groups $R^2$, $R^3$, $R^4$, $R^5$, $R^6$, $R^7$, $R^8$ $R^9$ and $R^{10}$ in the compounds of the formulae X1, XII, XVI and XVII are defined as above in the compounds of the formula I.

The groups $R^{4a}$ and $R^{5a}$ in the compounds of formulae IX, XII, XIV, XV and XVII are, independently of each other, either defined as the groups $R^4$ and $R^5$ in formula I, or they are precursors of the groups $R^4$ and $R^5$ in formula I, they can for example contain functional groups in protected form or functional groups which can be converted to obtain the final groups $R^4$ and $R^5$. The group $G^1$ in the compounds of formula V is a protecting group for a carboxylic acid, such as, for example methyl, ethyl, propyl, tert-butyl or benzyl, preferably methyl or ethyl. The group $G^2$ in the compounds of formulae V, XII, XIII, XIV, XV and XVII is defined as a protecting group for a pyrazole nitrogen, such as, for example, a 2-tetrahydropyranyl-group, a trimethylsilylethoxymethyl-group, a benzyl group, a 4-methoxybenzyl, a 2,5-dimethoxybenzyl group, a trialkylsilyl-group such as tert-butyldimethylsilyl-group. The group $G^4$ in the compounds of formulae XI and XII is defined as a hydrogen or a protecting group for a phenolic hydroxyl group, such as, for example, a trialkylsilyl-group such as tert-butyldimethylsilyl-group, a 2-tetrahydropyranyl-group, a benzyl group, a 4-methoxybenzyl or a 2,5-dimethoxybenzyl group. The group $G^5$ in the compounds of the formula XI is a boronic acid or a boronic ester or cyclic boronic ester. The group $G^6$ in the compound of formula XVI is a leaving group, that can be replaced in a Heck-type reaction, such as a halide, e.g. iodide, bromide or chloride or as a sulfonate, e.g. a trifluoromethanesulfonate.

Compounds of the formula XIII are obtained by submitting compounds of the formula V to carboxylic acid deprotection for example in aqueous sodium hydroxide. Subsequent reaction of the compounds of the formula XIII with an amine of the formula IX form an amide of the formula XIV is generally performed in the presence of activating agents, such as CDI, DCC, EDC, HOAt, HOBt, HATU, TOTU, TBTU, BEP or combinations thereof, and optionally an additional base, such as TEA, DIPEA or N-methylmorpholine in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyrrolidinone or a in mixture of solvents. The reaction temperature in this case is generally from 30° C. to 200° C., preferably from −20° C. to 80° C., more preferably from 0° C. to 20° C. The reaction time is generally from 15 min to 6 days, preferably from 15 min to 16 h, depending on the composition of the mixture and the chosen temperature range. The acids of formula XIII can be subjected to the reaction in form of their salts, for example their sodium salts. They can also be transformed into an activated derivative prior to the coupling with the amine, for example into an acid chloride or an acid anhydride by standard transformations. The amines of formula IX can be subjected to the reaction in form of their salts, for example as hydrochloride or triflate salts, in which case usually an additional equivalent of the base is added to the reaction.

Subsequently, the C-3 position of the pyrazole ring can be elaborated to a desired vinyl group to lead to compounds of the formula XV by treatment of compounds of the formula XIV with a suitable $CH_2=CH$-organometallic reagent such as a $CH_2=CH$-tin reagent, for example tributyl(vinyl)stannane, or a $CH_2=CH$-boron reagent, for example potassium vinyltrifluoroborate, and a suitable catalyst, for example a palladium complex such as tetrakis(triphenylphosphine)palladium(0), or bis(triphenylphosphine)palladium(II) chloride, or (diphenyphosphinoferrocene)palladium(II) chloride in a suitable organic solvent such as tetrahydrofurane, dioxane, N,N-dimethylformamide, N-methylpyrrolidinone or a mixture of solvents, at temperatures from about 20° C. to about 120° C., preferably in presence of a base when using a $CH_2=CH$-boron reagent such as potassium vinyltrifluoroborate, for example a tertiary amine, such as triethylamine, or N,N-ethyldiisopropylamine. A Heck-type reaction is conducted by heating compounds of the formula XV with compounds of the formula XVI in the presence of catalyst such as palladium(II) acetate, a ligand such as tri-o-tolylphosphine, a suitable base such as triethylamine or N,N-diisopropylethylamine, and a solvent such as acetonitrile or dimethylformamide to provide compounds of the formula XII. The reaction of the compound of the formula XVII with compounds of the formula XI to a compound of formula XII is a Suzuki-type reaction and is generally carried out as already described above in the presence of catalytic palladium compound, for example a palladium(II) salt such as palladium(II) acetate or palladium(II) chloride, which can be employed in the presence of a phosphine such as tricyclohexylphosphine or triphenylphosphine, or a palladium complex such as tetrakis(triphenylphosphine)palladium(0), palladium(0) bis(tri-tert-butylphosphin) or bis(triphenylphosphine)palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 120° C. The reaction time is generally from 30 min to 48 h, preferably from 30 min to 16 h, depending on the composition of the mixture and the chosen temperature range. Compounds of the formula XII can be trans-formed into compounds of the formula I in one or several steps as already described above in the first process of the present invention (see Scheme 1).

Additionally, Schemes 3 and 4 show two examples of alternative processes that are also part of the invention where the order of the various synthetic steps shown in Scheme 2 is modified to prepare compounds of the formula I

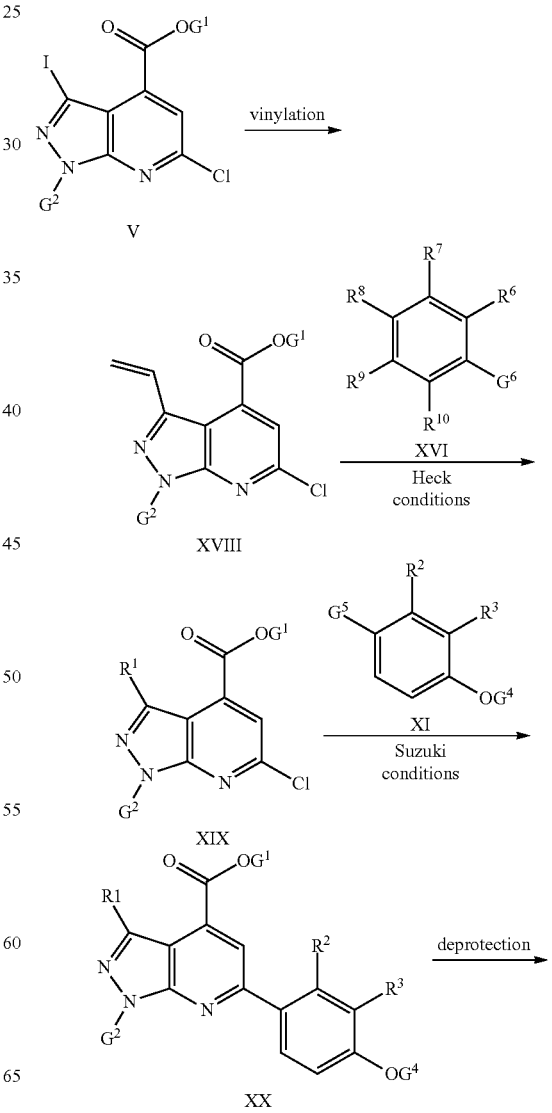

117
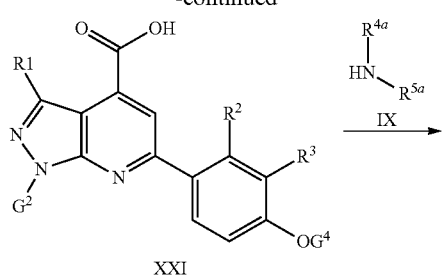
XXI
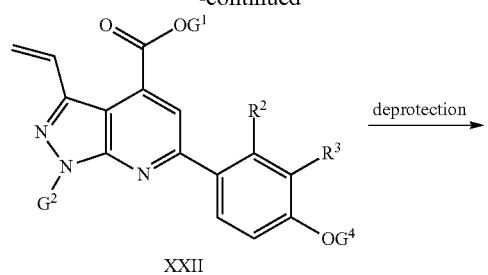
XXII
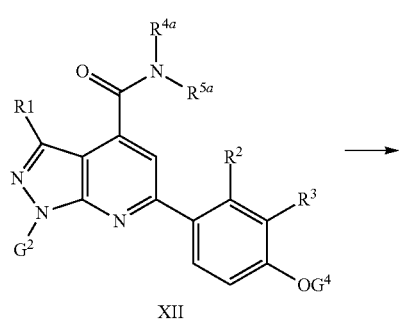
XII
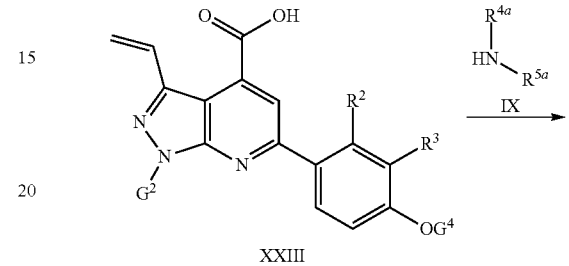
XXIII
118
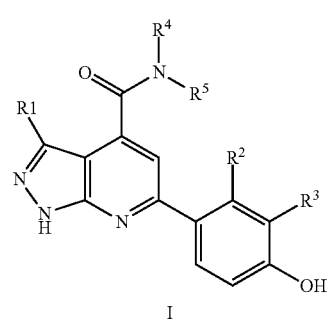
I
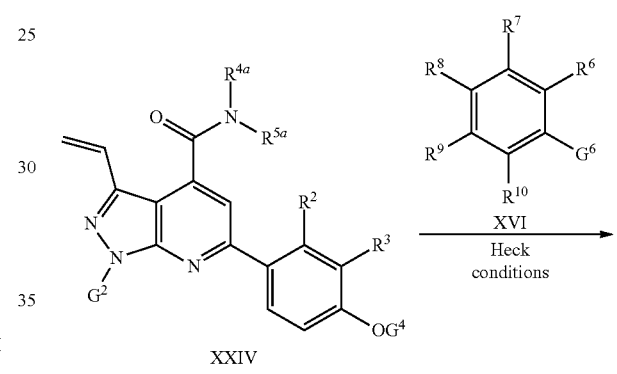
XXIV
Scheme 4
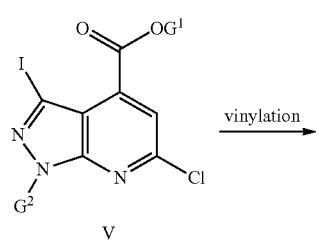
V
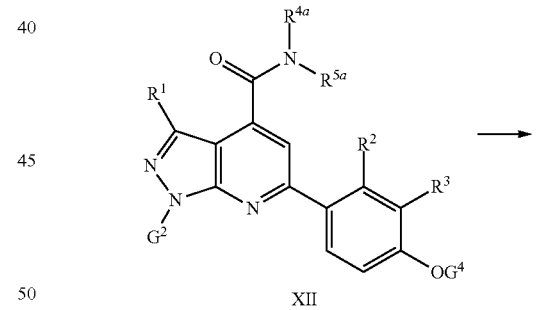
XII
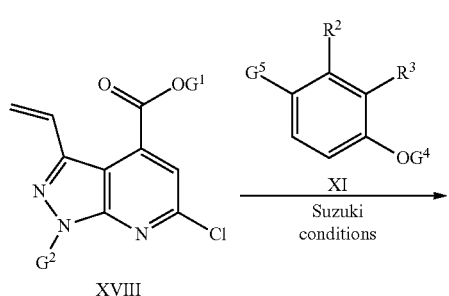
XVIII
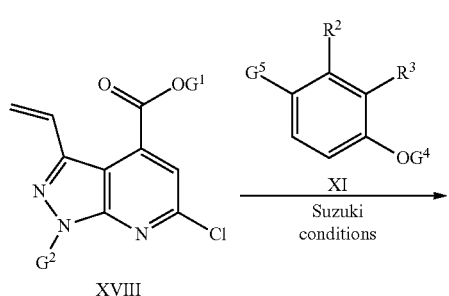
I
wherein in Scheme 3 and in Scheme 4 R¹ is a residue of the formula Ia

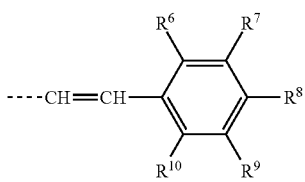

Ia and the groups $R^2$, $R^3$, $R^4$, $R^5$, $R^6$, $R^7$, $R^8$ $R^9$ and $R^{10}$ in the compounds of formulae XI, XII, XVI, XIX, XX, XXI, XXII, XXIII and XXIV are defined as above in the compounds of the formula I. The groups $R^{4a}$ and $R^{5a}$ in the compounds of formulae IX, XII and XXIII are, independently of each other, either defined as the groups $R^4$ and $R^5$ in formula I, or they are precursors of the groups $R^4$ and $R^5$ in formula I, they can for example contain functional groups in protected form or functional groups which can be converted to obtain the final groups $R^4$ and $R^5$. The group $G^1$ in the compounds of formulae V, XVIII, XIX, XX and XXII is a protecting group for a carboxylic acid, such as, for example methyl, ethyl, propyl, tert-butyl or benzyl, preferably methyl or ethyl. The group $G^2$ in the compounds of formulae V, XII, XVIII, XIX, XX, XXI, XXII, XXIII and XXIV is defined as a protecting group for a pyrazole nitrogen, such as, for example, a 2-tetrahydropyranyl-group, a trimethylsilylethoxymethyl-group, a benzyl group, a 4-methoxybenzyl, a 2,5-dimethoxybenzyl group, a trialkylsilyl-group such as tert-butyldimethylsilyl-group. The group $G^4$ in the compounds of formulae XI, XII, XX, XXI, XXII, XXIII and XIV is defined as a hydrogen or a protecting group for a phenolic hydroxyl group, such as, for example, a trialkylsilyl-group such as tert-butyldimethylsilyl-group, a 2-tetrahydropyranyl-group, a benzyl group, a 4-methoxybenzyl or a 2,5-dimethoxybenzyl group. The group $G^5$ in the compounds of the formula XI is a boronic acid or a boronic ester or cyclic boronic ester. The group $G^6$ in the compound of formula XVI is a leaving group, that can be replaced in a Heck-type reaction, such as a halide, e.g. iodide, bromide or chloride or as a sulfonate, e.g. a trifluoromethanesulfonate.

As depicted in Scheme 3 and using procedures similar to those described in the previous process, compounds of the formula V can undergo a direct vinylation at C-3 position to give compounds of the formula XVIII followed by a Heck-type reaction with a suitable compound of the formula XVI lead to compounds of the formula XIX. Using procedures previously presented in the invention, a Suzuki-type reaction with a suitable compound of the formula XI affords compounds of the formula XX which undergo deprotection of the carboxylic acid group to give compounds of the formula XXI which are transformed to amides of formula XII by coupling with amines of the formula IX. Compounds of the formula XII can be transformed into compounds of the formula I in one or several steps as already described above in the first process of the present invention (see Scheme 1).

As depicted in Scheme 4 and using procedures described previously in the invention, compounds of the formula XVIII obtained through vinylation of V can be submitted to a Suzuki-type reaction with a compound of the formula XI to give compounds of the formula XXII. Subsequent cleavage of $G^2$ protective group to obtain compounds of formula XXIII is followed by coupling with an amine of the formula IX to afford amides of the formula XXIV. Subsequent Heck-type reaction with a compound of the formula XVI give compounds of the formula XII which are subsequently transformed to the desired compounds of the formula I in one or several steps as described in the first process of the present invention (see Scheme 1).

As another part of the invention, compounds of the formula I wherein $R^1$ is ethylene-phenyl, wherein phenyl is unsubstituted or substituted by one or two identical or different substituents selected from F, Cl, $CH_3$, $O-CH_3$, $CF_3$, $O-CF_3$, CN, $SO_2CH_3$, $CO-CH_3$, and $CO-N((CH_3)_2$ can be obtained in one step by reduction, for example by catalytic hydrogenation, of the corresponding vinylic compounds of the formula I which can be prepared following the synthetic sequences outlined in Schemes 1, 2, 3 and 4.

As another part of the invention, Scheme 5 shows a process of preparing compounds of the formula I

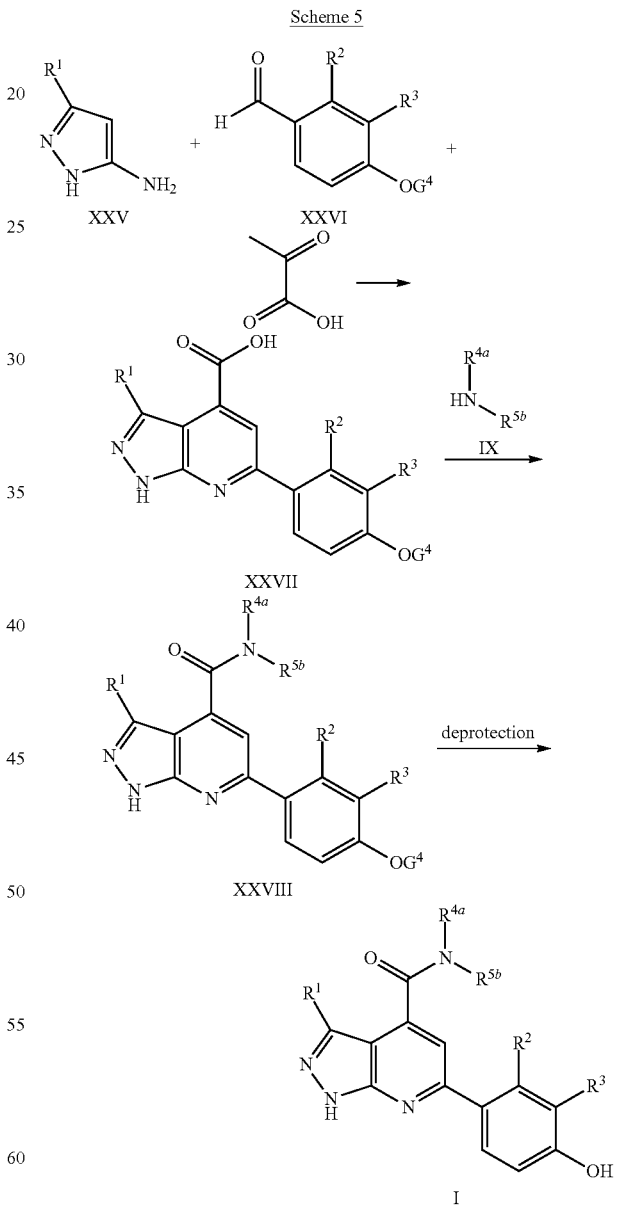

wherein $R^1$ is 2-phenylcyclopropyl, wherein phenyl is unsubstituted or substituted by one or two identical or different substituents selected from F, Cl, $CH_3$, $O-CH_3$, $CF_3$, $O-CF_3$, CN, $SO_2CH_3$, $CO-CH_3$, and $CO-N((CH_3)_2$, and the groups $R^2$, $R^3$ in the compounds of formulae XXVI, XXVII and XXVIII are defined as in the compounds of the formula I. The groups $R^{4a}$ and $R^{5a}$ in the compounds of formulae IX and XXVIII are, independently of each other, either defined as the groups $R^4$ and $R^5$ in formula I, or they are precursors of the groups $R^4$ and $R^5$ in formula I, they can for example contain functional groups in protected form or functional groups which can be converted to obtain the final groups $R^4$ and $R^5$. The group $G^4$ in the compounds of formulae XXVI, XXVII and XXVIII are defined as a hydrogen or a protecting group for a phenolic hydroxyl group, such as, for example, a trialkylsilyl-group such as tert-butyldimethylsilyl-group, a 2-tetrahydropyranyl-group, a benzyl group, a 4-methoxybenzyl or a 2,5-dimethoxybenzyl group.

The reaction of an aminopyrazole compound of the formula XXV (prepared as described in WO2008021924) with a benzaldehyde of the formula XXVI and pyruvic acid is conducted in the presence of acids, preferably at reflux in glacial acetic acid. Depending on the solvents and conditions applied the preferred regioisomer of formula XXVII can be easily isolated by precipitation from the reaction mixture. A compound of formula XXVII is transformed to amide of the formula XXVIII by coupling with an amine of formula IX using a coupling procedure as described previously in Scheme 1 to transform compounds of the formula VIII into compounds of the formula XII.

A compound of the formula XXVIII can already be a compound of formula I, if $G^4$ is H and if $R^{4a}$ is $R^4$ and $R^{5a}$ is $R^5$. If a compound of formula XXVIII is not already a compound of formula I, it can be transformed into a compound of formula I in one step or in several steps depending of the meaning of the groups $G^4$, $R^{4a}$ and $R^{5a}$. If the groups $R^{4a}$ and/or $R^{5a}$ contain or if the group $G^4$ consist of a protecting group that can be cleaved by hydrogenation, e.g. a benzyl group or a 4-methoxybenzyl group, one step in the transformation of a compound of formula XXVIII to a compound of formula I can be a catalytic hydrogenation or a transfer hydrogenation. If the groups $R^{4a}$ and/or $R^{5a}$ contain or if the group $G^4$ consist of a protecting group that can be cleaved by treatment with acid, e.g. a 2-tetrahydropyranyl group, a trialkylsilyl-group such as tert-butyldimethylsilyl-group, a 4-methoxybenzyl group, a 2,4-dimethoxybenzyl group or a tert-butoxycarbonyl group, one step in the transformation of a compound of formula XXVII to a compound of formula I can be an acidic deprotection. If the groups $R^{4a}$ and/or $R^{5a}$ contain or if the group $G^4$ consist of protecting group that can be cleaved by treatment with a suitable fluoride source, for example tetrabutylammonium fluoride, e.g. a trialkylsilyl-group such as tert-butyldimethylsilyl-group, one step in the transformation of a compound of formula XXVII to a compound of formula I can be an deprotection with a suitable fluoride source. All deprotection reactions used in the above-described transformations of compounds of the formula XII, in which the groups $R^{4a}$ and/or $R^{5a}$ contain or in which the group $G^4$ consist of protecting groups, to compounds of formula I are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

As another part of the invention, Scheme 6 shows a process of preparing compounds of the formula I

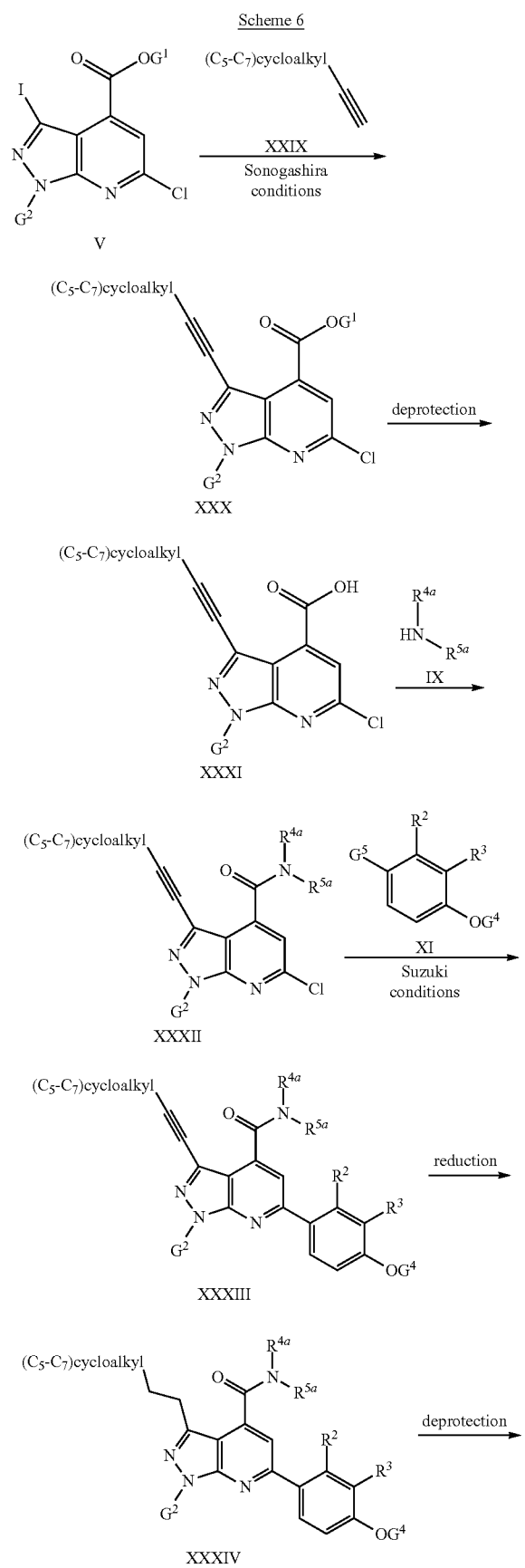

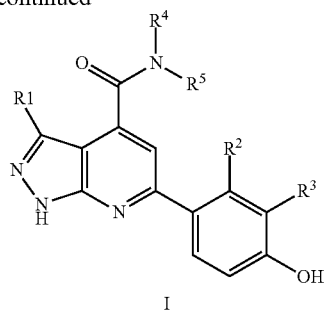

wherein $R^1$ is ethylene-($C_5$-$C_7$)cycloalkyl, and the groups $R^2$ and $R^3$ in the compounds of formulae XI, XXXIII and XXXIV are defined as above in the compounds of the formula I. The groups $R^{4a}$ and $R^{5a}$ in the compounds of formulae IX, XXXII, XXXIII and XXXIV are, independently of each other, either defined as the groups $R^4$ and $R^5$ in formula I, or they are precursors of the groups $R^4$ and $R^5$ in formula I, they can for example contain functional groups in protected form or functional groups which can be converted to obtain the final groups $R^4$ and $R^5$. The group $G^1$ in the compounds of formulae V and XXX is a protecting group for a carboxylic acid, such as, for example methyl, ethyl, propyl, tert-butyl or benzyl, preferably methyl or ethyl. The group $G^2$ in the compounds of formulae V, XXX, XXXI, XXXII, XXXIII and XXXIV is defined as a protecting group for a pyrazole nitrogen, such as, for example, a 2-tetrahydropyranyl-group, a trimethylsilylethoxymethyl-group, a benzyl group, a 4-methoxybenzyl, a 2,5-dimethoxybenzyl group, a trialkylsilyl-group such as tert-butyldimethylsilyl-group. The group $G^4$ in the compounds of formulae XI, XXXIII and XXXIV is defined as a hydrogen or a protecting group for a phenolic hydroxyl group, such as, for example, a trialkylsilyl-group such as tert-butyldimethylsilyl-group, a 2-tetrahydropyranyl-group, a benzyl group, a 4-methoxybenzyl or a 2,5-dimethoxybenzyl group. The group $G^5$ in the compounds of the formula XI is a boronic acid or a boronic ester or cyclic boronic ester. The alkyne linkage of compounds of the formula XXX can be installed under typical Sonogashira reaction conditions by heating a compound of the formula V with an oalkyne derivative of the formula XXIX in the presence of catalytic palladium compound, for example a palladium complex such as tetrakis(triphenylphosphine)palladium(0), and favourably in the presence of a base, for example a tertiary amine, such as triethylamine, and favourably in the presence of a copper (I) halide, for example copper(I) iodide, in an inert solvent, for example an ether, such as THF, dioxane or an amide, such as N,N-dimethylformamide or a mixture of solvents, at temperatures from about 20° C. to about 200° C., for example at temperatures from about 20° C. to about 110° C. The reaction time is generally from 30 min to 24 h, preferably from min to 16 h, depending on the composition of the mixture and the chosen temperature range. Subsequent removal of $G^1$ protecting group preferably under basic conditions (e.g., aqueous sodium hydroxyde) affords compounds of the formula XXXI which are converted to amides of the formula XXXII by coupling with amines of the formula IX followed by a typical Suzuki-type reaction with compounds of the formula XI to afford compounds of the formula XXXIII by using conditions described above to transform compounds of the formula X to compounds of the formula XII in the first process of the present invention (see Scheme 1). Compounds of the formula XXXIII are transformed to compounds of the formula XXXIV through reduction, for example catalytic hydrogenation in presence of a palladium compound. A compound of formula XXXIV can be transformed into a compound of formula I in one step or in several steps depending of the meaning of the groups $G^2$, $G^4$, $R^{4a}$ and $R^{5a}$. If the groups $R^{4a}$ and/or $R^{5a}$ contain or if the groups $G^2$ and/or $G^4$ consist of protecting groups that can be cleaved by hydrogenation, e.g. a benzyl group or a 4-methoxybenzyl group, one step in the transformation of a compound of formula Ia to a compound of formula I can be a catalytic hydrogenation or a transfer hydrogenation. If the groups $R^{4a}$ and/or $R^{5a}$ contain or if the groups $G^2$ and/or $G^4$ consist of protecting groups that can be cleaved by treatment with acid, e.g. a 2-tetrahydropyranyl group, trimethylsilylethoxymethyl-group, a trialkylsilyl-group such as tert-butyldimethylsilyl-group, a 4-methoxybenzyl group, a 2,4-dimethoxybenzyl group or a tert-butoxycarbonyl group, one step in the transformation of a compound of formula XII to a compound of formula I can be an acidic deprotection. If the groups $R^{4a}$ and/or $R^{5a}$ contain or if the groups $G^2$ and/or $G^4$ consist of protecting groups that can be cleaved by treatment with a suitable fluoride source, for example tetrabutylammomium fluoride, e.g. a 2-trimethylsilylethoxymethyl-group, a trialkylsilyl-group such as tert-butyldimethylsilyl-group, one step in the transformation of a compound of formula XII to a compound of formula I can be an deprotection with a suitable fluoride source. All deprotection reactions used in the above-described transformation of compounds of the formula XXXIV, in which the groups $R^{4a}$ and/or $R^{5a}$ contain or in which the groups $G^2$ and/or $G^4$ consist of protecting groups, to compounds of formula I are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

A another part of the invention, the compounds of the formula I, II, III, IV, XXVII and XXVIII may also be present in another tautomeric form as 2H-pyrazolo[3,4-b]pyridine derivatives in which the mobile hydrogen atom, which in formula I, II, III, IV, XXVII and XXVIII is bonded to the ring nitrogen atom in the 1-position of the pyrazolo-[3,4-b]pyridine ring system, is bonded to the ring nitrogen atom in the 2-position of the pyrazolo[3,4-b]pyridine ring system. As far as applicable, it applies to all compounds occurring in the preparation of the compounds of the formula I that they can be present in any other tautomeric form than the one represented in their formulae. As far as applicable and unless otherwise indicated, it applies to all acidic or basic compounds occurring in the preparation of the compounds of the formula I that they can be present in form of their salts.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed into the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae II, IIa, III, IV, V, VI, VII, VIII, X, XI, XII, XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII and XXXIV wherein $R^1$, $R^2$, $R^3$, $R^4$, $R^5$, $R^{4a}$, $R^{5a}$, $G^1$, $G^2$, $G^3$, $G^4$ $G^5$ and $G^6$ are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I apply correspondingly to the said intermediates and starting compounds. Another subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such contained trifluoroacetic acid is not specified. When example compounds containing a basic group were obtained after an acidic deprotection step, they were in part obtained in the form of their acid addition salt with hydrochloric acid, depending on the details of the workup such as washing steps with bases or evaporation or lyophilization conditions. In the names of the example compounds and their structural formulae any such contained hydrochloric acid may or may not be specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the NMR characterization, the chemical shift 6 (in ppm), the number of hydrogen atoms and the multiplicity (s=singlet, d=doublet, dd=double doublet, t=triplet, dt=double triplet, q=quartet, m=multiplet; br=broad) of the peaks is given. In the MS characterization, in general the mass number (m/z) of the peak of the molecular ion M, e.g. $M^+$, or of a related ion such as the ion M+1, e.g. $[M+1]^+$, i.e. the protonated molecular ion $[M+H]^+$, which was formed depending on the ionization method used, is given. Generally, the ionization method was electrospray ionization (ESI). The LC/MS conditions used were as follows.

Method LC1:
Column: Waters Xbridge C18 4.6 mm×50 mm, 2.5 µM; flow: 1.7 ml/min; solvent A: water+0.05% trifluoroacetic acid; solvent B: acetonitrile+0.05% trifluoroacetic acid; gradient 95% A+5% B for 0.2 min, then from 95% A+5% B to 5% A+95% B in 2.2 min, then 5% A+95% B for 1.1 min; MS ionisation method: $ESI^+$.

Method LC2:
Column Waters Xbridge C18 4.6 mm×50 mm, 2.5 µM; flow: 1.3 ml/min; solvent A: water+0.1% formic acid; solvent B: acetonitrile+0.1% formic acid; gradient from 97% A+3% B to 40% A+60% B in 3.5 min, then to 2% A+98% B in 0.5 min; then 2% A+98% B for 1.0 min; then to 97% A+3% B in 0.2 min, then 97% A+3% B for 1.3 min; MS ionisation method: $ESI^+$.

Method LC3:
Column: BEH C18 2.1×50 mm; 1.7 pm; flow: 0.9 ml; solvent A: water+0.1% formic acid; solvent B: acetonitrile+ 0.08% formic acid; gradient from 95% A+5% B to 5% A+95% B in 1.1 min; then 5% A+95% B for 0.6 min; MS ionisation method: $ESI^+$.

Method LC8:
Instrument: Waters Acquity UPLC/SQD; column: BEH C18 (2.1*50 mm, 1.7 µm); 50° C.; 0.8 mL/min; solvent: A: H2O+0.1% HCO2H; solvent B: ACN+0.1% HCO2H: gradient: t=0: 5% B; t=0.05 min: 6% B; t=2.5 min: 100% B; MS ionisation method: ESI+ or ESI−.

Method LC9:
UPLC/TOF—Column Acquity BEH C18 (50×2.1 mm; 1.7 µm); 40° C.; gradient 3 min; 1.0 ml/min; solvent A: H2O+ 0.05% TFA; solvent B: ACN+0.035% TFA; gradient: T0: 98% A—T1.6 to T2.1 min: 100% B—T2.5 to T3 min: 98% A; MS ionisation method: ESI+ or ESI−.

Method LC10:
Instrument: HPLC/ZQ; column Kromasil C18 (50*2.1 mm; 3.5 µm); 40° C.; 0.8 mL/min; solvent A: CH3COONH4 5 mM+3% ACN; solvent B: ACN; gradient: T0: 100% A—T5, 5 à T7 min: 100% B—T7.1 à T10 min: 100% A; MS ionisation method: ESI+ or ESI−.

Method LC11
Instrument: HPLC/ZMD; column XBridge 4.6×30 mm, 3 µm, 1 ml/min; gradient 10 min; 1.0 ml/min; gradient A (0.1% HCO2H dans H2O)/B (0.1% HCO2H dans ACN):t=0: 5% B; t=5.5 min: 100% B; t=7 min: 100% B; MS ionisation method: ESI+ or ESI−.

List of Abbreviations
BEP 2-bromo-1-ethyl-pyridinium tetrafluoroborate
BOC tert.butoxy carbonyl
CDI N,N'-carbonyldiimidazole
DCC 1,3-dicyclohexylcarbodiimide
DCM dichloromethane DEA diethylamine
DMF N,N-dimethylformamide
EDC 1-(3-dimethylaminopropyl)-3-ethylcarbodiimide hydrochloride
EtOAc ethyl acetate
EtOH ethanol
Exp. No. Example number
h hour/s
HOAt 1-hydroxy-aza-benzotriazole
HOBt 1-hydroxy-benzotirazole
HATU O-(7-azabenzotriazol-1-yl)-N,N,N',N'-tetramethyluronium hexafluorophosphate
HPLC high pressure liquid chromatography
LC liquid chromatography
MeOH methanol
Min minutes
MS mass spectroscopy
Rt retention time
r.t. room temperature
sep. separation
TBTU [(benzotriazol-1-yloxy)-dimethylamino-methylene]-dimethyl-ammonium tetrafluoroborate
TEA triethylamine
TFA trifluoroacetic acid
THF tetrahydrofurane
TOTU O-(cyano(ethoxycarbonyl)methyleneamino)-N,N,N',N'-tetramethyluronium tetrafluoroborate

EXAMPLE 1

[3-[(E)-2-(4-Chloro-phenyl)-vinyl]-6-(4-hydroxy-phenyl)-1H-pyrazolo[3,4-b]pyridin-4-yl]-piperazin-1-yl-methanone

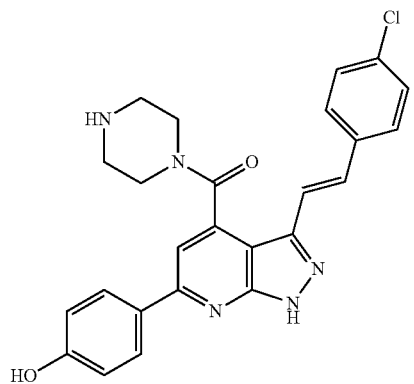 [SMILES: O=C(c1cc(-c2ccc(O)cc2)nc2[nH]nc(/C=C/c3ccc(Cl)cc3)c12)N1CCNCC1]

1.1:
6-Hydroxy-1H-pyrazolo[3,4-b]pyridine-4-carboxylic acid ethyl ester

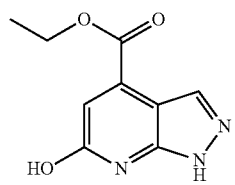

To a solution of 3-aminopyrazole (224 g, 2.7 mol) in water (1 L) were added a solution of diethyl oxalacetate sodium salt (567 g, 2.7 mol) in water (1.3 L) and then acetic acid in 4 portions (0.8 L). The reaction mixture was heated at 85° C. for 15 hours then cooled to room temperature and filtered. The precipitate was washed with water and then dried to afford the title compound as an orange solid (159 g, 28%). 1H NMR (250 MHz, DMSO): δ 1.35 (t, 3H), 4.36 (q, 2H), 6.69 (s, 1H), 8.16 (s, 1H).

1.2:
6-chloro-1H-pyrazolo[3,4-b]pyridine-4-carboxylic acid ethyl ester

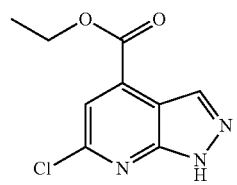

A mixture of 6-hydroxy-1H-pyrazolo[3,4-b]pyridine-4-carboxylic acid ethyl ester (116.4 g, 0.562 mol) and phosphorus oxychloride (500 mL) was heated at 110° C. for 6 hours then cooled to room temperature before being evaporated under reduced pressure. The residue was taken up in EtOAc and the precipitate filtered. The filtrate was neutralized using triethylamine (500 mL) and the resulting salt filtered. The filtrate was concentrated under vacuum and the residue subjected to silica gel column chromatography using a 9/1 mixture of toluene/EtOAc to afford the title compound as a yellow solid (26.3 g, 21%).

1H NMR (200 MHz, DMSO): δ 1.4 (t, 3H), 4.43 (q, 2H), 7.60 (s, 1H), 8.37 (s, 1H).

1.3: 6-chloro-3-iodo-1H-pyrazolo[3,4-b]pyridine-4-carboxylic acid ethyl ester

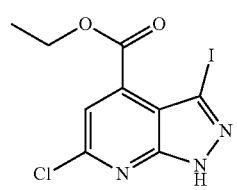 [SMILES: CCOC(=O)c1cc(Cl)nc2[nH]nc(I)c12]

In a 1 L single necked flask were charged 6-chloro-1H-pyrazolo[3,4-b]pyridine-4-carboxylic acid ethyl ester (10 g, 44.3 mmol) and dioxane (400 ml). To this resulting suspension were added a saturated solution of sodium hydrogen carbonate (0.5M, 260 ml) and iodine (11.2 g, 44.3 mmol). The reaction mixture was stirred at room temperature for 24 hours, iodine was then added (25 g, 97.5 mmol) and stirring was pursued for 48 hours. Next an aqueous sodium thiosulfate solution (0.9M) was added until complete decolouration and was poured into a solution of ice and HCl at pH=2. The mixture was filtered to afford the title compound as a yellow solid (14.7 g, 95%).

LC/MS (Method LC8): Rt=1.53 min; m/z=351 [M+H]⁺.

1.4: 6-chloro-3-iodo-1-(tetrahydro-pyran-2-yl)-1H-pyrazolo[3,4-b]pyridine-4-carboxylic acid ethyl ester

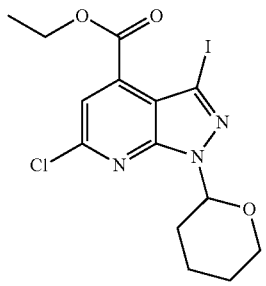 [SMILES: CCOC(=O)c1cc(Cl)nc2c1c(I)nn2C1CCCCO1]

To a solution of 6-chloro-3-iodo-1H-pyrazolo[3,4-b]pyridine-4-carboxylic acid ethyl ester (14 g, 39.8 mmol) and p-toluenesulfonic acid monohydrate (0.75 g, 3.9 mmol) in anhydrous chloroform (200 ml) at 0° C. was added dropwise 3,4-dihydro-2H-pyran (5.45 ml, 59.7 mmol). The reaction mixture was allowed to warm to room temperature, stirred overnight and concentrated under reduced pressure. The residue was subjected to silica gel column chromatography using a stepwise gradient of ethyl acetate (0-20%) in cyclohexane to afford the title compound as a yellow solid (9.4 g, 54%). LC/MS (Method LC8): Rt=2.08 min; m/z=351 [M+H-THP]$^+$.

1.5: 6-chloro-3-[(E)-2-(4-chloro-phenyl)-vinyl]-1-(tetrahydro-pyran-2-yl)-1H-pyrazolo-[3,4-b]pyridine-4-carboxylic acid

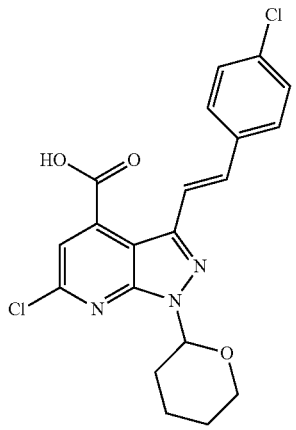 [SMILES: O=C(O)c1cc(Cl)nc2c1c(/C=C/c1ccc(Cl)cc1)nn2C1CCCCO1]

To a solution of 6-chloro-3-iodo-1-(tetrahydro-pyran-2-yl)-1H-pyrazolo[3,4-b]pyridine-4-carboxylic acid ethyl ester (2 g, 4.59 mmol) in dioxane (51 ml) were added trans-2-(4-chlorophenyl)vinylboronic acid (0.83 g, 4.59 mmol) and an aqueous solution of cesium carbonate (0.3M, 8.26 mmol). The resulting solution was degassed using argon, tetrakis(triphenylphosphine)palladium (0.26 g, 0.23 mmol) was then added and the reaction mixture was refluxed overnight. Dioxane was removed under vacuum, methylene chloride and water were added, and the mixture was acidified until pH=2. The organic layer was washed with water and the aqueous phase was extracted using methylene chloride. The resulting organic layers were combined, dried over anhydrous sodium sulfate, filtered and concentrated under reduced pressure to give the title compound (2g) as a yellow foam which was used without any further purification.

LC/MS (Method LC8): Rt=2.10 min; m/z=334 [M+H-THP]$^+$.

1.6: 4-[6-chloro-3-[(E)-2-(4-chloro-phenyl)-vinyl]-1-(tetrahydro-pyran-2-yl)-1H-pyrazolo[3,4-b]pyridine-4-carbonyl]-piperazine-1-carboxylic acid tert-butyl ester

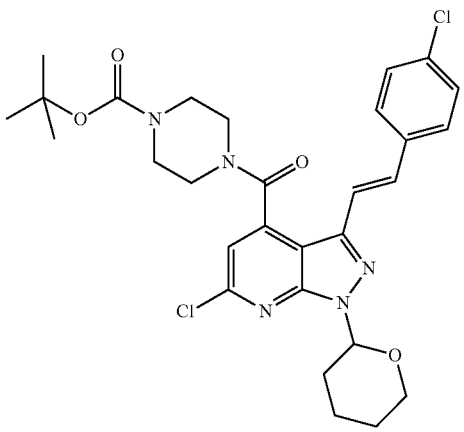 [SMILES: CC(C)(C)OC(=O)N1CCN(C(=O)c2cc(Cl)nc3c2c(/C=C/c2ccc(Cl)cc2)nn3C2CCCCO2)CC1]

To a solution of 6-chloro-3-[(E)-2-(4-chloro-phenyl)-vinyl]-1-(tetrahydro-pyran-2-yl)-1H-pyrazolo[3,4-b]pyridine-4-carboxylic acid (2 g, 4.79 mmol) in a mixture of anhydrous tetrahydrofuran (42 ml) and N,N-dimethylacetamide (10 ml) were added 1-boc-piperazine (0.98 g, 5.27 mmol), 1-hydroxybenzotriazole (0.06 g, 0.48 mmol), and N-(3-dimethylaminopropyl)-N'-ethylcarbodiimide hydrochloride (0.91 g, 4.79 mmol). The reaction mixture was stirred at room temperature for 4 hours, tetrahydrofuran was evaporated under reduced pressure, water and dichloromethane were then added. The organic phase was separated, dried over anhydrous sodium sulfate, filtered and concentrated in vacuum. The crude residue was purified on a silica gel column chromatography using a gradient of ethyl acetate (0-45%) in cyclohexane to yield the title compound as a yellow foam (1.51 g, 54%).

LC/MS (Method LC8): Rt=2.34 min; m/z=586 [M+H]$^+$.

1.7: 4-[3-[(E)-2-(4-chloro-phenyl)-vinyl]-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester

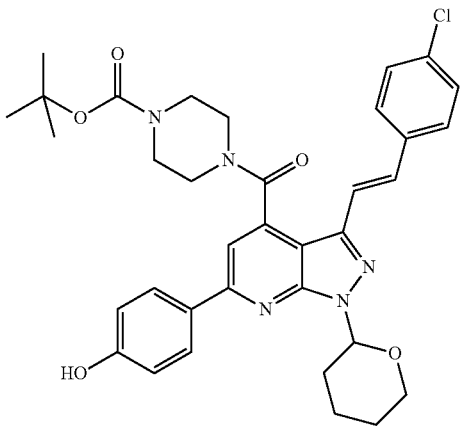 [SMILES: CC(C)(C)OC(=O)N1CCN(C(=O)c2cc(-c3ccc(O)cc3)nc3c2c(/C=C/c2ccc(Cl)cc2)nn3C2CCCCO2)CC1]

To a solution of 4-[6-chloro-3-[(E)-2-(4-chloro-phenyl)-vinyl]-1-(tetrahydro-pyran-2-yl)-1H-pyrazolo[3,4-b]pyridine-4-carbonyl]-piperazine-1-carboxylic acid tert-butyl ester (1.5 g, 2.56 mmol) in dioxane (38 ml) were added 4-hydroxyphenylboronic acid (0.39 g, 2.81 mmol) and an aqueous solution of cesium carbonate (0.3M, 4.6 mmol). The resulting solution was degassed using argon, tetrakis(triphenylphosphine)palladium (0.14 g, 0.13 mmol) was then added and the reaction mixture was refluxed for 3 hours. Solvents were removed under vacuum. The resulting crude mixture was submitted to a silica gel column chromatography using a gradient of ethyl acetate (0-45%) in cyclohexane to give the title compound (1.32 g, 80%) as a white solid.

LC/MS (Method LC8): Rt=2.25 min; m/z=644 [M+H]$^+$.

1.8: [3-[(E)-2-(4-chloro-phenyl)-vinyl]-6-(4-hydroxy-phenyl)-1H-pyrazolo[3,4-b]pyridin-4-yl]-piperazin-1-yl-methanone

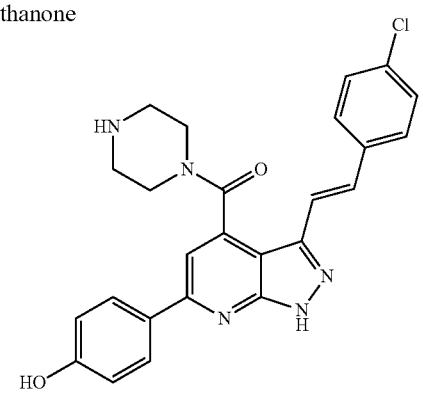

To a solution of 4-[3-[(E)-2-(4-chloro-phenyl)-vinyl]-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester (1.32 g, 2.05 mmol) in dry methanol (20 ml) was added 4N HCl in dioxane (5.1 ml, 20 mmol). The reaction mixture was heated to reflux for 30 minutes then cooled to room temperature and filtered. The precipitate was isolated and dried to afford a chlorhydrate salt of the title compound as an orange solid (0.9 g, 90%).

LC/MS (Method LC10): Rt=3.47 min; m/z=458 [M−H]$^+$.

The following examples have been prepared in a similar fashion as the synthesis for [3-[(E)-2-(4-chloro-phenyl)-vinyl]-6-(4-hydroxy-phenyl)-1H-pyrazolo[3,4-b]pyridin-4-yl]-piperazin-1-yl-methanone described immediately above. In the fifth step trans-stryrylboronic acid instead of trans-2-(4-chlorophenyl)vinylboronic acid was employed to yield 6-chloro-3-((E)-styryl)-1-(tetrahydro-pyran-2-yl)-1H-pyrazolo[3,4-b]pyridine-4-carboxylic acid (LC/MS (Method LC8): Rt=1.88 min; m/z=300.1 [M+H-THP]$^+$). This was reacted in the sixth step with the respective piperazines and the respective phenylboronic acids in the seventh step and deprotected in the eighth step:

| Exp. No. | Name | Structure | LC/MS method | m/z [M + H]+ | Rt [min] |
|---|---|---|---|---|---|
| 2 | [6-(4-Hydroxy-phenyl)-3-((E)-styryl)-1H-pyrazolo[3,4-b]pyridin-4-yl]-piperazin-1-yl-methanone | 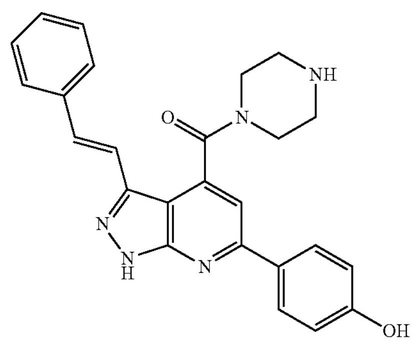 [SMILES: O=C(c1cc(-c2ccc(O)cc2)nc2[nH]nc(/C=C/c3ccccc3)c12)N1CCNCC1] | LC3 | 426.27 | 0.83 |
| 3 | (2,2-Dimethyl-piperazin-1-yl)-[6-(4-hydroxy-phenyl)-3-((E)-styryl)-1H-pyrazolo[3,4-b]pyridin-4-yl]-methanone | 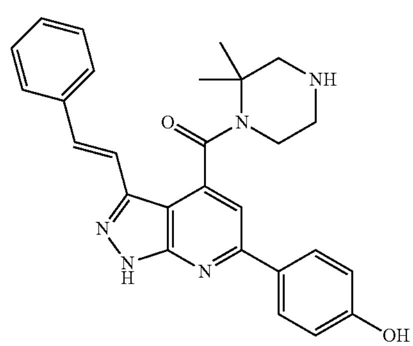 [SMILES: CC1(C)CNCCN1C(=O)c1cc(-c2ccc(O)cc2)nc2[nH]nc(/C=C/c3ccccc3)c12] | LC9 | 454 | 0.89 |

| Exp. No. | Name | Structure | LC/MS method | m/z [M + H]+ | Rt [min] |
|---|---|---|---|---|---|
| 4 | (3,3-Dimethyl-piperazin-1-yl)-[6-(4-hydroxy-phenyl)-3-((E)-styryl)-1H-pyrazolo[3,4-b]pyridin-4-yl]-methanone | 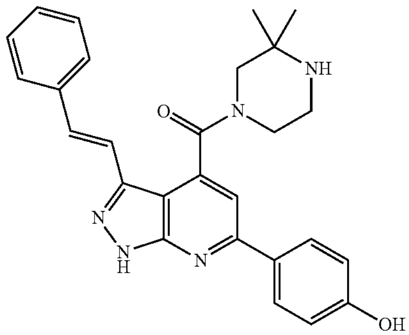 [SMILES: CC1(C)CN(C(=O)c2cc(-c3ccc(O)cc3)nc3[nH]nc(/C=C/c4ccccc4)c23)CCN1] | LC9 | 454 | 0.79 |
| 5 | [6-(4-Hydroxy-phenyl)-3-((E)-styryl)-1H-pyrazolo[3,4-b]pyridin-4-yl]-((S)-3-isobutyl-piperazin-1-yl)-methanone | 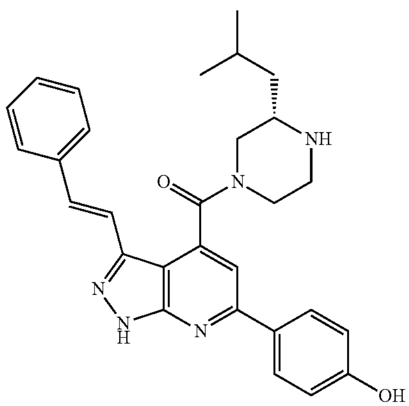 [SMILES: CC(C)C[C@H]1CN(C(=O)c2cc(-c3ccc(O)cc3)nc3[nH]nc(/C=C/c4ccccc4)c23)CCN1] | LC3 | 482.33 | 0.92 |
| 6 | [6-(4-Hydroxy-phenyl)-3-((E)-styryl)-1H-pyrazolo[3,4-b]pyridin-4-yl]-((S)-2-methyl-piperazin-1-yl)-methanone | 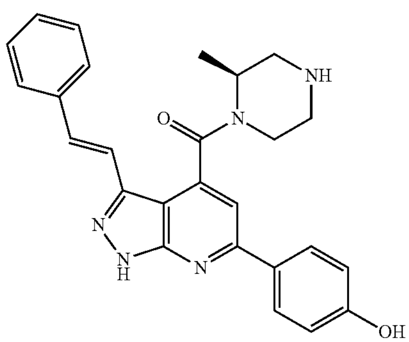 [SMILES: C[C@H]1CNCCN1C(=O)c1cc(-c2ccc(O)cc2)nc2[nH]nc(/C=C/c3ccccc3)c12] | LC3 | 440.29 | 0.85 |
| 7 | [6-(4-Hydroxy-2-methyl-phenyl)-3-((E)-styryl)-1H-pyrazolo[3,4-b]pyridin-4-yl]-piperazin-1-yl-methanone | 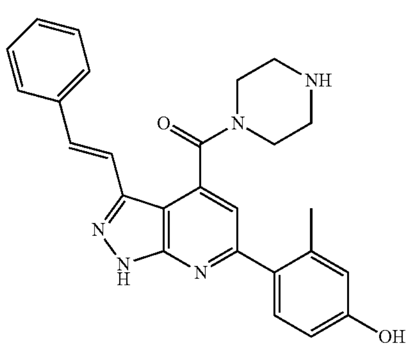 [SMILES: Cc1cc(O)ccc1-c1cc(C(=O)N2CCNCC2)c2c(/C=C/c3ccccc3)n[nH]c2n1] | LC3 | 440.27 | 0.84 |

-continued

| Exp. No. | Name | Structure | LC/MS method | m/z [M + H]+ | Rt [min] |
|---|---|---|---|---|---|
| 8 | ((2S,5R)-2,5-Dimethyl-piperazin-1-yl)-[6-(4-hydroxy-phenyl)-3-((E)-styryl)-1H-pyrazolo[3,4-b]pyridin-4-yl]-methanone | 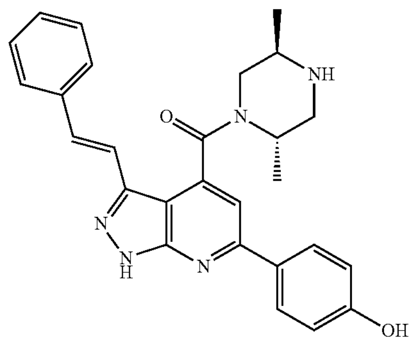 [SMILES: C[C@@H]1CN(C(=O)c2cc(-c3ccc(O)cc3)nc3[nH]nc(/C=C/c4ccccc4)c23)[C@@H](C)CN1] | LC3 | 454.28 | 0.86 |
| 9 | [6-(4-Hydroxy-3-methoxy-phenyl)-3-((E)-styryl)-1H-pyrazolo[3,4-b]pyridin-4-yl]-piperazin-1-yl-methanone | 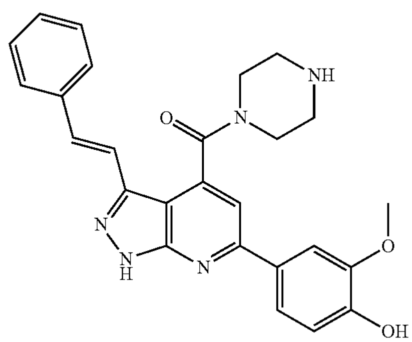 [SMILES: COc1cc(-c2cc(C(=O)N3CCNCC3)c3c(/C=C/c4ccccc4)n[nH]c3n2)ccc1O] | LC9 | 456 | 0.82 |
| 10 | ((S)-2-Ethyl-piperazin-1-yl)-[6-(4-hydroxy-phenyl)-3-((E)-styryl)-1H-pyrazolo[3,4-b]pyridin-4-yl]-methanone | 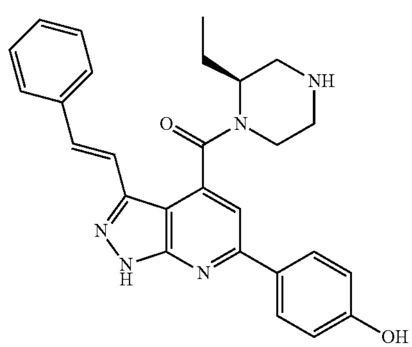 [SMILES: CC[C@H]1CNCCN1C(=O)c1cc(-c2ccc(O)cc2)nc2[nH]nc(/C=C/c3ccccc3)c12] | LC9 | 454 | 0.87 |
| 11 | [6-(2-Fluoro-4-hydroxy-phenyl)-3-((E)-styryl)-1H-pyrazolo[3,4-b]pyridin-4-yl]-((S)-2-methyl-piperazin-1-yl)-methanone | 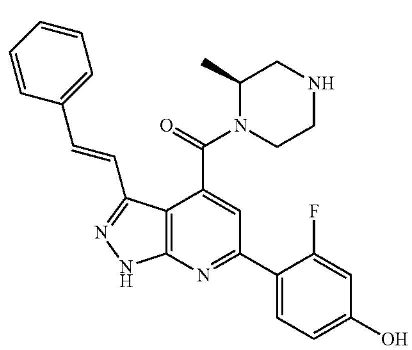 [SMILES: C[C@H]1CNCCN1C(=O)c1cc(-c2ccc(O)cc2F)nc2[nH]nc(/C=C/c3ccccc3)c12] | LC9 | 458 | 0.86 |

| Exp. No. | Name | Structure | LC/MS method | m/z [M + H]+ | Rt [min] |
|---|---|---|---|---|---|
| 12 | [6-(3-Fluoro-4-hydroxy-phenyl)-3-((E)-styryl)-1H-pyrazolo[3,4-b]pyridin-4-yl]-piperazin-1-yl-methanone | 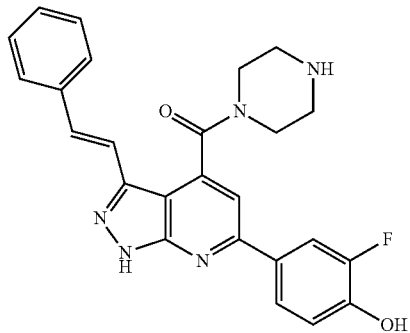 [SMILES: O=C(c1cc(-c2ccc(O)c(F)c2)nc2[nH]nc(/C=C/c3ccccc3)c12)N1CCNCC1] | LC9 | 444 | 0.88 |
| 13 | [6-(2-Chloro-4-hydroxy-phenyl)-3-((E)-styryl)-1H-pyrazolo[3,4-b]pyridin-4-yl]-piperazin-1-yl-methanone | 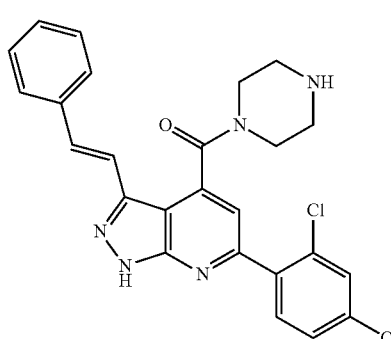 | LC9 | 460 | 0.75 |

EXAMPLE 14

[3-[(E)-2-(3-Dimethylaminomethyl-phenyl)-vinyl]-6-(4-hydroxy-phenyl)-1H-pyrazolo[3,4-b]pyridin-4-yl]-piperazin-1-yl-methanone 14.1: 6-chloro-3-iodo-1-(tetrahydro-pyran-2-yl)-1H-pyrazolo[3,4-b]pyridine-4-carboxylic acid

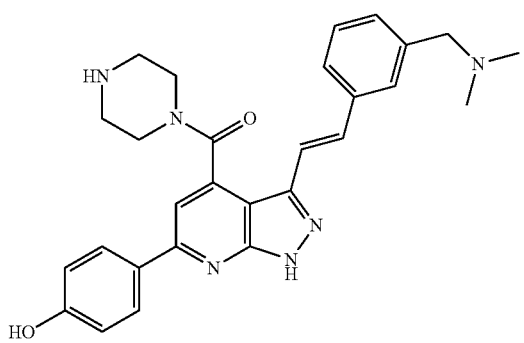 [SMILES: CN(C)Cc1cccc(/C=C/c2n[nH]c3nc(-c4ccc(O)cc4)cc(C(=O)N4CCNCC4)c23)c1]

To a solution of 6-chloro-3-iodo-1-(tetrahydro-pyran-2-yl)-1H-pyrazolo[3,4-b]pyridine-4-carboxylic acid ethyl ester (25 g, 57 mmol) in 1,4-dioxane (200 mL) was added an aqueous sodium hyroxide solution (1M, 180 mL). The reaction mixture was stirred at room temperature for 7 hours and then an aqueous HCl solution (1M, 200 mL) was carefully added. Water (140 mL) was added, and after 5 minutes of stirring the precipitate was filtered, washed with water, cyclohexane and then dried to afford the title compound as a yellow solid (17.1 g, 73%).

LC/MS (Method LC8): Rt=1.48 min; m/z=324 [M+H-THP]+.

14.2: 4-[6-chloro-3-iodo-1-(tetrahydro-pyran-2-yl)-1H-pyrazolo[3,4-b]pyridine-4-carbonyl]-piperazine-1-carboxylic acid tert-butyl ester

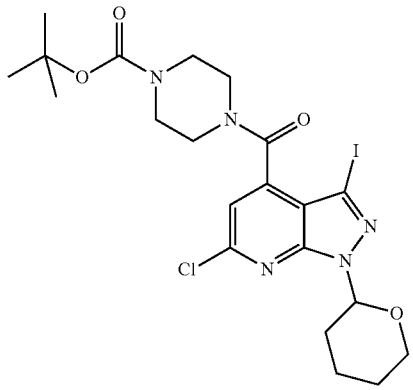 [SMILES: CC(C)(C)OC(=O)N1CCN(C(=O)c2cc(Cl)nc3c2c(I)nn3C2CCCCO2)CC1]

To a solution of 6-chloro-3-iodo-1-(tetrahydro-pyran-2-yl)-1H-pyrazolo[3,4-b]pyridine-4-carboxylic acid (17 g, 42 mmol) in a mixture of tetrahydrofuran (250 mL) and N,N-dimethylacetamide (40 mL) were added 1-boc-piperazine (8.6 g, 46 mmol), 1-hydroxybenzotriazole (0.56 g, 4.2 mmol), and N-(3-dimethylaminopropyl)-N'-ethylcarbodiimide hydrochloride (8.03 g, 42 mmol). The reaction mixture was stirred at room temperature for 20 hours and then the THF was evaporated under vacuum. An aqueous solution of bicarbonate (200 mL) was then added and the mixture stirred for 1 hour. The precipitate was filtered, washed with water, and then dried to afford the title compound as a yellow solid (24 g, 100%).

LC/MS (Method LC8): Rt=1.75 min; m/z=436 [M+H−THP−tBu]+.

14.3: 4-[6-chloro-1-(tetrahydro-pyran-2-yl)-3-vinyl-1H-pyrazolo[3,4-b]pyridine-4-carbonyl]-piperazine-1-carboxylic acid tert-butyl ester

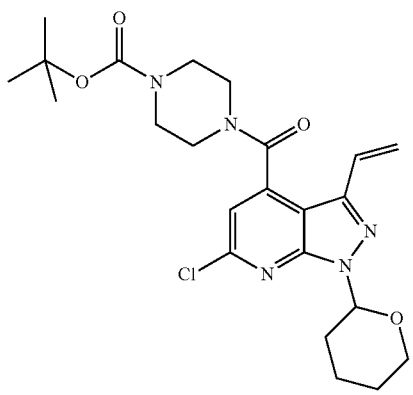 [SMILES: C=Cc1nn(C2CCCCO2)c2nc(Cl)cc(C(=O)N3CCN(C(=O)OC(C)(C)C)CC3)c12]

In a 1 L single necked flask were charged 4-[6-chloro-3-iodo-1-(tetrahydro-pyran-2-yl)-1H-pyrazolo[3,4-b]pyridine-4-carbonyl]-piperazine-1-carboxylic acid tert-butyl ester (21.3 g, 37 mmol), anhydrous tetrahydrofuran (370 ml), and tributyl(vinyl)stannane (11.9 ml, 40.7 mmol). The mixture was degassed for 15 minutes using argon, dichlorobis(triphenylphosphine)palladium (1.3 g, 1.8 mmol) was then added. The resulting solution was heated at 80° C. overnight under argon, then evaporated under reduced pressure. Ethyl acetate and a 5% aqueous potassium fluoride solution were added to the residue, the resulting precipitate was filtered. The filtrate was recovered and the two layers separated, the organic phase was washed with water, dried over anhydrous sodium sulfate, filtered and concentrated under vacuum. The crude product was purified on a silica gel column chromatography using a gradient of ethyl acetate (0-40%) in cyclohexane to afford the title compound as a brown foam (12.3 g, 70%).

LC/MS (Method LC8): Rt=1.74 min; m/z=475 [M+H]+.

14.4: (3-iodo-benzyl)-dimethyl-amine

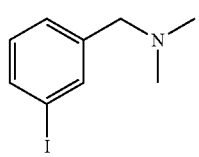

To a cold (0° C.) solution of 3-iodo-benzaldehyde (3 g, 12.9 mmol) in anhydrous dichloromethane (130 ml) were added acetic acid (1.9 ml) and N,N-dimethylacetamide. The yellow solution is stirred 10 minutes at 0° C. and sodium triacetoxyborohydride (6.85 g, 32.33 mmoles) is added by portions. The resulting mixture is stirred at room temperature for 90 minutes and evaporated to dryness under reduced pressure. Ethyl acetate and a saturated aqueous hydrogen carbonate solution were added to the residue and the two layers were separated The organic phase was washed with water, dried over anhydrous sodium sulfate, filtered and concentrated under vacuum to yield (3-iodo-benzyl)-dimethyl-amine (3.05 g, 90%) as a brown oil.

LC/MS (Method LC8): Rt=0.86 min; m/z=262 [M+H]+.

14.5: 4-[6-chloro-3-[(E)-2-(3-dimethylaminomethyl-phenyl)-vinyl]-1-(tetrahydro-pyran-2-yl)-1H-pyrazolo[3,4-b]pyridine-4-carbonyl]-piperazine-1-carboxylic acid tert-butyl ester

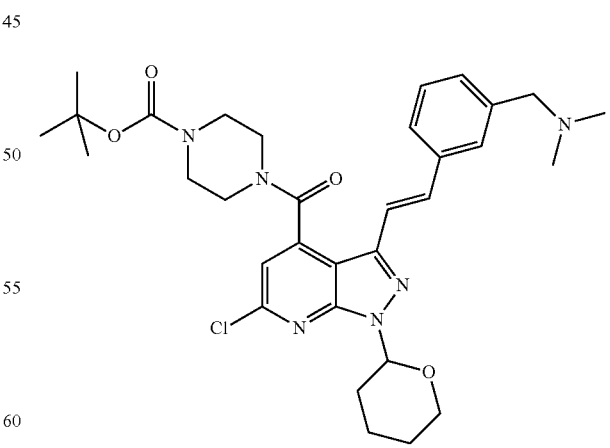

In a 250 ml round bottom flask were charged 4-[6-chloro-1-(tetrahydro-pyran-2-yl)-3-vinyl-1H-pyrazolo[3,4-b]pyridine-4-carbonyl]-piperazine-1-carboxylic acid tert-butyl ester (1.2 g, 2.52 mmol), (3-iodo-benzyl)-dimethyl-amine (1.64 g, 6.3 mmol), tetrabutylammonium bromide (0.32 g, 1 mmol), sodium hydrogen carbonate (0.53 g, 6.3 mmol) and anhydrous dimethylformamide (42 ml). The mixture was degassed during 10 minutes using argon, palladium acetate (0.05 g, 0.25 mmol) was then added. The resulting solution was heated at 100° C. under argon overnight. Dimethylformamide was eliminated under vacuum, dichloromethane and water were added to the residue, after extraction the organic layer was dried over anhydrous sodium sulfate, filtered and concentrated under reduced pressure to give the crude product. Further purification on a silica gel column chromatography using a gradient of methanol (0-5%) in dichloromethane afforded the title compound as brown solid (0.44 g, 29%).

LC/MS (Method LC8): Rt=1.17 min; m/z=609 [M+H]+.

14.6: 4-[3-[(E)-2-(3-dimethylaminomethyl-phenyl)-vinyl]-6-(4-hydroxy-phenyl)-1-(tetrahydropyran-2-yl)-1H-pyrazolo[3,4-b]pyridine-4-carbonyl]-piperazine-1-carboxylic acid tert-butyl ester

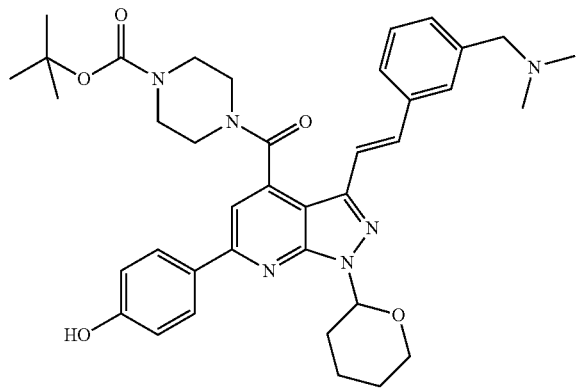 [SMILES: CN(C)Cc1cccc(/C=C/c2nn(C3CCCCO3)c3nc(-c4ccc(O)cc4)cc(C(=O)N4CCN(C(=O)OC(C)(C)C)CC4)c23)c1]

Utilizing the procedure described in example 1.7 except substituting 4-[6-chloro-3-[(E)-2-(4-chloro-phenyl)-vinyl]-1-(tetrahydro-pyran-2-yl)-1H-pyrazolo[3,4-b]pyridine-4-carbonyl]-piperazine-1-carboxylic acid tert-butyl ester with 4-[6-chloro-3-[(E)-2-(3-dimethylaminomethyl-phenyl)-vinyl]-1-(tetrahydro-pyran-2-yl)-1H-pyrazolo[3,4-b]pyridine-4-carbonyl]-piperazine-1-carboxylic acid tert-butyl ester, 4-[3-[(E)-2-(3-dimethylaminomethyl-phenyl)-vinyl]-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester was obtained (0.25 g, 52%) as a yellow solid.

LC/MS (Method LC8): Rt=1.22 min; m/z=667 [M+H]+.

14.7: [3-[(E)-2-(3-dimethylaminomethyl-phenyl)-vinyl]-6-(4-hydroxy-phenyl)-1H-pyrazolo[3,4-b]pyridin-4-yl]-piperazin-1-yl-methanone

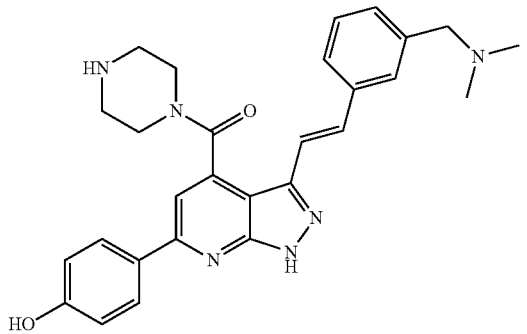 [SMILES: CN(C)Cc1cccc(/C=C/c2n[nH]c3nc(-c4ccc(O)cc4)cc(C(=O)N4CCNCC4)c23)c1]

To a cold solution (0° C.) of 4-[3-[(E)-2-(3-dimethylaminomethyl-phenyl)-vinyl]-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester (0.25 g, 0.37 mmol) in dry methanol (5 ml) was added dropwise a solution of aqueous 6N HCl (0.7 ml, 3.8 mmol). The reaction mixture was allowed to warm to room temperature and stirring was pursued for 2 hours before being concentrated under reduced pressure. Aqueous 6N HCl (0.7 ml, 3.8 mmol) was added to the crude mixture and stirring was pursued for another hour. Solvents were evaporated under vacuum, methanol and diethyl ether were added, the resulting precipitate was filtered and dried to give a chlorhydrate salt of the title compound as an orange solid (0.21 g; 95%).

LC/MS (Method LC9): Rt=0.68 min; m/z=483 [M+H]+.

EXAMPLE 15

{6-(4-Hydroxy-phenyl)-3-[(E)-2-(3-methanesulfonylmethyl-phenyl)-vinyl]-1H-pyrazolo[3,4-b]pyridin-4-yl}-piperazin-1-yl-methanone

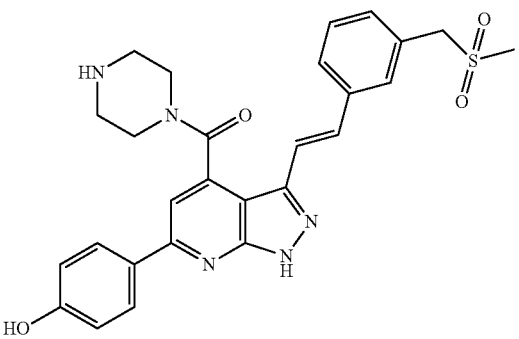 [SMILES: CS(=O)(=O)Cc1cccc(/C=C/c2n[nH]c3nc(-c4ccc(O)cc4)cc(C(=O)N4CCNCC4)c23)c1]

Using the same synthetic sequence described in example 14 except substituting (3-iodo-benzyl)-dimethyl-amine with 1-iodo-3-[(methylsulfonyl)methyl]-benzene (preparation described in WO0015609), {6-(4-Hydroxy-phenyl)-3-[(E)-2-(3-methanesulfonylmethyl-phenyl)-vinyl]-1H-pyrazolo[3,4-b]pyridin-4-yl}-piperazin-1-yl-methanone was obtained as a chlorhydrate salt.

LC/MS (Method LC9): Rt=0.8 min; m/z=518 [M+H]+.

EXAMPLE 16

((R)-2-Hydroxymethyl-piperazin-1-yl)-[6-(4-hydroxy-phenyl)-3-((E)-styryl)-1H-pyrazolo[3,4-b]pyridin-4-yl]-methanone

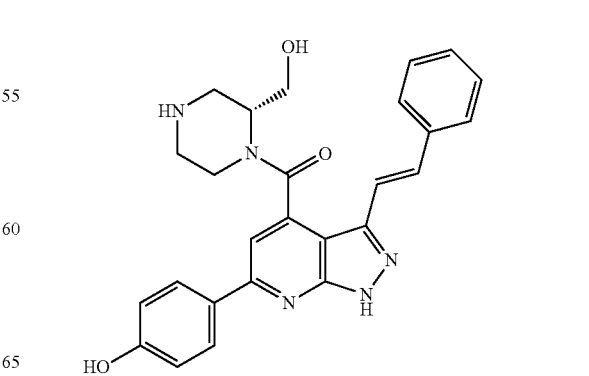

16.1: 6-chloro-1-(tetrahydro-pyran-2-yl)-3-vinyl-1H-pyrazolo[3,4-b]pyridine-4-carboxylic acid ethyl ester

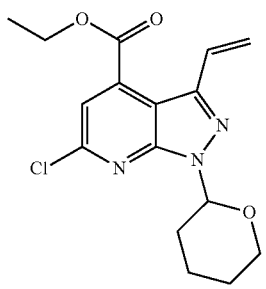 [SMILES: C=Cc1nn(C2CCCCO2)c2nc(Cl)cc(C(=O)OCC)c12]

To a solution of 6-chloro-3-iodo-1-(tetrahydro-pyran-2-yl)-1H-pyrazolo[3,4-b]pyridine-4-carboxylic acid ethyl ester (5.00 g, 11.48 mmol) in anhydrous tetrahydrofuran (115 ml) was added tributyl(vinyl)stannane (3.52 ml, 12.05 mmol). The mixture was degassed for 15 minutes using argon, dichlorobis(triphenylphosphine)palladium (0.40 g, 0.57 mmol) was then added. The resulting solution was heated at 80° C. overnight under argon, then evaporated under reduced pressure. Ethyl acetate and a 5% aqueous potassium fluoride solution were added to the residue, the resulting precipitate was filtered. The filtrate was recovered and the two layers separated, the organic phase was washed with brine, dried (Na$_2$SO$_4$), filtered and concentrated under vacuum. The crude product was purified on a silica gel column chromatography using a gradient of ethyl acetate (0-10%) in cyclohexane to afford the title compound as a yellow solid (3.24 g, 84%).

LC/MS (Method LC8): Rt=1.97 min; m/z=251 [M+H-THP]$^+$.

16.2: 6-chloro-3-((E)-styryl)-1-(tetrahydro-pyran-2-yl)-1H-pyrazolo[3,4-b]pyridine-4-carboxylic acid ethyl ester

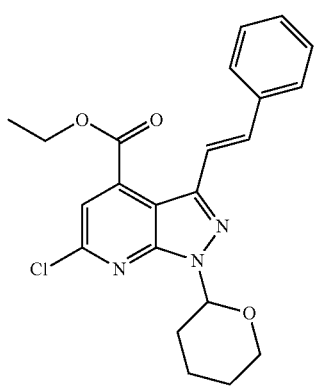 [SMILES: CCOC(=O)c1cc(Cl)nc2c1c(/C=C/c1ccccc1)nn2C1CCCCO1]

Utilizing the procedure described in example 14.5 except substituting 4-[6-chloro-1-(tetrahydro-pyran-2-yl)-3-vinyl-1H-pyrazolo[3,4-b]pyridine-4-carbonyl]-piperazine-1-carboxylic acid tert-butyl ester with 6-chloro-1-(tetrahydro-pyran-2-yl)-3-vinyl-1H-pyrazolo[3,4-b]pyridine-4-carboxylic acid ethyl ester and substituting (3-iodo-benzyl)-dimethyl-amine for iodobenzene, 6-chloro-3-((E)-styryl)-1-(tetrahydro-pyran-2-yl)-1H-pyrazolo[3,4-b]pyridine-4-carboxylic acid ethyl ester was obtained (2.8 g, 65%) as a yellow solid.

LC/MS (Method LC8): Rt=2.22 min; m/z=412 [M+H]$^+$.

16.3: 6-(4-hydroxy-phenyl)-3-((E)-styryl)-1-(tetrahydro-pyran-2-yl)-1H-pyrazolo[3,4-b]-pyridine-4-carboxylic acid

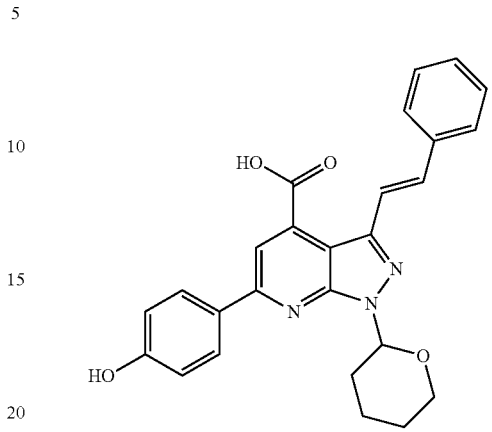

To a solution of 6-chloro-3-((E)-styryl)-1-(tetrahydro-pyran-2-yl)-1H-pyrazolo[3,4-b]pyridine-4-carboxylic acid ethyl ester (2.8 g, 6.80 mmol) in dioxane (60 ml) were added 4-hydroxyphenylboronic acid (1.03 g, 7.48 mmol) and an aqueous solution of cesium carbonate (0.4M, 30 mL). The resulting solution was degassed using argon, tetrakis(triphenylphosphine)palladium (0.71 g, 0.61 mmol) was then added and the reaction mixture was refluxed overnight. Dioxane was removed under vacuum, methylene chloride and water were added, and the mixture was acidified until pH=2. The organic layer was washed with water and the aqueous phase was extracted using methylene chloride. The resulting organic layers were combined, dried over anhydrous sodium sulfate, filtered and concentrated under reduced pressure to give the title compound (2.37 g, 79%) as a yellow solid which was used without any further purification.

LC/MS (Method LC8): Rt=1.92 min; m/z=442 [M+H]$^+$.

16.4: (R)-3-hydroxymethyl-4-[6-(4-hydroxy-phenyl)-3-((E)-styryl)-1-(tetrahydro-pyran-2-yl)-1H-pyrazolo[3,4-b]pyridine-4-carbonyl]-piperazine-1-carboxylic acid tert-butyl ester

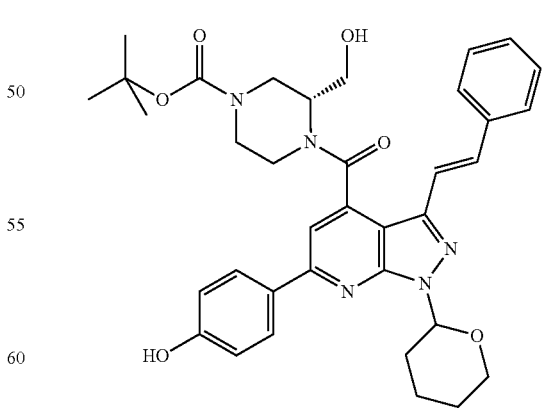

Utilizing the procedure described in example 1.6 except substituting 6-chloro-3-[(E)-2-(4-chloro-phenyl)-vinyl]-1-(tetrahydro-pyran-2-yl)-1H-pyrazolo[3,4-b]pyridine-4-carboxylic acid with 6-(4-hydroxy-phenyl)-3-((E)-styryl)-1-

(tetrahydro-pyran-2-yl)-1H-pyrazolo[3,4-b]pyridine-4-carboxylic acid and 1-boc-piperazine with (R)-3-hydroxymethyl-piperazine-1-carboxylic acid tert-butyl ester, (R)-3-hydroxymethyl-4-[6-(4-hydroxy-phenyl)-3-((E)-styryl)-1-(tetrahydro-pyran-2-yl)-1H-pyrazolo[3,4-b]pyridine-4-carbonyl]-piperazine-1-carboxylic acid tert-butyl ester (0.16 g, 28%) was obtained as a yellow solid.

LC/MS (Method LC8): Rt=1.86 min; m/z=640 [M+H]$^+$.

16.5: ((R)-2-hydroxymethyl-piperazin-1-yl)-[6-(4-hydroxy-phenyl)-3-((E)-styryl)-1H-pyrazolo[3,4-b]pyridin-4-yl]-methanone

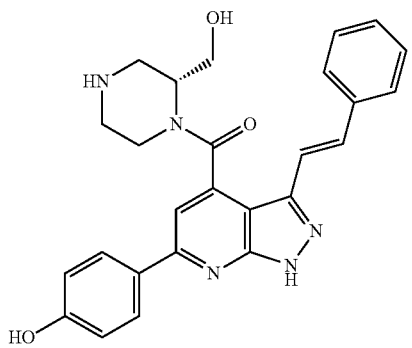 [SMILES: O=C(c1cc(-c2ccc(O)cc2)nc2[nH]nc(/C=C/c3ccccc3)c12)N1CCNC[C@@H]1CO]

Utilizing the procedure described in example 1.8 except substituting 4-[3-[(E)-2-(4-chloro-phenyl)-vinyl]-6-(4-hydroxy-phenyl)-1-(tetrahydro-pyran-2-yl)-1H-pyrazolo-[3,4-b]pyridine-4-carbonyl]-piperazine-1-carboxylic acid tert-butyl ester with (R)-3-hydroxymethyl-4-[6-(4-hydroxy-phenyl)-3-((E)-styryl)-1-(tetrahydro-pyran-2-yl)-1H-pyrazolo[3,4-b]pyridine-4-carbonyl]-piperazine-1-carboxylic acid tert-butyl ester, hydrochloride salt of ((R)-2-hydroxymethyl-piperazin-1-yl)-[6-(4-hydroxy-phenyl)-3-((E)-styryl)-1H-pyrazolo[3,4-b]pyridin-4-yl]-methanone was obtained (0.12 g, 91%) as a red solid.

LC/MS (Method LC9): Rt=0.8 min; m/z=456 [M+H]$^+$.

EXAMPLE 17

[6-(4-Hydroxy-phenyl)-3-phenethyl-1H-pyrazolo[3,4-b]pyridin-4-yl]-piperazin-1-yl-methanone

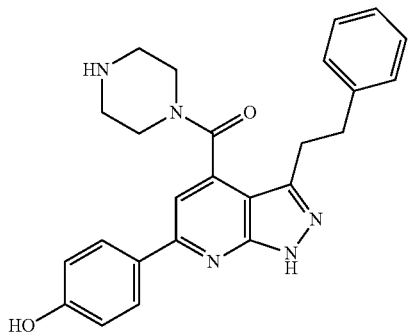 [SMILES: O=C(c1cc(-c2ccc(O)cc2)nc2[nH]nc(CCc3ccccc3)c12)N1CCNCC1]

17.1: 4-[6-(4-Hydroxy-phenyl)-3-((E)-styryl)-1-(tetrahydro-pyran-2-yl)-1H-pyrazolo[3,4-b]pyridine-4-carbonyl]-piperazine-1-carboxylic acid tert-butyl ester

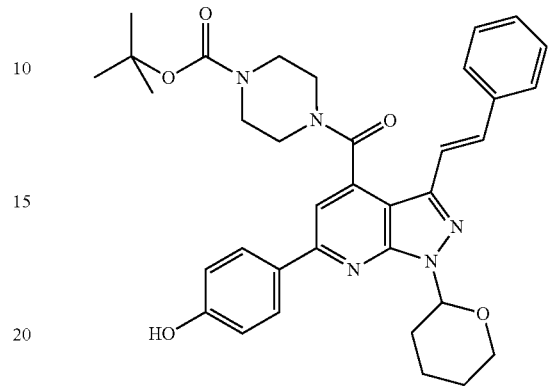

Utilizing the procedure described in example 1 until the seventh step except substituting trans-2-(4-chlorophenyl)vinylboronic acid with trans-2-phenylvinylboronic acid, (4-[6-(4-hydroxy-phenyl)-3-((E)-styryl)-1-(tetrahydro-pyran-2-yl)-1H-pyrazolo[3,4-b]-pyridine-4-carbonyl]-piperazine-1-carboxylic acid tert-butyl ester was obtained as a yellow solid.

LC/MS (Method LC8): Rt=1.99 min; m/z=610 [M+H]$^+$.

17.2: 4-[6-(4-hydroxy-phenyl)-3-phenethyl-1-(tetrahydro-pyran-2-yl)-1H-pyrazolo[3,4-b]pyridine-4-carbonyl]-piperazine-1-carboxylic acid tert-butyl ester

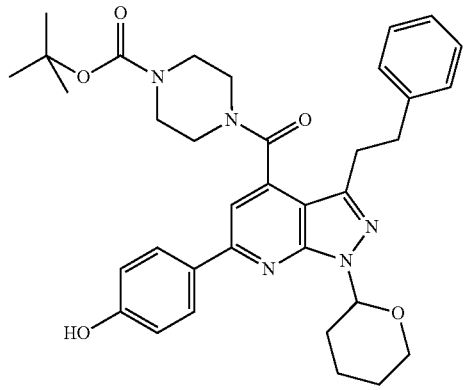 [SMILES: CC(C)(C)OC(=O)N1CCN(C(=O)c2cc(-c3ccc(O)cc3)nc3c2c(CCc2ccccc2)nn3C2CCCCO2)CC1]

To a solution of 4-[6-(4-hydroxy-phenyl)-3-((E)-styryl)-1-(tetrahydro-pyran-2-yl)-1H-pyrazolo[3,4-b]pyridine-4-carbonyl]-piperazine-1-carboxylic acid tert-butyl ester (0.74 g, 1.22 mmol) in dry methanol (40 ml) was added Pd/C (150 mg). The reaction mixture was stirred under a hydrogen atmosphere for 1 hour, filtered and concentrated under reduced pressure. The crude residue was taken in dry methanol (30 ml) and Pd/C (150 mg) was added. The mixture was submitted to a hydrogen pressure of 1 bar and was stirred for 1 hour, filtered and concentrated under vacuum to yield the title compound (0.72 g, 96%).

LC/MS (Method LC8): Rt=2.10 min; m/z=612 [M+H]$^+$.

17.3: [6-(4-hydroxy-phenyl)-3-phenethyl-1H-pyrazolo[3,4-b]pyridin-4-yl]-piperazin-1-yl-methanone

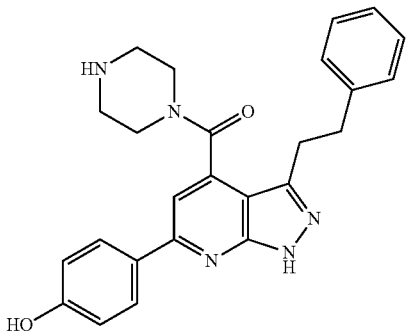 [SMILES: O=C(c1cc(-c2ccc(O)cc2)nc2[nH]nc(CCc3ccccc3)c12)N1CCNCC1]

Utilizing the procedure described in example 1.8 except substituting 4-[3-[(E)-2-(4-chloro-phenyl)-vinyl]-6-(4-hydroxy-phenyl)-1-(tetrahydro-pyran-2-yl)-1H-pyrazolo-[3,4-b]pyridine-4-carbonyl]-piperazine-1-carboxylic acid tert-butyl ester with 4-[6-(4-hydroxy-phenyl)-3-phenethyl-1-(tetrahydro-pyran-2-yl)-1H-pyrazolo[3,4-b]pyridine-4-carbonyl]-piperazine-1-carboxylic acid tert-butyl ester, a chlorhydrate salt of [6-(4-hydroxy-phenyl)-3-phenethyl-1H-pyrazolo[3,4-b]pyridin-4-yl]-piperazin-1-yl-methanone was obtained (0.5 g, quantitative) as a yellow solid.

LC/MS (Method LC9): Rt=0.73 min; m/z=428 [M+H].

EXAMPLE 18

(±)-[6-(4-Hydroxy-phenyl)-3 trans-(2-phenyl-cyclopropyl)-1H-pyrazolo[3,4-b]pyridin-4-yl]-piperazin-1-yl-methanone

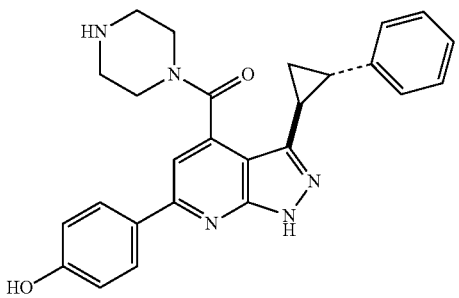

18.1: (±)-3-oxo-3 trans-(2-phenyl-cyclopropyl)-propionitrile

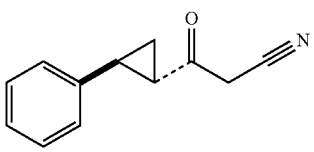

To a suspension of sodium hydride (60% in oil, 2.03 g, 50.78 mmol) in dry dioxane (60 mL) was added dropwise acetonitrile (2.65 mL, 50.78 mmol). After 30 min, a solution of (±)-ethyl trans-2-phenylcyclopropanecarboxylate (8.05 g, 42.31 mmol) in dry dioxane (30 ml) was added dropwise to the reaction mixture. The suspension was heated at 100° C. for 3 hours, cooled down to 0° C. prior to the addition of water and dichloromethane. Aqueous 1M HCl solution was added to acidified the mixture to pH=5. The organic layer was separated and the aqueous layer extracted with dichloromethane. The combined organic extracts were dried (MgSO₄), filtered, concentrated under vacuum. The crude residue was purified on a silica gel column chromatography using a gradient of EtOAc (0-30%) in cyclohexane to yield the title compound (3.17 g, 40%) as a colourless oil.

LC/MS (Method LC8): Rt=1.28 min; m/z=186 [M+H]⁺.

18.2: (±)-5 trans-(2-phenyl-cyclopropyl)-2H-pyrazol-3-ylamine

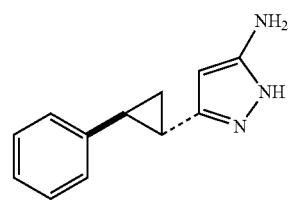

To a solution of (±)-3-oxo-3 trans-(2-phenyl-cyclopropyl)-propionitrile (3.15 g, 17 mmol) in ethanol (70 mL) was added hydrazine monohydrate (0.82 mL, 17 mmol). The reaction mixture was heated at 85° C. for 2.5 hours and then concentrated under vacuum. The residue was taken up in EtOAc and the organic layer was then washed with brine, dried (Na₂SO₄), filtered, concentrated under vacuum to give the title compound (3.25 g, 96%) as a yellow oil.

LC/MS (Method LC8): Rt=0.71 min; m/z=200 [M+H]⁺.

18.3: (±)-6-(4-Hydroxy-phenyl)-3-(trans-2-phenyl-cyclopropyl)-1H-pyrazolo[3,4-b]pyridine-4-carboxylic acid

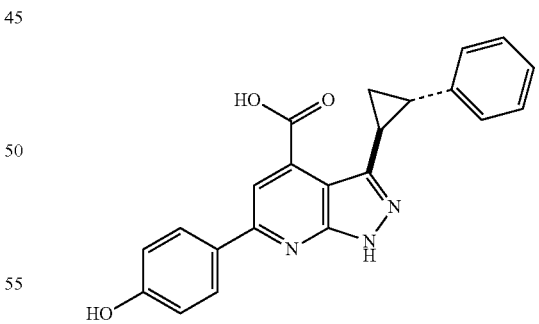

(±)-5-trans-(2-Phenyl-cyclopropyl)-2H-pyrazol-3-ylamine (3.24 g, 16.26 mmol), 4-hydroxybenzaldehyde (1.98 g, 16.26 mmol), pyruvic acid (1.13 ml, 16.26 mmol) and glacial acetic acid (25 ml) were heated to reflux under nitrogen for 1.5 hours and then evaporated under reduced pressure. The residue was taken up in diethyl ether, the precipitate was filtered and washed with diethyl ether to afford the crude title compound (4 g, 67%) as a brown solid.

LC/MS (Method LC8): Rt=1.53 min; m/z=372 [M+H]⁺.

18.4: (±)-4-[6-(4-Hydroxy-phenyl)-3 trans-(2-phenyl-cyclopropyl)-1H-pyrazolo[3,4-b]-pyridin-4-yl]-piperazine-1-carboxylic acid tert-butyl ester

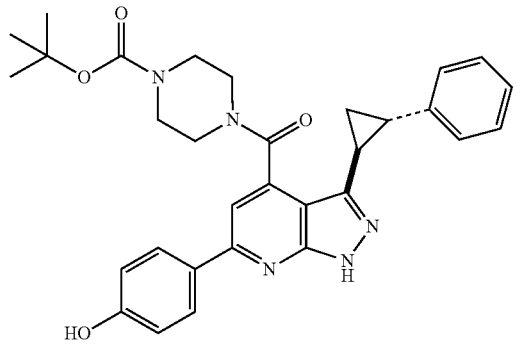

To a solution of (±)-6-(4-hydroxy-phenyl)-3-(trans-2-phenyl-cyclopropyl)-1H-pyrazolo-[3,4-b]pyridine-4-carboxylic acid (1.2 g, 3.23 mmol) in a mixture of tetrahydrofuran (29 mL) and N,N-dimethylacetamide (3 mL) were added 1-boc-piperazine (0.72 g, 3.88 mmol), 1-hydroxybenzotriazole (52 mg, 0.39 mmol), and N-(3-dimethylaminopropyl)-N'-ethyl-carbodiimide hydrochloride (0.74 g, 3.88 mmol). The reaction mixture was stirred at room temperature for 18 hours, EtOAc and an aqueous solution of citric acid were added. The organic layer was separated and the aqueous layer extracted with EtOAc. The combined organic extracts were washed with brine, dried (MgSO$_4$), filtered, concentrated under vacuum. The crude residue was purified on a silica gel column chromatography using a gradient of EtOAc (20-60%) in cyclohexane to yield the title compound as a yellow wax (0.09 g, 9%).

LC/MS (Method LC8): Rt=1.68 min; m/z=540 [M+H]$^+$.

18.5: (±)-[6-(4-Hydroxy-phenyl)-3 trans-(2-phenyl-cyclopropyl)-1H-pyrazolo[3,4-b]-pyridin-4-yl]-piperazin-1-yl-methanone (SAR240501A)

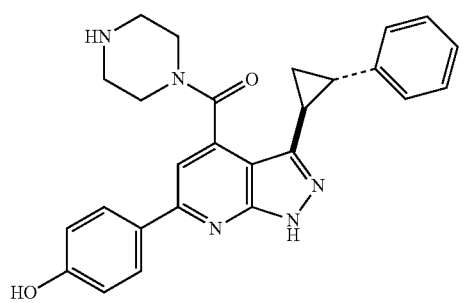

To a solution of (±)-4-[6-(4-hydroxy-phenyl)-3 trans-(2-phenyl-cyclopropyl)-1H-pyrazolo[3,4-b]pyridin-4-yl]-piperazine-1-carboxylic acid tert-butyl ester (0.12 g, 0.23 mmol) in methanol (3.3 ml) was added 4N HCl in dioxane (0.3 ml). The reaction mixture was stirred at room temperature for 18 hours, diethyl ether was then added, the resulting precipitated was filtered and washed once with diethyl ether to afford the hydrochloride salt of the title compound (0.09 g, 80%) as an orange solid.

LC/MS (Method LC9): Rt=0.82 min; m/z=440 [M+H]$^+$.

EXAMPLE 19

(6-(4-Hydroxy-phenyl)-3-{(E)-2-[4-(piperidine-1-carbonyl)-phenyl]-vinyl}-1H-pyrazolo[3,4-b]pyridin-4-yl)-piperazin-1-yl-methanone

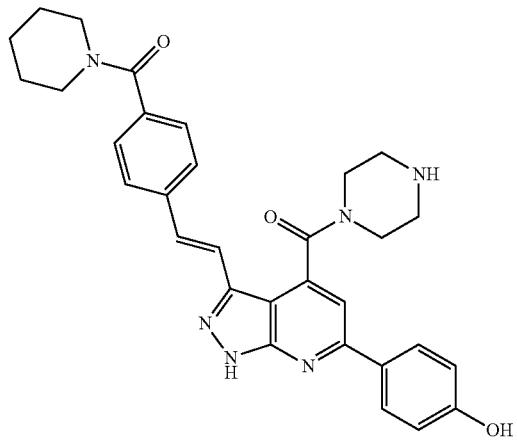 [SMILES: O=C(c1ccc(/C=C/c2n[nH]c3nc(-c4ccc(O)cc4)cc(C(=O)N4CCNCC4)c23)cc1)N1CCCCC1]

19.1: (4-iodo-phenyl)-piperidin-1-yl-methanone

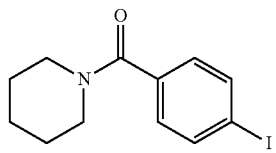 [SMILES: O=C(c1ccc(I)cc1)N1CCCCC1]

To a suspension of 4-iodo-benzoyl chloride (2.00 g, 7.51 mmol) in dichloromethane (25 mL) was added piperidine (1.85 mL, 18.76 mmol). The reaction mixture was heated at reflux for 1.5 hour and then cooled to room temperature. The organic layer was washed with an aqueous 1M HCl solution, brine, dried (Na$_2$SO$_4$), filtered, concentrated under vacuum to give the title compound (2.37 g, 100%) as a white solid.

1H NMR (400 MHz, CDCl$_3$): δ 1.40-1.65 (m, 6H), 3.18-3.68 (m, 4H), 7.06-7.10 (m, 2H), 7.66-7.70 (m, 2H).

19.2: 6-(4-hydroxy-phenyl)-1-(tetrahydro-pyran-2-yl)-3-vinyl-1H-pyrazolo[3,4-b]pyridine-4-carboxylic acid

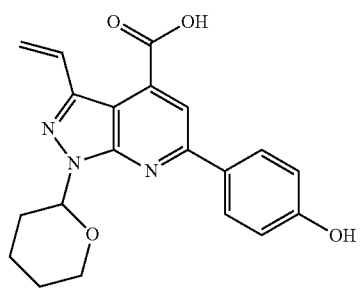 [SMILES: C=Cc1nn(C2CCCCO2)c2nc(-c3ccc(O)cc3)cc(C(=O)O)c12]

To a solution of 6-chloro-1-(tetrahydro-pyran-2-yl)-3-vinyl-1H-pyrazolo[3,4-b]pyridine-4-carboxylic acid ethyl ester (2.00 g, 5.96 mmol), described in example 16.1, in dioxane (54 mL) were added 4-hydroxyphenylboronic acid (0.90 g, 6.55 mmol) and an aqueous solution of cesium carbonate (0.4 M, 27 mL, 10.8 mmol). The resulting solution was degassed using argon, tetrakis(triphenylphosphine)palladium (0.62 g, 0.54 mmol) was then added and the reaction mixture was refluxed overnight. Dioxane was removed under vacuum, water was added and then the mixture was acidified to pH=2. The aqueous phase was extracted with a mixture of tetrahydrofuran and EtOAc. The combined organic extracts were washed with brine, dried ($Na_2SO_4$), filtered, concentrated under vacuum to give the title compound (3.13 g) as a brown foam which was used without further purification.

LC/MS (Method LC8): Rt=1.57 min; m/z=366 $[M+H]^+$.

19.3: 4-[6-(4-hydroxy-phenyl)-1-(tetrahydro-pyran-2-yl)-3-vinyl-1H-pyrazolo[3,4-b]pyridine-4-carbonyl]-piperazine-1-carboxylic acid tert-butyl ester

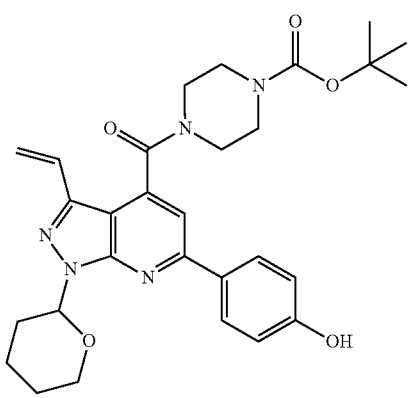 [SMILES: C=Cc1nn(C2CCCCO2)c2nc(-c3ccc(O)cc3)cc(C(=O)N3CCN(C(=O)OC(C)(C)C)CC3)c12]

To a solution of 6-(4-hydroxy-phenyl)-1-(tetrahydro-pyran-2-yl)-3-vinyl-1H-pyrazolo[3,4-b]pyridine-4-carboxylic acid (3.12 g, 6.62 mmol) in tetrahydrofuran (44 mL) were added 1-boc-piperazine (1.35 g, 7.28 mmol), 1-hydroxybenzotriazole (0.09 g, 0.66 mmol), and N-(3-dimethylaminopropyl)-N'-ethylcarbodiimide hydrochloride (1.27 g, 6.62 mmol). After 2 hours, N,N-dimethylacetamide (3 ml), 1-boc-piperazine (0.24 g, 1.32 mmol) and N-(3-dimethylaminopropyl)-N'-ethylcarbodiimide hydrochloride (0.25 g, 1.32 mmol) were added to the reaction mixture. After 1 hour, tetrahydrofuran was evaporated under reduced pressure, water and dichloromethane were then added. The organic layer was washed with an aqueous 1M HCl solution, water, brine, dried ($Na_2SO_4$), filtered, concentrated under vacuum. The crude residue was purified on a silica gel column chromatography using a gradient of methanol (0-5%) in dichloromethane to yield the title compound as a yellow foam (3.17 g, 90%).

LC/MS (Method LC8): Rt=1.77 min; m/z=534 $[M+H]^+$.

19.4: 4-[6-[4-(tert-butyl-dimethyl-silanyloxy)-phenyl]-1-(tetrahydro-pyran-2-yl)-3-vinyl-1H-pyrazolo[3,4-b]pyridine-4-carbonyl]-piperazine-1-carboxylic acid tert-butyl ester

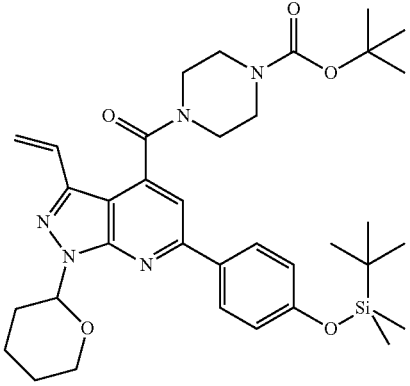 [SMILES: C=Cc1nn(C2CCCCO2)c2nc(-c3ccc(O[Si](C)(C)C(C)(C)C)cc3)cc(C(=O)N3CCN(C(=O)OC(C)(C)C)CC3)c12]

To a solution of 4-[6-(4-hydroxy-phenyl)-1-(tetrahydro-pyran-2-yl)-3-vinyl-1H-pyrazolo[3,4-b]pyridine-4-carbonyl]-piperazine-1-carboxylic acid tert-butyl ester (3.15 g, 5.90 mmol) in dichloromethane (22 ml) were added imidazole (0.96 g, 14.17 mmol) and tert-butyl(chloro)dimethylsilane (1.07 g, 7.08 mmol). The reaction mixture was stirred at room temperature for 5 hours, water and dichloromethane were then added. The aqueous layer was separated and the organic layer was washed with water, brine, dried ($Na_2SO_4$), filtered, concentrated under vacuum. The crude residue was purified on a silica gel column chromatography using a gradient of EtOAc (0-30%) in cyclohexane to yield the title compound as a yellow foam (2.05 g, 53%).

LC/MS (Method LC8): Rt=2.41 min; m/z=648 $[M+H]^+$.

19.5: 4-[6-(4-Hydroxy-phenyl)-3-{(E)-2-[4-(piperidine-1-carbonyl)-phenyl]-vinyl}-1-(tetrahydro-pyran-2-yl)-1H-pyrazolo[3,4-b]pyridine-4-carbonyl]-piperazine-1-carboxylic acid tert-butyl ester

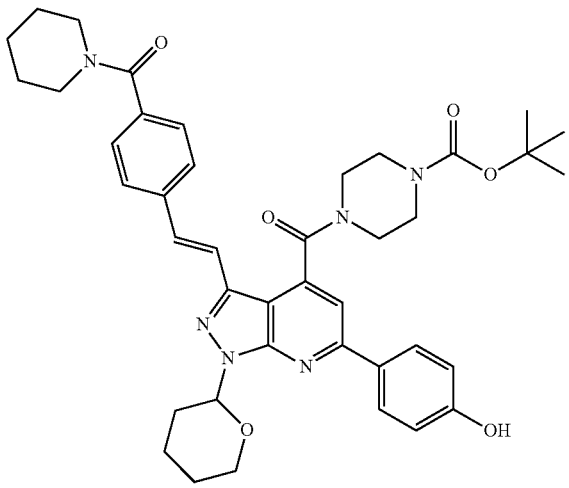 [SMILES: CC(C)(C)OC(=O)N1CCN(C(=O)c2cc(-c3ccc(O)cc3)nc3c2c(/C=C/c2ccc(C(=O)N4CCCCC4)cc2)nn3C2CCCCO2)CC1]

To a solution of 4-[6-[4-(tert-butyl-dimethyl-silanyloxy)-phenyl]-1-(tetrahydro-pyran-2-yl)-3-vinyl-1H-pyrazolo[3,4-b]pyridine-4-carbonyl]-piperazine-1-carboxylic acid tert-butyl ester (0.3 g, 0.46 mmol) in DMF (2.1 mL) were added (4-iodo-phenyl)-piperidin-1-yl-methanone (0.175 g, 0.56 mmol), tri(o-tolyl)phosphine (28 mg, 0.09 mmol) and triethylamine (2.1 mL). The resulting solution was degassed using argon, palladium acetate (5 mg, 0.02 mmol) was then added and the reaction mixture was heated at 125° C. overnight. The reaction mixture was concentrated under vacuum and the residue taken up in water and then acidified to pH=1. The precipitate was filtered, washed with water and then dried under vacuum. The crude residue was purified on a silica gel column chromatography using a gradient of methanol (0-3%) in dichloromethane to yield the title compound as a light brown solid (0.25 g, 65%).

LC/MS (Method LC8): Rt=1.92 min; m/z=721 [M+H]$^+$.

19.6: (6-(4-Hydroxy-phenyl)-3-{(E)-2-[4-(piperidine-1-carbonyl)-phenyl]-vinyl}-1H-pyrazolo[3,4-b]pyridin-4-yl)-piperazin-1-yl-methanone

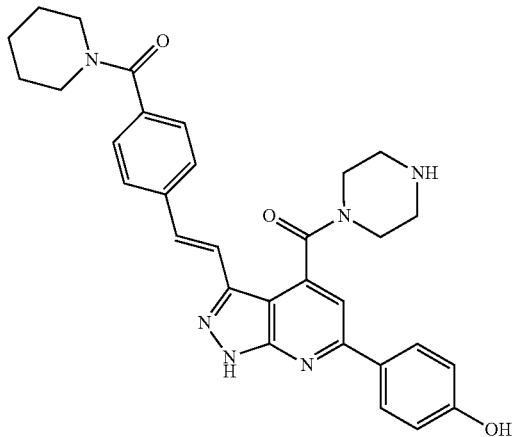 [SMILES: O=C(c1ccc(/C=C/c2n[nH]c3nc(-c4ccc(O)cc4)cc(C(=O)N4CCNCC4)c23)cc1)N1CCCCC1]

To a solution of 4-[4-[6-(4-Hydroxy-phenyl)-3-{(E)-2-[4-(piperidine-1-carbonyl)phenyl]-vinyl}-1-(tetrahydro-pyran-2-yl)-1H-pyrazolo[3,4-b]pyridine-4-carbonyl]-piperazine-1-carboxylic acid tert-butyl ester (0.25 g, 0.35 mmol) in methanol (5 ml) was added 4N HCl in dioxane (0.9 ml). The reaction mixture was stirred at room temperature for 18 hours, diethyl ether was then added, the resulting precipitated was filtered and washed once with diethyl ether to afford the hydrochloride salt of the title compound (0.175 g, 82%) as an orange solid.

LC/MS (Method LC9): Rt=0.89 min; m/z=537 [M+H]$^+$.

EXAMPLE 20

1-(3-{(E)-2-[6-(4-Hydroxy-phenyl)-4-(piperazine-1-carbonyl)-1H-pyrazolo[3,4-b]pyridin-3-yl]-vinyl}-phenyl)-pyrrolidin-2-one

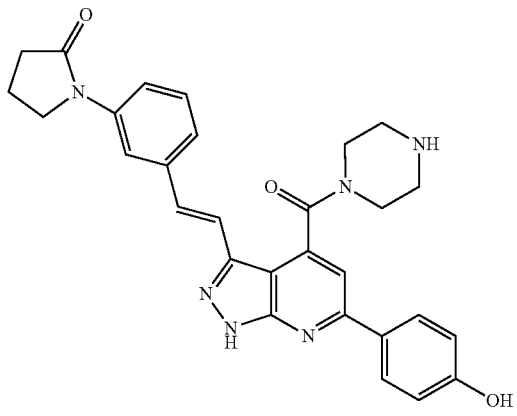 [SMILES: O=C(c1cc(-c2ccc(O)cc2)nc2[nH]nc(/C=C/c3cccc(N4CCCC4=O)c3)c12)N1CCNCC1]

20.1: 4-Bromo-N-(3-iodo-phenyl)-butyramide

To a solution of 3-iodoaniline (1.5 g, 6.85 mmol) and triethylamine (1.34 mL, 9.59 mmol) in dichloromethane (28 mL) at 0° C. was added dropwise 4-bromobutyryl chloride (0.99 mL, 8.56 mmol). The reaction mixture was then stirred at room temperature overnight. The organic extract was washed with an aqueous 1M HCl solution, aqueous 1M NaOH solution and brine, dried (Na$_2$SO$_4$), filtered, concentrated under vacuum. The crude residue was purified by silica gel column chromatography using a gradient of EtOAc (0-15%) in cyclohexane to yield a sticky solid. Trituration in a mixture of cyclohexane and ether and then filtration give the title compound as a solid (1.61 g, 64%).

1H NMR (400 MHz, CDC$_3$): δ 2.17-2.33 (m, 2H), 2.58 (t, 2H), 3.54 (t, 1H), 3.68 (t, 1H), 7.03-7.08 (m, 1H), 7.32-7.51 (m, 3H), 7.96 (s, 1H).

20.2: 1-(3-Iodo-phenyl)-pyrrolidin-2-one

To a solution of 4-bromo-N-(3-iodo-phenyl)-butyramide (1.60 g, 4.36 mmol) in dry DMF (20 mL) at 0° C. was added portionwise sodium hydride (60% in oil, 0.20 g, 5.01 mmol). After 15 min at 0° C., the reaction mixture was then stirred at room temperature overnight. As the reaction was incomplete as judged by TLC, sodium hydride (60% in oil, 45 nmg, 1.09 mmol) was added. After two hours, water (40 mL) and an aqueous solution of saturated ammonium chloride (40 mL) were added to the reaction mixture. The aqueous phase was extractred with EtOAc and then the organic extracts were washed with brine, dried (Na$_2$SO$_4$), filtered, concentrated under vacuum. The crude residue was purified on a silica gel column chromatography using a gradient of EtOAc (0-30%) in cyclohexane to yield the title compound as a yellow solid (0.94 g, 75%).

1H NMR (400 MHz, CDCl$_3$): δ 2.14-2.23 (m, 2H), 2.63 (t, 2H), 3.85 (t, 2H), 7.1 (t, 1H), 7.48-7.51 (m, 1H), 7.66-7.70 (m, 1H), 7.96 (t, 1H).

155

20.3: 4-[6-(4-Hydroxy-phenyl)-3-{(E)-2-[3-(2-oxo-pyrrolidin-1-yl)-phenyl]-vinyl}-1-(tetrahydropyran-2-yl)-1H-pyrazolo[3,4-b]pyridine-4-carbonyl]-piperazine-1-carboxylic acid tert-butyl ester

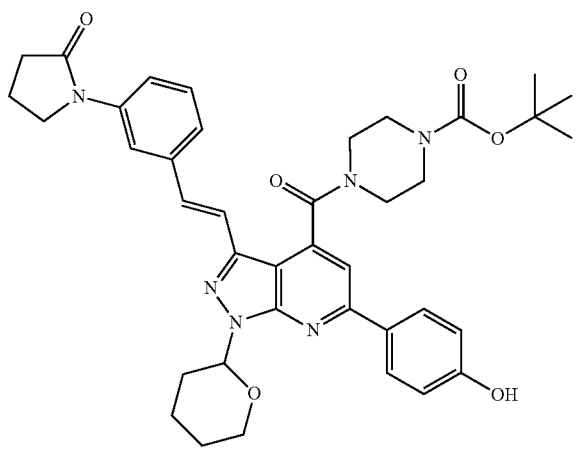 [SMILES: CC(C)(C)OC(=O)N1CCN(C(=O)c2cc(-c3ccc(O)cc3)nc3c2c(/C=C/c2cccc(N4CCCC4=O)c2)nn3C2CCCCO2)CC1]

To a solution of 4-[6-(4-hydroxy-phenyl)-1-(tetrahydro-pyran-2-yl)-3-vinyl-1H-pyrazolo[3,4-b]pyridine-4-carbonyl]-piperazine-1-carboxylic acid tert-butyl ester (0.30 g, 0.56 mmol) in DMF (2.55 mL) were added 1-(3-iodo-phenyl)-pyrrolidin-2-one (0.19 g, 0.67 mmol), tri(o-tolyl)phosphine (34 mg, 0.11 mmol) and triethylamine (2.55 mL). The resulting solution was degassed using argon, palladium acetate (6 mg, 0.03 mmol) was then added and the reaction mixture was heated at 125° C. overnight. The reaction mixture was concentrated under vacuum and the residue taken up in water and then acidified to pH=1. The precipitate was filtered, washed with water and then dried under vacuum. The crude residue was purified by silica gel column chromatography using a gradient of EtOAc (0-100%) in cyclohexane to yield the title compound as a beige solid (0.26 g, 66%).

LC/MS (Method LC8): Rt=1.89 min; m/z=693 [M+H]$^+$.

156

20.4: 1-(3-{(E)-2-[6-(4-Hydroxy-phenyl)-4-(piperazine-1-carbonyl)-1H-pyrazolo[3,4-b]-pyridin-3-yl]-vinyl}-phenyl)-pyrrolidin-2-one

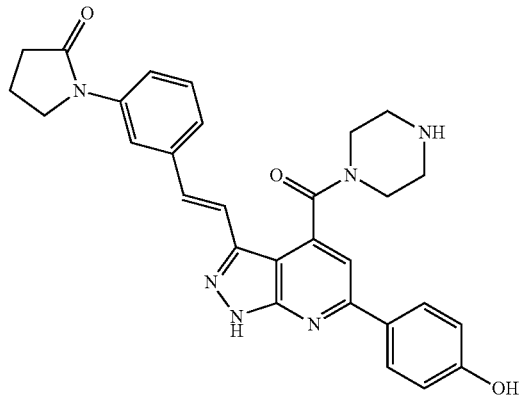 [SMILES: O=C(c1cc(-c2ccc(O)cc2)nc2[nH]nc(/C=C/c3cccc(N4CCCC4=O)c3)c12)N1CCNCC1]

To a solution of 4-[6-(4-Hydroxy-phenyl)-3-{(E)-2-[3-(2-oxo-pyrrolidin-1-yl)-phenyl]-vinyl}-1-(tetrahydro-pyran-2-yl)-1H-pyrazolo[3,4-b]pyridine-4-carbonyl]-piperazine-1-carboxylic acid tert-butyl ester (0.246 g, 0.36 mmol) in methanol (5 ml) was added 4N HCl in dioxane (0.9 ml). The reaction mixture was stirred at room temperature for 18 hours, diethyl ether was then added, the resulting precipitated was filtered and washed once with diethyl ether to afford the hydrochloride salt of the title compound (0.19 g, 93%) as an orange solid.

LC/MS (Method LC10): Rt=2.98 min; m/z=509 [M+H]$^+$.

The following examples have been prepared in a similar fashion as the synthesis for 1-(3-{(E)-2-[6-(4-Hydroxy-phenyl)-4-(piperazine-1-carbonyl)-1H-pyrazolo[3,4-b]pyridin-3-yl]-vinyl}-phenyl)-pyrrolidin-2-one described immediately above. In the third step 4-[6-(4-hydroxy-phenyl)-1-(tetrahydro-pyran-2-yl)-3-vinyl-1H-pyrazolo[3,4-b]pyridine-4-carbonyl]-piperazine-1-carboxylic acid tert-butyl ester was reacted with the respective aryl halides, and deprotected in the forth step:

| Exp. No. | Name | Structure | LC/MS method | m/z [M + H]+ | Rt [min] |
|---|---|---|---|---|---|
| 21 | [6-(4-Hydroxy-phenyl)-3-((E)-2-p-tolyl-vinyl)-1H-pyrazolo[3,4-b]-pyridin-4-yl]-piperazin-1-yl-methanone | 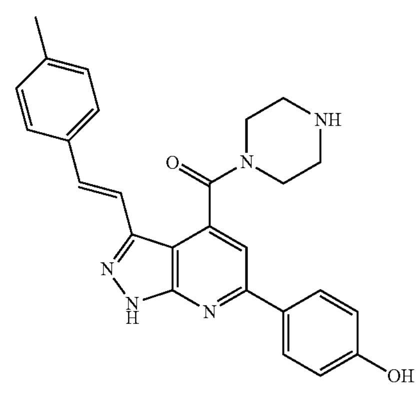 [SMILES: Cc1ccc(/C=C/c2n[nH]c3nc(-c4ccc(O)cc4)cc(C(=O)N4CCNCC4)c23)cc1] | LC3 | 440.15 | 0.88 |

-continued

| Exp. No. | Name | Structure | LC/MS method | m/z [M + H]+ | Rt [min] |
|---|---|---|---|---|---|
| 22 | {6-(4-Hydroxy-phenyl)-3-[(E)-2-(3-methane-sulfonyl-phenyl)-vinyl]-1H-pyrazolo[3,4-b]-pyridin-4-yl}-piperazin-1-yl-methanone | 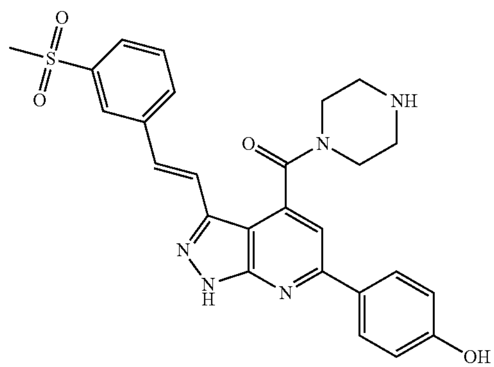 [SMILES: CS(=O)(=O)c1cccc(/C=C/c2n[nH]c3nc(-c4ccc(O)cc4)cc(C(=O)N4CCNCC4)c23)c1] | LC9 | 504 | 0.75 |
| 23 | [3-[(E)-2-(3-Dimethylamino-phenyl)-vinyl]-6-(4-hydroxy-phenyl)-1H-pyrazolo[3,4-b]pyridin-4-yl]-piperazin-1-yl-methanone | 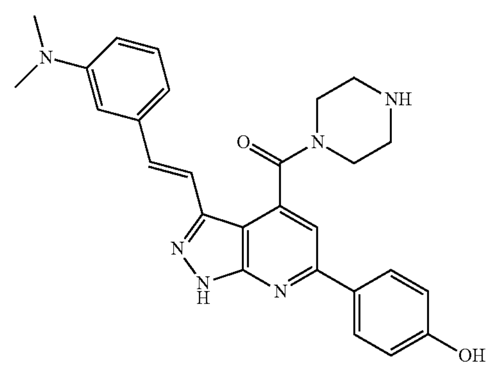 [SMILES: CN(C)c1cccc(/C=C/c2n[nH]c3nc(-c4ccc(O)cc4)cc(C(=O)N4CCNCC4)c23)c1] | LC9 | 469 | 0.65 |
| 24 | {6-(4-Hydroxy-phenyl)-3-[(E)-2-(4-methane-sulfonyl-phenyl)-vinyl]-1H-pyrazolo[3,4-b]pyridin-4-yl}-piperazin-1-yl-methanone | 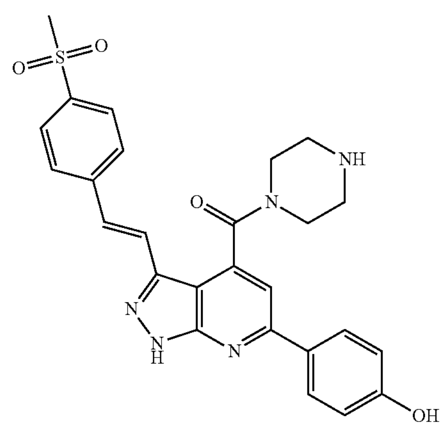 [SMILES: CS(=O)(=O)c1ccc(/C=C/c2n[nH]c3nc(-c4ccc(O)cc4)cc(C(=O)N4CCNCC4)c23)cc1] | LC9 | 504 | 0.75 |
| 25 | 3-{(E)-2-[6-(4-Hydroxy-phenyl)-4-(piperazine-1-carbonyl)-1H-pyrazolo[3,4-b]pyridin-3-yl]-vinyl}-benzonitrile | 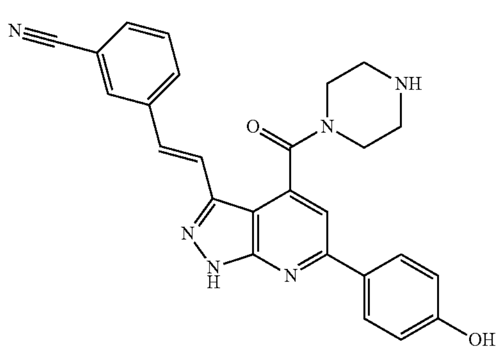 [SMILES: N#Cc1cccc(/C=C/c2n[nH]c3nc(-c4ccc(O)cc4)cc(C(=O)N4CCNCC4)c23)c1] | LC9 | 451 | 0.81 |

| Exp. No. | Name | Structure | LC/MS method | m/z [M + H]+ | Rt [min] |
|---|---|---|---|---|---|
| 26 | {6-(4-Hydroxy-phenyl)-3-[(E)-2-(3-piperidin-1-yl-phenyl)-vinyl]-1H-pyrazolo[3,4-b]pyridin-4-yl}-piperazin-1-yl-methanone | 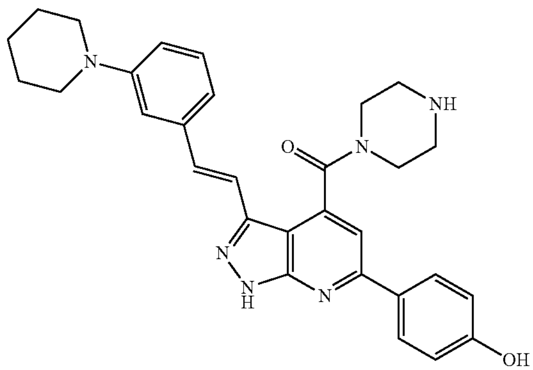 [SMILES: O=C(c1cc(-c2ccc(O)cc2)nc2[nH]nc(/C=C/c3cccc(N4CCCCC4)c3)c12)N1CCNCC1] | LC9 | 509 | 0.69 |
| 27 | {6-(4-Hydroxy-phenyl)-3-[(E)-2-(3-morpholin-4-yl-phenyl)-vinyl]-1H-pyrazolo[3,4-b]pyridin-4-yl}-piperazin-1-yl-methanone | 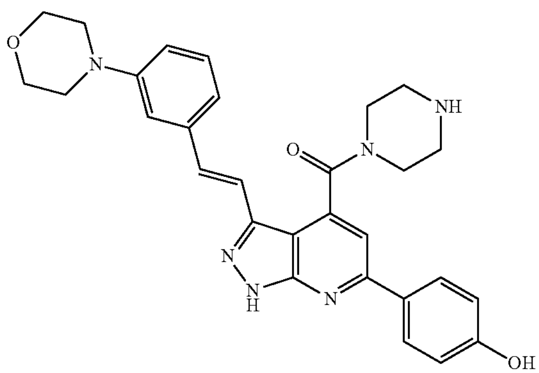 [SMILES: O=C(c1cc(-c2ccc(O)cc2)nc2[nH]nc(/C=C/c3cccc(N4CCOCC4)c3)c12)N1CCNCC1] | LC9 | 511 | 0.80 |
| 28 | {6-(4-Hydroxy-phenyl)-3-[(E)-2-(3-pyrrolidin-1-yl-phenyl)-vinyl]-1H-pyrazolo[3,4-b]pyridin-4-yl}-piperazin-1-yl-methanone | 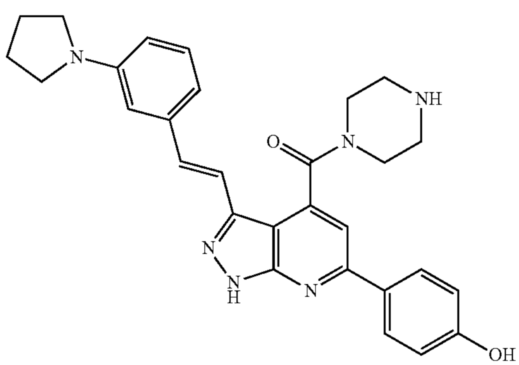 [SMILES: O=C(c1cc(-c2ccc(O)cc2)nc2[nH]nc(/C=C/c3cccc(N4CCCC4)c3)c12)N1CCNCC1] | LC9 | 495 | 0.90 |
| 29 | 4-{(E)-2-[6-(4-Hydroxy-phenyl)-4-(piperazine-1-carbonyl)-1H-pyrazolo[3,4-b]pyridin-3-yl]-vinyl}-2-methyl-benzonitrile | 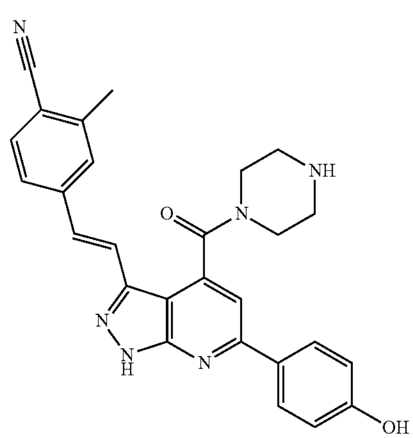 [SMILES: Cc1cc(/C=C/c2n[nH]c3nc(-c4ccc(O)cc4)cc(C(=O)N4CCNCC4)c23)ccc1C#N] | LC9 | 465 | 0.92 |

-continued

| Exp. No. | Name | Structure | LC/MS method | m/z [M + H]+ | Rt [min] |
|---|---|---|---|---|---|
| 30 | [3-[(E)-2-(3-Chloro-5-piperidin-1-yl-phenyl)-vinyl]-6-(4-hydroxy-phenyl)-1H-pyrazolo[3,4-b]pyridin-4-yl]-piperazin-1-yl-methanone | 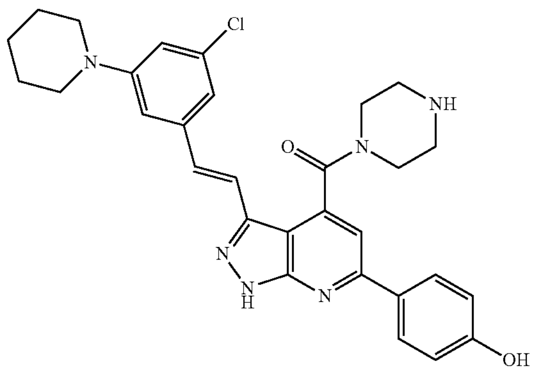 [SMILES: O=C(c1cc(-c2ccc(O)cc2)nc2[nH]nc(/C=C/c3cc(Cl)cc(N4CCCCC4)c3)c12)N1CCNCC1] | LC9 | 543 | 0.88 |
| 31 | 3-{(E)-2-[6-(4-Hydroxy-phenyl)-4-(piperazine-1-carbonyl)-1H-pyrazolo[3,4-b]pyridin-3-yl]-vinyl}-N,N-dimethyl-benzamide | 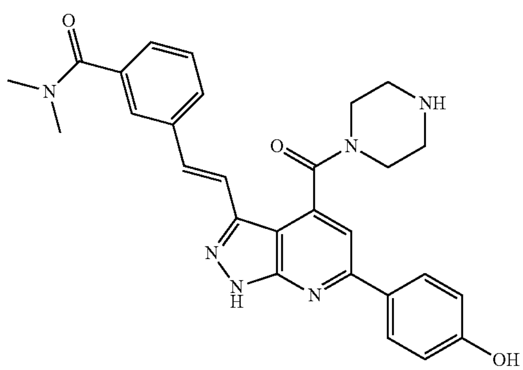 [SMILES: CN(C)C(=O)c1cccc(/C=C/c2n[nH]c3nc(-c4ccc(O)cc4)cc(C(=O)N4CCNCC4)c23)c1] | LC9 | 497 | 0.80 |
| 32 | 5-{(E)-2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one | 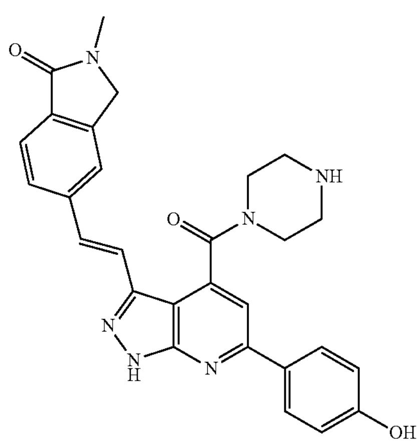 [SMILES: CN1Cc2cc(/C=C/c3n[nH]c4nc(-c5ccc(O)cc5)cc(C(=O)N5CCNCC5)c34)ccc2C1=O] | LC9 | 495 | 0.68 |
| 33 | [3-[(E)-2-(2,3-Dihydro-1H-indol-7-yl)-vinyl]-6-(4-hydroxy-phenyl)-1H-pyrazolo[3,4-b]pyridin-4-yl]-piperazin-1-yl-methanone | 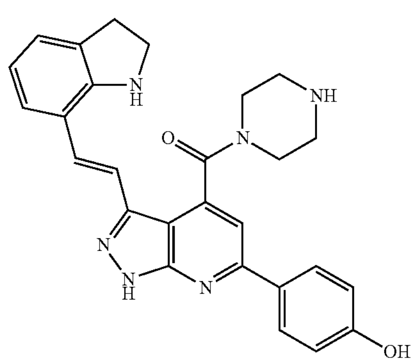 [SMILES: O=C(c1cc(-c2ccc(O)cc2)nc2[nH]nc(/C=C/c3cccc4c3NCC4)c12)N1CCNCC1] | LC9 | 467 | 0.61 |

EXAMPLE 34

3-{(E)-2-[4-(2,2-Dimethyl-piperazine-1-carbonyl)-6 (4-hydroxy-phenyl)-1H-pyrazolo[3,4-b]pyridin-3-yl]-vinyl}-N,N-dimethyl-benzamide

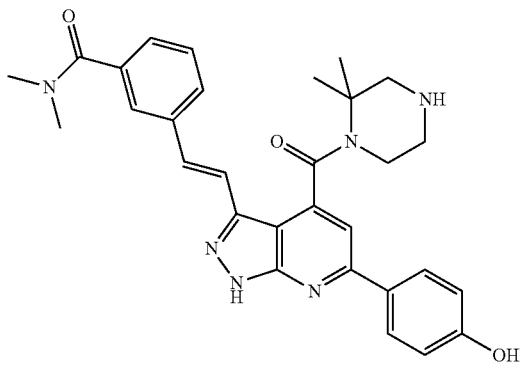 [SMILES: CN(C)C(=O)c1cccc(/C=C/c2n[nH]c3nc(-c4ccc(O)cc4)cc(C(=O)N4CCNCC4(C)C)c23)c1]

34.1: 4-[6-(4-Hydroxy-phenyl)-1-(tetrahydro-pyran-2-yl)-3-vinyl-1H-pyrazolo[3,4-b]-pyridine-4-carbonyl]-3,3-dimethyl-piperazine-1-carboxylic acid tert-butyl ester

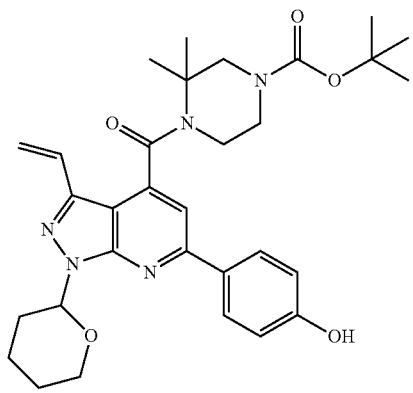 [SMILES: C=Cc1nn(C2CCCCO2)c2nc(-c3ccc(O)cc3)cc(C(=O)N3CCN(C(=O)OC(C)(C)C)CC3(C)C)c12]

4-[6-(4-Hydroxy-phenyl)-1-(tetrahydro-pyran-2-yl)-3-vinyl-1H-pyrazolo[3,4-b]pyridine-4-carbonyl]-3,3-dimethyl-piperazine-1-carboxylic acid tert-butyl ester was obtained in a similar fashion as 4-[6-(4-hydroxy-phenyl)-1-(tetrahydro-pyran-2-yl)-3-vinyl-1H-pyrazolo[3,4-b]pyridine-4-carbonyl]-piperazine-1-carboxylic acid tert-butyl ester employing 3,3-Dimethyl-piperazine-1-carboxylic acid tert-butyl ester instead of piperazine-1-carboxylic acid tert-butyl ester.

LC/MS (Method LC8): Rt=1.86 min; m/z=562.3 [M+H]$^+$.

34.2: 3-{(E)-2-[4-(2,2-Dimethyl-piperazine-1-carbonyl)-6-(4-hydroxy-phenyl)-1H-pyrazolo[3,4-b]pyridin-3-yl]-vinyl}-N,N-dimethyl-benzamide

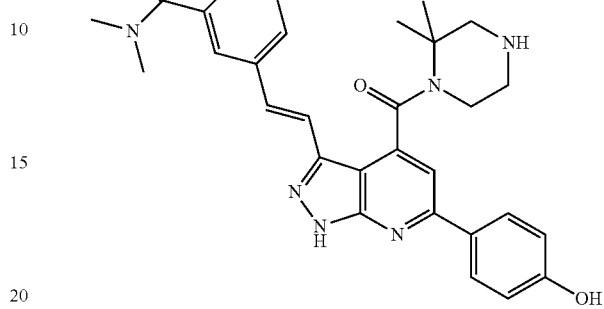

3-{(E)-2-[4-(2,2-Dimethyl-piperazine-1-carbonyl)-6-(4-hydroxy-phenyl)-1H-pyrazolo-[3,4-b]pyridin-3-yl]-vinyl}-N,N-dimethyl-benzamide has been prepared in a similar fashion as the synthesis for 1-(3-{(E)-2-[6-(4-Hydroxy-phenyl)-4-(piperazine-1-carbonyl)-1H-pyrazolo[3,4-b]pyridin-3-yl]-vinyl}-phenyl)-pyrrolidin-2-one. In the third step instead of 4-[6-(4-hydroxy-phenyl)-1-(tetrahydro-pyran-2-yl)-3-vinyl-1H-pyrazolo[3,4-b]-pyridine-4-carbonyl]-piperazine-1-carboxylic acid tert-butyl ester 4-[6-(4-Hydroxyphenyl)-1-(tetrahydro-pyran-2-yl)-3-vinyl-1H-pyrazolo[3,4-b]pyridine-4-carbonyl]-3,3-dimethyl-piperazine-1-carboxylic acid tert-butyl ester was reacted with 3-Iodo-N,N-dimethyl-benzamide, and deprotected in the forth step.

LC/MS (Method LC9): Rt=0.78 min; m/z=525 [M+H]$^+$.

EXAMPLE 35

6-{(E)-2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one

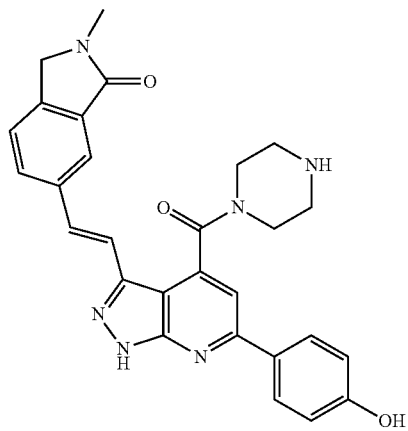 [SMILES: CN1Cc2ccc(/C=C/c3n[nH]c4nc(-c5ccc(O)cc5)cc(C(=O)N5CCNCC5)c34)cc2C1=O]

35.1: 6-Bromo-2-methylisoindolin-1-one

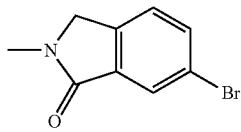

To a solution of 5-bromo-2-bromomethyl-benzoic acid methyl ester (1.00 g, 3.25 mmol) in THF (6.5 mL) was a solution of methylamine in THF (2M, 8.12 mL, 16.24 mmol). The reaction mixture was heated at 50° C. for 4 hours and then concentrated under vacuum. The residue was taken up in EtOAc and the organic layer was then washed with an aqueous 1M HCl solution, brine, dried ($Na_2SO_4$), filtered, concentrated under vacuum to give the title compound (0.73 g, 100%) as a yellow solid.

1H NMR (400 MHz, $CDCl_3$): δ 3.19 (m, 3H), 4.32 (s, 2H), 7.31 (d, 1H), 7.63 (dd, 1H), 7.96 (d, 1H).

35.2: 4-[6-(4-Hydroxy-phenyl)-3-[(E)-2-(2-methyl-3-oxo-2,3-dihydro-1H-isoindol-5-yl)vinyl]-1-(tetrahydro-pyran-2-yl)-1H-pyrazolo[3,4-b]pyridine-4-carbonyl]-piperazine-1-carboxylic acid tert-butyl ester

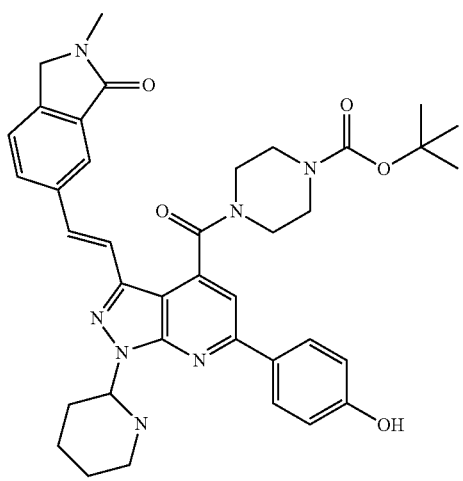 [SMILES: CN1Cc2ccc(/C=C/c3nn(C4CCCCN4)c4nc(-c5ccc(O)cc5)cc(C(=O)N5CCN(C(=O)OC(C)(C)C)CC5)c34)cc2C1=O]

Utilizing the procedure described in example 20.3 except substituting 1-(3-iodophenyl)-pyrrolidin-2-one with 6-bromo-2-methylisoindolin-1-one lead to the title compound as a yellow solid.

LC/MS (Method LC8): Rt=2.62 min; m/z=679 [M+H]$^+$.

35.3: 6-{(E)-2-[6-(4-Hydroxy-phenyl)-4-(piperazine-1-carbonyl)-1H-pyrazolo[3,4-b]pyridin-3-yl]-vinyl}-2-methyl-2,3-dihydro-isoindol-1-one

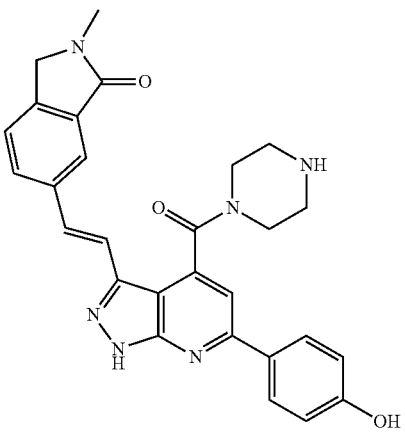 [SMILES: CN1Cc2ccc(/C=C/c3n[nH]c4nc(-c5ccc(O)cc5)cc(C(=O)N5CCNCC5)c34)cc2C1=O]

To a solution of 4-[6-(4-Hydroxy-phenyl)-3-[(E)-2-(2-methyl-3-oxo-2,3-dihydro-1H-isoindol-5-yl)-vinyl]-1-(tetrahydro-pyran-2-yl)-1H-pyrazolo[3,4-b]pyridine-4-carbonyl]-piperazine-1-carboxylic acid tert-butyl ester (0.19 g, 0.28 mmol) in methanol (4 ml) was added 4N HCl in dioxane (0.7 ml). The reaction mixture was stirred at room temperature for 3 days, diethyl ether was then added, the resulting precipitated was filtered and washed once with diethyl ether to afford the hydrochloride salt of the title compound (0.15 g, 96%) as an orange solid.

LC/MS (Method LC10): Rt=2.82 min; m/z=495 [M+H]$^+$.

EXAMPLE 36

[3-(2-cyclohexyl-ethyl)-6-(4-hydroxy-phenyl)-1H-pyrazolo[3,4-b]pyridin-4-yl]-piperazin-1-yl-methanone

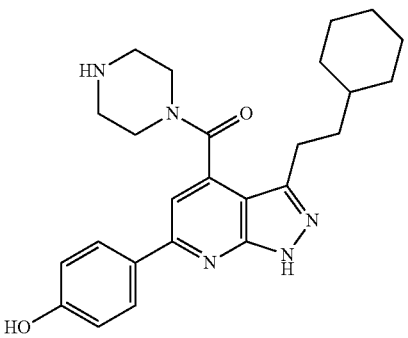 [SMILES: O=C(c1cc(-c2ccc(O)cc2)nc2[nH]nc(CCC3CCCCC3)c12)N1CCNCC1]

36.1: 6-chloro-3-cyclohexylethynyl-1-(tetrahydro-pyran-2-yl)-1H-pyrazolo[3,4-b]pyridine-4-carboxylic acid ethyl ester

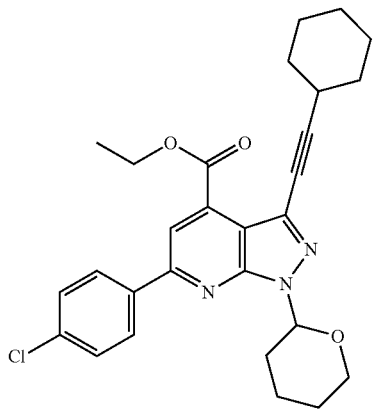 [SMILES: CCOC(=O)c1cc(-c2ccc(Cl)cc2)nc2c1c(C#CC1CCCCC1)nn2C1CCCCO1]

A solution of 6-chloro-3-iodo-1-(tetrahydro-pyran-2-yl)-1H-pyrazolo[3,4-b]pyridine-4-carboxylic acid ethyl ester (1.0 g, 2.30 mmol) and triethylamine (1.92 mL, 13.77 mmol) in THF (7.65 mL) was degassed using argon during 3 min. Cyclohexylacetylene (0.45 mL, 3.44 mmol), copper(I) iodide (0.08 g, 0.46 mmol) and tetrakis(triphenylphosphine)palladium (0.13 g, 0.11 mmol) were then added and the reaction mixture was stirred at room temperature overnight. The reaction mixture was concentrated under vacuum and the residue purified on a silica gel column chromatography using a gradient of ethyl acetate (0-5%) in cyclohexane to afford the title compound as a beige solid (0.93 g, 97%).

LC/MS (Method LC8): Rt=2.27 min; m/z=416 [M+H]$^+$.

36.2: 3-cyclohexylethynyl-6-(4-hydroxy-phenyl)-1-(tetrahydro-pyran-2-yl)-1H-pyrazolo[3,4-b]pyridine-4-carboxylic acid

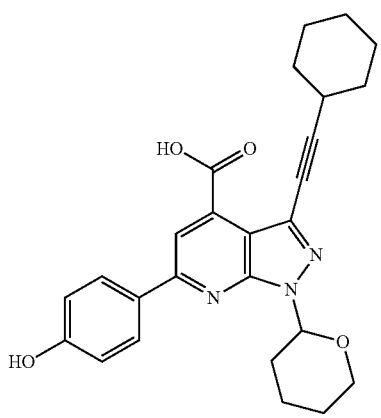 [SMILES: O=C(O)c1cc(-c2ccc(O)cc2)nc2c1c(C#CC1CCCCC1)nn2C1CCCCO1]

Utilizing the procedure described in example 16.3 except substituting 6-chloro-3-((E)styryl)-1-(tetrahydro-pyran-2-yl)-1H-pyrazolo[3,4-b]pyridine-4-carboxylic acid ethyl ester with 6-chloro-3-cyclohexylethynyl-1-(tetrahydro-pyran-2-yl)-1H-pyrazolo[3,4-b]-pyridine-4-carboxylic acid ethyl ester, 3-cyclohexylethynyl-6-(4-hydroxy-phenyl)-1-(tetrahydro-pyran-2-yl)-1H-pyrazolo[3,4-b]pyridine-4-carboxylic acid (0.93 g, 97%) was obtained as a beige solid.

LC/MS (Method LC8): Rt=1.91 min; m/z=446 [M+H]$^+$.

36.3: 4-[3-cyclohexylethynyl-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester

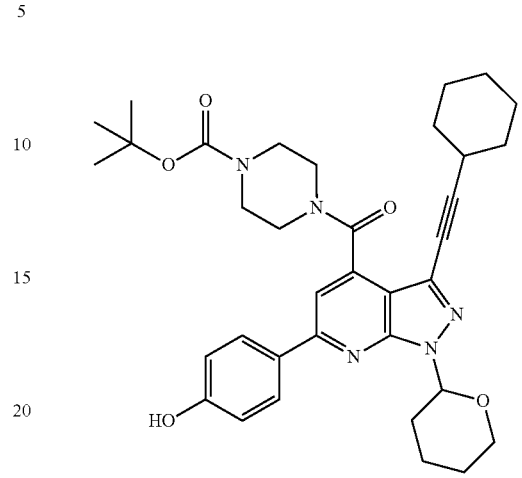

Utilizing the procedure described in example 1.6 except substituting 6-chloro-3-[(E)-2-(4-chloro-phenyl)-vinyl]-1-(tetrahydro-pyran-2-yl)-1H-pyrazolo[3,4-b]pyridine-4-carboxylic acid with 3-cyclohexylethynyl-6-(4-hydroxy-phenyl)-1-(tetrahydro-pyran-2-yl)-1H-pyrazolo[3,4-b]pyridine-4-carboxylic acid, 4-[3-cyclohexylethynyl-6-(4-hydroxyphenyl)-1-(tetrahydro-pyran-2-yl)-1H-pyrazolo[3,4-b]pyridine-4-carbonyl]-piperazine-1-carboxylic acid tert-butyl ester (0.72 g, 96%) was obtained as a yellow solid.

LC/MS (Method LC8): Rt=2.06 min; m/z=614 [M+H]$^+$.

36.4: 4-[3-(2-cyclohexyl-ethyl)-6-(4-hydroxy-phenyl)-1-(tetrahydro-pyran-2-yl)-1H-pyrazolo[3,4-b]pyridine-4-carbonyl]-piperazine-1-carboxylic acid tert-butyl ester

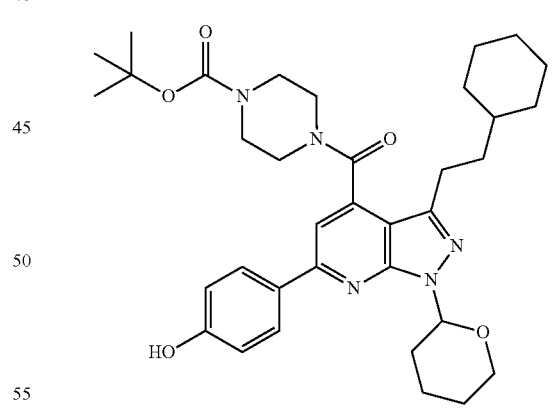

To a solution of 4-[3-cyclohexylethynyl-6-(4-hydroxyphenyl)-1-(tetrahydro-pyran-2-yl)-1H-pyrazolo[3,4-b]pyridine-4-carbonyl]-piperazine-1-carboxylic acid tert-butyl ester (0.34 g, 0.56 mmol) in methanol (15 ml) was added Pd/C (10%, 12 mg, 0.01 mmol). The reaction mixture was hydrogenated at 4 bar for 18 h, Pd/C (10%, 12 mg, 0.01 mmol) was added and hydrogenation pursued for an additional 8 hours. The reaction mixture was then filtered and concentrated under reduced pressure to yield the title compound (0.33 g, 95%) as a grey solid.

LC/MS (Method LC8): Rt=2.17 min; m/z=618 [M+H]$^+$.

36.5: [3-(2-cyclohexyl-ethyl)-6-(4-hydroxy-phenyl)-1H-pyrazolo[3,4-b]pyridin-4-yl]-piperazin-1-yl-methanone

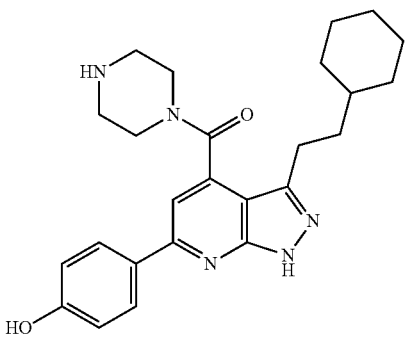 [SMILES: O=C(c1cc(-c2ccc(O)cc2)nc2[nH]nc(CCC3CCCCC3)c12)N1CCNCC1]

Utilizing the procedure described in example 1.8 except substituting 4-[3-[(E)-2-(4-chloro-phenyl)-vinyl]-6-(4-hydroxy-phenyl)-1-(tetrahydro-pyran-2-yl)-1H-pyrazolo-[3,4-b]pyridine-4-carbonyl]-piperazine-1-carboxylic acid tert-butyl ester with 4-[3-(2-cyclohexyl-ethyl)-6-(4-hydroxy-phenyl)-1-(tetrahydro-pyran-2-yl)-1H-pyrazolo[3,4-b]-pyridine-4-carbonyl]-piperazine-1-carboxylic acid tert-butyl ester, a chlorhydrate salt of [3-(2-cyclohexyl-ethyl)-6-(4-hydroxy-phenyl)-1H-pyrazolo[3,4-b]pyridin-4-yl]-piperazin-1-yl-methanone was obtained (0.15 g, 58%) as a yellow solid.

LC/MS (Method LC10): Rt=3.47 min; m/z=434 [M+H]$^+$.

EXAMPLE 37

[3-[(E)-2-(4-Fluoro-phenyl)-vinyl]-6-(4-hydroxy-phenyl)-1H-pyrazolo[3,4-b]pyridin-4-yl]-piperazin-1-yl-methanone

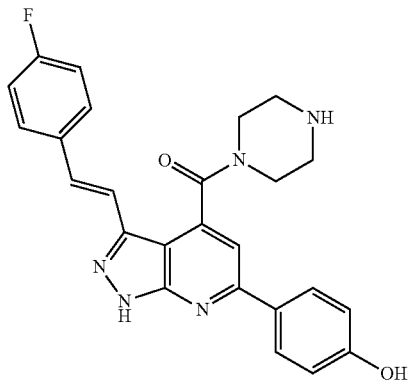 [SMILES: O=C(c1cc(-c2ccc(O)cc2)nc2[nH]nc(/C=C/c3ccc(F)cc3)c12)N1CCNCC1]

0.25 mmol of 1-fluoro-4-iodo-benzene were weighted into a reaction tube. 2.5 mmol sodium hadrogencarbonate was added as solid, followed by 0.25 mmol tetrabutylammonium fluoride in 0.5 ml DMF and 0.1 mmol of 4-[6-(4-hydroxy-phenyl)-1-(tetrahydro-pyran-2-yl)-3-vinyl-1H-pyrazolo[3,4-b]pyridine-4-carbonyl]-piperazine-1-carboxylic acid tert-butyl ester in 1 ml DMF. The tube was purged with Argon. 0.01 mmol palladium(II) acetate in 0.25 mmol DMF was added, the tube was closed with a screw cap and stirred for 8 h at 80° C. New palladium(II) acetate (0.01 mmol) was added and heating continued for 1 h at 100° C. The reaction mixture was diluted with 20 ml ethyl acetate and washed with 20 ml water, dried and evaporated. The residue was dissolved in 5 ml THF and 1 ml methanol and shaken with 100 mg silica-bound propane thiol scavenger for 4 h at RT. The mixture was filtered, the filter washed with THF, the filtrate evaporated and the residue submitted to SFC purification. The purified product was dissolved in 3 ml methanol and 0.5 ml 4N HCl in dioxane. The mixture was stirred for 30 min at 65° C. The cooled solution was diluted slowly with ml diethyl ether to precipitate the product, which was filtered off, washed with 1 ml diethyl ether, and dried in vacuo to afford [3-[(E)-2-(4-Fluoro-phenyl)-vinyl]-6-(4-hydroxy-phenyl)-1H-pyrazolo[3,4-b]pyridin-4-yl]-piperazin-1-yl-methanone (18 mg, 37%).

LC/MS (Method LC1): Rt=1.74 min; m/z=444.17 [M+H]$^+$.

$^1$H-NMR (500 MHz, d6-DMSO): 2.72-3.27 (bm, 4H), 3.4-3.5 (bm, 3H), 4.22-4.44 (bm, 1H) 6.92 (d, 2H), 7.11 (d, 1H), 7.23 (m, 2H), 7.32 (d, 1H), 7.61 (m, 2H), 7.79 (s, 1H), 8.09 (d, 2H), 9.2 (bs, 1H), 9.5 (bs, 1H)

The following examples have been prepared in a similar fashion as the synthesis for [3-[(E)-2-(4-fluoro-phenyl)-vinyl]-6-(4-hydroxyphenyl)-1H-pyrazolo[3,4-b]pyridin-4-yl]-piperazin-1-yl-methanone described immediately above employing 4-[6-(4-hydroxyphenyl)-1-(tetrahydro-pyran-2-yl)-3-vinyl-1H-pyrazolo[3,4-b]pyridine-4-carbonyl]-piperazine-1-carboxylic acid tert-butyl ester and the respective aryl iodides or bromides:

| Exp. No. | Name | Structure | LC/MS method | m/z [M + H]+ | Rt [min] |
|---|---|---|---|---|---|
| 38 | [6-(4-Hydroxy-phenyl)-3-((E)-2-m-tolyl-vinyl)-1H-pyrazolo[3,4-b]pyridin-4-yl]-piperazin-1-yl-methanone | 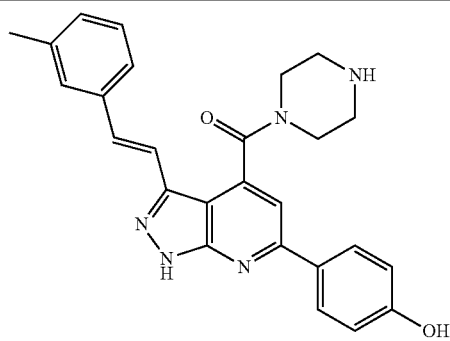 | LC2 | 440.04 | 2.82 |

-continued

| Exp. No. | Name | Structure | LC/MS method | m/z [M + H]+ | Rt [min] |
|---|---|---|---|---|---|
| 39 | [3-[(E)-2-(2,4-Dichloro-phenyl)-vinyl]-6-(4-hydroxy-phenyl)-1H-pyrazolo[3,4-b]pyridin-4-yl]-piperazin-1-yl-methanone | 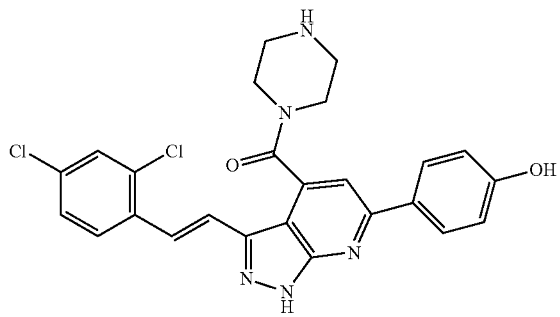 [SMILES: O=C(c1cc(-c2ccc(O)cc2)nc2[nH]nc(/C=C/c3ccc(Cl)cc3Cl)c12)N1CCNCC1] | LC1 | 494.21 | 1.95 |
| 40 | [3-[(E)-2-(3,5-Dimethyl-phenyl)-vinyl]-6-(4-hydroxy-phenyl)-1H-pyrazolo[3,4-b]pyridin-4-yl]-piperazin-1-yl-methanone | 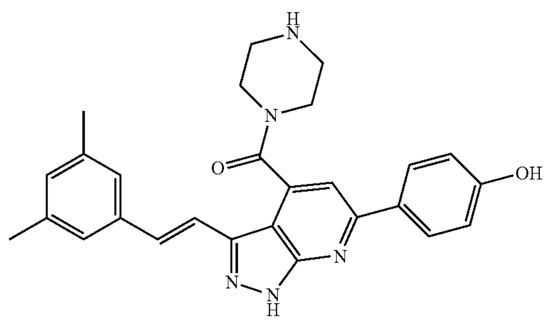 [SMILES: Cc1cc(C)cc(/C=C/c2n[nH]c3nc(-c4ccc(O)cc4)cc(C(=O)N4CCNCC4)c23)c1] | LC1 | 454.29 | 1.89 |
| 41 | [3-[(E)-2-(4-Difluoromethoxy-phenyl)-vinyl]-6-(4-hydroxy-phenyl)-1H-pyrazolo[3,4-b]pyridin-4-yl]-piperazin-1-yl-methanone | 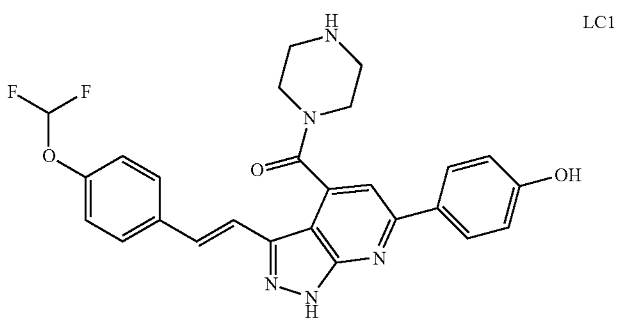 | LC1 | 492.23 | 1.87 |
| 42 | {6-(4-Hydroxy-phenyl)-3-[(E)-2-(4-trifluoromethyl-phenyl)-vinyl]-1H-pyrazolo[3,4-b]pyridin-4-yl}-piperazin-1-yl-methanone | 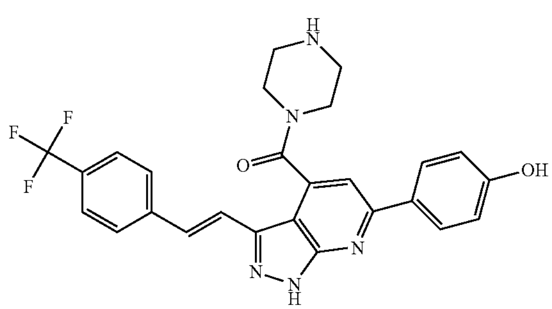 [SMILES: O=C(c1cc(-c2ccc(O)cc2)nc2[nH]nc(/C=C/c3ccc(C(F)(F)F)cc3)c12)N1CCNCC1] | LC1 | 494.22 | 1.95 |
| 43 | [3-[(E)-2-(2,4-Dimethoxy-phenyl)-vinyl]-6-(4-hydroxy-phenyl)-1H-pyrazolo[3,4-b]pyridin-4-yl]-piperazin-1-yl-methanone | 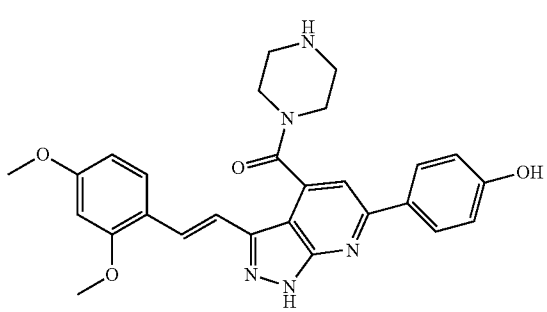 [SMILES: COc1ccc(/C=C/c2n[nH]c3nc(-c4ccc(O)cc4)cc(C(=O)N4CCNCC4)c23)c(OC)c1] | LC1 | 486.25 | 1.8 |

| Exp. No. | Name | Structure | LC/MS method | m/z [M + H]+ | Rt [min] |
|---|---|---|---|---|---|
| 44 | {6-(4-Hydroxy-phenyl)-3-[(E)-2-(4-phenoxy-phenyl)-vinyl]-1H-pyrazolo[3,4-b]pyridin-4-yl}-piperazin-1-yl-methanone | 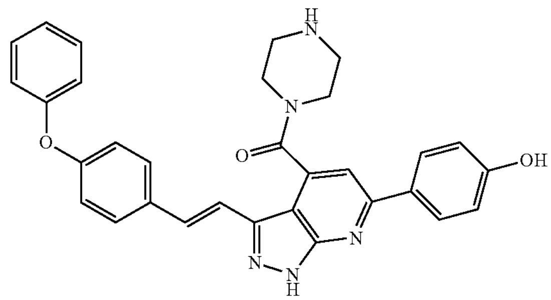 [SMILES: O=C(c1cc(-c2ccc(O)cc2)nc2[nH]nc(/C=C/c3ccc(Oc4ccccc4)cc3)c12)N1CCNCC1] | LC1 | 518.25 | 2 |
| 45 | [3-[(E)-2-(3,4-Dichloro-phenyl)-vinyl]-6-(4-hydroxy-phenyl)-1H-pyrazolo[3,4-b]pyridin-4-yl]-piperazin-1-yl-methanone | 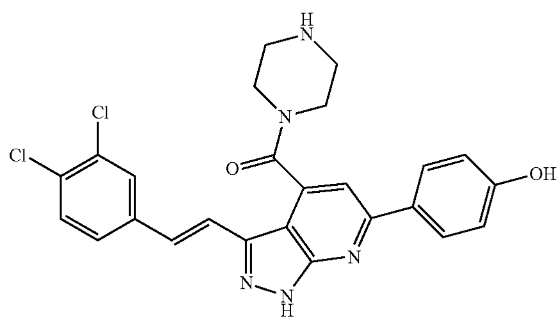 [SMILES: O=C(c1cc(-c2ccc(O)cc2)nc2[nH]nc(/C=C/c3ccc(Cl)c(Cl)c3)c12)N1CCNCC1] | LC1 | 494.14 | 1.95 |
| 46 | {6-(4-Hydroxy-phenyl)-3-[(E)-2-(3-trifluoromethyl-phenyl)-vinyl]-1H-pyrazolo[3,4-b]pyridin-4-yl}-piperazin-1-yl-methanone | 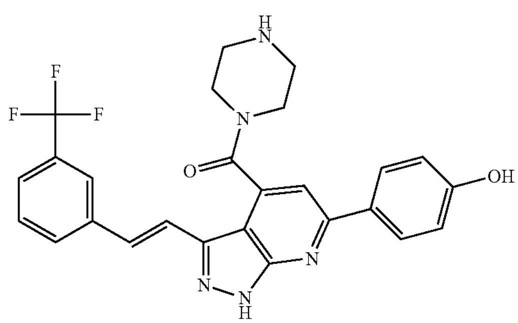 [SMILES: O=C(c1cc(-c2ccc(O)cc2)nc2[nH]nc(/C=C/c3cccc(C(F)(F)F)c3)c12)N1CCNCC1] | LC1 | 494.17 | 1.93 |
| 47 | [3-[(E)-2-(4-Hydroxy-3-methyl-phenyl)-vinyl]-6-(4-hydroxy-phenyl)-1H-pyrazolo[3,4-b]pyridin-4-yl]-piperazin-1-yl-methanone | 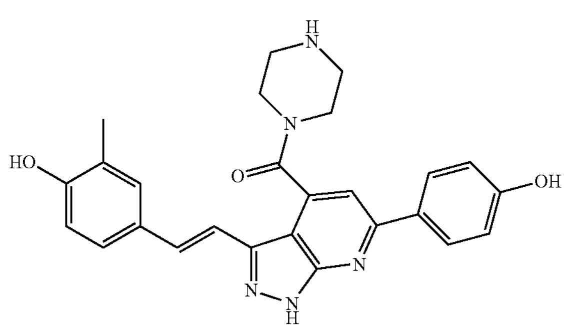 [SMILES: Cc1cc(/C=C/c2n[nH]c3nc(-c4ccc(O)cc4)cc(C(=O)N4CCNCC4)c23)ccc1O] | LC1 | 456.22 | 1.69 |

-continued

| Exp. No. | Name | Structure | LC/MS method | m/z [M + H]+ | Rt [min] |
|---|---|---|---|---|---|
| 48 | [3-[(E)-2-(3-Chloro-phenyl)-vinyl]-6-(4-hydroxy-phenyl)-1H-pyrazolo[3,4-b]pyridin-4-yl]-piperazin-1-yl-methanone | 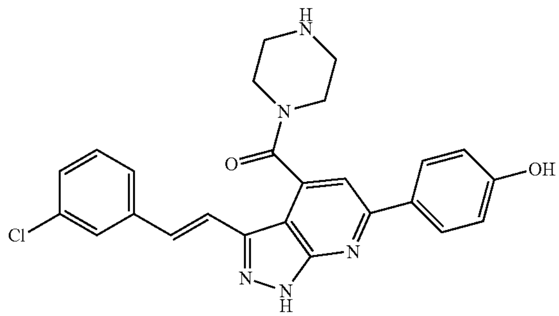 [SMILES: O=C(c1cc(-c2ccc(O)cc2)nc2[nH]nc(/C=C/c3cccc(Cl)c3)c12)N1CCNCC1] | LC1 | 460.17 | 1.85 |
| 49 | [3-[(E)-2-(2,4-Dimethyl-phenyl)-vinyl]-6-(4-hydroxy-phenyl)-1H-pyrazolo[3,4-b]pyridin-4-yl]-piperazin-1-yl-methanone | 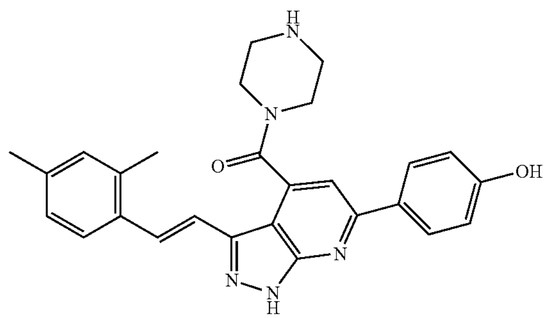 [SMILES: Cc1ccc(/C=C/c2n[nH]c3nc(-c4ccc(O)cc4)cc(C(=O)N4CCNCC4)c23)c(C)c1] | LC1 | 454.22 | 1.89 |
| 50 | [3-[(E)-2-(2,5-Dimethyl-phenyl)-vinyl]-6-(4-hydroxy-phenyl)-1H-pyrazolo[3,4-b]pyridin-4-yl]-piperazin-1-yl-methanone | 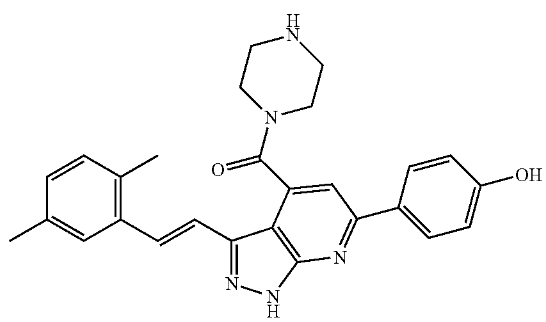 [SMILES: Cc1ccc(C)c(/C=C/c2n[nH]c3nc(-c4ccc(O)cc4)cc(C(=O)N4CCNCC4)c23)c1] | LC1 | 454.22 | 1.87 |
| 51 | {6-(4-Hydroxy-phenyl)-3-[(E)-2-(4-isopropyl-phenyl)-vinyl]-1H-pyrazolo[3,4-b]pyridin-4-yl}-piperazin-1-yl-methanone | 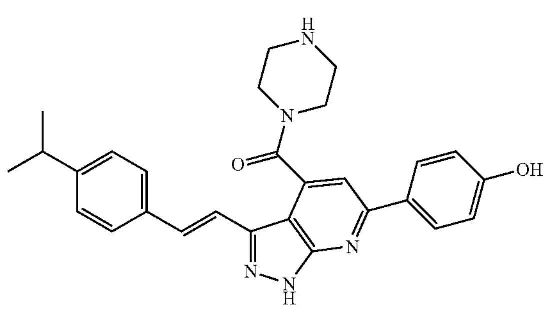 [SMILES: CC(C)c1ccc(/C=C/c2n[nH]c3nc(-c4ccc(O)cc4)cc(C(=O)N4CCNCC4)c23)cc1] | LC1 | 468.23 | 1.97 |
| 52 | [3-[(E)-2-(2-Chloro-4-fluoro-phenyl)-vinyl]-6-(4-hydroxy-phenyl)-1H-pyrazolo[3,4-b]pyridin-4-yl]-piperazin-1-yl-methanone | 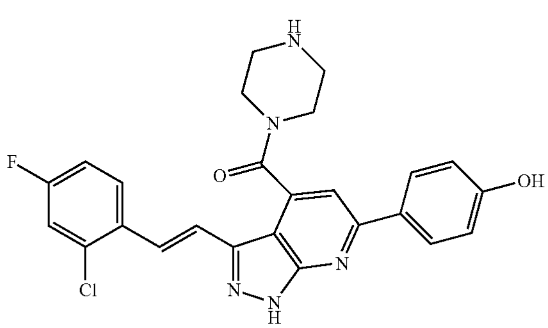 [SMILES: O=C(c1cc(-c2ccc(O)cc2)nc2[nH]nc(/C=C/c3ccc(F)cc3Cl)c12)N1CCNCC1] | LC1 | 478.15 | 1.88 |

| Exp. No. | Name | Structure | LC/MS method | m/z [M + H]+ | Rt [min] |
|---|---|---|---|---|---|
| 53 | [3-[(E)-2-(4-Ethyl-phenyl)-vinyl]-6-(4-hydroxy-phenyl)-1H-pyrazolo[3,4-b]pyridin-4-yl]-piperazin-1-yl-methanone | 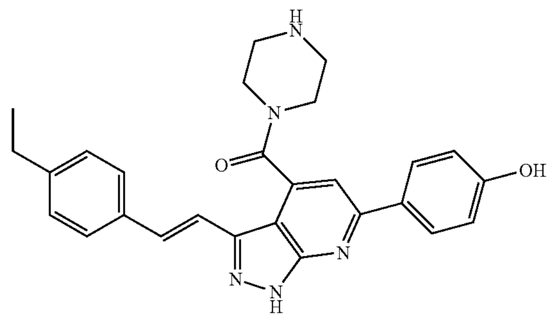 [SMILES: CCc1ccc(/C=C/c2n[nH]c3nc(-c4ccc(O)cc4)cc(C(=O)N4CCNCC4)c23)cc1] | LC2 | 454.01 | 3.01 |
| 54 | [3-[(E)-2-(4-tert-Butyl-phenyl)-vinyl]-6-(4-hydroxy-phenyl)-1H-pyrazolo[3,4-b]pyridin-4-yl]-piperazin-1-yl-methanone | 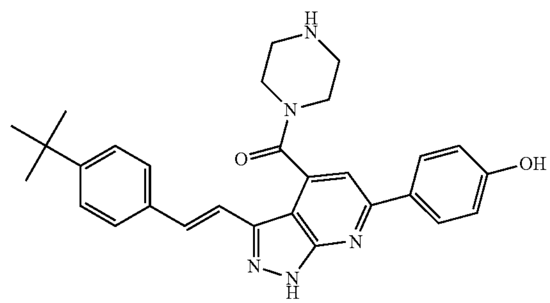 [SMILES: CC(C)(C)c1ccc(/C=C/c2n[nH]c3nc(-c4ccc(O)cc4)cc(C(=O)N4CCNCC4)c23)cc1] | LC2 | 482.02 | 3.31 |
| 55 | [3-[(E)-2-(3-Fluoro-4-methyl-phenyl)-vinyl]-6-(4-hydroxy-phenyl)-1H-pyrazolo[3,4-b]pyridin-4-yl]-piperazin-1-yl-methanone | 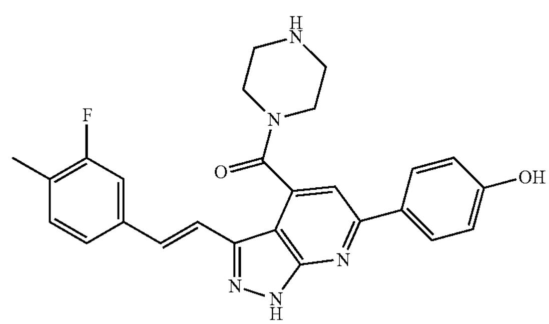 [SMILES: Cc1ccc(/C=C/c2n[nH]c3nc(-c4ccc(O)cc4)cc(C(=O)N4CCNCC4)c23)cc1F] | LC2 | 457.98 | 2.92 |
| 56 | {6-(4-Hydroxy-phenyl)-3-[(E)-2-(3-methoxy-phenyl)-vinyl]-1H-pyrazolo[3,4-b]pyridin-4-yl}-piperazin-1-yl-methanone | 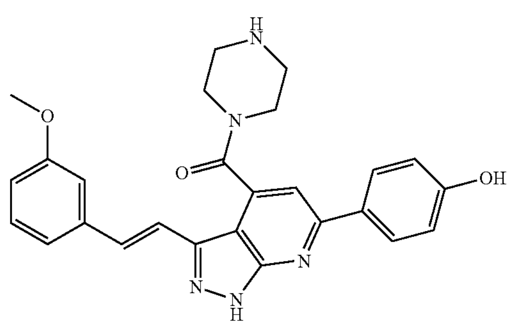 [SMILES: COc1cccc(/C=C/c2n[nH]c3nc(-c4ccc(O)cc4)cc(C(=O)N4CCNCC4)c23)c1] | LC1 | 456.23 | 1.77 |
| 57 | 1-(4-{(E)-2-[6-(4-Hydroxy-phenyl)-4-(piperazine-1-carbonyl)-1H-pyrazolo[3,4-b]pyridin-3-yl]-vinyl}-phenyl)-ethanone | 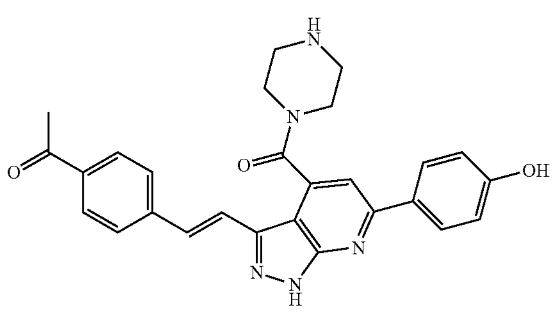 [SMILES: CC(=O)c1ccc(/C=C/c2n[nH]c3nc(-c4ccc(O)cc4)cc(C(=O)N4CCNCC4)c23)cc1] | LC1 | 468.25 | 1.72 |

| Exp. No. | Name | Structure | LC/MS method | m/z [M + H]+ | Rt [min] |
|---|---|---|---|---|---|
| 58 | {6-(4-Hydroxy-phenyl)-3-[(E)-2-(4-trifluorome-thoxy-phenyl)-vinyl]-1H-pyrazo-lo[3,4-b]pyridin-4-yl}-piperazin-1-yl-methanone | 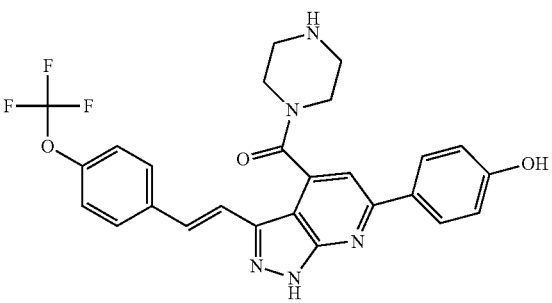 [SMILES: O=C(c1cc(-c2ccc(O)cc2)nc2[nH]nc(/C=C/c3ccc(OC(F)(F)F)cc3)c12)N1CCNCC1] | LC1 | 510.26 | 1.96 |
| 59 | [3-[(E)-2-(3,4-Difluoro-phenyl)-vinyl]-6-(4-hydroxy-phenyl)-1H-pyrazolo[3,4-b]pyridin-4-yl]-piperazin-1-yl-methanone | 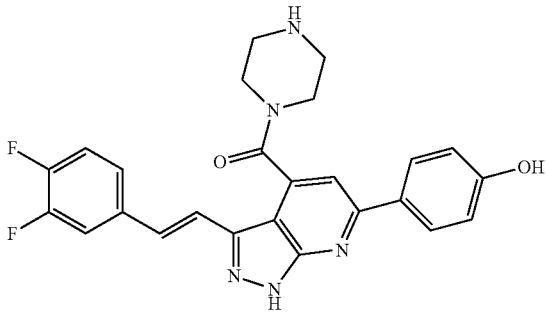 [SMILES: O=C(c1cc(-c2ccc(O)cc2)nc2[nH]nc(/C=C/c3ccc(F)c(F)c3)c12)N1CCNCC1] | LC1 | 462.27 | 1.83 |
| 60 | {6-(4-Hydroxy-phenyl)-3-[(E)-2-(2-methoxy-phenyl)-vinyl]-1H-pyrazolo[3,4-b]pyridin-4-yl}-piperazin-1-yl-methanone | 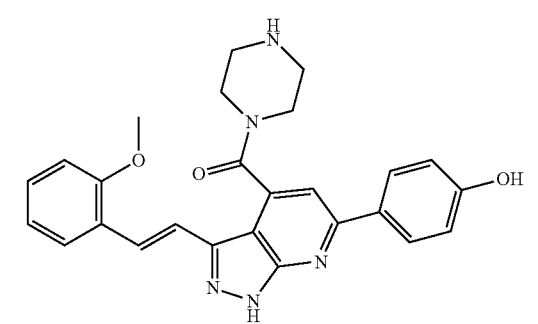 [SMILES: COc1ccccc1/C=C/c1n[nH]c2nc(-c3ccc(O)cc3)cc(C(=O)N3CCNCC3)c12] | LC1 | 456.28 | 1.75 |
| 61 | [3-[(E)-2-(4-Fluoro-2-methyl-phenyl)-vinyl]-6-(4-hydroxy-phenyl)-1H-pyrazolo[3,4-b]pyridin-4-yl]-piperazin-1-yl-methanone | 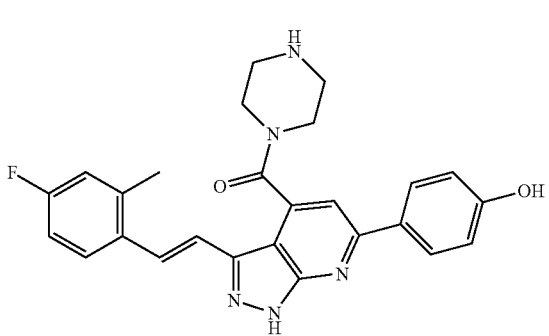 [SMILES: Cc1cc(F)ccc1/C=C/c1n[nH]c2nc(-c3ccc(O)cc3)cc(C(=O)N3CCNCC3)c12] | LC1 | 458.27 | 1.84 |

-continued

| Exp. No. | Name | Structure | LC/MS method | m/z [M + H]+ | Rt [min] |
|---|---|---|---|---|---|
| 62 | {6-(4-Hydroxy-phenyl)-3-[(E)-2-(3,4,5-trimethoxy-phenyl)-vinyl]-1H-pyrazolo[3,4-b]pyridin-4-yl}-piperazin-1-yl-methanone | 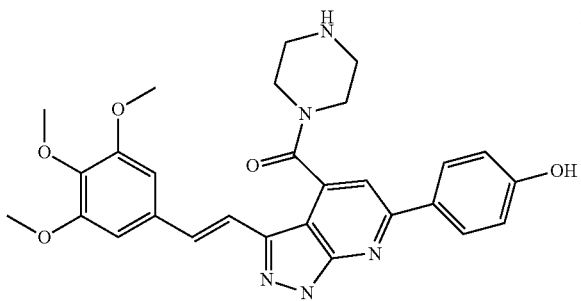 | LC1 | 516.31 | 1.74 |
| 63 | [3-[(E)-2-(2-Fluoro-4-methyl-phenyl)-vinyl]-6-(4-hydroxy-phenyl)-1H-pyrazolo[3,4-b]pyridin-4-yl]-piperazin-1-yl-methanone | 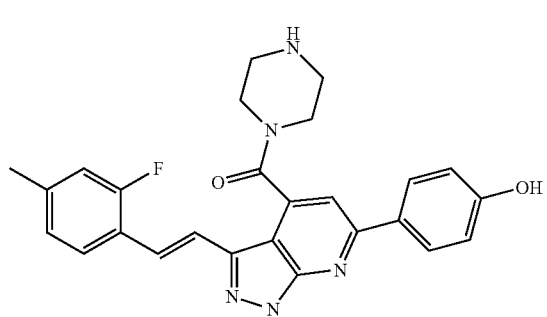 | LC1 | 458.26 | 1.86 |
| 64 | [3-[(E)-2-(2,3-Dihydro-benzofuran-5-yl)-vinyl]-6-(4-hydroxy-phenyl)-1H-pyrazolo[3,4-b]pyridin-4-yl]-piperazin-1-yl-methanone | 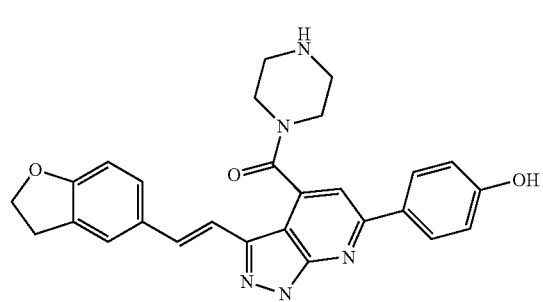 | LC1 | 468.27 | 1.74 |
| 65 | [3-((E)-2-Benzo[1,3]dioxol-5-yl-vinyl)-6-(4-hydroxy-phenyl)-1H-pyrazolo[3,4-b]pyridin-4-yl]-piperazin-1-yl-methanone | 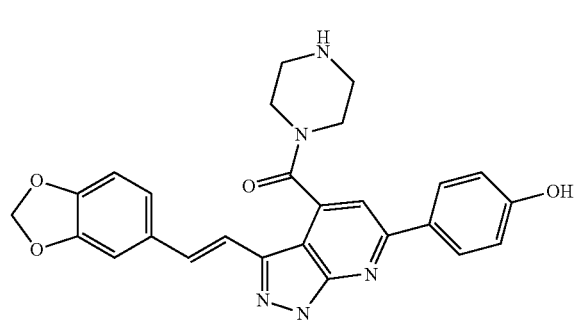 | LC1 | 470.24 | 1.76 |
| 66 | 4-{(E)-2-[6-(4-Hydroxy-phenyl)-4-(piperazine-1-carbonyl)-1H-pyrazolo[3,4-b]pyridin-3-yl]-vinyl}-N,N-dimethyl-benzamide | 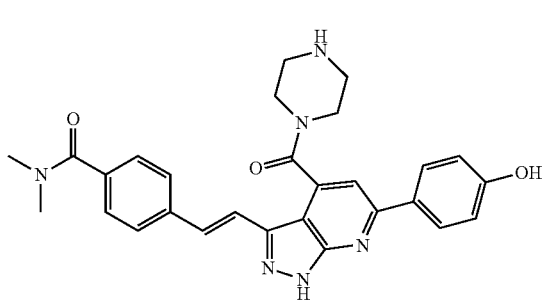 [SMILES: CN(C)C(=O)c1ccc(/C=C/c2n[nH]c3nc(-c4ccc(O)cc4)cc(C(=O)N4CCNCC4)c23)cc1] | LC1 | 497.29 | 1.63 |

| Exp. No. | Name | Structure | LC/MS method | m/z [M + H]+ | Rt [min] |
|---|---|---|---|---|---|
| 67 | [3-[(E)-2-(4-Ethoxy-phenyl)-vinyl]-6-(4-hydroxy-phenyl)-1H-pyrazolo[3,4-b]pyridin-4-yl]-piperazin-1-yl-methanone | 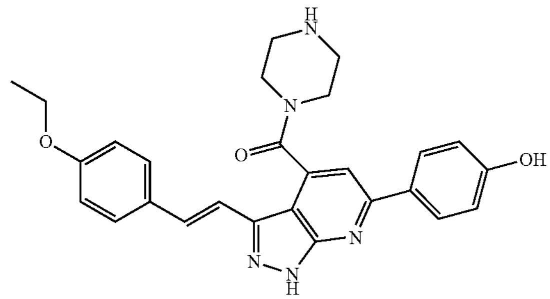 [SMILES: CCOc1ccc(/C=C/c2n[nH]c3nc(-c4ccc(O)cc4)cc(C(=O)N4CCNCC4)c23)cc1] | LC1 | 470.26 | 1.84 |
| 68 | {6-(4-Hydroxy-phenyl)-3-[(E)-2-(2-trifluoromethyl-phenyl)-vinyl]-1H-pyrazolo[3,4-b]pyridin-4-yl}-piperazin-1-yl-methanone | 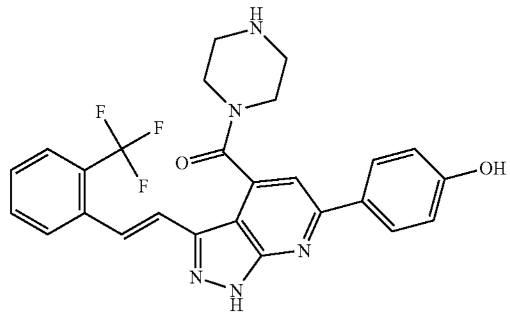 [SMILES: O=C(c1cc(-c2ccc(O)cc2)nc2[nH]nc(/C=C/c3ccccc3C(F)(F)F)c12)N1CCNCC1] | LC1 | 494.21 | 1.89 |
| 69 | [6-(4-Hydroxy-phenyl)-3-((E)-2-o-tolyl-vinyl)-1H-pyrazolo[3,4-b]pyridin-4-yl]-piperazin-1-yl-methanone | 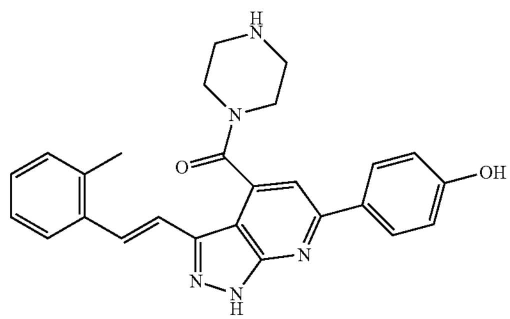 [SMILES: Cc1ccccc1/C=C/c1n[nH]c2nc(-c3ccc(O)cc3)cc(C(=O)N3CCNCC3)c12] | LC1 | 440.22 | 1.82 |
| 70 | [3-[(E)-2-(3,5-Dichloro-phenyl)-vinyl]-6-(4-hydroxy-phenyl)-1H-pyrazolo[3,4-b]pyridin-4-yl]-piperazin-1-yl-methanone | 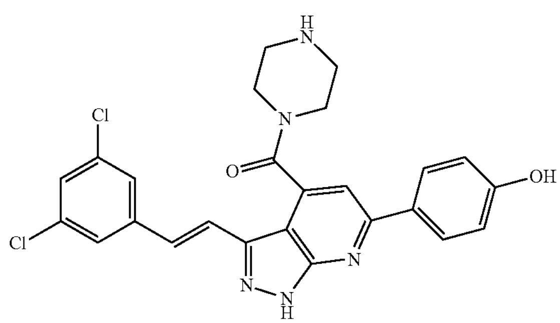 [SMILES: O=C(c1cc(-c2ccc(O)cc2)nc2[nH]nc(/C=C/c3cc(Cl)cc(Cl)c3)c12)N1CCNCC1] | LC1 | 494.15 | 1.96 |
| 71 | [3-[(E)-2-(3-Fluoro-phenyl)-vinyl]-6-(4-hydroxy-phenyl)-1H-pyrazolo[3,4-b]pyridin-4-yl]-piperazin-1-yl-methanone | 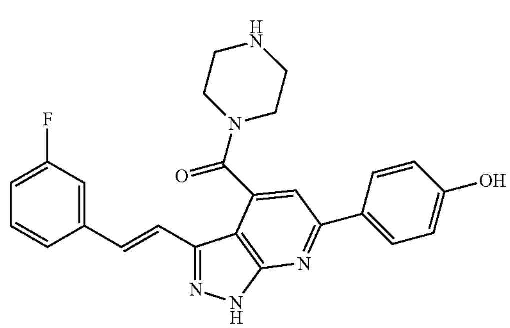 [SMILES: O=C(c1cc(-c2ccc(O)cc2)nc2[nH]nc(/C=C/c3cccc(F)c3)c12)N1CCNCC1] | LC1 | 444.20 | 1.80 |

| Exp. No. | Name | Structure | LC/MS method | m/z [M + H]+ | Rt [min] |
|---|---|---|---|---|---|
| 72 | [3-[(E)-2-(2-Fluoro-phenyl)-vinyl]-6-(4-hydroxy-phenyl)-1H-pyrazolo[3,4-b]pyridin-4-yl]-piperazin-1-yl-methanone | 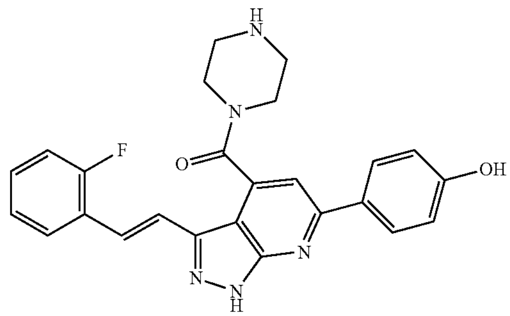 [SMILES: O=C(c1cc(-c2ccc(O)cc2)nc2[nH]nc(/C=C/c3ccccc3F)c12)N1CCNCC1] | LC1 | 444.19 | 1.76 |
| 73 | {6-(4-Hydroxy-phenyl)-3-[(E)-2-(4-methoxy-3-methyl-phenyl)-vinyl]-1H-pyrazolo[3,4-b]pyridin-4-yl}-piperazin-1-yl-methanone | 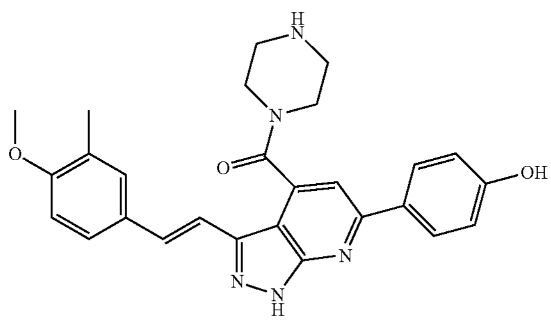 [SMILES: COc1ccc(/C=C/c2n[nH]c3nc(-c4ccc(O)cc4)cc(C(=O)N4CCNCC4)c23)cc1C] | LC1 | 470.21 | 1.84 |

EXAMPLE 74

4-[6-(4-Hydroxy-phenyl)-3-((E)-styryl)-1H-pyrazolo[3,4-b]pyridine-4-carbonyl]-piperazine-1-carboxylic acid dimethylamide

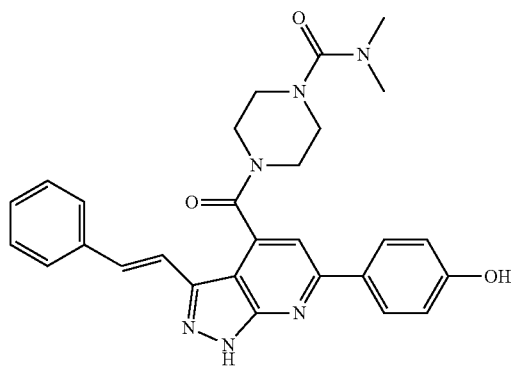 [SMILES: CN(C)C(=O)N1CCN(C(=O)c2cc(-c3ccc(O)cc3)nc3[nH]nc(/C=C/c4ccccc4)c23)CC1]

0.24 mmol of piperazine-1-carboxylic acid dimethylamide were weighted into a reaction tube and dissolved/suspended in 1 ml THF. 1 ml of a DMF stock solution containing 0.24 mmol of 6-(4-Hydroxy-phenyl)-3-((E)-styryl)-1-(tetrahydro-pyran-2-yl)-1H-pyrazolo[3,4-b]pyridine-4-carboxylic acid, 1 mmol N-methyl morpholine, 0.01 mmol 4-dimethylaminopyridine, and 0.3 mmol 1-hydroxybenzotriazole were added, followed by 0.3 mmol EDC. The tube was closed and shaken at 50° C. overnight. The THF was left to evaporate, 0.1 ml TFA was added, the volume was adjusted to 2 ml with DMF. The solution was filtered and submitted to prep. RP HPLC purification to give 4-[6-(4-Hydroxy-phenyl)-3-((E)-styryl)-1-(tetrahydro-pyran-2-yl)-1H-pyrazolo[3,4-b]pyridine-4-carbonyl]-piperazine-1-carboxylic acid dimethylamide. In order to transform the trifluoro acetic acid salt into a hydrochloric acid salt and—for other examples to cleave acid labile protecting groups—the product obtained above was shaken with 3 ml methanol and 0.5 ml 4M HCl in dioxane at 65° C. for 30 minutes. Then 10 ml diethyl ether was slowly added to the cooled solution, and the formed precipitate was filtered off, washed with 1 ml diethyl ether, and dried in vacuo to afford 0.085 mmol of 4-[6-(4-Hydroxy-phenyl)-3-((E)-styryl)-1H-pyrazolo[3,4-b]pyridine-4-carbonyl]-piperazine-1-carboxylic acid dimethylamide (35%).

LC/MS (Method LC2): Rt=3.82 min; m/z=497.26 [M+H]$^+$, $^1$H-NMR (400 MHz, d6-DMSO): 2.70 (s, 6H), 2.14-2.34 (m, 1H), 2.90-3.40 (bm, 4H), 3.30-4.0 (bm, 4H), 6.91 (d, 2H), 7.20 (d, 1H), 7.29-7.42 (m, 4H), 7.56 (d, 2H), 7.70 (s, 1H), 8.09 (d, 2H), 10 (bs, 1H).

The following examples have been prepared in a similar fashion as the synthesis for 4-[6-(4-hydroxy-phenyl)-3-((E)-styryl)-1H-pyrazolo[3,4-b]pyridine-4-carbonyl]-piperazine-1-carboxylic acid dimethylamide described immediately above employing 6-(4-hydroxy-phenyl)-3-((E)-styryl)-1-(tetrahydro-pyran-2-yl)-1H-pyrazolo[3,4-b]pyridine-4-carboxylic acid and the respective amines:

| Exp. No. | Name | Structure | LC/MS method | m/z [M + H]⁺ | R$_t$ [min] |
|---|---|---|---|---|---|
| 75 | 6-(4-Hydroxy-phenyl)-3-((E)-styryl)-1H-pyrazolo[3,4-b]-pyridine-4-carboxylic acid (4-methyl-piperidin-4-yl)-amide | 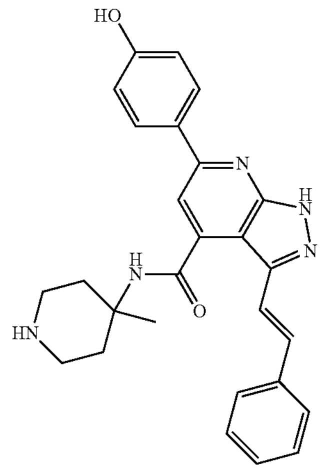 [SMILES: CC1(NC(=O)c2cc(-c3ccc(O)cc3)nc3[nH]nc(/C=C/c4ccccc4)c23)CCNCC1] | LC2 | 454.30 | 3.04 |
| 76 | ((S)-2-Butyl-piperazin-1-yl)-[6-(4-hydroxy-phenyl)-3-((E)-styryl)-1H-pyrazolo[3,4-b]-pyridin-4-yl]-methanone | 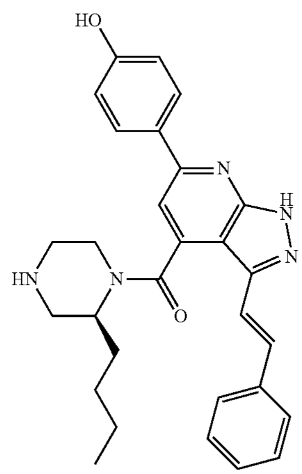 [SMILES: CCCC[C@H]1CNCCN1C(=O)c1cc(-c2ccc(O)cc2)nc2[nH]nc(/C=C/c3ccccc3)c12] | LC2 | 482.25 | 3.27 |
| 77 | ((R)-2-Butyl-piperazin-1-yl)-[6-(4-hydroxy-phenyl)-3-((E)-styryl)-1H-pyrazolo[3,4-b]-pyridin-4-yl]-methanone | 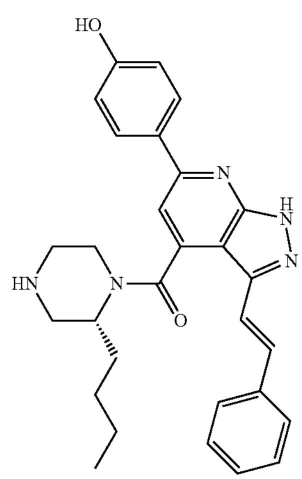 [SMILES: CCCC[C@@H]1CNCCN1C(=O)c1cc(-c2ccc(O)cc2)nc2[nH]nc(/C=C/c3ccccc3)c12] | LC2 | 482.25 | 3.19 |

| Exp. No. | Name | Structure | LC/MS method | m/z [M + H]+ | R_t [min] |
|---|---|---|---|---|---|
| 78 | (2,7-Diaza-spiro[4.4]non-2-yl)-[6-(4-hydroxyphenyl)-3-((E)-styryl)-1H-pyrazolo[3,4-b]pyridin-4-yl]-methanone | 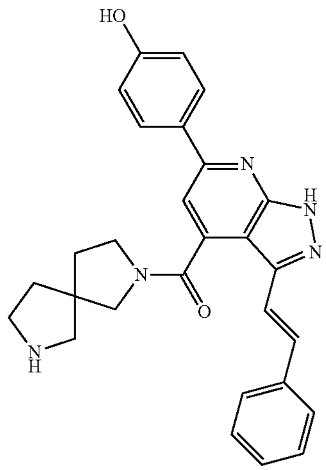 [SMILES: O=C(c1cc(-c2ccc(O)cc2)nc2[nH]nc(/C=C/c3ccccc3)c12)N1CCC2(CCNC2)C1] | LC2 | 466.26 | 2.75 |
| 79 | (6,9-Diaza-spiro[4.5]dec-9-yl)-[6-(4-hydroxyphenyl)-3-((E)-styryl)-1H-pyrazolo[3,4-b]pyridin-4-yl]-methanone | 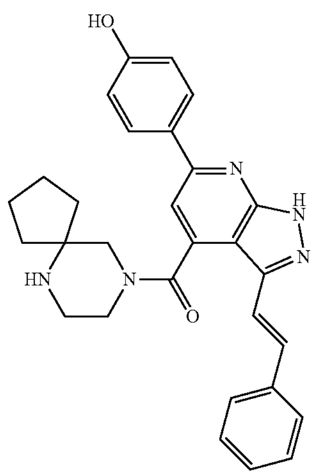 [SMILES: O=C(c1cc(-c2ccc(O)cc2)nc2[nH]nc(/C=C/c3ccccc3)c12)N1CCNC2(CCCC2)C1] | LC2 | 480.30 | 3.10 |
| 80 | 2-Ethyl-1-{4-[6-(4-hydroxyphenyl)-3-((E)-styryl)-1H-pyrazolo[3,4-b]pyridine-4-carbonyl]-piperazin-1-yl}-butan-1-one | 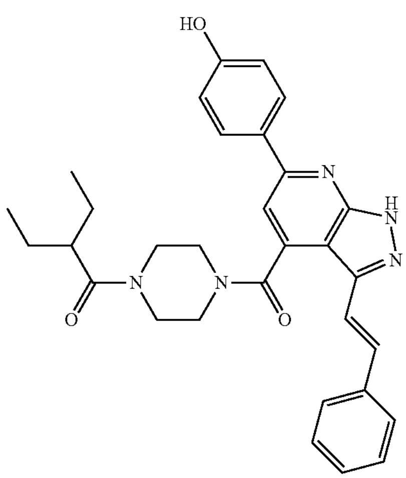 [SMILES: CCC(CC)C(=O)N1CCN(C(=O)c2cc(-c3ccc(O)cc3)nc3[nH]nc(/C=C/c4ccccc4)c23)CC1] | LC2 | 524.29 | 4.27 |

-continued

| Exp. No. | Name | Structure | LC/MS method | m/z [M + H]⁺ | R$_t$ [min] |
|---|---|---|---|---|---|
| 81 | 1-{4-[6-(4-Hydroxy-phenyl)-3-((E)-styryl)-1H-pyrazolo[3,4-b]-pyridine-4-carbonyl]-piperazin-1-yl}-2-morpholin-4-yl-ethanone | 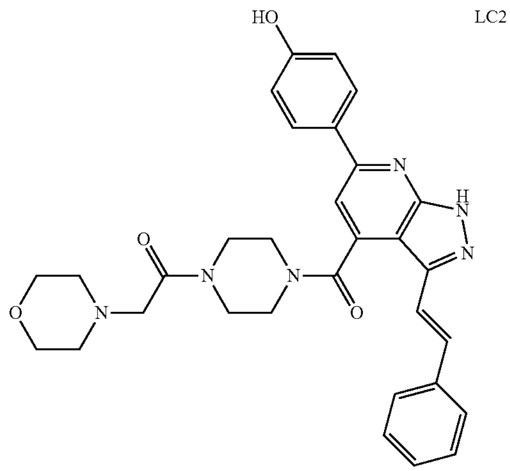 | LC2 | 553.27 | 2.83 |
| 82 | 4-[6-(4-Hydroxy-phenyl)-3-((E)-styryl)-1H-pyrazolo[3,4-b]pyridine-4-carbonyl]-piperazine-1-carboxylic acid methyl ester | 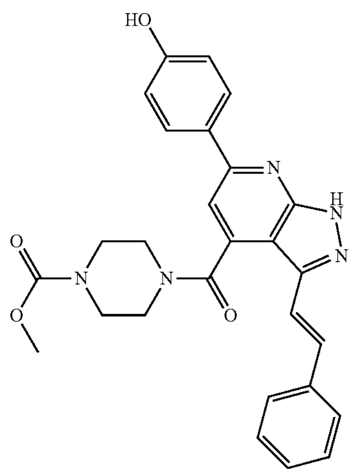 [SMILES: COC(=O)N1CCN(C(=O)c2cc(-c3ccc(O)cc3)nc3[nH]nc(/C=C/c4ccccc4)c23)CC1] | LC2 | 484.20 | 3.86 |
| 83 | [6-(4-Hydroxy-phenyl)-3-((E)-styryl)-1H-pyrazolo[3,4-b]pyridin-4-yl]-[4-(pyridine-3-carbonyl)-piperazin-1-yl]-methanone | 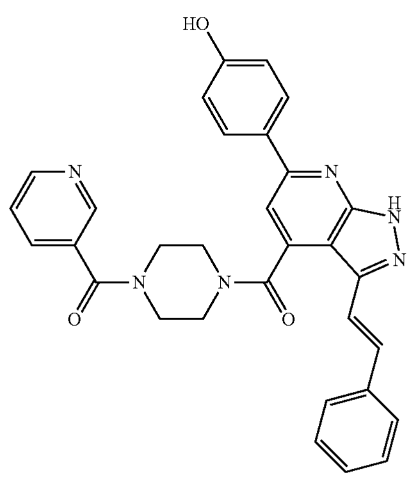 [SMILES: O=C(c1cccnc1)N1CCN(C(=O)c2cc(-c3ccc(O)cc3)nc3[nH]nc(/C=C/c4ccccc4)c23)CC1] | LC2 | 531.18 | 3.37 |

-continued

| Exp. No. | Name | Structure | LC/MS method | m/z [M + H]+ | R_t [min] |
|---|---|---|---|---|---|
| 84 | 2-{4-[6-(4-Hydroxy-phenyl)-3-((E)-styryl)-1H-pyrazolo[3,4-b]-pyridine-4-carbonyl]-piperazin-1-yl}-N,N-dimethyl-acetamide | 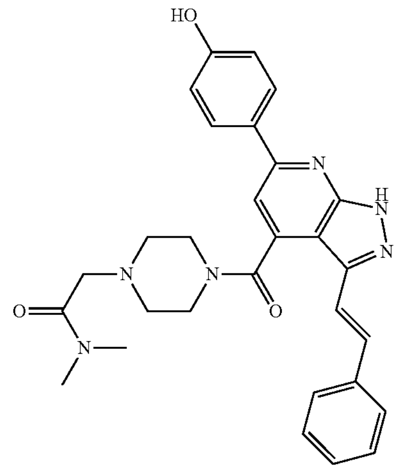 [SMILES: CN(C)C(=O)CN1CCN(C(=O)c2cc(-c3ccc(O)cc3)nc3[nH]nc(/C=C/c4ccccc4)c23)CC1] | LC2 | 511.23 | 2.90 |
| 85 | (4-Cyclopropyl-piperazin-1-yl)-[6-(4-hydroxy-phenyl)-3-((E)-styryl)-1H-pyrazolo[3,4-b]pyridin-4-yl]-methanone | 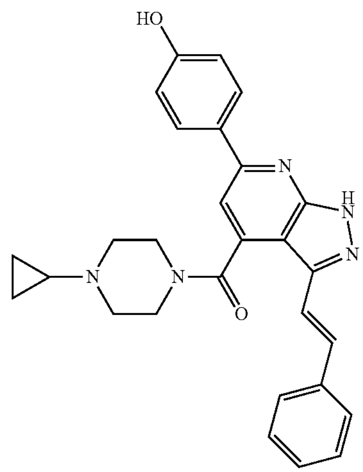 [SMILES: O=C(c1cc(-c2ccc(O)cc2)nc2[nH]nc(/C=C/c3ccccc3)c12)N1CCN(C2CC2)CC1] | LC2 | 466.26 | 3.03 |
| 86 | 2-Hydroxy-1-{4-[6-(4-hydroxy-phenyl)-3-((E)-styryl)-1H-pyrazolo[3,4-b]pyridine-4-carbonyl]-piperazin-1-yl}-2-methyl-propan-1-one | 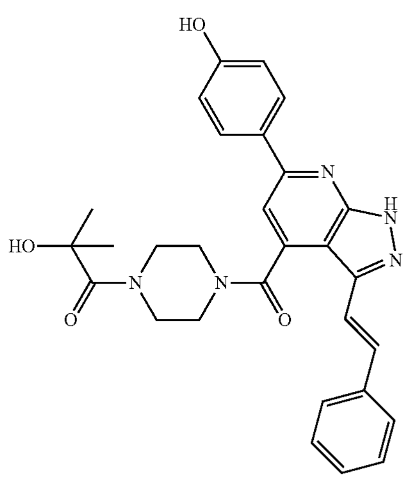 [SMILES: CC(C)(O)C(=O)N1CCN(C(=O)c2cc(-c3ccc(O)cc3)nc3[nH]nc(/C=C/c4ccccc4)c23)CC1] | LC2 | 512.27 | 3.55 |

| Exp. No. | Name | Structure | LC/MS method | m/z [M + H]+ | R_t [min] |
|---|---|---|---|---|---|
| 87 | 3-Hydroxy-1-{4-[6-(4-hydroxy-phenyl)-3-((E)-styryl)-1H-pyrazolo[3,4-b]pyridine-4-carbonyl]-piperazin-1-yl]-2,2-dimethyl-propan-1-one | 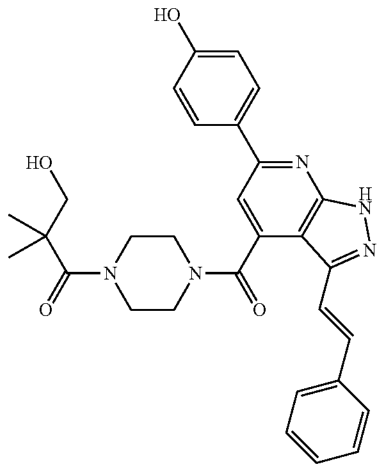 [SMILES: CC(C)(CO)C(=O)N1CCN(C(=O)c2cc(-c3ccc(O)cc3)nc3[nH]nc(/C=C/c4ccccc4)c23)CC1] | LC2 | 526.24 | 3.59 |
| 88 | 1-{4-[6-(4-Hydroxy-phenyl)-3-((E)-styryl)-1H-pyrazolo[3,4-b]-pyridine-4-carbonyl]-piperazin-1-yl}-3-methoxy-propan-1-one | 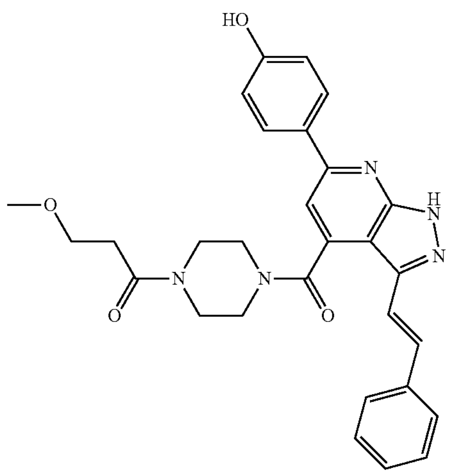 [SMILES: COCCC(=O)N1CCN(C(=O)c2cc(-c3ccc(O)cc3)nc3[nH]nc(/C=C/c4ccccc4)c23)CC1] | LC2 | 512.27 | 3.54 |

Determination of PKC βII Inhibition

PKC βII inhibition was determined according to the following protocol:

Active human full-length recombinant PKC βII and the peptide substrate, FluoresceinRFARKGSLRQKNV, were purchased from Invitrogen GmbH, Darmstadt, Germany. Adenosine-5'-triphosphate (ATP), bovine serum albumine (BSA), dimethylsulphoxide (DMSO), 4-(2-hydroxyethyl)piperazine-1-ethanesulfonic acid (Hepes), Triton X-100, 1,2-Dioleoyl-sn-glycerol (DAG), L-α-Phosphatidyl-L-serine (PS), calcium chloride ($CaCl_2$), and Pluronic F-68 were purchased from Sigma-Aldrich, Munich, Germany. Magnesium chloride, 1 M sodium hydroxide solution, 1M hydrochloric acid solution and EDTA were obtained from Merck Biosciences, Darmstadt, Germany. Test compounds were diluted to three times the test concentration in buffer 1 (30 mM Hepes-NaOH, pH 7.4, 0.01% Pluronic F-68 and 3% (v/v) DMSO). The PKC βII enzyme was diluted to a concentration of 30 ng/ml in buffer 2 (30 mM Hepes-NaOH, pH 7.4, 15 mM $MgCl_2$, 150 μM $CaCl_2$, 150 pg/ml PS, 60 μg/ml DAG, and 0.045% (w/v) Triton X-100). The peptide substrate and ATP were diluted to concentrations of 3 μM and 120 μM, respectively, in buffer 2. Two μl of the compound solution were mixed with 2 μl of the diluted enzyme in a 384-well small volume microtiter plate (Greiner, Bio-One, Frickenhausen, Germany), and the kinase reaction was initiated by addition of 2 μl of the solution containing peptide substrate and ATP. After 60 min incubation at 32° C., the reaction was stopped by addition of 20 μl of a solution containing 130 mM Hepes-NaOH, pH 7.4, 0.0195% (v/v) Brij-35, 6.5 mM EDTA, 0.13% chip coating reagent 3 (Caliper Lifescience Inc, Hopkinton, Mass.) and 6.5% (v/v) DMSO. Phosphorylation of the substrate peptide was then detected on a Caliper 3000 instrument essentially as described by Pommereau et al (J. Biomol. Screening 2004, 9(5), 409-416). Separation conditions were as follows: Pressure −0.8 psi, upstream voltage −3000 V, downstream voltage −800 V. Positive controls (buffer 1 instead of compound) and negative controls (buffer 1 instead of compound and buffer 2 instead of kinase solution) were run in parallel on each plate. Fractional turnover (R) was determined as the height of the peak of the phosphorylated peptide product divided by the sum of the unphosphorylated substrate and phosphorylated product peak heights. Percent-inhibition values for the test compounds were determined using the formula $$\% \text{ Inhibition} = 100 * (1 - (R_{compound} - R_{negative\ control}) / (R_{positive\ control} - R_{negative\ control})).$$

In the following table % inhibition values observed with example compounds at a final concentration of 1.14 μM (±0.15 μM) are listed:

| Exp. No. | % Inhibition |
|---|---|
| 1 | 86 |
| 2 | 97 |
| 3 | 88 |
| 4 | 99 |
| 5 | 85 |
| 6 | 98 |
| 7 | 96 |
| 8 | 97 |
| 9 | 55 |
| 10 | 87 |
| 11 | 99 |
| 12 | 97 |
| 13 | 110 |
| 14 | 100 |
| 15 | 99 |
| 16 | 96 |
| 17 | 94 |
| 18 | 94 |
| 19 | 99 |
| 20 | 115 |
| 21 | 98 |
| 22 | 100 |
| 23 | 99 |
| 24 | 99 |
| 25 | 99 |
| 26 | 96 |
| 27 | 98 |
| 28 | 94 |
| 29 | 96 |
| 30 | 90 |
| 31 | 99 |
| 32 | 99 |
| 33 | 99 |
| 34 | 98 |
| 35 | 98 |
| 36 | 81 |
| 37 | 97 |
| 38 | 98 |
| 39 | 39 |
| 40 | 99 |
| 41 | 97 |
| 42 | 66 |
| 43 | 87 |
| 44 | 97 |
| 45 | 61 |
| 46 | 97 |
| 47 | 98 |
| 48 | 97 |
| 49 | 88 |
| 50 | 92 |
| 51 | 94 |
| 52 | 91 |
| 53 | 95 |
| 54 | 95 |
| 55 | 76 |
| 56 | 100 |
| 57 | 98 |
| 58 | 89 |
| 59 | 97 |
| 60 | 98 |
| 61 | 86 |
| 62 | 98 |
| 63 | 97 |
| 64 | 99 |
| 65 | 97 |
| 66 | 99 |
| 67 | 99 |
| 68 | 60 |
| 69 | 94 |
| 70 | 98 |
| 71 | 96 |
| 72 | 99 |
| 73 | 98 |
| 74 | 27 |
| 75 | 93 |
| 76 | 57 |
| 77 | 79 |
| 78 | 94 |
| 79 | 97 |
| 80 | 26 |
| 81 | 45 |
| 82 | 56 |
| 83 | 90 |
| 84 | 54 |
| 85 | 19 |
| 86 | 93 |
| 87 | 94 |
| 88 | 89 |

The invention claimed is:

1. A compound of formula I

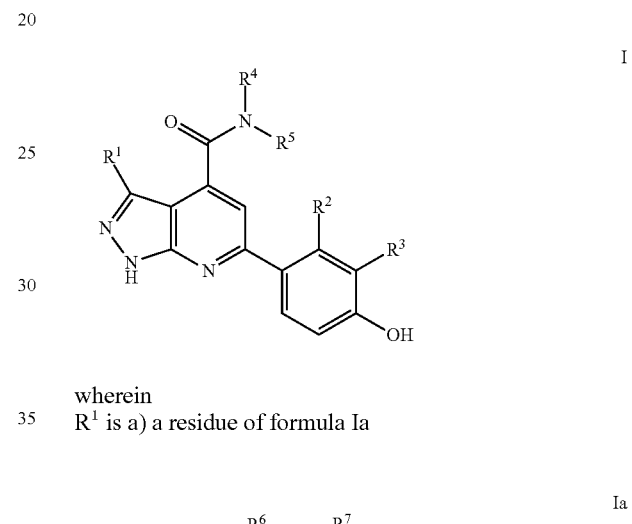

wherein
$R^1$ is a) a residue of formula Ia

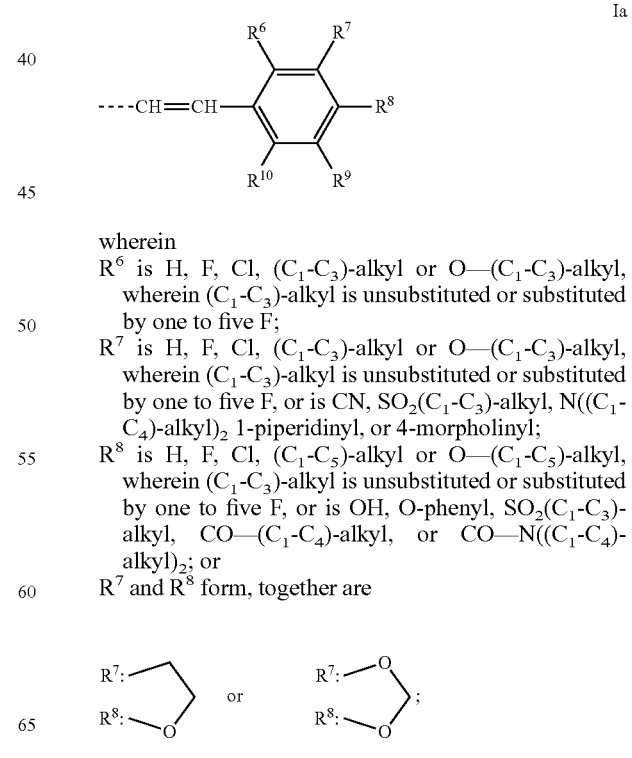

wherein
$R^6$ is H, F, Cl, $(C_1-C_3)$-alkyl or O—$(C_1-C_3)$-alkyl, wherein $(C_1-C_3)$-alkyl is unsubstituted or substituted by one to five F;
$R^7$ is H, F, Cl, $(C_1-C_3)$-alkyl or O—$(C_1-C_3)$-alkyl, wherein $(C_1-C_3)$-alkyl is unsubstituted or substituted by one to five F, or is CN, $SO_2(C_1-C_3)$-alkyl, $N((C_1-C_4)$-alkyl$)_2$ 1-piperidinyl, or 4-morpholinyl;
$R^8$ is H, F, Cl, $(C_1-C_5)$-alkyl or O—$(C_1-C_5)$-alkyl, wherein $(C_1-C_3)$-alkyl is unsubstituted or substituted by one to five F, or is OH, O-phenyl, $SO_2(C_1-C_3)$-alkyl, CO—$(C_1-C_4)$-alkyl, or CO—N$((C_1-C_4)$-alkyl$)_2$; or
$R^7$ and $R^8$ form, together are $R^9$ is H, F, $CH_3$, or $O-CH_3$; and
$R^{10}$ is H; or b) ethylene-phenyl, wherein phenyl is unsubstituted or substituted by one or two identical or different substituents selected from F, Cl, $CH_3$, $O-CH_3$, $CF_3$, $O-CF_3$, CN, $SO_2CH_3$, $CO-CH_3$, and $CO-N((CH_3)_2$; and $R^2$ is H, or $CH_3$;
$R^3$ is H, or $O-CH_3$; and
$R^4$ is piperidin-4-yl, piperidin-3-yl or pyrrolidin-3-yl, which are unsubstituted or monosubstituted by $(C_1-C_3)$-alkyl, which is unsubstituted or substituted by one to five F, and
$R^5$ is H, or
$R^4$ and $R^5$ together with the nitrogen carrying them form
a) a residue of formula Ib

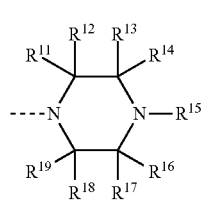

wherein
$R^{11}$ is H, $CH_3$, $(C_3-C_5)$-cycloalkyl, or $(C_3-C_4)$-alkyl, and
$R^{12}$ is H, or
$R^{11}$ and $R^{12}$ together with the C-atoms form 1'-spiro-cyclopentyl;
$R^{13}$ is H, $(C_1-C_4)$-alkyl, or $(C_3-C_5)$-cycloalkyl, and
$R^{14}$ is H, or $CH_3$ or
$R^{13}$ and $R^{14}$ together with the C-atom carrying them is 1'-spiro-cyclo-$(C_3-C_6)$-alkyl;
$R^{15}$ is H, $CH_2-CO-N((C_1-C_4)\text{-alkyl})_2$, $CO-(C_1-C_6)$-alkyl, $CO-(C_1-C_4)$-alkylene-OH, $CO-(C_1-C_4)$-alkylene-O-$CH_3$, $CO-CH_2$-4-morpholinyl, $CO-O-(C_1-C_4)$-alkyl, $CO-N((C_1-C_4)\text{-alkyl})_2$, $(C_3-C_6)$-cycloalkyl, or pyridyl;
$R^{16}$ is H, or $(C_1-C_4)$-alkyl;
$R^{17}$ is H;
$R^{18}$ is H; and
$R^{19}$ is H; or b) a 9 to 11 membered spiro-heterocycloalkyl containing 2 nitrogen atoms, which is attached via a nitrogen atom; or a pharmaceutically acceptable salt thereof.

2. A compound of formula I as claimed in claim 1, wherein $R^1$ is a) a residue of formula Ia

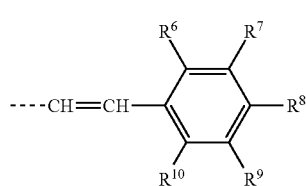

wherein
$R^4$ is 4 methyl-piperidin-4-yl and
$R^5$ is H, or
$R^4$ and $R^5$ together with the nitrogen carrying them form
a) a residue of formula Ib

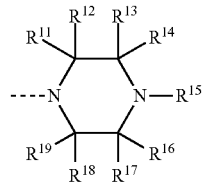

wherein
$R^{11}$ is H, $CH_3$, $(C_3-C_4)$-alkyl, or $(C_3-C_4)$-cycloalkyl; and
$R^{12}$ is H;
or a pharmaceutically acceptable salt thereof.

3. A compound of formula I as claimed in claim 1, wherein $R^1$ is a) a residue of formula Ia

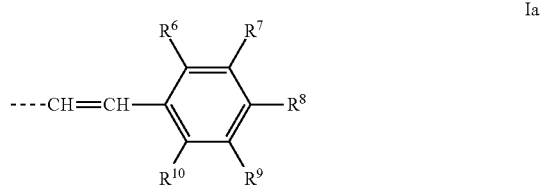

wherein
$R^6$ is H, F, Cl, $CH_3$, $CF_3$, or $O-CH_3$; and
$R^7$ is H, F, Cl, $CH_3$, $CF_3$, CN, $O-CH_3$, $SO_2CH_3$, $N(CH_3)_2$, 1-piperidinyl, or 4-morpholinyl;
$R^8$ is H, F, Cl, $CH_3$, $CH_2CH_3$, $CH(CH_3)_2$, $C(CH_3)_3$, $CF_3$, OH, $O-CH_3$, $O-C_2H_5$, $O-CHF_2$, $O-CF_3$, O-phenyl, $SO_2CH_3$, $CO-CH_3$, or $CO-N(CH_3)_2$; or
$R^7$ and $R^8$ together are

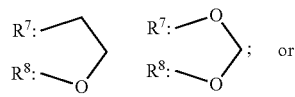

b) phenethyl; and
$R^4$ is 4-methyl-piperidin-4-yl, and
$R^5$ is H, or
$R^4$ and $R^5$ together with the nitrogen carrying them form
a) a residue of formula Ib

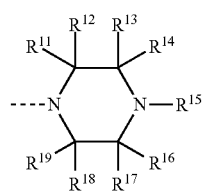

wherein
$R^{11}$ is H, $CH_3$, or $(CH_2)_3-CH_3$, and
$R^{12}$ is H, or
$R^{11}$ and $R^{12}$ together with the C-atoms form 1'-spiro-cyclopentyl;
$R^{13}$ is H, $CH_3$, or $CH_2-CH(CH_3)_2$, and
$R^{14}$ is H, or $CH_3$, or
$R^{13}$ and $R^{14}$ together with the C-atom carrying them is 1'-spiro-cyclopentyl; and $R^{15}$ is H, $CH_2$—CO—$N(CH_3)_2$, CO—$CH(C_2H_5)_2$, CO—$C(CH_3)_2$—OH, CO—$C(CH_3)_2$—$CH_2$—OH, CO—$(CH_2)_2$—O—$CH_3$, CO—$CH_2$—4-morpholinyl, CO—$OCH_3$, CO—$N(CH_3)_2$, cyclopropyl, or 3-pyridyl; and $R^{16}$ is H, or $CH_3$; or b) (2,7-Diaza-spiro[4.4]non-2-yl), or a pharmaceutically acceptable salt thereof.

4. A compound of formula I as claimed in claim 1, wherein $R^1$ is a residue of formula Ia

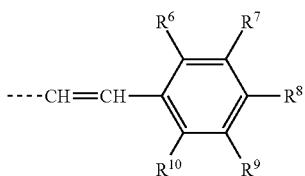

wherein
$R^6$ is H, F, Cl, $CH_3$, $CF_3$, or O—$CH_3$;
$R^7$ is H, F, Cl, $CH_3$, $CF_3$, CN, O—$CH_3$, $SO_2CH_3$, $N(CH_3)_2$, 1-piperidinyl, or 4-morpholinyl;
$R^8$ is H, F, Cl, $CH_3$, $CH_2CH_3$, $CH(CH_3)_2$, $C(CH_3)_3$, $CF_3$, OH, O—$CH_3$, O—$C_2H_5$, O—$CHF_2$, O—$CF_3$, O-phenyl, $SO_2CH_3$, CO—$CH_3$, or CO—$N(CH_3)_2$; and
$R^2$ is H;
$R^3$ is H; and
$R^4$ and $R^5$ together with the nitrogen carrying them form a residue of formula Ib

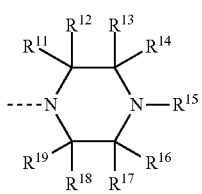

wherein
$R^{11}$ is H, $CH_3$, or $(CH_2)_3$—$CH_3$, and
$R^{12}$ is H, or
$R^{11}$ and $R^{12}$ together with the C-atoms carrying them are 1'-spiro-cyclopentyl;
$R^{13}$ is H, $CH_3$, or $CH_2$—$CH(CH_3)_2$, and
$R^{14}$ is H, or $CH_3$, or
$R^{13}$ and $R^{14}$ together with the C-atom carrying them is 1'-spiro-cyclopentyl; and
$R^{15}$ is H; and
$R^{16}$ is H, or $CH_3$;
or a pharmaceutically acceptable salt thereof.

5. A compound selected from
[3-[(E)-2-(4-Chloro-phenyl)-vinyl]-6-(4-hydroxy-phenyl)-1H-pyrazolo[3,4-b]pyridin-4-yl]-piperazin-1-yl-methanone,
[6-(4-Hydroxy-phenyl)-3-((E)-styryl)-1H-pyrazolo[3,4-b]pyridin-4-yl]-piperazin-1-yl-methanone,
(3,3-Dimethyl-piperazin-1-yl)-[6-(4-hydroxy-phenyl)-3-((E)-styryl)-1H-pyrazolo[3,4-b]pyridin-4-yl]-methanone,
[6-(4-Hydroxy-phenyl)-3-((E)-styryl)-1H-pyrazolo[3,4-b]pyridin-4-yl]-(S)-3-isobutyl-piperazin-1-yl)-methanone,
[6-(4-Hydroxy-phenyl)-3-((E)-styryl)-1H-pyrazolo[3,4-b]pyridin-4-yl]-((S)-2-methyl-piperazin-1-yl)-methanone,
[6-(4-Hydroxy-2-methyl-phenyl)-3-((E)-styryl)-1H-pyrazolo[3,4-b]pyridin-4-yl]-piperazin-1-yl-methanone,
((2S,5R)-2,5-Dimethyl-piperazin-1-yl)-[6-(4-hydroxy-phenyl)-3-((E)-styryl)-1H-pyrazolo[3,4-b]pyridin-4-yl]-methanone,
[6-(4-Hydroxy-3-methoxy-phenyl)-3-((E)-styryl)-1H-pyrazolo[3,4-b]pyridin-4-yl]-piperazin-1-yl-methanone,
[6-(4-Hydroxy-phenyl)-3-phenethyl-1H-pyrazolo[3,4-b]pyridin-4-yl]-piperazin-1-yl-methanone,
[6-(4-Hydroxy-phenyl)-3-((E)-2-p-tolyl-vinyl)-1H-pyrazolo[3,4-b]pyridin-4-yl]-piperazin-1-yl-methanone,
{6-(4-Hydroxy-phenyl)-3-[(E)-2-(3-methanesulfonyl-phenyl)-vinyl]-1H-pyrazolo[3,4-b]pyridin-4-yl}-piperazin-1-yl-methanone,
[3-[(E)-2-(3-Dimethylamino-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(4-methanesulfonyl-phenyl)-vinyl]-1H-pyrazolo[3,4-b]pyridin-4-yl}-piperazin-1-yl-methanone,
3-{(E)-2-[6-(4-Hydroxy-phenyl)-4-(piperazine-1-carbonyl)-1H-pyrazolo[3,4-b]pyridin-3-yl]-vinyl}-benzonitrile,
{6-(4-Hydroxy-phenyl)-3-[(E)-2-(3-piperidin-1-yl-phenyl)-vinyl]-1H-pyrazolo[3,4-b]pyridin-4-yl}-piperazin-1-yl-methanone,
{6-(4-Hydroxy-phenyl)-3-[(E)-2-(3-morpholin-4-yl-phenyl)-vinyl]-1H-pyrazolo[3,4-b]pyridin-4-yl}-piperazin-1-yl-methanone,
[3-[(E)-2-(4-Fluoro-phenyl)-vinyl]-6-(4-hydroxy-phenyl)-1H-pyrazolo[3,4-b]pyridin-4-yl]-piperazin-1-yl-methanone,
[6-(4-Hydroxy-phenyl)-3-((E)-2-m-tolyl-vinyl)-1H-pyrazolo[3,4-b]pyridin-4-yl]-piperazin-1-yl-methanone,
[3-[(E)-2-(2,4-Dichloro-phenyl)-vinyl]-6-(4-hydroxy-phenyl)-1H-pyrazolo[3,4-b]pyridin-4-yl]-piperazin-1-yl-methanone,
[3-[(E)-2-(3,5-Dimethyl-phenyl)-vinyl]-6-(4-hydroxy-phenyl)-1H-pyrazolo[3,4-b]pyridin-4-yl]-piperazin-1-yl-methanone,
[3-[(E)-2-(4-Difluoromethoxy-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(4-trifluoromethyl-phenyl)-vinyl]-1H-pyrazolo[3,4-b]pyridin-4-yl}-piperazin-1-yl-methanone,
[3-[(E)-2-(2,4-Dimethoxy-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(4-phenoxy-phenyl)vinyl]-1H-pyrazolo[3,4-b]pyridin-4-yl}-piperazin-1-yl-methanone,
[3-[(E)-2-(3,4-Dichloro-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(3-trifluoromethyl-phenyl)-vinyl]-1H-pyrazolo[3,4-b]pyridin-4-yl}piperazin-1-yl-methanone,
[3-[(E)-2-(4-Hydroxy-3-methyl-phenyl)-vinyl]-6-(4-hydroxy-phenyl)-1H-pyrazolo[3,4-b]pyridin-4-yl]-piperazin-1-yl-methanone,

[3-[(E)-2-(3-Chloro-phenyl)vinyl]-6-(4-hydroxy-phenyl)-1H-pyrazolo[3,4-b]pyridin-4-yl]-piperazin-1-yl-methanone,
[3-[(E)-2-(2,4-Dimethyl-phenyl)-vinyl]-6-(4-hydroxy-phenyl)-1H-pyrazolo[3,4-b]pyridin-4-yl]-piperazin-1-yl-methanone,
[3-[(E)-2-(2,5-Dimethyl-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(4-isopropyl-phenyl)-vinyl]-1H-pyrazolo[3,4-b]pyridin-4-yl}-piperazin-1-yl-methanone,
[3-[(E)-2-(2-Chloro-4-fluoro-phenyl)-vinyl]-6-(4-hydroxy-phenyl)-1H-pyrazolo[3,4-b]pyridin-4-yl]-piperazin-1-yl-methanone,
[3-[(E)-2-(4-Ethyl-phenyl)-vinyl]-6-(4-hydroxy-phenyl)-1H-pyrazolo[3,4-b]pyridin-4-yl]-piperazin-1-yl-methanone
[3-[(E)-2-(4-tert-Butyl-phenyl)-vinyl]-6-(4-hydroxy-phenyl)-1H-pyrazolo[3,4-b]pyridin-4-yl]-piperazin-1-yl-methanone,
[3-[(E)-2-(3-Fluoro-4-methyl-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(3-methoxy-phenyl)-vinyl]-1H-pyrazolo[3,4-b]pyridin-4-yl}-piperazin-1-yl-methanone,
1-(4-{(E)-2-[6-(4-Hydroxy-phenyl)-4-(piperazine-1-carbonyl)-1H-pyrazolo[3,4-b]pyridin-3-yl]vinyl}-phenyl)-ethanone,
{6-(4-Hydroxy-phenyl)-3-[(E)-2-(4-trifluoromethoxy-phenyl)-vinyl]-1H-pyrazolo[3,4-b]pyridin-4-yl}-piperazin-1-yl-methanone,
[3-[(E)-2-(3,4-Difluoro-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(2-methoxy-phenyl)-vinyl]-1H-pyrazolo[3,4-b]pyridin-4-yl}-piperazin-1-yl-methanone,
[3-[(E)-2-(4-Fluoro-2-methyl-phenyl)-vinyl]-6-(4-hydroxy-phenyl)-1H-pyrazolo[3,4-b]pyridin-4-yl]piperazin-1-yl-methanone,
{6-(4-Hydroxy-phenyl)-3-[(E)-2-(3,4,5-trimethoxy-phenyl)-vinyl]-1H-pyrazolo[3,4-b]pyridin-4-yl}-piperazin-1-yl-methanone,
[3-[(E)-2-(2-Fluoro-4-methyl-phenyl)-vinyl]-6-(4-hydroxy-phenyl)-1H-pyrazolo[3,4-b]pyridin-4-yl]-piperazin-1-yl-methanone,
[3-[(E)-2-(2,3-Dihydro-benzofuran-5-yl)-vinyl]-6-(4-hydroxy-phenyl)-1H-pyrazolo[3,4-b]pyridin-4-yl]-piperazin-1-yl-methanone,
[3-((E)-2-Benzo[1,3]dioxol-5-yl-vinyl)-6-(4-hydroxy-phenyl)-1H-pyrazolo[3,4-b]pyridin-4-yl]-piperazin-1-yl-methanone,
4-{(E)-2[6-(4-Hydroxy-phenyl)-4-(piperazine-1-carbonyl)-1H-pyrazolo[3,4-b]pyridin-3-yl]-vinyl}-N,N-dimethyl-benzamide,
[3-[(E)-2-(4-Ethoxy-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(2-trifluoromethyl-phenyl)-vinyl]-1H-pyrazolo[3,4-b]pyridin-4-yl}-piperazin-1-yl-methanone,
[6-(4-Hydroxy-phenyl)-3-((E)-2-o-tolyl-vinyl)-1H-pyrazolo[3,4-b]pyridin-4-yl]-piperazin-1-yl-methanone,
[3-[(E)-2-(3-Fluoro-phenyl)-vinyl]-6-(4-hydroxy-phenyl)-1H-pyrazolo[3,4-b]pyridin-4-yl]-piperazin-1-yl-methanone,
[3-[(E)-2-(2-Fluoro-phenyl)-vinyl]-6-(4-hydroxy-phenyl)-1H-pyrazolo[3,4-b]pyridin-4-yl]-piperazin-1-yl-methanone,
{6-(4-Hydroxy-phenyl)-3-[(E)-2-(4-methoxy-3-methyl-phenyl)-vinyl]-1H-pyrazolo[3,4-b]pyridin-4-yl}-piperazin-1-yl-methanone,
4-[6-(4-Hydroxy-phenyl)-3-((E)-styryl)-1H-pyrazolo[3,4-b]pyridine-4-carbonyl]-piperazine-1-carboxylic acid dimethylamide,
6-(4-Hydroxy-phenyl)-3-((E)-styryl)-1H-pyrazolo[3,4-b]pyridine-4-carboxylic acid (4-methyl-piperidin-4-yl)-amide,
((S)-2-Butyl-piperazin-1-yl)-[6-(4-hydroxy-phenyl)-3-((E)-styryl)-1H-pyrazolo[3,4-b]pyridin-4-yl]-methanone,
((R)-2-Butyl-piperazin-1-yl)-[6-(4-hydroxy-phenyl)-3-((E)-styryl)-1H-pyrazolo[3,4-b]pyridin-4-yl]-methanone,
(2,7-Diaza-spiro[4.4]non-2-yl)-[6-(4-hydroxy-phenyl)-3-((E)-styryl)-1H-pyrazolo[3,4-b]pyridin-4-yl]-methanone,
(6,9-Diaza-spiro[4.5]dec-9-yl)-[6-(4-hydroxy-phenyl)-3-((E)-styryl)-1H-pyrazolo[3,4-b]pyridin-4-yl]-methanone,
2-Ethyl-1-{4[-(4-hydroxy-phenyl)-3-((E)-styryl)-1H-pyrazolo[3,4-b]pyridine-4-carbonyl]-piperazin-1-yl}-butan-1-one,
1-{4-[6-(4-Hydroxy-phenyl)-3-((E)-styryl)-1H-pyrazolo[3,4-b]pyridine-4-carbonyl]-piperazin-1-yl}-2-morpholin-4-yl-ethanone,
4-[6-(4-Hydroxy-phenyl)-3-((E)-styryl)-1H-pyrazolo[3,4-b]pyridine-4-carbonyl]-piperazine-1-carboxylic acid methyl ester,
[6-(4-Hydroxy-phenyl)-3-((E)-styryl)-1H-pyrazolo[3,4-b]pyridin-4-yl]-[4-(pyridine-3-carbonyl)-piperazin-1-yl]-methanone,
2-{4-[6-(4-Hydroxy-phenyl)-3-((E)-styryl)-1H-pyrazolo[3,4-b]pyridine-4-carbonyl]-piperazin-1-yl}-N,N-dimethyl-acetamide,
(4-Cyclopropyl-piperazin-1-yl)-[6-(4-hydroxy-phenyl)-3-((E)-styryl)-1H-pyrazolo[3,4-b]pyridin-4-yl]-methanone,
2-Hydroxy-1-{4-[6-(4-hydroxy-phenyl)-3-((E)-styryl)-1H-pyrazolo[3,4-b]pyridine-4-carbonyl]-piperazin-1-yl}-2-methyl-propan-1-one,
3-Hydroxy-1-{4-[6-(4-hydroxy-phenyl)-3-((E)-styryl)-1H-pyrazolo[3,4-b]pyridine-4-carbonyl]piperazin-1-yl}-2,2-dimethyl-propan-1-one, or
1-{4-[6-(4-Hydroxy-phenyl)-3-((E)-styryl)-1H-pyrazolo[3,4-b]pyridine-4-carbonyl]-piperazin-1-yl}-3-methoxy-propan-1-one,
or a pharmaceutically acceptable salt thereof.

6. A pharmaceutical composition, comprising at least one compound of formula I as claimed in claim 1, or as claimed in claim 5; or a pharmaceutically acceptable salt thereof, and a pharmaceutically acceptable carrier.

7. The compound of formula I as claimed in claim 2, wherein $R^{13}$ and $R^{14}$ together with the C-atom carrying them is 1'-spiro-cyclopentyl.

\* \* \* \* \*